(12) United States Patent
Zimmerman et al.

(10) Patent No.: US 11,648,257 B2
(45) Date of Patent: *May 16, 2023

(54) PHARMACEUTICAL CARRIERS CAPABLE OF PH DEPENDENT RECONSTITUTION AND METHODS FOR MAKING AND USING SAME

(71) Applicant: PLx Opco Inc., Sparta, NJ (US)

(72) Inventors: Ronald R. Zimmerman, Sparta, NJ (US); Efthymios Deliargyris, Sparta, NJ (US); Robert W. Strozier, Sparta, NJ (US); Jeffrey W. Moore, Sparta, NJ (US)

(73) Assignee: PLx Opco Inc., Sparta, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/378,458

(22) Filed: Jul. 16, 2021

(65) Prior Publication Data

US 2022/0000886 A1 Jan. 6, 2022

Related U.S. Application Data

(63) Continuation of application No. PCT/US2021/024061, filed on Mar. 25, 2021.

(60) Provisional application No. 63/000,287, filed on Mar. 26, 2020.

(51) Int. Cl.
| | | |
|---|---|---|
| *A61K 31/616* | (2006.01) |
| *A61K 31/192* | (2006.01) |
| *A61K 31/4439* | (2006.01) |
| *A61K 47/12* | (2006.01) |
| *A61K 47/14* | (2017.01) |
| *A61K 47/24* | (2006.01) |
| *A61K 47/26* | (2006.01) |
| *A61K 47/42* | (2017.01) |
| *A61K 47/44* | (2017.01) |
| *A61K 47/38* | (2006.01) |

(52) U.S. Cl.
CPC .......... *A61K 31/616* (2013.01); *A61K 31/192* (2013.01); *A61K 31/4439* (2013.01); *A61K 47/12* (2013.01); *A61K 47/14* (2013.01); *A61K 47/24* (2013.01); *A61K 47/26* (2013.01); *A61K 47/38* (2013.01); *A61K 47/42* (2013.01); *A61K 47/44* (2013.01)

(58) Field of Classification Search
None
See application file for complete search history.

(56) References Cited

U.S. PATENT DOCUMENTS

| | | |
|---|---|---|
| 4,079,131 A | 3/1978 | Lin et al. |
| 4,079,132 A | 3/1978 | Lin et al. |
| 4,309,420 A | 1/1982 | Ghyczy et al. |
| 4,332,795 A | 6/1982 | Ghyczy et al. |
| 4,369,182 A | 1/1983 | Ghyczy et al. |
| 4,378,354 A | 3/1983 | Ghyczy et al. |
| 4,421,747 A | 12/1983 | Ghyczy et al. |
| 4,474,798 A | 10/1984 | Inagi et al. |
| 4,684,632 A | 8/1987 | Schulz et al. |
| 4,687,762 A | 8/1987 | Fukushima et al. |
| 4,849,227 A | 7/1989 | Cho |
| 4,918,063 A | 4/1990 | Lichtenberger |
| 4,950,656 A | 8/1990 | Lichtenberger |
| 5,032,585 A | 7/1991 | Lichtenberger |
| 5,043,329 A | 8/1991 | Lichtenberger |
| 5,059,626 A | 10/1991 | Park et al. |
| 5,091,188 A | 2/1992 | Haynes |
| 5,110,606 A | 5/1992 | Geyer et al. |
| 5,145,684 A | 9/1992 | Liversidge et al. |
| 5,154,930 A | 10/1992 | Popescu et al. |
| 5,213,804 A | 5/1993 | Martin et al. |
| 5,314,909 A | 5/1994 | Dollerup |
| 5,505,960 A | 4/1996 | Lucchetti et al. |
| 5,518,738 A | 5/1996 | Eickhoff |
| 5,552,160 A | 9/1996 | Liversidge et al. |
| 5,560,931 A | 10/1996 | Eickhoff |
| 5,603,959 A | 2/1997 | Horrobin et al. |
| 5,763,422 A | 6/1998 | Lichtenberger et al. |
| 5,807,541 A | 9/1998 | Aberg et al. |
| 5,891,466 A | 4/1999 | Yesair |
| 5,916,591 A | 6/1999 | Bierdel-Willkommen et al. |
| 5,942,248 A | 8/1999 | Barnwell |

(Continued)

FOREIGN PATENT DOCUMENTS

| | | |
|---|---|---|
| CN | 1585644 A | 2/2005 |
| EP | 51833 A1 | 5/1982 |

(Continued)

OTHER PUBLICATIONS

Salicylic Acid PubChem ID 338 [online], PubChem [retrieved on Feb. 11, 2022], Retrieved from the internet: <https://pubchem.ncbi.nlm.nih.gov/compound/Salicylic-acid#:~:text=Salicylic%20Acid%20is%20a%20beta,white%20to%20light%20tan% 20solid.> (Year: 2022).*
Jain et al. AAPS PharmSciTech vol. 10 No 4. (Year: 2009).*
Trimaille et al. Journal of Biomedical Materials Research Part A; pp. 55-65. (Year: 2006).*
International Search Report and Written Opinion issued in International Patent Application No. PCT/US2021/024061, dated Jul. 7, 2021.
Lichtenberger et a., "Surface phospholipids in gastric injury and protection when a selective cyclooxygenase-2 inhibitor (Coxib) is used in combination with aspirin," *British Journ. Of Pharmacology*, vol. 150, pp. 913-919 (2007).

(Continued)

*Primary Examiner* — Katherine Peebles
(74) *Attorney, Agent, or Firm* — Foley & Lardner LLP

(57) ABSTRACT

Disclosed herein are novel drug carriers including a non-aqueous pH dependent release system and a non-aqueous pH dependent reassembly/assembly and reabsorption/absorption system. The carriers are capable of pH dependent release of biologically active agents and assembly or reassembly when the carrier transitions from a low pH environment, to a high pH environment and back to a low pH environment.

20 Claims, 37 Drawing Sheets

(56) References Cited

U.S. PATENT DOCUMENTS

| | | | |
|---|---|---|---|
| 5,955,451 | A | 9/1999 | Lichtenberger |
| 6,045,821 | A | 4/2000 | Garrity et al. |
| 6,096,336 | A | 8/2000 | Cao et al. |
| 6,096,338 | A | 8/2000 | Lacy et al. |
| 6,120,800 | A | 9/2000 | Forssen et al. |
| 6,248,363 | B1 | 6/2001 | Patel et al. |
| 6,569,463 | B2 | 5/2003 | Patel et al. |
| 6,759,057 | B1 | 7/2004 | Weiner et al. |
| 6,923,988 | B2 | 8/2005 | Patel et al. |
| 7,374,779 | B2 | 5/2008 | Chen et al. |
| 7,473,432 | B2 | 1/2009 | Cevc et al. |
| 8,663,692 | B1 | 3/2014 | Muller |
| 9,216,150 | B2 * | 12/2015 | Marathi ............... A61K 31/192 |
| 9,226,892 | B2 * | 1/2016 | Marathi ............... A61K 31/196 |
| 9,730,884 | B2 * | 8/2017 | Marathi ............... A61K 31/196 |
| 10,179,104 | B2 * | 1/2019 | Marathi ................ A61K 47/14 |
| 10,646,431 | B2 * | 5/2020 | Marathi ................ A61K 47/12 |
| 10,656,431 | B2 | 5/2020 | Marathi et al. |
| 10,786,444 | B2 * | 9/2020 | Marathi ............... A61K 31/405 |
| 2002/0035264 | A1 | 3/2002 | Kararli et al. |
| 2003/0219461 | A1 | 11/2003 | Britten et al. |
| 2004/0077604 | A1 | 4/2004 | Lichtenberger |
| 2004/0109894 | A1 | 6/2004 | Shefer et al. |
| 2004/0146537 | A1 | 7/2004 | Radhakrishnan et al. |
| 2005/0147659 | A1 | 7/2005 | Carli et al. |
| 2006/0100263 | A1 | 5/2006 | Basile et al. |
| 2006/0188607 | A1 | 8/2006 | Schramm |
| 2006/0210622 | A1 | 9/2006 | Pace et al. |
| 2007/0154559 | A1 | 7/2007 | Pai et al. |
| 2007/0196396 | A1 * | 8/2007 | Pilgaonkar ........... A61K 9/2027 514/217 |
| 2008/0260819 | A1 | 10/2008 | Fleming |
| 2010/0136105 | A1 | 6/2010 | Chen et al. |
| 2011/0034568 | A1 | 2/2011 | Lichtenberger |
| 2011/0065677 | A1 | 3/2011 | Lichtenberger |
| 2011/0071118 | A1 | 3/2011 | Lichtenberger |
| 2012/0276194 | A1 | 11/2012 | Besins et al. |
| 2013/0296933 | A1 * | 11/2013 | Kashiwabuchi ..... D01D 5/0076 606/231 |
| 2017/0304190 | A1 * | 10/2017 | Marathi .................. A61P 29/00 |
| 2018/0169061 | A1 * | 6/2018 | Gumudavelli ........... A61K 9/50 |

FOREIGN PATENT DOCUMENTS

| | | |
|---|---|---|
| EP | 0 287 036 A2 | 10/1988 |
| EP | 0 407 815 A2 | 1/1991 |
| JP | 57108021 | 7/1982 |
| JP | 3176425 | 7/1991 |
| JP | 2007-22881 A | 2/2007 |
| WO | WO 87/07506 A1 | 12/1987 |
| WO | WO 92/06680 | 4/1992 |
| WO | WO 92/06680 A1 | 4/1992 |
| WO | WO 1996/022780 | 8/1996 |
| WO | WO 1998/013073 A2 | 4/1998 |
| WO | WO 2000/02554 A2 | 1/2000 |
| WO | WO 2000/022909 A2 | 4/2000 |
| WO | WO 2000/022909 A3 | 4/2000 |
| WO | WO 2000/067728 A2 | 11/2000 |
| WO | WO 02/083099 | 10/2002 |
| WO | WO 2002/085414 A2 | 10/2002 |
| WO | WO 2005/044254 A1 | 5/2005 |
| WO | WO 2008/025819 A2 | 3/2008 |
| WO | WO 2008/068276 A1 | 6/2008 |
| WO | WO 2009/063500 A2 | 5/2009 |
| WO | WO 2011/082384 A2 | 7/2011 |
| WO | WO 2011/095814 A1 | 8/2011 |
| WO | WO 2013/049749 A2 | 4/2013 |

OTHER PUBLICATIONS

Tarnawaski et al., "Protection of the Gastric Mucosa by Linoleic Acid-A Nutrient Essential Fatty Acid," *Clin. Invest. Med.*, vol. 10, No. 3, pp. 132-135 (1987) [ABSTRACT].

Kim et al., "Skin Permeation Enhancement of Diclofenac by Fatty Acids," *Drug Delivery*, vol. 15, pp. 303-309 (2008).
Takamura et al., "Determination of Higher Fatty Acids in Fats and Oils by High-Performance Liquid Chromatography with Electrochemical Detection," *The Elecrochemical Society*, pp. 568, 571, 575, 576 in part (1997).
Chakrabarty et al., "The Fatty Acids and Glycerides of an Indian sesame Oil," *J. Sci. Food Agric.*, vol. 2, pp. 255-259 (1951).
Russell, "Protection from NSAID-Induced Gastrointestinal Damage," *Inflammopharmacology*, vol. 3, pp. 327-333 (1995).
Anderson, et al., "Lack of drug-drug interaction between three different non-steroidal anti-inflammatory drugs and omeprazole," (Abstract of Euro. J. Clin. Pharmacol. 1998; 54(5) pp. 399-404).
Chang et al., "Effect of dissolution media and additives on the drug release from cubic delivery systems," Journal of Controlled Release, 1997, vol. 46, pp. 215-222.
Fernandez et al., "Aspirin, Salicylate and Gastrointestinal Injury," Nature Medicine, vol. 1, No. 7, Jul. 1995, pp. 602-603.
Allison MC, Howatson AG, Torrance CJ, Lee FD, Russel RI: "Gastrointestinal damage associated with the use of nonsteroidal anti-inflammatory drugs," N, Engl J. Med, 327:749-754, 1992.
Anand BS, Romero JI, Sanduja SK, Lichtenberger LM: Phospholipid association reduces the gastric toxicity of aspirin in human subjects. *Am J Gastroenterol* 94: 1818-1822, 1999.
Basso, D.M., M.S. Beattie, and J.C. Bresnahan, "A sensitive and reliable locomotor rating scale for open field testing in rats." *J Neurotrauma*, 1995. 12(1): p. 1-21.
Benedict, et al., "New variant of human tissue plasminigen activator (TPA) with enhanced efficacy and lower incidence of bleeding compared with recombinant human TPA." *Circulation* 92: 3032-3040, 1995.
Bergstrom S, Duner H, von Euler US, Pernow B, Sjovall J, "Observations on the effects of infusions of prostaglandin E in man," *Acta Physiol Scand*, 45: 145-151, 1959.
Bjarnason I, Macpherson A, Rotman H, Schupp, Hayllar J. "A randomized double-blind, cross-over study on the gastroduodenal tolerability of a highly specific cyclo-oxygenase-2 inhibitor, flosulide and naproxen," *Scand J Gastroentero/32*: 126-130, 1997.
Blake PR, Summers MF. "NOESY-1-1 Ech spectroscopy with eliminated radiation damping." *J Magn Res* 86: 622-625, 1990.
Bogentoft et al., "Influence of food on the absorption of acetylsalicylic acid from enteric-coated dosage forms," *European J Clin Pharmacol*, 14(5), 351-355, 1978.
Butler BD, Lichtenberger LM, Hills BA. "Distribution of surfactants in the canine GI tract and their ability to lubricate." *Am. J. Physiol: Gastointestinal and Liver Physiology* 7:G645-651, 1983.
Cryer, et al., "Low-Dose Aspirin-Induced Ulceration Is Attenuated by Aspirin-Phosphatidylcholine: G.K.I A Randomized Clinical Trial," *The American Journal of Gastroenterology*, Nov. 16, 2010, pp. 1-6.
Canadian Cooperative Study Group. "A randomized trial of aspirin and sulfide pyrazone in threatened stroke." *New Eng J Med* 299:53-59, 1978.
Carlson, S.L., et al., "Acute inflammatory response in spinal cord following impact injury." *Exp Neurol*, 1998. 151(1): p. 77-88.
Clatworthy, A.L., et al., "Role of peri-axonal inflammation in the development of thermal hyperalgesia and guarding behavior in a rat model of neuropathic pain." *Neurosci Lett*, 1995. 184(1): p. 5-8.
Coggeshall, RE., et al., "Is large myelinated fiber loss associated with hyperalgesia in a model of experimental peripheral neuropathy in the rat?," Pain, vol. 52, pp. 233-242 (1993).
Croffie et al., "Sclerosing agents for use in GI endoscopy," Gastrointestinal Endoscopy, 66, Jan. 6, 2007.
Cryer B, Feldman M. "Effects of very low dose daily, long term aspirin therapy on gastric, duodenal, and rectal prostaglandin levels and on mucosal injury." *Gastroenterology* 117: 17-25, 1999.
Daveport, "Gastric mucosal injury by fatty and acetylsalicyclic acids," *Gastroenterology*, 46, 245-253, 1964.
Dial EJ, Lichtenberger LM. "A role for milk phospholipids in protection against gastric acid." *Gastroenterology* 87: 379-385, 1984.
Edwards MH, Pierangeli S, Liu X, Barker JH, Anderson G, Harris EN. "Hydroxychloroquine reverses thrombogenic antibodies in mice." *Circulation* 96: 4380-4384, 1997.

(56) References Cited

OTHER PUBLICATIONS

Faden, A.I., "Experimental neurobiology of central nervous system trauma." *Grit Rev Neurobiol*, 1993. 7(3-4): p. 175-86.
Ferreira SH Vane JR, "New aspects of the mode of action of NSAIDs," *Ann Rev Pharmaco/14*: 57-70, 1974.
Fields WS, Lemak NA, Frankowsk RF, Hardy RJ. "Controlled trial of aspirin in cerebral ischemia" *Stroke* 8:301-314, 1977.
Fuster V, Chesbro JH. "Series on Pharmacology in Practice 10. Antithrombotic Therpay: Role of Platelet inhibitor drugs in management of arterial thromboembolic and atherosclerotic disease." *Mayo Clinic Proc*. 56:265, 1981.
Gabriel SE, Fehring RA. "Trends in the utilization of non-steroidal anti-inflammatory drugs in the United States, 1986-1990." *J Clin Epidemiol* 45:1041-1044, 1992.
Gabriel SE, Jaakkimainen R, Bombardier C. "Risk for serious gastrointestinal complications related to the use of nonsteroidal anti-inflammatory drugs." *Ann Int Med* 115:787-796, 1991.
Gambino, et al., "Slow Intravenous Administration of Low Dose Aspirin Inhibits Both Vascular and Platelet Cyclooxygenase Activity: An Experimental Study in the Rat (42340)," *Proceeding of the Society for Experimental Biology and Medicine*, vol. 182, pp. 287-290 (1986).
Go MF, Lew GM, Lichtenberger LM, Genta RM, Graham DY. "Gastric mucosal hydrophobicity and Helicobacter pylori: response to antimicrobial therapy." *Am J Gastroenterol* 88: 1362-65, 1993.
Goddard, et al., "Does aspirin damage the canine gastric mucosa by reducing its surface hydrophobicity?" *Am. J. Physiology: Gastrointestinal and Liver Physiology* 15: G421-430, 1987.
Goddard PJ, Kao Y-CJ, Lichtenberger LM. "Luminal surface hydrophobicity of canine gastric mucosa is dependent on a surface mucous gel." *Gastroenterology* 98:361-370, 1990.
Googman & Gillman's Manual of Pharmacology and Therapeutics, 12th Edition, Section IV, Inflammation, Immunomodulation, and Analgesic Agents: Pharmacotherapy of Gout, Nonsteroidal Anti-Inflammatory Drugs; Figure 34-1; 1999.
Grill, R, et al., "Cellular delivery of neurotrophin-3 promotes corticospinal axonal growth and partial functional recovery after spinal cord injury." *J Neurosci*, 1997. 17(14): p. 5560-5572.
Hains, B.C., JA Yucra, and C.E. Hulsebosch, "Reduction of pathological and behavioral deficits following spinal cord contusion injury with the selective cyclooxygenase-2 inhibitor NS-398." *J Neurotrauma*, 2001. 18(4): p. 409-423.
Hennekens, et al., "Aspirin and cardiovascular disease." *Bull NY Acad Med* 65:57-68, 1989.
Henry, et al., "Fatal peptic ulcer complications and the use of non-steroidal anti-inflammatory drugs, aspirin and corticosteroids," *Br, Med J*, 295:1227-1229, 1987.
Hills BA, Butler BD, Lichtenberger LM. "Gastric Mucosal Barrier: The hydrophobic lining to the lumen of the stomach." *Am. J. Physiol.: Gastrointestinal and Liver Physiology* 7:G561-68, 1983.
Hirst, W.D., et al., "Expression of COX-2 by normal and reactive astracytes in the adult rat central nervous system." *Mol Cell Neurosci*, 1999. 13(1): p. 57-68.
Hsiao, K., "Transgenic mice expressing Alzheimer amyloid precursor proteins." *Exp Gerontol*, 1998. 33(7-8): pp. 883-889.
Hsiao, K., et al., "Correlative memory deficits, A beta elevation, and amyloid plaques in transgenic mice." *Science*, 274(5284): pp. 99-102 (1996).
Ivey KK, Paone DB, Krause WI. "Acute effect of systemic aspirin on gastric mucosa in man," Dig, Dis Sci. 25:97-99 (1980).
Jiang Y, Zhao J, Genant HK, Dequeker J, Geusens P, "Bone mineral density and biomechanical properties of spine and femur of ovariectomized rats treated with naproxen." *Bone* 22: 509-514 (1996).
Ya-Chu, et al., "A method to preserve extracellular surfactant-like phospholipids on the luminal surface of the rodent gastric mucosa." *J. Histochem. Cytochem*. 38, pp. 427-431 (1990).
Ya-Chu, "Phospholipid and neutral-lipid-containing organelles of rat gastroduodenal mucous cells." *Gastroenterology* 101:7-21, 1991.
Katare, O.P et al., "Proliposomes of Indomethacin for Oral Administration", Journal of Microencapsulation, vol. 8, No. 1, 1991, pp. 1-7.
Konturek JW, Dembinski A, Konturek SJ, Stachura J, Domschke W, "Infection of Helicobacter pylori in gastricadaptation to continued aspirin administration in human subjects," Gastroenterology: IV 114: 245-255, 1998.
Kurata JR, Abbey DE, "The effect of chronic aspirin use on duodenal and gastric ulcer hospitalizations," *J, Clin. Gastroenterol*, 12(3):260-266, 1990.
Laine L, Harper S, Simon T, Bath T, Johanson J, Schwartz H, Stem S, Quan H, Bolognese J. "A randomized trial comparing the effect of Rofecoxib, a cyclooxygenase-2 specific inhibitor, with that of ibuprofen on the gastroduodenal mucosa of patients with osteoarthritis," *Gastroenteroloav* 117: 776-783, 1999.
Laneuville O, Breuer D.K, DeWitt DL et. al. "Differential inhibition of human prostaglandin endoperoxide H synthase-1 and -2 by non steroidal anti-inflammatory drugs." *J Pharm Exp Ther* 271:927-934, 1994.
Langenbach R, Morham SG, Tiano HF, Loftin CD et al. "Prostaglandin synthase 1 gene disruption in mice reduces arachidonic acid-induced inflammation and indomethacin-induced gastric ulceration," *Cell* 83:483-492, 1995.
Lekstrom JA, Bell WR. "Aspirin in the prevention of thrombosis." *Med* 70:161, 1991.
Lewis HD Jr, Davis JW, Arclirbald DO, et al. "Protective effects of aspirin against acute myocardial infarction and death in man with unstable anginas. Results of a VA cooperative study." *N Eng J Med* 313: 396, 1983.
Lichtenberger, et al., "Role of surface-active phospholipids in gastric cytoprotection." *Science* 219:1327-1329,1983.
Lichtenberger, et al., "Gastric protective activity of mixtures of saturated polar and neutral lipids in rats." *Gastroenterology* 99:311-326 (1990).
Lichtenberger, et al., "Zwitterionic phospholipids enhance aspirin's therapeutic activity, as demonstrated in rodent model systems." *J Pharm Exp Therap* 277:1221-1227 (1996).
Lichtenberger, et al., "NSAIDs associate with zwitterionic phospholipids: Insight into the mechanism and reversal of NSAID-Induced G.I. injury." *Nature Medicine* 1: 154-158, 1995.
Lichtenberger, et al., Phosphatidylcholine association increases the anti-inflammatory and analgesic activity of ibuprofen in acute and chronic rodent models of joint inflammation: relationship to alterations in bioavailability and cyclooxygenase-inhibitory potency. *J Pharmacol Exp Ther*, 2001. 298(1): p. 279-287.
Lichtenberger, "Effect of luminal damaging agents on the gastric mucosal barrier and prostaglandin metabolism in cyclooxygenase (COX) knockout mice." *Gastroenterology*, 2001. 120: p. A-143.
Lichtenberger, "The hydrophobic barrier properties of gastrointestinal mucus." *Ann. Rev. Physiol*. 57:565-583, 1995.
Ligumsky M, Golanska EM, Hansen DG, Kauffman Jr GL, "Aspirin can inhibit gastric mucosal cyclo-oxygenase without causing lesions in the rat." *Gastroenterology* 84; 756-761, 1983.
Ligumsky M, Grossman MI, Kauffman Jr GL, "Endogenous gastric mucosal prostaglandins: their role in mucosal integrity," *Am, J, Physiol*, 242: G337-341, 1982.
Ligumsky, et al., "Rectal administration of nonsteroidal antiinflammatory drugs," *Gastroenterology* 98: 1245-1249, 1990.
Lim, G.P., et al., "Ibuprofen suppresses plaque pathology and inflammation in a mouse model for Alzheimer's disease." *J Neurosci*, 2000. 20(15): p. 5709-5714.
Lipsky PE, Isakson PC. "Outcome of specific COX-2 inhibition in rheumatoid arthritis," *J Rheumatol* 24(Suppl 49): Sep. 14, 1997.
Mahmud T, Rati, SS, Scott, DL, Wrigglesworth JM, Bjarnason I. "Nonsteroidal antiinflammatory drugs and uncoupling of mitochondria oxidative phosphorylation." *Arthritis Rheum* 39: 1998-2003, 1996.
Masferrer, et al., "Selective inhibition of inducible cyclo-oxygenase-2 in vivo is anti-inflammatory and non-ulcerogenic," *P.N.AS*, 91:3228-3232, 1994.
McCafferty D-M, Granger DN, Wallace JL. "Indomethacin-induced gastric injury and leukocyte adherence in arthritic vs healthy rats." *Gastroenterology* 109; 1173-1180, 1995.

(56) References Cited

OTHER PUBLICATIONS

McCormack K, Brune K. "Classical absorption theory and the development of gastric mucosal damage associated with non-steroidal anti-inflammatory drugs." Arch Toxico 160: 261-269, 1987.
Meade EA, Smith WL, Dewitt DL. "Differential inhibition of prostaglandin endoperoxide synthase (cyclooxygenase) isozymes by aspirin and other nonsteroidal anti-inflammatory drugs," *J Biol Chem* 268: 6610-6614, 1993.
Mitchell JA, Akarasreenont P, Thiemermann C, Flower RJ, Vane JR. "Selectivity of NSAIDs as inhibitors of constitutive and inducible cyclo-oxygenase," *P.N.AS*, 90:11693-11697, 1993.
Mizuno H, Sakamoto C, Matsuda K et. al. "Induction of COX-2 in gastric mucosal lesions and its inhibition by the specific antagonist delays healing in mice." *Gastroenterology* 112: 387-397,1997.
Morham SG, Langenbach R, Loftin CD et al. "Prostaglandin synthase 2 gene disruption causes severe renal pathology in the mouse," *Cell* 83: 473-482, 1995.
Morris, R, "Developments of a water-maze procedure for studying spatial learning in the rat." *J Neurosci Met*, 1984.11 (1): p. 47-60.
O'Banion MK, Sardowski HB, Winn V, Young DA, "A serum and glucocorticoid regulated 4-kilobase RNA encodes a cyclooxygenase-related protein," *J Biol Chem* 266:23261-7, 1991.
Pelletier J-P, Pathological pathways of osteoarthritis, In: *Nonsteroidal Anti-inflammatory Drugs: A Research and Clinical Perspective*, Royal Society of Medicine Press, London, Jan. 14, 1994.
Pierangeli SS, Barker JH, Stikovac D, Ackerman D, Anderson G, Barquinero J, Acland R, Harris EN. "Effect of human IgG anti phospholipid antibodies on an in vivo thrombosis model in mice." *Thromb Haemost* 71: 670-674, 1994.
Pierangeli SS, Liu X, Antonov IT, Sparrow IT, Harris EN, Myones BL. "Induction of pathogenic anticardiolipin antibodies in a murine model." *Arthritis Rheum* 41: S135, 1998.
Pinon JF. "In vivo study of platelet aggregation in rats." *J Pharmaco Methods* 12:79-84, 1984.
Plunkett, J.A., et al., Effects of interleukin-10 (IL-10) on pain behavior and gene expression following excitotoxic spinal cord injury in the rat. *Exp Neurol*, 2001. 168(1): p. 144-54.
Rabchevsky, A.G., et al., "Cyclosporin A treatment following spinal cord injury to the rat: behavioral effects and stereological assessment of tissue sparing." *J Neurotrauma*, 2001. 18(5):p. 513-22.
Randall LO, Selitto JJ. "A method for measurement of analgesic activity of inflamed tissue." *Arch. Int. Pharmacodyn*. 111: 409-411, 1957.
Resnick, D.K., et al., "Role of cyclooxygenase 2 in acute spinal cord injury." *J Neurotrauma*, 1998. 15(12): p. 1005-13.
Reuter BK, Asfaha S, Buret A, Sharkey KA, Wallace JL. "Exacerbation of inflammation-associated colonic injury in rat through inhibition of cyclooxygenase-2." *J Clin Invest* 98: 2076.2085, 1996.
Robert A, Nezamis JE, Lancaster C, Hanchar AJ: "Cytoprotection by prostaglandins in rats: prevention of gastric necrosis produced by alcohol, HCL, NaOH, hypertonic NaCl and thermal injury," *Gastroenterology* 70: 359-370, 1979.
Rogers, J., et al., "Inflammation and Alzheimer's disease pathogenesis." *Neurobiol Aging*, 1996. 17(5): p. 681-6.
Rome LH, Lands WEM. "Structure requirements for time dependent inhibition of prostaglandin biosynthesis by anti-inflammatory drugs." *Proc Natl Acad Sci USA* 72:4863-4865, 1975.
ROTH GI, Majerus PW. "The mechanism of the effect of aspirin on human platelets I. Acetylation of a particular fraction protein." *J Clin Invest* 56:624-632, 1975.
Sanduja, et al., "Differentiation associated expression of prostaglandin Hand thromboxane A synthases in monocytoid leukemia cell lines." *Blood* 78:3178-3185,1991.
Sanduja, et al., "Kinetic of Prostacyclin Synthesis in PGHS-1 Overexpressed Endothelial cells." *Am. J Physiol*. 267: C1459-1466, 1994.
SCHAFER AI, Handin RI. "The role of platelets in thrombotic and vascular disease." *Progr Cardiovasc Dis* 22:31-52, 1979.
Simon LS, Lanza FL, Lipsky PE et al. "Preliminary safety and efficacy of SC-58635, a novel COX-2 inhibitor," *Arthritis Rheum* 41: 1591-1602, 1998.
Smith WL, DeWitt DL. Biochemistry of prostaglandin endoperoxide H synthase-1 and synthase-2 and their differential susceptibility to non-steroidal anti-inflammatory drugs. *Seminars in Nephro*. 15:179-194, 1995.
Spychal RT, Marrero JM, Saverymuttu SH, Northfield TC. "Measurement of the surface hydrophobicity of human gastrointestinal mucosa." *Gastroenterology* 97: 104-111, 1989.
Stewart, W.F., et al., "Risk of Alzheimer's disease and duration of NSAID use." *Neurology*, 1997. 48(3): p. 626-32.
Symmons, "Mortality in rheumatoid arthritis." *Br, J, Rheum*, 27 (Suppl): 44-54, 1988.
Final Report on the Aspirin Component of the Ongoing Physicians Health Study, Steering Committee of the Physicians Health Study Research Group, *N Eng J Med* 321, No. 3, pp. 129-135 (1989).
Vane J. "Towards a better aspirin." *Nature* 367:215-216,1994.
Vane JR, "Inhibition of prostaglandin synthesis as a mechanism of action of aspirin-like drugs," *Nature* 231:232-251,1971.
Velasquez et al., "Fatty acid-induced injury in developing piglet intestine: effect of degree of saturation and carbon chain length," *Pediatr. Res.* 33, 543-547, 1993.
Velasquez et al., "Oleic acid-induced mucosal injury in developing piglets intestine," *Am. J. Physiol*, 64, pp. 576-581, 1993.
Viinikka L. "Acetylsalicylic acid and the balance between prostacyclin and thromboxane." *Scand J Clin Lab Invest* 50 (supple 201): Oct. 31, 2008, 1990.
Wallace JL, Keenan CM, Granger DN. "Gastric ulceration induced by nonsteroidal anti-inflammatory drugs is a neutrophil-dependent process." Am *J. Physio/259*: G462-467, 1990.
Wallace JL. "Nonsteroidal anti-inflammatory drugs and gastroenteropathy: the second hundred years," *Gastroenterology* 112: 1000-1016, 1997.
Walt R, Katschinski B, Logan R, Ashley J, Longman M, "Rising frequency of ulcer perforation in elderly people in the United Kingdom." *Lancet* 489-492, 1986.
Whittle BJR, Higgs GA, Eakin KE, Moncada S, Vane JR, "Selective inhibition of prostaglandin production in inflammatory exudates arid gastric mucosa," *Nature* 284:271-273, 1980.
Whittle BJR. "Temporal relationship between cyclooxygenase inhibition, as measured by prostacyclin biosynthesis and the gastrointestinal damage induced by indomethacin in the rat." *Gastroenterology* 80:94-98, 1981.
Xie W, Chipman JG, Robertson DL, Erikson RL, Simmons DL, Expression of a mitogen responsive gene encoding prostaglandin synthesis is regulated by mRNA splicing, *P.N.AS*, 88: 2692-2696, 1991.
Pathan et al., "Chemical Penetration Enhancers for Transdermal Drug Delivery System," *Tropical Journ. Of Pharm. Research*, vol. 8, No. 2, pp. 173-179 (2009).
Notice of Reasons for Rejection which issued in related Japanese Patent Application No. 2014-533449, dated Jan. 10, 2017.
Chinese Office Action issued in related Chinese Patent Application No. 201280058596, dated Jul. 26, 2016.
Notice of Reasons for Rejection issued in related Japanese Patent Application No. 2014-533449, dated May 24, 2016.
Piao et al., "Oral Delivery of Diclofenac Sodium Using a Novel Solid-in-oil Suspension," *International Journal of Pharm..*, vol. 313, pp. 159-162 (2006).
Advisory Action and references cited by the Examiner issued in related U.S. Appl. No. 13/731,189, dated Jun. 9, 2015.
European Extended Search Report issued in related European Patent Application No. EP 12 83 7423, dated Jun. 3, 2015.
Advisory Action and references cited by the Examiner issued in related U.S. Appl. No. 13/908,233, dated Jun. 11, 2015.
Office Action issued in related U.S. Appl. No. 13/908,233, dated Jan. 26, 2015.
Office Action issued in related U.S. Appl. No. 13/791,189, dated Jan. 26, 2015.

(56) References Cited

OTHER PUBLICATIONS

Lichtenberger et al., "Surface phospholipids in gastric injury and protection when a selective cyclooxygenase-2 inhibitor (Coxib) is used in combination with aspirin," *British Journ. of Pharmacology*, vol. 150, pp. 913-919 (2007).
Sokovic et al., "Antibacterial Effects of the Essential Oils of Commonly Consumed Medicinal Herbs Using an Vitro Model," *Molecules*, vol. 15, pp. 7532-7546 (2010).
Strickley, "Solubilizing Excipients in Oral and Injectable Formulations," *Pharm. Res.*, vol. 21, No. 2, pp. 201-230 (2004).
Mandel et al., "Fatty-Acid-Mediated Gastroprotection Does Not Correlate with Prostaglandin Elevation in Rats Exposed to Various Chemical Insults," *Vet. Pathol.*, vol. 31, pp. 679-688 (1994).
Tarnawaski et al., "Protection of the Gastric Mucosa by Linoleic Acid-A Nutrient Essential Fatty Acid," *Clin. Invest. Med.*, vol. 10, No. 3, pp. 132-5 (1987 [Abstract].
Kim et al., "Skin Permeation Enhancement of Diclofenac by Fatty Acids," *Drug Delivery*, vol. 14, pp. 303-309 (2008).
Hollander et al., "The Role of Nutrient Essential Fatty Acids in Gastric Mucosal Protection," *Gastric Cytoprotection*, pp. 187-195 (1989).
Office Action issued in related U.S. App. No. 13/908,233, dated Sep. 2, 2014.
Takamura et al., "Determination of Higher Fatty Acids in Fats and Oils by High-Performance Liquid Chromatography with Electrochemical Detection," *The Electrochemical Society*, pp. 568, 571, 575, 576 in part (1997).
Yen, "Influence of Seed Roasting Process on the Changes in Composition and Quality of Sesame (Sesame indicum) Oil,"*J. Sci. Food Agric.*, vol. 50, pp. 563-570 (1990).
Carvalho et al., "Extraction, Fatty Acid Profile and Antioxidant Activity of Sesame Extract," *Brazilian Journ. of Chem. Eng.*, vol. 29, No. 2, pp. 409-420 (2012).
Nzikou et al., "Chemical Composition on the Seeds and Oil of Sesame (*Sesamum indicum* L.) Grown in Congo-Brazzaville," *Advance Journ. of Food Science and Technology*, vol. 1, No. 1, pp. 6-11 (2009).
Lecithin (Medical dictionary [online] retrieved on Sep. 2, 2014 from: http://medical-dictionary.thefreedictionary.com/lecithin.
Sesame Seed Oil [online] retrieved Sep. 2, 2014 from http://www.oilsandplants.com/sesameseed.htm; 2 pages.
Cakrabarty et al., "The Fatty Acids and Glycerides of an Indian sesame Oil," *J. Sci. Food Agric.*, vol. 2, pp. 255-259 (1951).
Matthaus et al., "Comparison of Different Methods for the Determination of the Oil Content in Oilseeds," *JAOCS*, vol. 78, pp. 95-201 (2001).
Office Action issued in related U.S. Appl. No. 13/791,189, dated Sep. 4, 2014.
Stomach Acid Medline Plus [online] retrieved on Feb. 18, 2014 from http://www.nlm.nih.gov/medlineplus/ency/article/003883.htm; 2 pages.
Shiratori et al., Intestinal Fat Digestion Plays a Significant Role in Fat-Induced Suppression of Gastric Acid Secretion and Gastrin Release in the Rat, *Digestive Diseases and Sciences*, vol. 38, No. 12, pp. 2267-2272 (1993).
Russel, "Protection from NSAID-Induced Gastrointestinal Damage," *Inflammopharmacology*, vol. 3, pp. 327-333 (1995).
Wiseman, "Non-Steroidal Anti-Inflammatory Drugs: Facts and Fallacies," *CME*, vol. 21, No. 2, pp. 80-84 (2003).
Final Office Action cited in related U.S. Appl. No. 13/731,189, dated Feb. 20, 2014.
Smith et al., Introduction to the Principles of Drug Design and Action, Fourth Edition, CRC Press, 2005, pp. 40-41). [Abstract].
Anderson et al., "Lack of drug-drug interaction between three different non-steroidal anti-inflammatory drugs and omeprazol," (Abstract of Euro. J. Clin. Pharmacol. 1998; 54(5) pp. 399-404).
Helmenstine (Stomach pH [online] retrieved on Aug. 27, 2014 from http://chemistry.about.com/b/2013/07/08/what-is-the-ph-of-the-stomach.htm 1 page).
Chang et al., "Effect of dissolution media and additives on the drug release from cubic delivery systems," Journal of Controlled Release, 1997, vol. 46, pp. 215-22.
Hazemoto et al., "pH-sensitive liposome composed of phosphatidylethanolamine and fatty acid," Chem. Pharm. Bull., 1990, vol. 38, No. 3, pp. 748-751.
Phoeung et al., "pH-triggered release from nonphospholipid LUVs modulated by the pKa of the included fatty acid," 2010, vol. 26, No. 15, pp. 12769-12776.
Fernandez et al., "Aspirin, Salicyclate and Gastrointestinal Injury," Nature Medicine, vol. 1, No. 7, Jul. 1995, pp. 602-603.
Rosdahl (Textbook of Basic Nursing 2008; p. 308, 3 pages).
Takeshi Azuma, "Adverse Effects of NSAIDs to The Stomach and Preventions to Them," Therapeutic Research, vol. 3, No. 4, pp. 538-540 (1995).
Nakamura, et al., "Clinical problems of NSAID-associated uncer," Journ. of Japanese Society of Gastroenterology, vol. 97, No. 5, pp. 551-559 (2000).
Notice of Reasons for Rejection issued in co-pending Japanese Patent Application No. 2017-114115, dated Mar. 6, 2018.
Huang, et al., "Short- and medium-chain fatty acids exhibit antimicrobial activity for oral microorganisms," *Archives of Oral Biology*, vol. 56, pp. 650-654 (2011).

\* cited by examiner

Photographs Showing Mixing, Temperature Monitoring, and pH Monitoring

Photographs of the Control Composition during a pH Cycle

Initial pH 1        pH 7        Final pH 1

Photographs of Aspirin-Containing Composition Sample during a pH Cycle

Initial pH 1          pH 7          Final pH 1

Photographs of the Aspirin-Containing Composition during Two pH 7 Adjustment Cycles

Photographs Comparing the Control Composition at pH 1 and the Aspirin-Containing Composition at Different pH Values

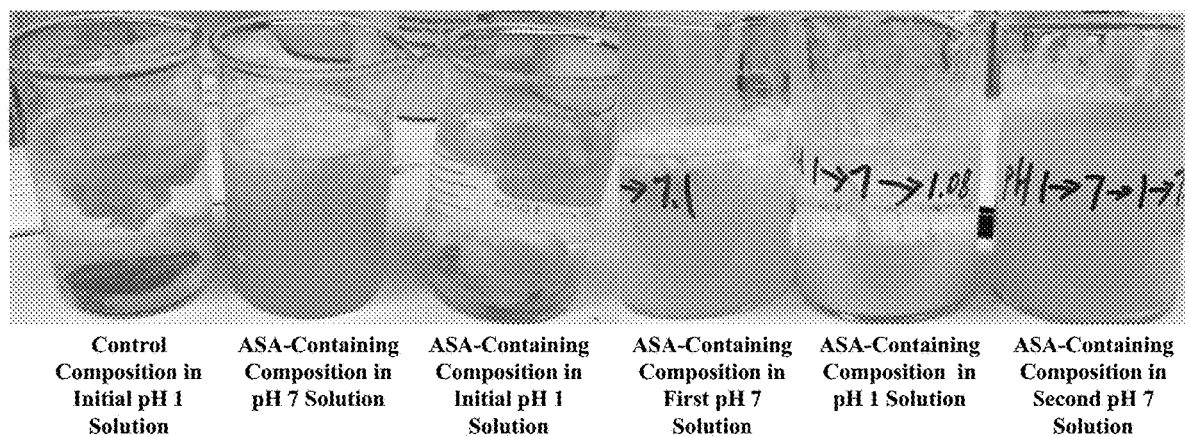

| Control Composition in Initial pH 1 Solution | ASA-Containing Composition in pH 7 Solution | ASA-Containing Composition in Initial pH 1 Solution | ASA-Containing Composition in First pH 7 Solution | ASA-Containing Composition in pH 1 Solution | ASA-Containing Composition in Second pH 7 Solution |

FIG. 7

Photographs of the Ibuprofen-Containing Composition during a pH Cycle

Photographs of the Ibuprofen-Containing Sample during a pH Cycle after 1 Day and after a 4 Days Rest

Day 1          Day 4

Plot of UV Ibuprofen Concentration Values in Both Phases for the Ibuprofen-Containing Composition during a pH Cycle

Photographs of the Preparation of the Omeprazole-Containing Composition before and after Citric Acid Addition

Photographs of the Omeprazole-Containing Composition Addition to the Initial pH 1 Solution
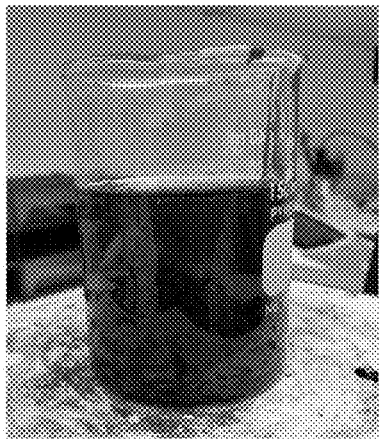  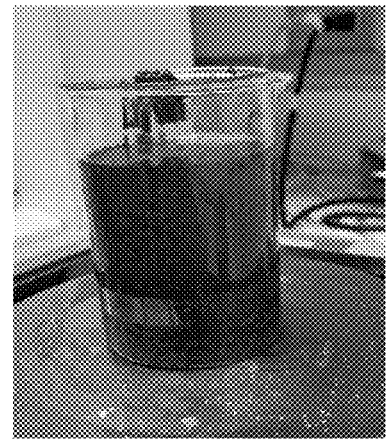
Initial pH of pH 1 Solution and the Omeprazole-Containing Composition
Initial pH 1 Solution Turned Brown within a Minute after Addition of the Omeprazole-Containing Composition and the Omeprazole-Containing Composition Sank to the Bottom
FIG. 13

Photographs of Omeprazole-Containing Composition in the Initial pH 1 Solution Adjusted to pH 7

Photographs of the Control Composition and the Omeprazole-Containing Composition during a pH Cycle

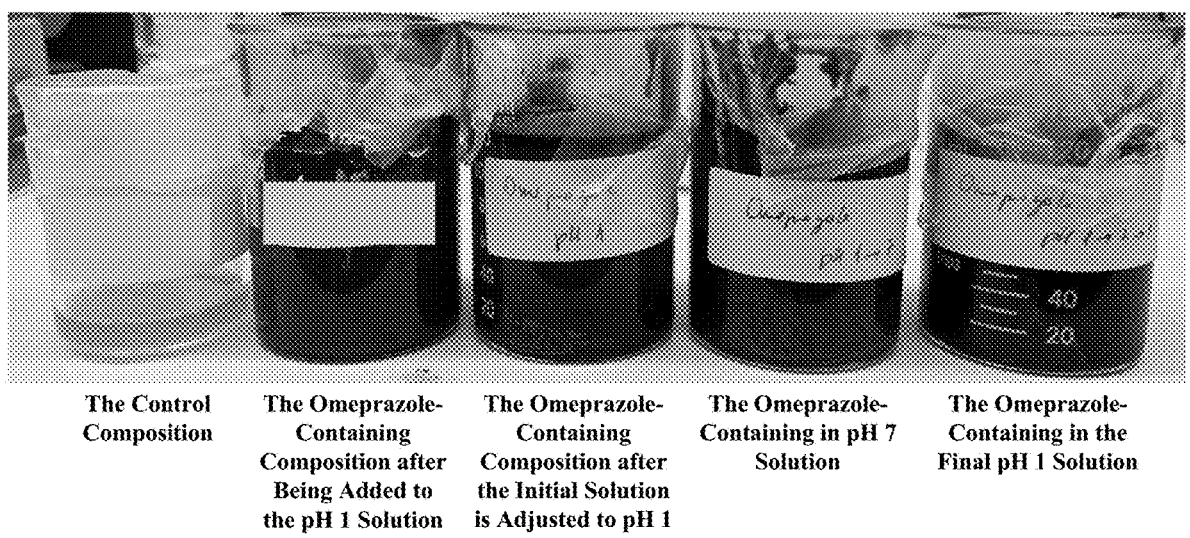

| The Control Composition | The Omeprazole-Containing Composition after Being Added to the pH 1 Solution | The Omeprazole-Containing Composition after the Initial Solution is Adjusted to pH 1 | The Omeprazole-Containing in pH 7 Solution | The Omeprazole-Containing in the Final pH 1 Solution |

FIG. 15

Plot of UV Omeprazole Percentage Values in Both Phases for the Omeprazole-Containing Composition during a pH Cycle

Photographs of the High Oleic Acid-Ibuprofen-Containing Composition during pH Cycle

Photographs of the Control Composition and
the High Oleic Acid-Ibuprofen-Containing Composition at pH 7

Control Composition at pH 7 | High Oleic Acid-Ibuprofen-Containing Composition at pH 7 | High Oleic Acid-Ibuprofen-Containing Composition at pH 7

Plot of UV Concentration Values in Both Phases for Ibuprofen from the High Oleic Acid-Ibuprofen-Containing Composition during a pH Cycle

Photographs of the Nonionic Surfactant-Ibuprofen-Containing Composition during pH Cycle

Photographs of the Preparation of the Whey Isolate Protein-Containing Composition Compared to the Control Composition

Photographs of the Whey Isolate Protein-Containing Sample after Being Added to the Initial pH 1 Solution and After Raising the pH to pH 7 with NaOH

Initial pH 1 Solution          pH 7 Solution

Photographs of the Whey Isolate Protein-Containing Sample during a pH Cycle

Photographs of the High Oleic Acid, Nonionic Surfactant-Whey Isolate Protein-Containing Composition in a pH Cycle

Initial pH 1 Solution      pH 7 Solution      Final pH 1 Solution

Plot of UV WIP Percentage Values in Both Phases for HA, NIS Whey Isolate Protein-Containing Composition during a pH Cycle Plot of a Comparison of UV API Percentage Values in Aqueous Phase for Aspirin, Ibuprofen, Omeprazole, and WIP Compositions during a pH Cycle

Photographs of the Preparation of the Nonionic Surfactant-Aspirin-Containing Composition Compared to the Control Composition

Photographs of the Nonionic Surfactant-Aspirin-Containing Composition during a pH Cycle

Initial pH 1 Solution | pH 7 Solution | Final pH 1 Solution

PHARMACEUTICAL CARRIERS CAPABLE OF PH DEPENDENT RECONSTITUTION AND METHODS FOR MAKING AND USING SAME

CROSS-REFERENCE TO RELATED APPLICATIONS

This application is a continuation of International Patent Application No. PCT/US2021/024061, filed Mar. 25, 2021, which claims the benefit of priority from U.S. Provisional Patent Application No. 63/000,287, filed Mar. 26, 2020, the contents of which are incorporated by reference herein in their entirety.

BACKGROUND OF THE DISCLOSURE

One problem associated with many pharmaceuticals that are injurious to the stomach or are susceptible to degradation in the stomach is that such pharmaceuticals do not simply proceed from the stomach to the small intestine, through the pyloric sphincter, and into the duodenum. Rather, a portion of such pharmaceuticals flows backward from the duodenum and through the pyloric sphincter, while the sphincter is opened into the stomach (duodenal reflux). Thus, injurious pharmaceuticals contained in the back flow may cause injury to the lining of the stomach, e.g., nonsteroidal anti-inflammatory drugs (NSAIDs), while degradable pharmaceuticals may be subject to further loss due to degradation in the stomach, e.g., heparin or insulin.

There is a need in the art for improved pharmaceutical formulations. The present disclosure satisfies this need.

SUMMARY OF THE DISCLOSURE

In one aspect of the disclosure, described are pharmaceutical carrier compositions comprising: (a) a non-aqueous pH dependent release system; and (b) a non-aqueous pH dependent reassembly/assembly and reabsorption/absorption system. The pharmaceutical carrier compositions are characterized by: (i) the carrier composition has a low pH form and a high pH form; (ii) the carrier composition is formulated to release one or more biologically active agents minimally from a low pH form and maximally from a high pH form due to the non-aqueous pH dependent release system; (iii) the carrier composition is formulated to either reassemble into the low pH form or assembly into a new low pH form due to the non-aqueous pH dependent reassembly/assembly and reabsorption/absorption system; and (iv) the carrier composition is formulated to either reabsorb the one or more biologically active agents in its reassembled form or absorb the one or more biologically active agents in the newly assembled form.

In another aspect, for the compositions of the disclosure, the non-aqueous pH dependent reassembly/assembly and reabsorption/absorption system comprises one or more nonionic surfactants. For example, the one or more nonionic surfactants can be present in the composition in an amount of about 0.05 wt. % to about 20 wt. %. Further, the one or more nonionic surfactants can comprise an ethylene glycol mono fatty acid ester, a propylene glycol mono fatty acid ester, or a combination of two or more thereof. In addition, the one or more nonionic surfactants can comprise (a) one or more selected from sorbitan mono, di, and tri fatty acid esters; and/or (b) propylene glycol monolaurate; and/or (c) sorbitan trioleate (STO), sorbitan monooleate, or sorbitan tristearate, or a combination thereof.

In one aspect, for the compositions of the disclosure, the non-aqueous pH dependent reassembly/assembly and reabsorption/absorption system can comprise one or more zwittterionic surfactants.

In another aspect, for the compositions of the disclosure, the one or more zwittterionic surfactants comprise one or more zwittterionic phospholipids. For example, the one or more zwitterionic surfactants can comprise phosphatidic acid, phosphatidylethanolamine, phosphatidylcholine, phosphatidylserine, phosphatidylinositol, phosphatidylinositol phosphate, phosphatidylinositol bisphosphate, phosphatidylinositol triphosphate, ceramide phosphorylcholine, ceramide phosphorylethanolamine, ceramide phosphorylglycerol, dimyristoylphosphatidylcholine, di stearoylphosphatidylcholine, dilinoleoylphosphatidylcholine, dipalmitoylphosphatidylcholine, or a combination of two or more thereof. In another aspect, the one or more zwitterionic surfactants can comprise lecithin.

In a further aspect, for the compositions of the disclosure, the one or more zwittterionic surfactants can be present in the composition in an amount of at least about 10 wt. %. In another aspect, the one or more zwitterionic surfactants are present in the composition in an amount of about 5 wt. % to about 25 wt. %.

In one embodiment, for the compositions of the disclosure, the pH dependent release system can comprise a carboxylic acid having at least 8 carbon atoms. In another aspect, the carboxylic acid having at least 8 carbon atoms can be present in the composition in an amount of at least about 5 wt. %, at least about 10 wt. %, at least about 15 wt. %, at least about 20 wt. %, or in an amount of about 5 wt. % to about 50 wt. %.

In another embodiment, for the compositions of the disclosure, the carboxylic acid having at least 8 carbon atoms is a monocarboxylic acid.

In one aspect of the disclosure for the compositions described herein, the carboxylic acid having at least 8 carbon atoms is selected from the group consisting of as octenoic acid, decenoic acid, decadienoic acid, lauroleic acid, laurolinoleic acid, myristovaccenic acid, myristolinoleic acid, myristolinolenic acid, palmitolinolenic acid, palmitidonic acid, α-linolenic acid, stearidonic acid, dihomo-α-linolenic acid, eicosatetraenoic acid, eicosapentaenoic acid, clupanodonic acid, docosahexaenoic acid, 9,12,15,18,21-tetracosapentaenoic acid, 6,9,12,15,18,21-tetracosahexaenoic acid, myristoleic acid, palmitovaccenic acid, α-eleostearic acid, β-eleostearic acid, punicic acid, 7,10,13-octadecatrienoic acid, 9,12,15-eicosatrienoic acid, β-eicosatetraenoic acid, 8-tetradecenoic acid, 12-octadecenoic acid, linoleic acid, linolelaidic acid, γ-linolenic acid, calendic acid, pinolenic acid, dihomo-linoleic acid, dihomo-γ-linolenic acid, arachidonic acid, adrenic acid, osbond acid, palmitoleic acid, vaccenic acid, rumenic acid, paullinic acid, 7,10,13-eicosatrienoic acid, oleic acid, elaidic acid, gondoic acid, erucic acid, nervonic acid, 8,11-eicosadienoic acid, mead acid, sapienic acid, gadoleic acid, 4-hexadecenoic acid, petroselinic acid, and 8-eicosenoic acid, or a combination of two or more thereof.

In another aspect of the disclosure for the compositions described herein, the non-aqueous pH dependent reassembly/assembly and reabsorption/absorption system further comprises one or more polyacids, one or more water insoluble oligomers, one or more water insoluble polymers, or any combination thereof.

In a further aspect of the disclosure for the compositions described herein, the polyacids can comprise, for example, a biocompatible fatty poly acid. In another aspect, the one or more polyacids can comprise glutaric acid (GA), poly(methacrylic acid-co-methyl methacrylate), or hypromellose phthalate (HPMC-P), or a combination of two or more thereof. In addition, the one or more polyacids can be present in the composition in an amount of about 1 wt. % to about 10 wt. %.

In another aspect of the disclosure for the compositions described herein, the one or more water insoluble oligomers can comprise low molecular weight poly(hexyl substituted lactides) (PHLA), low molecular weight polyethylene, polyvinyl chloride, ethyl cellulose, or acrylate polymers and copolymers thereof, or a combination of two or more thereof. In addition, the one or more water insoluble oligomers are present in the composition in an amount of about 1 wt. % to about 5 wt. %. Further, the one or more water insoluble polymers can comprise a copolymer of ethyl acrylate and methyl methacrylate, lactide-coglycolide, cellulose, or ethyl cellulose, or a combination of two or more thereof. Moreover, the one or more water insoluble polymers can be present in the composition in an amount of about 1 wt. % to about 5 wt. %.

In another aspect of the disclosure for the compositions described herein, (a) the non-aqueous pH dependent release system is present in an amount between 10 wt. % and 95 wt. %; and (b) the non-aqueous pH dependent reassembly/assembly and reabsorption/absorption system is present in an amount between about 5 wt. % and 90 wt. %.

In a further aspect of the disclosure for the compositions described herein, (a) the non-aqueous pH dependent release system is present in an amount between 20 wt. % and 95 wt. %; and (b) the non-aqueous pH dependent reassembly/assembly and reabsorption/absorption system is present in an amount between about 5 wt. % and 80 wt. %.

In yet another aspect of the disclosure for the compositions described herein, (a) the non-aqueous pH dependent release system is present in an amount between 30 wt. % and 95 wt. %; and (b) the non-aqueous pH dependent reassembly/assembly and reabsorption/absorption system is present in an amount between about 5 wt. % and 70 wt. %.

In one embodiment of the disclosure for the compositions described herein, (a) the non-aqueous pH dependent release system is present in an amount between 40 wt. % and 95 wt. %; and (b) the non-aqueous pH dependent reassembly/assembly and reabsorption/absorption system is present in an amount between about 5 wt. % and 60 wt. %.

In a further embodiment of the disclosure for the compositions described herein, the non-aqueous pH dependent release system comprises: (a) at least 15 wt. % of one or more monocarboxylic acids having at least 8 carbon atoms, (b) at least 20 wt. % of one or more monocarboxylic acids having at least 8 carbon atoms, or (c) at least 30 wt. % of one or more monocarboxylic acids having at least 8 carbon atoms.

In one aspect of the disclosure for the compositions described herein, the non-aqueous pH dependent release system comprises: (a) at least 15 wt. % of a mixture of (i) one or more low melting point monocarboxylic acids, (ii) one or more medium melting point monocarboxylic acids, (iii) one or more high melting point monocarboxylic acids, or (iv) any combination thereof, and (b) wherein: (i) the low melting point monocarboxylic acids have melting point temperatures less than or equal to room temperature, (ii) the medium melting point monocarboxylic acids have melting point temperatures greater than room temperature and less than or equal to a body temperature of a mammal, or a human, and (iii) the high melting point monocarboxylic acids have melting point temperatures above the body temperature of a mammal, or a human.

In one embodiment of the disclosure for the compositions described herein, the non-aqueous pH dependent release system further comprises one or more neutral lipids. For example, the one or more neutral lipids can comprise one or more biocompatible oils. In addition, the one or more biocompatible oils can comprise peanut oil, canola oil, avocado oil, safflower oil, olive oil, corn oil, soybean oil, sesame oil, vitamin A, vitamin D, vitamin E, animal oils, fish oils, or krill oil, or a combination of two or more thereof. In another aspect, the one or more neutral lipids can comprise a fatty acid ester. For example, the fatty acid ester can be a fatty acid methyl ester. Further, the fatty acid methyl ester can be methyl linolenate, methyl oleate, or methyl palmitate, or a combination of thereof. In a further aspect, the one or more neutral lipids can be present in the composition in an amount of about 30 wt. % to about 75 wt. %.

In another embodiment of the disclosure for the compositions described herein, the non-aqueous pH dependent release system further comprises (a) one or more low melting point neutral lipids; and/or (b) one or more medium melting point neutral lipids; and/or (c) one or more high melting point neutral lipids.

In a further embodiment of the disclosure for the compositions described herein, the composition comprises less than 10 wt. % of one or more selected from (1) fatty acid salts, (2) secondary complexing agents, (3) protective agents, (4) excipients, (5) adjuvants, (6) drying agents, (7) antioxidants, (8) preservatives, (9) chelating agents, (10) viscomodulators, (11) tonicifiers, (12) flavorants and taste masking agents, (13) colorants, (14) odorants, (15) opacifiers, (16) suspending agents, and (17) binders.

In one aspect of the disclosure for the compositions described herein, the pharmaceutical composition comprises (a) a carrier composition according to any one of claims 1 to 20; and (b) one or more biologically active agents, wherein a weight ratio of the carrier composition to the one or more biologically active agents is between about 10:1 and about 1:2. For this composition, the one or more biologically active agents can be, for example, suspended in the carrier composition. Further, the one or more biologically active agents can be, for example, crystalline solid particles. Additionally, the biologically active agent can comprise at least one agent selected from the group consisting of an acid-labile pharmaceutical agent, an anti-depressant, an anti-diabetic agent, an anti-epileptic agent, an anti-fungal agent, an anti-malarial agent, an anti-muscarinic agent, an anti-neoplastic agent, an immunosuppressant, an anti-protozoal agent, an anti-tussive, a neuroleptics, a beta-blocker, a cardiac inotropic agent, a corticosteroid, an anti-parkinsonian agent, a gastrointestinal agent, histamine, a histamine receptor antagonist, a keratolytic, a lipid regulating agent, a muscle relaxant, a nitrate, an anti-anginal agent, a non-steroidal anti-inflammatory agent, a nutritional agent, an opioid analgesic, a sex hormone, a stimulant, a nutraceutical, a peptide, a protein, a therapeutic protein, a nucleoside, a nucleotide, DNA, RNA, a glycosaminoglycan, an acid-labile drug, (+)-N{3-[3-(4-fluorophenoxy)phenyl]-2-cyclopenten-1-yl}-N-hydroxyurea, amylase, aureomycin, bacitracin, beta carotene, cephalosporins, chloromycetin, cimetidine, cisapride, cladribine, clorazepate, deramciclane, didanosine, digitalis glycosides, dihydrostreptomycin, erythromycin, etoposide, famotidine, a hormone, estrogen, insulin, adrenalin, heparin, lipase, milameline, novobiocin, pancreatin, penicillin salts, polymyxin, pravastatin, progabide, protease, quinapril, quinoxaline-2-carboxylic acid, [4-

(R)carbamoyl-1-(S-3-fluorobenzyl-2-(S),7-dihydroxy-7-methyloctyl]amide, quinoxaline-2-carboxylic acid[1-benzyl-4-(4,4-difluoro-1-hydroxy-cyclohexyl)-2-hydroxy-4-hydroxycarbamoyl-butyl]-amide ranitidine, streptomycin, subtilin, sulphanilamide, a proton pump inhibitors, esomeprazole, lansoprazole, minoprazole, omeprazole, pantoprazole and rabeprazole. In another aspect, the one or more biologically active agents can be hydrophobic.

Further, the one or more biologically active agents can include an acid labile drug. For example, the acid-labile drug can be selected from the group consisting of heparin, insulin, erythropoietin, pancreatin, lansoprazole, omeprazole, pantoprazole, rabeprazole, penicillin salts, benzathine penicillin, polymyxin, sulphanilamide, and erythromycin.

In another aspect, the one or more biologically active agents can include a non-steroidal anti-inflammatory agent (NSAID). For example, the NSAID can be selected from the group consisting of ibuprofen, piroxicam, salicylate, aspirin, naproxen, indomethacin, diclofenac, mefenamic acid, COX2 inhibitors, and any mixture thereof. In addition, the NSAID can be selected from the group consisting of aspirin, naproxen, indomethacin and mefenamic acid. Further, the NSAID can be aspirin.

Both the foregoing summary and the following description of the drawings and detailed description are exemplary and explanatory. They are intended to provide further details of the invention, but are not to be construed as limiting. Other objects, advantages, and novel features will be readily apparent to those skilled in the art from the following detailed description of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 depicts photographs comparing the control composition at pH 1 and the aspirin-containing composition at different pH values.

FIG. 13 depicts photographs of the omeprazole-containing composition after initial addition to the pH 1 solution, after pH adjustment, and after sitting for a little while.

FIG. 15 depicts photographs of the control composition, the omeprazole-containing composition, the omeprazole-containing composition in the pH 1 solution, the omeprazole-containing composition in the pH 7 solution, and the omeprazole-containing composition in the final pH 1 solution.

DETAILED DESCRIPTION OF THE DISCLOSURE

I. Overview

Figure 1:
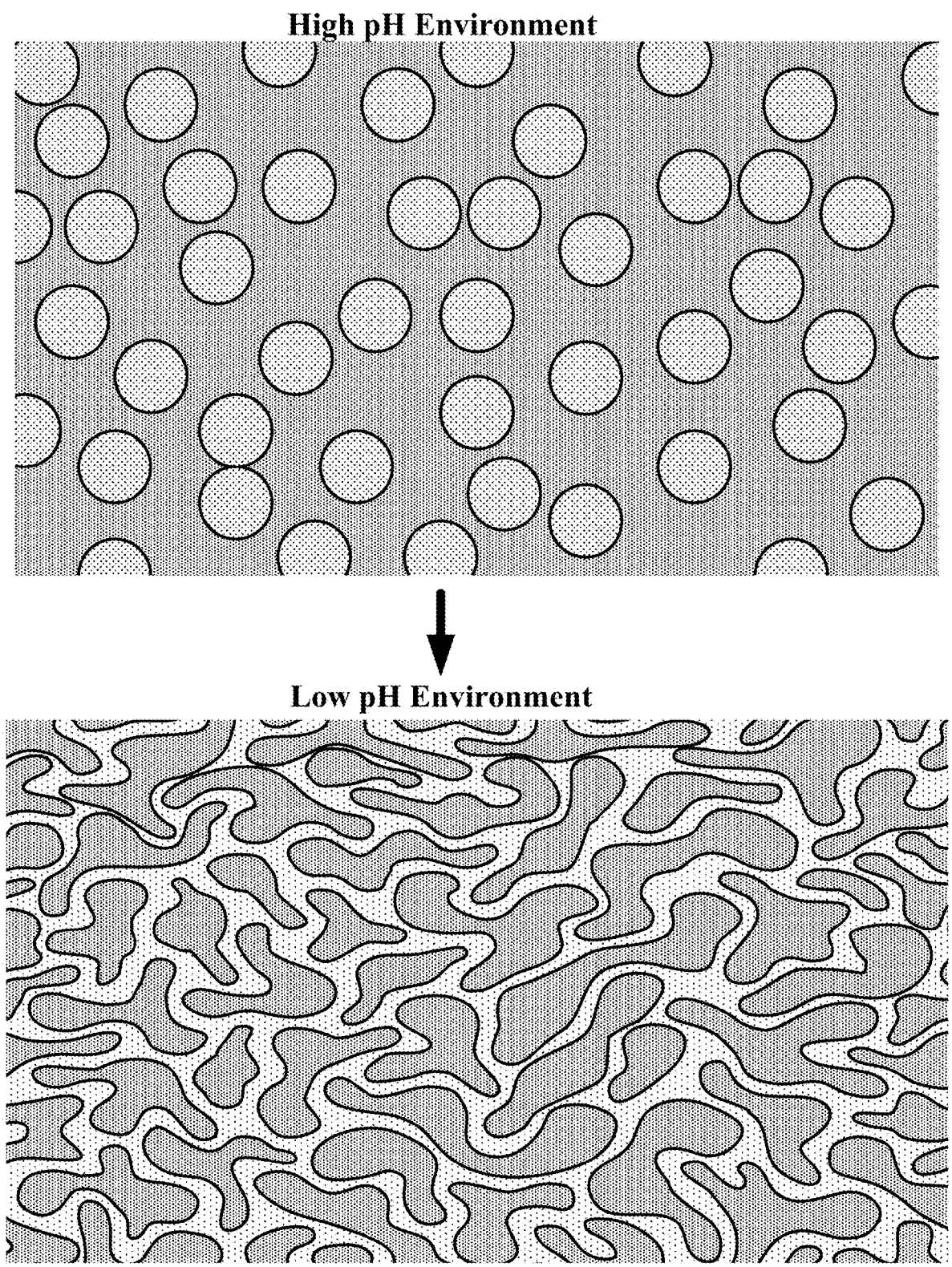
FIG. 1 illustrates the change for a high pH form (shown here as an emulsion comprising oil droplets in a high pH aqueous fluid or high pH environment) into a low pH form, shown here as an oil phase of amorphous structures in the low pH aqueous fluid or low pH environment. In the top frame, the BAI concentration is shown higher in the higher pH aqueous phase (higher dot pattern shading) and lower in the oil droplets (lower dot pattern shading). In the bottom frame, the BAI concentration is shown higher in the amorphous oil phase (higher dot pattern shading) and lower in the low pH fluid (lower dot pattern shading).

Certain embodiments of the present disclosure relate to systems and compositions including a nonaqueous carrier and one or more biologically active agents (BAIs) to form a tailored biologically active agent release non-aqueous matrix having improved GI protection due to duodenal reflux and to methods for making and using same.

A. Reassembling Drug Carriers

The carriers of this disclosure include one or more non-aqueous targeted release agents and one or more non-aqueous reconstitutive agents to form unique non-aqueous matrices for targeted release of one or more biologically active agents (BAIs) and targeted matrix reassembly or targeted matrix assembly. The reassembled matrix or newly assembled matrix are capable of absorbing BAIs via partitioning. The carriers are formulated to: (a) have a first form or low pH form in low pH environments such as aqueous fluids having a pH less than or equal to about pH 3 (≤about pH 3), (b) have a second form or high pH form in high pH environment such as aqueous fluids having a pH greater than about pH 3 (>pH 3), and (c) reassemble into the low pH form or assemble into a new low pH form after passing from a low pH environment to a high pH environment and back to a low pH environment such as passing through the stomach into the duodenum and back into the stomach due to duodenal reflux. In certain embodiments, the carriers may also include one or more neutral lipids.

Additionally, the carriers disclosed herein are designed to: (a) minimally release one or more biologically active agents from their low pH form in contact with low pH aqueous fluids; (b) maximally release one or more BAIs from their high pH form providing pH dependent targeted release of BAIs within tracts having different pH environments along the length of the tracts; and (c) absorb any BAI into their reassembled low pH form or their newly assembled low pH form to reduce injury or irritation to the low pH environment or to reduce decomposition of any BAI reentering the low pH environment from the high pH environment such as any biologically active agent present in duodenal reflux.

Thus, the carriers are capable of being formulated to target release of BAIs based on pH into a tissue tract having a pH profile across the length of the tract such as the gastrointestinal (GI) tract, urinary tract, reproductive tract, or other tracts that have mucosal gels and differ in pH along the tract. Carrier-mediated targeted release is particularly useful for: (a) BAIs injurious to certain portions of the tracts such as the esophagus or the stomach, (b) acid labile BAIs, e.g., BAIs that decompose or are destroyed in low pH or acidic environments such as gastric fluid, (c) biologically active agents that are impermeable/insoluble in low pH fluids, e.g., gastric fluid, (d) BAIs susceptible to first pass metabolism, and/or (e) BAIs that cause stomach ulceration, irritation, upset, or dyspepsia.

In certain embodiments, the targeted release carriers include one or more pH dependent release agents include at least one ionizable group such as a carboxylic acid group (—COOH), hydroxy group (—OH), thiol group (—SH), sulphonic acid group (—SO$_3$H), sulphonamide group (—SO$_2$NH$_2$), imide group (—C(O)NHC(O)R), amide group (—C(O)NHR), amine salt (—NR$_2$H$^+$X$^-$), etc. and/or protonatable group such as amino group (e.g., —NH$_2$, —NHR, or —NR$_2$), amide group (—C(O)NHR), imide group (—C(O)NHC(O)R), etc., wherein each of the R groups are hydrocarbyl groups. In certain embodiments, the release agents include one or more carboxylic acid groups. In other embodiments, the release agents include one or more oil soluble or oil miscible compounds including at least one carboxylic acid group.

In other embodiments, the pH dependent, oil soluble or oil miscible release agents include one or more fatty acids sometimes referred to herein as free fatty acids. The term free fatty acids (FFAs) refer to carboxylic acids having a hydrocarbon tail of generally formula R—COOH, wherein R is a hydrocarbon or hydrocarbyl group generally having at least 8 carbon atoms, sometimes between 8 and 40 carbon atoms. FFAs are to be distinguished from compounds that include fatty acids as a moiety in their molecular structure such as mono-glyceride, di-glycerides, tri-glycerides, or fatty acid esters such as methyl, ethyl, propyl, etc. esters of the general formula R—COOR', where R and R' are hydrocarbon or hydrocarbyl groups.

In certain embodiments, the one or more non-aqueous reconstitutive agents include, without limitation, (a) neutral lipids, (b) surfactants such as non-ionic surfactants, anionic surfactants, cationic surfactants, and/or zwitterionic surfactants, (c) compounds, oligomers, polymers, or copolymer including carboxylic acid moieties, and/or (d) any other component that stabilizes oil matrices or assists in matrix formation. Such matrices are capable of absorbing BAIs from low pH fluids due to partitioning. The absorption of BAIs from low pH fluids would reduce injury and/or irritation to low pH environment tissues due to the BAIs and/or would reduce decomposition or destruction of BAIs in low pH environments or low pH aqueous fluids. For example, the one or more non-aqueous reconstitutive agents are designed to assist in the reformation of the low pH matrix or formation of a new low pH matrix due to duodenal reflux, where the reformed low pH matrix and/or the newly formed low pH matrix absorb BAIs. In certain embodiments, the carriers may be taken without a BAI to absorb BAIs known to be injurious to the stomach (GI toxicity) or known to be destroyed or decompose in the stomach, especially BAIs that are injurious and persistent such as naproxen.

B. Compositions Including Targeted Release and Reconstitutive/Absorptive Carriers Some embodiments of the present disclosure provide compositions including a carrier of this disclosure and a therapeutically effective amount one or more BAIs, wherein the carrier is designed to effect a targeted release of the BAIs and/or to modify and/or alter the chemical properties, physical properties, and/or behavior of the BAIs in tissues and/or organs, when administered to an animal, mammal, or human. The carrier is also designed to facilitate reconstitution back into its low pH carrier structure or form, or newly form a low pH carrier structure or form due to duodenal reflux: the carrier transitions from its high pH form back into its low pH form(s) when changing from a high pH environment back into a low pH environment.

In certain embodiments, the compositions include a carrier of this disclosure and a therapeutically effective amount of one or more pharmaceutical active ingredients (APIs) and/or one or more nutraceutical agents, wherein the carrier is designed to effect a targeted release of the APIs and/or nutraceutical agents and/or to modify and/or alter the chemical properties, physical properties, and/or behavior of the agents in tissues and/or organs of the APIs or nutraceuticals, when administered to an animal, mammal, or human and to facilitate matrix reconstitution due to duodenal reflux.

The above compositions may be in the form of a solution of the BAIs in the carrier, a suspension of solid BAIs in the carrier, wherein some of the BAIs may be dissolved in the carrier, a suspension of the BAIs in the carrier, wherein no active agent is dissolved in the carrier, a paste of the BAIs in the carriers, or any other mixture or combination of the BAIs in the carriers or surrounded by the carriers. The BAIs may be present in the carrier in an amount sufficient to produce a solid-in-oil suspension, a paste like suspension, a coated solid material such as coated crystals or coated micro- or nano-particles, where the coating may be from a monolayer to millimeters in thickness, a matrix of coated solid material, or any other form including a carrier of this disclosure and one or more active agents.

In some embodiments, the present disclosure broadly relates to pharmaceutical compositions comprising (1) a carrier comprising: (a) a non-aqueous pH dependent release system; and (b) a non-aqueous pH dependent reassembly/assembly and reabsorption/absorption system, wherein the carrier composition has a low pH form and a high pH form, wherein the carrier composition is formulated to release one or more biologically active agents minimally from its low pH form and maximally or at a higher level from its high pH form due to the non-aqueous pH dependent release system, wherein the carrier composition is formulated to either reassembly into its low pH form and/or assembly into a new low pH form due to the non-aqueous pH dependent reassembly/assembly and reabsorption/absorption system, and wherein the carrier is formulated to either reabsorb the one or more biologically active agents in its reassembled form and/or absorb the one or more biologically active agents in its newly assembly form, and (2) one or more biologically active agents, wherein a weight ratio of the carrier to the one or more biologically active agents is between about 10:1 and about 1:2.

In certain embodiments, the non-aqueous pH dependent release system is present in an amount between 10 wt. % and 95 wt. %; and the non-aqueous pH dependent reassembly/assembly and reabsorption/absorption system is present in an amount between about 5 wt. % and 90 wt. %. In other embodiments, the non-aqueous pH dependent release system is present in an amount between 20 wt. % and 95 wt. %; and the non-aqueous pH dependent reassembly/assembly and reabsorption/absorption system is present in an amount between about 5 wt. % and 80 wt. %. In other embodiments, the non-aqueous pH dependent release system is present in an amount between 30 wt. % and 95 wt. %; and the non-aqueous pH dependent reassembly/assembly and reabsorption/absorption system is present in an amount between about 5 wt. % and 70 wt. %. In other embodiments, the non-aqueous pH dependent release system is present in an amount between 40 wt. % and 95 wt. %; and the non-aqueous pH dependent reassembly/assembly and reabsorption/absorption system is present in an amount between about 5 wt. % and 60 wt. %. In other embodiments, the non-aqueous pH dependent release system comprises: at least 15 wt. % of one or more monocarboxylic acids having at least 8 carbon atoms, at least 20 wt. % of one or more monocarboxylic acids having at least 8 carbon atoms, or at least 30 wt. % of one or more monocarboxylic acids having at least 8 carbon atoms.

In other embodiments, the non-aqueous pH dependent release system comprises at least 15 wt. % of a mixture of (a) one or more low melting point monocarboxylic acids, (b) one or more medium melting point monocarboxylic acids, (c) one or more high melting point monocarboxylic acids, or (d) any combination thereof, wherein the low melting point monocarboxylic acids have melting point temperatures less than or equal to room temperature, wherein the medium melting point monocarboxylic acids have melting point temperatures greater than room temperature and less than or equal to a body temperature of an animal, a mammal, or a human, and wherein the high melting point monocarboxylic acids have melting point temperatures above the body temperature of an animal, a mammal, or a human. In other embodiments, the non-aqueous pH dependent release system further comprises one or more neutral lipids. In other embodiments, the non-aqueous pH dependent release system further comprises: a mixture of (a) one or more low melting point neutral lipids, (b) one or more medium melting point neutral lipids, (c) one or more high melting point neutral lipids, or (d) any combination thereof, wherein the at low melting point neutral lipids have melting point temperatures less than or equal to room temperature, wherein the medium melting point neutral lipids have melting point temperatures greater than room temperature and less than or equal to a body temperature of an animal, a mammal, or a human, and wherein the high melting point neutral lipids have melting point temperatures greater than the body temperature of an animal, a mammal, or a human.

In other embodiments, the non-aqueous pH dependent reassembly/assembly and reabsorption/absorption system comprises: (a) one or more polyacids, (b) one or more polymers including a plurality of carboxylic acid moieties, (c) one or more surfactants, (d) one or more water insoluble oligomers, (e) one or more water insoluble polymers, or (f) any combination thereof. In other embodiments, the pharmaceutical compositions further comprise: less than 10 wt. % of one or more selected from (1) fatty acid salts, (2) secondary complexing agents, (3) protective agents, (4) excipients, (5) adjuvants, (6) drying agents, (7) antioxidants, (8) preservatives, (9) chelating agents, (10) viscomodulators, (11) tonicifiers, (12) flavorants, (13) colorants, (14) odorants, (15) opacifiers, (16) suspending agents, and (17) binders.

C. Methods for Making

Some embodiments of the present disclosure provide methods for making the carriers of this disclosure by contacting components together under conditions of mixing, temperature, pressure, and time sufficient to form a carrier having engineered BAI release, reconstitutive, and BAI absorptive properties. In certain embodiments, a solvent system may be used, but the solvent must be removed so that the carriers are substantially free solvent. The removal process may be distillation, evaporation, vacuum distillation, vacuum evaporation, any other solvent removal techniques, or any combination thereof.

Some embodiments of the present disclosure provide methods for making the compositions by contacting or admixing a therapeutically effective amount of one or more BAIs into a carrier of this disclosure under conditions of mixing, temperature, pressure, and time sufficient to form a composition, wherein the carrier is a liquid at biological temperatures and the carrier is engineered so that the BAIs are released in a pH dependent nature and the carrier is engineered to reconstitute capable of absorbing BAIs due to partitioning between an aqueous fluid and the non-aqueous matrix. In certain embodiments, the BAIs are simply admixed into the carrier under conditions of mixing, temperature, pressure, and time sufficient to form a composition for this disclosure.

In certain embodiments, the BAIs comprise one or more APIs and/or one or more nutraceutical agents.

It should be recognized by an ordinary artisan that the admixing method reduces step and eliminates any concern for solvent removal or trace solvent contamination allowing for lower manufacturing cost, environmental manufacturing concerns, etc. Alternatively, certain formulations may benefit from solvation of the ingredients. In certain embodiments, the APIs and/or nutraceutical agents are solids and the admixing method simply involves mixing the solid APIs and/or solid nutraceutical agents into the carrier to form solid-in-oil suspension or paste, i.e., a suspension of the solid APIs and/or solid nutraceutical agents in an oil matrix. In other embodiments, the APIs and/or nutraceutical agents are liquids and the admixing method simply involves mixing the liquid APIs and/or liquid nutraceutical agents into the carrier to form an oil matrix including the liquid APIs and/or liquid nutraceutical agents. In other embodiments, the APIs and/or nutraceutical agents are a mixture of solids and liquids. Again, if a solvent system is used, the solvent is removed so that the compositions are substantially free of solvent, wherein the removal techniques may be distillation, evaporation, vacuum distillation, vacuum evaporation, any other solvent removal technique, or any combination thereof.

Some embodiments of the present disclosure provide methods including administering an effective amount of a composition of this disclosure to a human, mammal, or animal, wherein the effective amount of the composition results in a therapeutically effective amount of the one or more BAIs such as APIs and/or one or more nutraceutical agents sufficient to illicit a desired response. The mode of administration may be oral administration, sublingual or rectal administration, or esophageal, gastric, intestinal instillation via endoscopy. In certain embodiments, the administration may be topical such as administration into ophthalmic, urinary, the reproductive, or other tract, tissue, or organ for which topical administration represents an effective treatment methodology. In other embodiments, the administration may be parenteral.

D. Further Characteristics of the Compositions and Carriers

More particularly, some embodiments of the present disclosure relate to systems and compositions including a non-aqueous carrier and one or more biologically active agents (BAIs) to form a tailored biologically active agent release non-aqueous matrix having improved GI protection due to duodenal reflux and to methods for making and using same. The carriers: (a) have a first or low pH form, wherein the low pH form is substantially insoluble in fluids having a pH less than or equal to about pH 3 and releases minimal amounts of the one or more biologically active agents in the low pH fluids, (b) have a second or high pH form, wherein the high pH form changes in fluids having a pH greater the pH 3 and releases substantial amounts of the one or more biologically active agents in the high pH fluids, (c) reassemble into the low pH form and/or assemble into a new low pH form after passing through the stomach into the duodenum and back into the stomach due to duodenal reflux, and (d) the reassembled low pH form and/or assembled new low pH form absorbs a portion of any biologically active agent present in the duodenal reflux to reduce stomach injury or irritation or to reduce the loss of any biologically active agent present in the duodenal reflux. In certain embodiments, the carriers may be administered to absorb a portion of one or more biologically active agents due to duodenal reflux, wherein the one or more biologically active agents are known gastric irritants, have known gastric stomach toxicity, have long therapeutic lifetimes, or are destroyed or decompose in the stomach.

Drug delivery systems have been studied for years. PLx Pharma Inc. has been instrumental in advancing the art of drug delivery systems by discovering that carriers may be designed that deliver biologically active agents to different parts of the GI tract based solely on pH. These carriers were based on using a sufficient amount of free fatty acid (long chained carboxylic acids), where the pH dependent behavior of the free fatty acid were thought to be based on the fact that at low pH values below about pH 3, the free fatty acids or carboxylic acids exist in their protonated form (R—COOH, where R is a hydrocarbyl group) and at high pH values above pH 3, especially a pH above the pKa of the free fatty acid, the free fatty acids or carboxylic acids exit in their ionized or deprotonated form as a salt ($R-COO^-A^+$, where R is as above and $A^+$ is a counterion like $Na^+$, $K^+$, $Ca_2^+$, $NH_4^+$, etc.) and act as surfactants.

Another class of drug delivery systems that release biologically active agents outside of the stomach are biologically active agents coated with polymers that breakdown in high pH environments or by the active of certain enzymes present in high pH environments of the GI tract. These polymeric coatings are not liquids and PLx Pharma has shown that aspirin released from such polymer-coated compositions is very slow and often unpredictable. Thus, so-called enteric coated aspirin are incapable of quickly releasing aspirin for patients that may be in immediate need of the anti-platelet activity of aspirin.

While there are compositions that show pH dependent release of biologically active agents, there is still a need in the art for new and novel pharmaceutical carriers and compositions based on the carriers that are capable of not only targeted release of biologically active agents, but are also capable of reconstitution and reabsorption of the biologically active agents upon back flow into the stomach to protect the stomach from injury from the biologically active agents or to protect the biologically active agents from further loss due to degradation in the stomach.

The present inventors have found that unique compositions may be prepared for pH dependent release of one or more biologically active agents (BAIs) including active pharmaceutical ingredients (APIs) and/or nutraceutical agents and for pH dependent reconstitution and absorption of BAIs, when the compositions transitions from a low pH environment, to a high pH environment and back to a low pH environment such as occurs in duodenal reflux. The inventors have found that pH dependent release of BAIs, pH dependent carrier assembly or reassembly, and BAI absorption or reabsorption is controlled by the nature of the carrier used in the compositions. The carriers are oil based, generally essentially free of water and/or solvents, and control the targeted release of BAIs in tracts in an animal, mammal, or human that have different pH values along a length of the tract such as the gastrointestinal (GI) tract, the urinary tract, the reproductive tract, or tissues such as ophthalmic tissue. Because the carriers are oil based and include pH dependent release agents, the carriers are also designed to assembly or reassembly when the carrier transitions from a high pH environment back to a low pH environment. Further, the assembled and/or reassembled carriers are designed to absorb and/or reabsorb BAIs in the low pH environments. The carriers of this disclosure are formulated to reduce injury to the stomach mucosa during initial passage through the stomach into the duodenum for BAIs known to be injurious or irritants to the stomach mucosa and to reduce injury due to duodenal reflux or to reduce loss of biologically active agents that decompose or are destroyed in gastric fluid.

1. NSAIDs

For example, non-steroidal anti-inflammatory drugs (NSAIDs) are known to cause significant gastrointestinal (GI) toxicity. This issue is particularly relevant to aspirin that in contrast to the other NSAIDs is indicated as a lifelong therapy for patients with cardiovascular disease. The GI symptoms from chronic aspirin use range from bloating and dyspepsia all the way to life threatening bleeding as a result of ulcer formation. The majority of the toxic side effects due to the use of aspirin includes the appearance of erosions or ulcers in the stomach. Other NSAIDs are also known to have the same or similar toxic effects on the stomach.

The ability, therefore, to deliver an NSAID past the stomach and into the duodenum instead is a logical approach to limit toxicity. One technique for accomplishing this delayed release is to utilize enteric coat tablets with that goal in mind and employ a pH-dependent coating decomposition to delay the release of the NSAID until the composition passes out of the stomach, a low pH environment, into the small intestines, a high pH environment. Accordingly, the polymer coating remains intact and only begins degrading and allowing the component NSAID, especially aspirin, to be released once the pH rises above pH 7 in the small intestines, a pH and environment necessary for the enteric coating degradation. Once released, the aspirin is free standing in the GI tract and available for absorption.

The degradation of enteric coatings is associated with significant inter- and intra-patient variability and results in unpredictable rates of aspirin release and absorption. More importantly, the promise of improved GI safety has not been fulfilled in clinical practice and studies have demonstrated that the risk of aspirin-induced GI bleeding is the same with enteric-coated aspirin formulations as compared to regular, immediate release aspirin formulations that deliver aspirin in the stomach. It appears therefore that the unidirectional, one-pass protection provided by the enteric polymer coating is insufficient to limit toxicity to the stomach.

The explanation for this observation relates to the normal digestive process that relies on continuous mixing of the luminal contents through ongoing peristalses. Accordingly, contents routinely reflux back into the stomach from the duodenum to allow for better mixing and digestion. Therefore, once the enteric-coated tablet arrives in the higher pH of the duodenum, it loses the polymer protection and releases the aspirin, which is then free to reflux back into the stomach and cause injury.

The NSAID compositions of this disclosure also employ a pH dependent release mechanism; however, rather than a polymer coating, the present compositions rely on the chemical nature of the carriers of this disclosure in which the NSAIDs are suspended, where the carriers minimally release the NSAIDs, or other biologically active agents, in low pH environments and efficiently or maximally release the NSAIDs or release the NSAIDs at a higher level, or other biologically active agents, in high pH environments.

Clinical studies have shown that aspirin absorption from compositions of this disclosure is both complete and reliable and in fact is bioequivalent to immediate release aspirin formulations. However, there is an additional very important differentiation of the compositions of this disclosure and it relates to the dynamic nature of the chemical nature of the carrier and its interaction with the solid NSAIDs, e.g., aspirin, or any other solid biologically active agent. Specifically, the carriers of this disclosure have been engineered both to release biologically active agents such as NSAIDs in a pH dependent manner and to reassemble or reconstitute when the carrier transitions from a high pH environment back into a low pH environment due to duodenal reflux. The reassembled or reconstituted carriers are then capable of reabsorbing any biologically active agents also refluxed back into the stomach from the duodenum. Accordingly, the protection from injury is maintained during the full digestive process compared with the one-pass protection from enteric coated tablets or other pH dependent carriers that only affect a pH dependent release, but not protection due to duodenal reflux. This differentiation in the mechanism of action of the engineered carriers of this disclosure is of very high clinical relevance since it allows for bidirectional stomach protection for the first time ever. This improved stomach protection not only lowers the risk for serious complications such ulcers or even life threatening bleeding, but the improved protection also reduces the dyspetic burden that frequently leads patients to discontinue this life saving therapy.

2. Acid Labile Biologically Active Agents

For compositions including acid labile biologically active agents or APIs, the reconstitution not only reduces the amount of API refluxed back into the stomach from causing stomach toxicity, but also reduces the loss of the API due to degradation in the stomach.

Thus, the inventors have found that by a very careful engineering of the carriers of this disclosure not only may the carriers affect a pH dependent release of the biologically active agents, but may also reconstitute during duodenal reflux affecting a reabsorption of the biologically active agents. The ability for the engineered carrier to reassemble or reconstitute, may also allow for the formulation of compositions that may be taken during administration of biologically active agents known to efficiently reflux from the duodenum back into the stomach such as naproxen or other persistent biologically active agents known to be injurious to the stomach. The ability of the engineered carrier to reassemble or reconstitute also further reduces any decomposition of acid labile biologically active agents.

As the population of the world and particularly the United States has increasing numbers of older citizens and citizens that are physically heavier than previous generations, the need for new delivery systems for biologically active agents or APIs that mitigate against certain adverse effects such as adverse GI affects increases, especially for non-steroidal, anti-inflammatory drugs (NSAIDs). NSAIDs are ubiquitously used drugs for managing pain, for reducing or managing cardiovascular disease, for reducing platelet aggregation, for reducing fever, for reducing or preventing cancer, and for a number of other uses. However, NSAIDs have a major drawback; they all have, to some extent, the ability to cause irritation, erosion, and/or ulceration of the stomach and upper GI tract.

Previous work showed that fatty acids were capable of controlling the release of biologically active agents in a pH dependent manner as set for in U.S. Pat. Nos. 10,179,104; 9,730,884; 9,226,892; and 9,216,150, each incorporated by reference herein in their entirety. However, no one recognized that such compositions could be designed to facilitate composition reconstitution and reabsorption biologically active agents due to duodenal reflux. It is believed that this reconstitution/reabsorption results in further reduction of possible stomach mucosa lining damage, irritation, or injury or further reduction in the loss of biologically active agents in low pH environment, especially for biologically active agents that decomposes or are destroyed in low pH environments.

II. Pharmaceutical Carrier Compositions

It was found that the compositions including one or more biologically active agents and a targeted release or pH dependent release carrier, which includes at least one compound that undergoes a change in at least one chemical property in a pH dependent manner such as undergoing protonation or deprotonation, may be further formulated to include at least one compound capable of pH dependent carrier reassembly or carrier assembly during duodenal reflux, wherein the reassembled or newly assembled carrier is capable of absorption or reabsorption of the one or more biologically active agents.

In some embodiments, the carriers of the present disclosure are designed to form hydrophobic matrices in which an active agent is mixed as a solid or liquid (depending on the nature of the active agent). These hydrophobic matrices operate to modify, alter, change, or augment chemical and/or physical characteristics of the active agent by providing an immiscible/different environment compared to an aqueous biofluid such as blood, gastric fluids, duodenal fluids, small intestinal fluids, large intestinal fluids, vaginal fluids, rectal solids/fluids, or any other biofluid setting up a situation where the active agent is free to partition between the two immiscible environments. Additionally, properties of the carriers of this disclosure such as viscosity, lipophilicity, hydrophobicity, dispersibility, dispensability, softening temperature, melting temperature, etc. also act to modify, alter, change, or augment the rate of partitioning of the active agent by sequestering the active agent in the immiscible carrier until the carrier matrix is dispersed to small enough particles to facilitate mass transfer from the immiscible carrier into the appropriate biofluid. For solid active agents sequestered in a carrier matrix of this disclosure, an added reduction in partitioning rate ensues because the active agent must migrate out of the matrix and dissolve as the particle size of the matrix reduces in the biofluid due to mechanic actions of the tissue and/or organ and/or due to biochemical processes occurring in the tissue and/or organ.

In some embodiments, the present disclosure broadly relates to compositions comprising: (1) a carrier as disclosed herein, and (2) at least one biologically active agent. The carrier includes an effective amount of a pH dependent release system sufficient for a targeted release of the biologically active agents at a desired pH and an effective amount of a carrier reassembly/assembly and biologically active agent reabsorption/absorption system sufficient to reassemble the carrier to its low pH form or assemble a new low pH carrier in low pH environments and to reabsorb or absorb the biologically active agents contained in the original carrier.

Generally, the pH dependent release systems cause the at least one biologically active agent to be released in a pH sensitive manner characterized in that less than 20% of the at least one biologically active agent is released into gastric fluid and greater than 50% of the at least one biologically active agent is released in an intestinal fluid such as duodenum fluid. In other embodiments, the carriers efficiently release the at least one biologically active agent in high pH environments and reassemble and reabsorption or assembly and absorb the at least one biologically active agent due to a transition from a high pH environment to a low pH environment as a result of duodenal reflux. In other embodiments, the carriers release the biologically active agents minimally at a first pH and efficiently at second pH and reconstitute and reabsorb or assembly and absorb the at least one biologically active agent at the first pH due to duodenal reflux. In other embodiments, the carriers release the biologically active agents minimally in the stomach and efficiently in the duodenum and reconstitute and reabsorb or form a new carrier and absorb the at least one biologically active agent in the stomach due to duodenal reflux.

In other embodiments, the present disclosure relates broadly to pharmaceutical compositions comprising a carrier and at least pharmaceutically active ingredient (API) such as one weak acid non-steroidal anti-inflammatory drug (NSAID). The carrier includes an effective amount of a pH dependent release system sufficient for a targeted release of the API at a desired pH and an effective amount of a reassembly/assembly and reabsorption/absorption system sufficient to reassemble the carrier into its low pH form or to form a new low pH carrier due to duodenal reflux with concurrent reabsorption or absorption of the API. Generally, the carrier releases the API in a pH sensitive manner characterized in that less than 20% of the API is released into gastric fluid and greater than 50% of the API is released in intestinal fluid having a pH value greater than pH 3 and reconstitutes and reabsorbs the API in gastric fluid or form a new low pH carrier that absorbs the API. In other embodiments, the compositions further include at least one secondary agent for the biologically active agents, which generally reduce the toxicity or reduce the acid induced hydrolysis of the biologically active agents. In other embodiments, the compositions of this disclosure are non-aqueous including only residual water and are immiscible in water or aqueous solutions, but are capable of being dispersed in aqueous solutions releasing the biologically active agent in a pH dependent manner. In other embodiments, the carriers of this disclosure are oil-based including only residual water and are immiscible in water or aqueous solutions, but the carriers are capable of being dispersed in aqueous solutions releasing the BAI or BAIs.

In other embodiments, the carriers of this disclosure may be tailored to have good targeted active agent release characteristics, to have reduced active agent toxicity or irritation, to have increased active agent bioavailability, and to have increased active agent migration across relatively hydrophobic barriers in a human, mammal or animal. In other embodiments, the carriers of this disclosure may be tailored to have good targeted active agent release characteristics, to have reduced active agent GI toxicity or irritation, to have increased active agent bioavailability, and to have increased active agent migration across relatively hydrophobic barriers in a human, mammal or animal.

Some embodiments of the present disclosure relate to compositions comprising a carrier including an effective amount of a least one targeted release agent and an effective amount of at least one reassembly/assembly and reabsorption/absorption agent and a therapeutically effective amount of at least one biologically active agent, where the carrier composition and/or its components are capable of controllably releasing the at least one biologically active agent into certain portions of the gastro-intestinal (GI) tract and controllable reassembly/assembly and reabsorption/absorption of the at least one biologically active agent due to duodenal reflux. In other embodiments, the carrier and/or its components modify and/or alter the chemical and/or physical properties and/or behavior of the at least one active agent in tissues and/or organs reducing and/or altering tissue and/or organ toxicity, improving and/or altering bioavailability, and/or improving and/or altering efficacy. In other embodiments, the carriers are capable of releasing the at least one BAI in a pH dependent manner. In other embodiments, the biocompatible targeted release agents comprise at least one biocompatible free fatty acid having at least 8 carbon atoms.

Some embodiments of the present disclosure relate to a composition comprising a carrier including up to 80 wt. % of one or more free fatty acids, up to 40 wt. % of one or more surfactants and up to 50 wt. % of one or more neutral lipids, where the weight percentages of all components in the composition add up to 100 wt. %, and an effective amount of at least one biologically active agent, where the carrier composition and/or its components are capable of controllably releasing at least one active agent into certain portions of the gastro-intestinal (GI) tract. In other embodiments, the carrier and/or its components modify and/or alter the chemical and/or physical properties and/or behavior of the at least one active agent in tissues and/or organs reducing and/or altering tissue and/or organ toxicity, improving and/or altering bioavailability, and/or improving and/or altering efficacy. In some embodiments, the one or more surfactants include a mixture of nonionic surfactants. In some embodiments, the one or more surfactants include a mixture of nonionic surfactants, cationic surfactants, and zwitterionic surfactants in a weight ratio of nonionic surfactants to cationic and zwitterionic surfactants between about 50:1 and 1:1. In some embodiments, the one or more surfactants include a mixture of nonionic surfactants, anionic surfactants, and zwitterionic surfactants in a weight ratio of nonionic surfactants to anionic and zwitterionic surfactants between about 50:1 and 1:1. In some embodiments, the one or more surfactants include a mixture of nonionic surfactants and cationic surfactants in a weight ratio of nonionic surfactants to cationic surfactants between about 50:1 and 1:1. In some embodiments, the one or more surfactants include nonionic surfactants and anionic surfactants in a weight ratio of nonionic surfactants to anionic surfactants between about 50:1 and 1:1. In some embodiments, the surfactants include a mixture of nonionic surfactants and zwitterionic surfactants is a weight ratio of nonionic surfactants to zwitterionic surfactants between about 50:1 and 1:1.

Some embodiments of the present disclosure relate to a composition comprising a carrier including greater than about 15 wt. % of at least one biocompatible free fatty acid having at least 8 carbon atoms, greater than about 20 wt. % of at least one biocompatible free fatty acid having at least 8 carbon atoms, or greater than about 30 wt. % of at least on biocompatible free fatty acid; greater than about 10 wt. % of a mixture of surfactants, greater than about 20 wt. % of a mixture of surfactants, or greater than about 30 wt. % of a mixture of surfactants; and a remainder comprising at least one neutral lipid, where the free fatty acids, the surfactants, and the neutral lipids are immiscible in water, where the weight percentages of all components in the composition add up to 100 wt. %, and an effective amount of at least one biologically active agent, where the carrier composition and/or its components are capable of controllably releasing at least one active agent into certain portions of the gastro-intestinal (GI) tract. In other embodiments, the carrier and/or its components modify and/or alter the chemical and/or physical properties and/or behavior of the at least one active agent in tissues and/or organs reducing and/or altering tissue and/or organ toxicity, improving and/or altering bioavailability, and/or improving and/or altering efficacy. In other embodiments, the mixture of surfactants comprises at least one nonionic surfactant and at least one zwitterionic surfactant is a weight ratio of the at least one nonionic surfactant to the at least one zwitterionic surfactants between about 50:1 and 1:1.

In other embodiments, the present disclosure relates broadly to pharmaceutical compositions including a carrier of this disclosure and an effective amount of a pharmaceutical agent or a mixture of pharmaceutical agents to form a solution and/or a suspension of the pharmaceutical agent or the mixture of pharmaceutical agents in the carrier. In certain embodiments, the pharmaceutical compositions may be tailored to have good targeted pharmaceutical release characteristics, to have reduced pharmaceutical toxicity or irritation, to have increased pharmaceutical bioavailability, and to have increased pharmaceutical migration across relatively hydrophobic barriers in a human, mammal or animal. In other embodiments, the pharmaceutical compositions may be tailored to have good targeted pharmaceutical release characteristics, to have reduced pharmaceuticals GI toxicity or irritation, to have increased pharmaceutical bioavailability, and to have increased pharmaceutical migration across relatively hydrophobic barriers in a human, mammal or animal.

In other embodiments, the present disclosure relates broadly to nutraceutical compositions including a carrier of this disclosure and an effective amount of a nutraceutical agent or a mixture of nutraceutical agents to form a solution and/or a suspension of the nutraceutical agent or a mixture of nutraceutical agents in the carrier. In certain embodiments, the nutraceutical compositions may be tailored to have good targeted nutraceutical release characteristics, to have reduced nutraceutical toxicity or irritation, to have increased nutraceutical bioavailability, and to have increased nutraceutical migration across relatively hydrophobic barriers in a human, mammal or animal. In other embodiments, the nutraceutical compositions may be tailored to have good targeted nutraceutical release characteristics, to have reduced nutraceutical GI toxicity or irritation, to have increased nutraceutical bioavailability, and to have increased nutraceutical migration across relatively hydrophobic barriers in a human, mammal or animal.

In other embodiments, the pharmaceutical agent is an NSAID. In other embodiments, the NSAID compositions of this disclosure may also include: (1) a pharmaceutically acceptable amount of antioxidant selected from the group consisting of Vitamin A, Vitamin C, Vitamin E or other antioxidants approved for a human, mammal or animal consumption by the FDA and mixtures or combinations thereof; (2) a pharmaceutically acceptable amount of a polyvalent cation selected from the group consisting of copper, zinc, gold, aluminum and calcium and mixtures or combinations thereof; (3) a pharmaceutically acceptable amount of an agent to promote fluidity, enhance viscosity, promote spreadability, promote dispersibility and/or promote permeability selected from the group consisting of dimethylsulfoxide (DMSO), propylene glycol (PPG), and medium chain triglyceride/MCT and mixtures or combination thereof; (4) a pharmaceutically acceptable amount of a food coloration or non-toxic dye; (5) a pharmaceutically acceptable amount of a flavor enhancer; (6) an excipient; and/or (7) an adjuvant.

In other embodiments, the pharmaceuticals and/or nutraceutical agent is acid labile. The carriers may be tailored to selectively minimize release of the acid labile active agents in the stomach and selectively target release of the acid labile active agent to the small intestines or the large intestines. This embodiment could be especially useful for patients at risk for cardiovascular (CV) disease and acid reflux disease, or an elevated risk of gastrointestinal bleeding that require the use of a proton pump inhibitor including but not limited to omeprazole or lansoprazole.

In other embodiments, the carriers comprise a least one targeted release agent, where the carrier composition and/or its components are capable of controllably releasing at least one active agent into certain portions of the gastro-intestinal (GI) tract. In other embodiments, the targeted release agents comprise pH dependent release agents capable of controllably releasing the active agents in a pH dependent manner. In other embodiments, the targeted release agents comprise pH dependent release agents capable of controllably releasing the active agents into certain portions of the GI tract based on a pH of the portions. In other embodiments, the pH dependent release agents include fatty acid having at least 8 carbon atoms. In other embodiments, the carrier further comprising at least one neutral lipid, where the neutral lipid is water immiscible. In other embodiments, the neutral lipids comprise mono-glycerides, diglycerides, triglycerides, or mixtures and combinations thereof, where the ester side chains have at least 6 carbon atoms. In other embodiments, carrier further comprising less than 10 wt. % of a phospholipid or a plurality of phospholipids.

Some embodiments of the present disclosure relate to a carrier composition comprising up to 80 wt. % one or more free fatty acids, up to 40 wt. % of a mixture of at least one nonionic surfactants and a cationic surfactant, an anionic surfactant, or a zwitterionic surfactant, and up to 50 wt. % one or more neutral lipids, where the carrier composition and/or its components are capable of controllably releasing at least one active agent into certain portions of the gastrointestinal (GI) tract. In some embodiments, the mixture of surfactants comprises at least one nonionic surfactant and at least one cationic, anionic, or zwitterionic surfactant is a weight ratio of the at least one nonionic surfactant to the at least one cationic, anionic, or zwitterionic surfactant between about 50:1 and 1:1. In some embodiments, the mixture of surfactants comprises at least one nonionic surfactant and at least one zwitterionic surfactant is a weight ratio of nonionic surfactants to zwitterionic surfactants between about 50:1 and 1:1.

Some embodiments of the present disclosure relate broadly to carriers including at least one targeted release agent. The carriers and/or their components modify and/or alter the chemical and/or physical properties of biologically active agents and/or behavior of biologically active agents in tissues and/or organs reducing and/or altering tissue and/or organ toxicity, improving and/or altering bioavailability, and/or improving and/or altering efficacy of biologically active agents. In certain embodiments, the carriers and/or their components modify and/or alter the chemical and/or physical properties of biologically active agents and/or behavior of biologically active agents in tissues and/or organs in a pH dependent manner to reduce and/or alter tissue and/or organ toxicity, improve and/or alter bioavailability, and/or improve and/or alter efficacy of biologically active agents. The carriers include all of the properties set forth above in addition to any other set forth below.

In certain embodiments, the carriers include: (1) pH dependent release system, (2) a pH dependent carrier reassembly/assembly and biologically active agent reabsorption/absorption due to duodenal reflux, (3) optionally one or more neutral lipids, (4) optionally one or more surfactants, (5) optionally a biologically active agent complexing agent, and (6) optionally a protective system including agents to reduce and/or eliminate biologically active agent toxicities, irritations or side effects. The carriers are generally viscous fluids capable of being orally administered, directly administered, internally administered and/or topically administered.

In other embodiments, the carriers may also include other components such as: (1) excipients, (2) adjuvants, (3) drying agents, (4) antioxidants, (5) preservatives, (6) chelating agents, (7) viscomodulators, (8) tonicifiers, (9) flavorants and taste masking agents, (10) colorants, (11) odorants, (12) opacifiers, (13) suspending agents, (14) binders, and (15) mixtures thereof.

The carriers disclosed herein are generally fluid and the composition made therefrom are generally solutions, pastes, semi-solids, dispersions, suspensions, colloidal suspensions or mixtures thereof and are capable of being orally administered, parenterally administered or topically administered. In some embodiments, the other components include citric acid.

Some embodiments of the present disclosure broadly relate to pharmaceutical carrier compositions comprising: (a) a non-aqueous pH dependent release system; and (b) a non-aqueous pH dependent reassembly/assembly and reabsorption/absorption system, wherein the carrier composition has a low pH form and a high pH form, wherein the carrier composition is formulated to release one or more biologically active agents minimally from its low pH form and maximally from its high pH form due to the non-aqueous pH dependent release system, wherein the carrier composition is formulated to either reassembly into its low pH form or assembly into a new low pH form due to non-aqueous pH dependent reassembly/assembly and reabsorption/absorption system, and wherein the carrier is formulated to either reabsorb the one or more biologically active agents in its reassembled form or absorb the one or more biologically active agents in its newly assembly form. In certain embodiments, the non-aqueous pH dependent release system is present in an amount between 10 wt. % and 95 wt. %; and the non-aqueous pH dependent reassembly/assembly and reabsorption/absorption system is present in an amount between about 5 wt. % and 90 wt. %. In other embodiments, the non-aqueous pH dependent release system is present in an amount between 20 wt. % and 95 wt. %; and the non-aqueous pH dependent reassembly/assembly and reabsorption/absorption system is present in an amount between about 5 wt. % and 80 wt. %. In other embodiments, the non-aqueous pH dependent release system is present in an amount between 30 wt. % and 95 wt. %; and the non-aqueous pH dependent reassembly/assembly and reabsorption/absorption system is present in an amount between about 5 wt. % and 70 wt. %. In other embodiments, the non-aqueous pH dependent release system is present in an amount between 40 wt. % and 95 wt. %; and the non-aqueous pH dependent reassembly/assembly and reabsorption/absorption system is present in an amount between about 5 wt. % and 60 wt. %. In some embodiments, when the carrier also comprises other components such as: (1) excipients, (2) adjuvants, (3) drying agents, (4) antioxidants, (5) preservatives, (6) chelating agents, (7) viscomodulators, (8) tonicifiers, (9) flavorants and taste masking agents, (10) colorants, (11) odorants, (12) opacifiers, (13) suspending agents, (14) binders, and (15) mixtures thereof, the total weight percentage of these other components along with that of the non-aqueous pH dependent release system and the non-aqueous pH dependent reassembly/assembly and reabsorption/absorption system is 100 wt. %.

In other embodiments, the non-aqueous pH dependent release system comprises: at least 15 wt. % of one or more monocarboxylic acids having at least 8 carbon atoms, at least 20 wt. % of one or more monocarboxylic acids having at least 8 carbon atoms, or at least 30 wt. % of one or more monocarboxylic acids having at least 8 carbon atoms.

In other embodiments, the non-aqueous pH dependent release system comprises: at least 15 wt. % of a mixture of (a) one or more low melting point monocarboxylic acids, (b) one or more medium melting point monocarboxylic acids, (c) one or more high melting point monocarboxylic acids, or (d) any combination thereof, wherein the low melting point monocarboxylic acids have melting point temperatures less than or equal to room temperature, wherein the medium melting point monocarboxylic acids have melting point temperatures greater than room temperature and less than or equal to a body temperature of an animal, a mammal, or a human, and wherein the high melting point monocarboxylic acids have melting point temperatures above the body temperature of an animal, a mammal, or a human. In other embodiments, the non-aqueous pH dependent release system further comprises one or more neutral lipids. In other embodiments, the non-aqueous pH dependent release system further comprises: a mixture of (a) one or more low melting point neutral lipids, (b) one or more medium melting point neutral lipids, (c) one or more high melting point neutral lipids, or (d) any combination thereof, wherein the at low melting point neutral lipids have melting point temperatures less than or equal to room temperature, wherein the medium melting point neutral lipids have melting point temperatures greater than room temperature and less than or equal to a body temperature of an animal, a mammal, or a human, and wherein the high melting point neutral lipids have melting point temperatures greater than the body temperature of an animal, a mammal, or a human.

In some embodiments, the base carriers of this disclosure include: (1) at least 10 wt. % of a non-aqueous pH dependent release system such as a mixture of free fatty acids; and (2) one or more reconstituting agents (i.e., compounds contributing to pH dependent reassembly/reabsorption).

In certain embodiments, the carrier may include one or more of the following additives: (a) one or more excipients, (b) one or more adjuvants, (c) one or more drying agents, (d) one or more antioxidants, (e) one or more preservatives, (f) one or more chelating agents, (g) one or more viscomodulators, (h) one or more tonicifiers, (i) one or more flavorants, (j) one or more colorants, (k) one or more odorants, (l) one or more opacifiers, (m) one or more of suspending agents, and (n) mixtures thereof.

TABLE A

| Reagent | wt. % range |
|---|---|
| Base Carrier | |
| pH dependent release system | 10 to 90 |
| reconstituting agents | 90 to 10 |
| Additive Weight Percentages Based on 100% of Base Carrier | |
| complexing agent | 0 to 10 |
| Excipients | 0 to 5 |
| Adjuvants | 0 to 5 |
| drying agents | 0 to 5 |
| Antioxidants | 0 to 5 |
| Preservatives | 0 to 5 |
| chelating agents | 0 to 5 |
| Viscomodulators | 0 to 5 |
| Opacifiers | 0 to 5 |
| suspending agents | 0 to 5 |

The carriers and/or the carrier components are designed to modify and/or alter the chemical and/or physical properties and/or behavior of at least one active agent in tissues and/or organs reducing and/or altering tissue and/or organ toxicity, improving and/or altering bioavailability, and/or improving and/or altering efficacy. In certain embodiments, the carriers and/or the biocompatible, hydrophobic agents modify and/or alter the chemical and/or physical properties and/or behavior of at least one active agent in tissues and/or organs in a pH dependent manner to reduce and/or alter tissue and/or organ toxicity, improve and/or alter bioavailability, and/or improve and/or alter efficacy. The carriers and/or carrier components are also designed to facilitate reconstitution of any carrier blow back from the duodenum to stomach and drug reabsorption of the blow back material.

It is believed that the carriers and/or their components interact with certain types of biologically active agents to affect particle size, morphology, other physical characteristics, physical/chemical properties and/or behavior and physical/chemical properties of the crystals of the active agent in the carrier. In certain embodiments, the biologically active agents are added to the carrier at an elevated temperature, where the temperature may be up to the melting temperature of the active ingredient, but below a decomposition temperature of any of the carrier components or biologically active agents. The inventors believe that the augmented properties result in increased bioavailability of the biologically active agents once the pH of the environment is at or near the pKa or pKb of the pH dependent release agents and/or the biologically active agents.

III. pH Dependent Release Agents pH dependent release compounds, as disclosed herein, generally include at least one ionizable group, i.e., a group that undergoes a change in at least one chemical property in a pH dependent manner. For example, carboxylic acids exist in two form depending on pH, a normal acid form, R—COOH, in pH environments below the acids' pKa values and a salt form, R—COO-A+, where A+ is a counterion, in environments at or above the acid's pKa values. Exemplary examples of other ionizable groups useful in the present carriers include, without limitation, a hydroxy group, an amino group, an amide group, other similarly ionizable groups, or mixtures and combinations thereof of these ionizable group with carboxylic acid groups. The targeted release agents are generally immiscible or insoluble in water and are generally soluble or miscible in oils. In certain embodiments, the compounds may be weak carboxylic acids such as fatty acids, i.e., acids that have a pKa value greater than or equal to about pH 3.5.

For targeted release agents that include groups that may be deprotonated such as COOH and OH groups, the targeted release agents are neutral below their pKa values, especially at pH values less than pH 3, and are ionized at pH values at or above their pKa values. More particularly, the targeted release agents are neutral in gastric fluid and ionized (deprotonated) in duodenum fluid. Such weak acid targeted release agents ionize as the pH rises converting them into surfactants, which assist in a rapid dissolution of the carrier releasing the biologically active agent or API in higher pH environments. Because the GI tract has a pH profile starting at the stomach and proceeding to the large intestines of increasing pH from a pH value in the stomach between about pH 1 and about pH 3 to a pH in the duodenum between about pH 3 and pH 7 to pH values as high as pH 8 or 9 in the large intestines, compositions may be formulated to release the biologically active agents at different pH values based on the pKa values of the release agents. Thus, the carriers disclosed herein are designed to efficiently and rapidly release a biologically active agents only when the pH of the environment is at or greater than the pKa value of the release agents. The carriers of this disclosure may include from an effective amount of the release agents to 100% of release agents. Fatty acids represent one class of targeted release agents that are immiscible in water and have pKa values generally greater than about pH 3 and are converted to surfactants upon ionization at pH values at or above their pKa values.

Free Fatty Acids

Suitable biocompatible fatty acids for use in this disclosure include, without limitation, any saturated fatty acid or unsaturated fatty acids or mixtures or combinations thereof suitable for a human, mammal or animal consumption. Exemplary fatty acids include short chain free fatty acids (SCFFA), medium chain free fatty acids (MCFFA), long chain free fatty acids (LCFFA), verylong-chain free fatty acids (VLCFFA) and mixtures or combinations thereof. SCFFA include free fatty acids having a hydrocarbyl tail group having 4 to 7 carbon atoms (C4 to C7). MCFFA include free fatty acids having a hydrocarbyl group having 8 to 13 carbon atoms (C8 to C13). LCFFA include free fatty acids having a hydrocarbyl group having 14 to 24 carbon atoms (C14-C24). VLCFFA include free fatty acids having a hydrocarbyl group having greater than 24 carbon atoms (>C24). Exemplary unsaturated fatty acids include, without limitation, myristoleic acid [$CH_3(CH_2)_3CH=CH(CH_2)_7COOH$, cis-Δ9, C:D 14:1, n-5], palmitoleic acid [$CH_3(CH_2)_5CH=CH(CH_2)_7COOH$, cis-Δ9, C:D 16:1, n-7], sapienic acid [$CH_3(CH_2)_8CH=CH(CH_2)_4COOH$, cis-Δ6, C:D 16:1, n-10], oleic acid [$CH_3(CH_2)_7CH=CH(CH_2)_7COOH$, cis-Δ9, C:D 18:1, n-9], linoleic acid [$CH_3(CH_2)_4CH=CHCH_2CH=CH(CH_2)_7COOH$, cis,cis-Δ9,Δ12, C:D 18:2, n-6], α-Linolenic acid [$CH_3CH_2CH=CHCH_2CH=CHCH_2CH=CH(CH_2)_7COOH$, cis,cis,cis-Δ9,Δ12,Δ15, C:D 18:3, n-3], arachidonic acid [$CH_3(CH_2)_4CH=CHCH_2CH=CHCH_2CH=CHCH_2CH=CH(CH_2)_3COOH$, cis,cis,cis,cis-Δ5Δ8,Δ11,Δ14, C:D 20:4, n-6], eicosapentaenoic acid [$CH_3CH_2CH=CHCH_2CH=CHCH_2CH=CHCH_2CH=CHCH_2CH=CH(CH2)3COOH$], cis,cis,cis,cis,cis-Δ5,Δ8,Δ11,Δ14,Δ17, 20:5, n-3], erucic acid [$CH_3(CH_2)_7CH=CH(CH_2)_{11}COOH$, cis-Δ13, C:D 22:1, n-9], docosahexaenoic acid [$CH_3CH_2CH=CHCH_2CH=CHCH_2CH=CHCH_2CH=CHCH_2CH=CHCH_2CH=CH(CH_2)_2COOH$, cis,cis,cis,cis,cis,cis-Δ4,Δ7,Δ10,Δ13,Δ16,Δ19, C:D 22:6, n-3], or mixtures and combinations thereof.

Exemplary saturated fatty acids include, without limitation, lauric acid [$CH_3(CH_2)_{10}COOH$, C:D 12:0], myristic acid [$CH_3(CH_2)_{12}COOH$, C:D 14:0], palmitic acid [$CH_3(CH_2)_{14}COOH$, C:D 16:0], stearic acid [$CH_3(CH_2)_{16}COOH$, C:D 18:0], arachidic acid [$CH_3(CH_2)_{18}COOH$, C:D 20:0], behenic acid [$CH_3(CH_2)_{20}COOH$, C:D 22:0], lignoceric acid [$CH_3(CH_2)_{22}COOH$, C:D 24:0], cerotic acid [$CH_3(CH_2)_{24}COOH$, C:D 26:0], or mixture or combinations thereof.

Exemplary saturated fatty acids include, without limitation, butyric (C4), valeric (C5), caproic (C6), enanthic (C7), caprylic (C8), pelargonic (C9), capric (C10), undecylic (C11), lauric (C12), tridecylic (C13), myristic (C14), pentadecylic (C15), palmitic (C16), margaric (C17), stearic (C18), nonadecylic (C19), arachidic (C20), heneicosylic (C21), behenic (C22), tricosylic (C23), lignoceric (C24), pentacosylic (C25), cerotic (C26), heptacosylic (C27), montanic (C28), nonacosylic (C29), melissic (C30), hentriacontylic (C31), lacceroic (C32), psyllic (C33), geddic (C34), ceroplastic (C35), hexatriacontylic (C36), heptatriacontylic acid (C37), octatriacontylic acid (C38), nonatriacontylic acid (C39), tetracontylic acid (C40), and mixtures or combinations thereof. Unsaturated fatty acids include, without limitation, n-3 unsaturated fatty acids such as α-linolenic acid, stearidonic acid, eicosapentaenoic acid, and docosahexaenoic acid, n-6 unsaturated fatty acids such as linoleic acid, γ-linolenic acid, dihomo-γ-linolenic acid, and arachidonic acid, n-9 unsaturated fatty acids oleic acid, elaidic acid, eicosenoic acid, erucic acid, nervonic acid, mead acid and mixtures or combinations thereof.

Exemplary unsaturated fatty acids include, without limitation, (a) ω-3 unsaturated fatty acids such as octenoic (8:1), decenoic (10:1), decadienoic (10:2), lauroleic (12:1), laurolinoleic (12:2), myristovaccenic (14:1), myristolinoleic (14:2), myristolinolenic (14:3), palmitolinolenic (16:3), palmitidonic (16:4), α-linolenic (18:3), stearidonic (18:4), dihomo-α-linolenic (20:3), eicosatetraenoic (20:4), eicosapentaenoic (20:5), clupanodonic (22:5), docosahexaenoic (22:6), 9,12,15,18,21-tetracosapentaenoic (24:5), 6,9,12,15, 18,21-tetracosahexaenoic (24:6), and mixtures or combinations thereof; (b) ω-5 unsaturated such as myristoleic (14:1), palmitovaccenic (16:1), α-eleostearic (18:3), β-eleostearic (trans-18:3) punicic (18:3), 7,10,13-octadecatrienoic (18:3), 9,12,15-eicosatrienoic (20:3), β-eicosatetraenoic (20:4), and mixtures or combinations thereof; (c) ω-6 unsaturated such as 8-tetradecenoic (14:1), 12-octadecenoic (18:1), linoleic (18:2), linolelaidic (trans-18:2), γ-linolenic (18:3), calendic (18:3), pinolenic (18:3), dihomo-linoleic (20:2), dihomo-γ-linolenic (20:3), arachidonic (20:4), adrenic (22:4), osbond (22:5), and mixtures or combinations thereof; (d) ω-7 unsaturated such as palmitoleic (16:1), vaccenic (18:1), rumenic (18:2), paullinic (20:1), 7,10,13-eicosatrienoic (20: 3), and mixtures or combinations thereof (e) ω-9 Unsaturated such as oleic (18:1), elaidic (trans-18:1), gondoic (20:1), erucic (22:1), nervonic (24:1), 8,11-eicosadienoic (20:2), mead (20:3), and mixtures or combinations thereof; (f) ω-10 Unsaturated such as Sapienic (16:1); (g) ω-11 unsaturated such as gadoleic (20:1); (h) ω-12 Unsaturated such as 4-Hexadecenoic (16:1) Petroselinic (18:1) 8-Eicosenoic (20:1), and mixtures or combinations thereof and (i) mixtures or combinations thereof.

Diacids

Exemplary examples of saturate diacids include, without limitation, ethanedioic acid (oxalic acid), propanedioic acid (malonic acid), butanedioic acid (succinic acid), pentanedioic acid (glutaric acid), hexanedioic acid (adipic acid), heptanedioic acid (pimelic acid), octanedioic acid (suberic acid, nonanedioic acid (azelaic acid), decanedioic acid (sebacic acid), undecanedioic acid, dodecanedioic acid, tridecanedioic acid (brassylic acid), hexadecanedioic acid (thapsic acid), heneicosa-1,21-dioic acid (japanic acid), docosanedioic acid (phellogenic acid), triacontanedioic acid (equisetolic acid), and mixtures or combinations thereof. Exemplary examples of unsaturated diacids include, without limitation, (Z)-butenedioic acid (maleic acid), (E)-butenedioic acid (fumaric acid), (Z and E)-pent-2-enedioic acid (glutaconic acid), 2-decenedioic acid, dodec-2-enedioic acid (traumatic acid), (2E,4E)-hexa-2,4-dienedioic acid (muconic acid), and mixtures or combinations thereof.

Poly Acids

Suitable poly carboxylic acid compounds for use a pH depending release agents include, without limitation, any poly carboxylic acid compound. Exemplary examples of water immiscible poly acids include, without limitation, dicarboxylic acids having carbyl or carbenyl groups having between 8 and 50 carbon atoms and mixtures or combinations thereof. Polymer carboxylic acids or polymers including carboxylic acid groups, where the polymers are oil soluble or are oils, not miscible with water. Exemplary example of hydrophilic poly acids include, without limitation, polyacrylic acid, polymethacrylic acid, polylactic acid, polyglycol acid, mixtures and combinations thereof, copolymers thereof, CARBOPOL® reagents available from Lubrizol Corporation (a registered trademark of the Lubrizol Corporation), other carboxylic acid containing polymers, or mixtures or combinations thereof.

Hydroxy Acids

Suitable hydroxy acids include, without limitation, 2-hydroxyoleic acid, 2-hydroxytetracosanoic acid (cerebronic acid), 2-hydroxy-15-tetracosenoic acid (hydroxynervonic acid), 2-hydroxy-9-cis-octadecenoic acid, 3-hydroxypalmitic acid methyl ester, 2-hydroxy palmitic acid, 10-hydroxy-2-decenoic acid, 12-hydroxy-9-octadecenoic acid (ricinoleic acid), 1,13-dihydroxy-tetracos-9t-enoic acid (axillarenic acid), 3,7-dihydroxy-docosanoic acid (byrsonic acid), 9,10-dihydroxyoctadecanoic acid, 9,14-dihydroxyoctadecanoic acid, 22-hydroxydocosanoic acid (phellonic acid), 2-oxo-5, 8,12-trihydroxydodecanoic acid (phaseolic acid), 9,10,18-trihydroxyoctadecanoic acid (phloionolic acid), 7,14-dihydroxydocosa-4Z,8,10,12,16Z,19Z-hexaenoic acid (Maresin 1), 5S,12R,18R-trihydroxy-6Z,8E,10E,14Z,16E-eicosapentaenoic acid (resolvin E1), resolvin D1, 10,17S-docosatriene, (neuroprotectin D1).

Fatty Acid Salts

Suitable biocompatible fatty acid salts for use in this disclosure include, without limitation, alkali metal salts of any of the above listed fatty acids, alkaline earth metals salts of any of the above listed fatty acids, transition metal salts of any of the above listed fatty acids or mixture or combinations thereof. In certain embodiments, the metal salts include lithium, sodium, potassium, cesium, magnesium, calcium, barium, copper, zinc, cobalt, iron, or mixture or combinations thereof.

Polymer Including Carboxylic Acids

Suitable water insoluble polymer including carboxylic acids include, without limitation, homo acrylic acid polymers, acrylic acid/acrylate copolymers, ethylene/acrylic acid copolymers, propylene/acrylic acid copolymers, unsaturated olefinic monomer/acrylic acid copolymers, methacrylic acid/acrylic acid copolymers, methacrylic acid/acrylate copolymers, ethylene/methacrylic acid copolymers, propylene/methacrylic acid copolymers, unsaturated olefinic monomer/methacrylic acid copolymers, acrylic acid/methacrylic acid/unsaturated olefinic monomer containing polymers, acid functionalized cellulose polymers, or mixtures and combinations thereof. Exemplary examples include, without limitation, poly(methacrylic acid-co-methyl methacrylate) (EUDRAGIT® L, S and F), hydroxypropylmethylcellulose phthalate (HPMC-P) and HPMC acetate succinate (HPMC-AS), which possess carboxyl groups on the polymer side chains, are insoluble at stomach low pH, but soluble at intestinal neutral pH.

In some embodiments, the carrier comprises one or more pH dependent release compounds in an amount of at least 5 wt. %. This includes an amount of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 wt. % or more, including increments therein. In some embodiments, the carrier comprises one or more pH dependent release compounds in an amount of at least 10 wt. % or at least 15 wt. % or at least 20 wt. %. In some embodiments, the carrier comprises one or more pH dependent release compounds in an amount of about 5 wt. % to about 50 wt. %. This includes an amount of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt. %, including increments therein. In some embodiments, the carrier comprises one or more pH dependent release compounds in an amount of about 5 wt. % to about 45 wt. %, about 5 wt. % to about 40 wt. %, about 10 wt. % to about 50 wt. %, about 10 wt. % to about 45 wt. %, about 10 wt. % to about 40 wt. %, about 15 wt. % to about 50 wt. %, about 15 wt. % to about 45 wt. %, about 15 wt. % to about 40 wt. %, about 20 wt. % to about 50 wt. %, about 20 wt. % to about 45 wt. %, about 20 wt. % to about 40 wt. %, about 25 wt. % to about 50 wt. %, about 25 wt. % to about 45 wt. %, or about 25 wt. % to about 40 wt. %.

In some embodiments, the carrier comprises a carboxylic acid having at least 8 carbon atoms in an amount of at least 5 wt. %. This includes an amount of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 wt. % or more, including increments therein. In some embodiments, the carrier comprises a carboxylic acid having at least 8 carbon atoms in an amount of at least 10 wt. % or at least 15 wt. % or at least 20 wt. %. In some embodiments, the carrier comprises a carboxylic acid having at least 8 carbon atoms in an amount of about 5 wt. % to about 50 wt. %. This includes an amount of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt. %, including increments therein. In some embodiments, the carrier comprises a carboxylic acid having at least 8 carbon atoms in an amount of about 5 wt. % to about 45 wt. %, about 5 wt. % to about 40 wt. %, about 10 wt. % to about 50 wt. %, about 10 wt. % to about 45 wt. %, about 10 wt. % to about 40 wt. %, about 15 wt. % to about 50 wt. %, about 15 wt. % to about 45 wt. %, about 15 wt. % to about 40 wt. %, about 20 wt. % to about 50 wt. %, about 20 wt. % to about 45 wt. %, about 20 wt. % to about 40 wt. %, about 25 wt. % to about 50 wt. %, about 25 wt. % to about 45 wt. %, or about 25 wt. % to about 40 wt. %.

In some embodiments, the non-aqueous carrier comprises a pH dependent releasing agent that has a low melting point (i.e., a temperature less than or equal to room temperature). In some embodiments, the pH dependent releasing agent has a melting point below 25° C. In some embodiments, the pH dependent releasing agent has a melting point below 20° C. In some embodiments, the pH dependent releasing agent has a melting point below 15° C. In some embodiments, the pH dependent releasing agent has a melting point below 10° C. In some embodiments, the pH dependent releasing agent has a melting point below 5° C. In some embodiments, the pH dependent releasing agent has a melting point below 0° C. In some embodiments, the pH dependent releasing agent is a carboxylic acid having at least 8 carbon atoms. In some embodiments, the carboxylic acid having at least 8 carbon atoms is a monocarboxylic acid.

In some embodiments, the pH dependent release agent has a medium melting point (i.e., melting point temperatures greater than room temperature and less than or equal to a body temperature of an animal, a mammal, or a human). In some embodiments, the melting point of the agent is above room temperature and less than or equal to a body temperature of a mammal. In some embodiments, the melting point of the agent is above room temperature and less than or equal to a body temperature of a human. In some embodiments, the pH dependent releasing agent has a melting point above 25° C. and below 37° C. In some embodiments, the pH dependent releasing agent has a melting point below 37° C. and above 30° C. In some embodiments, the pH dependent releasing agent has a melting point below 30° C. and above 25° C. In some embodiments, the pH dependent releasing agent is a carboxylic acid having at least 8 carbon atoms. In some embodiments, the carboxylic acid having at least 8 carbon atoms is a monocarboxylic acid.

In some embodiments, the pH dependent releasing agent has a high melting point (i.e., the melting point is above the body temperature of an animal, a mammal, or a human). In some embodiments, the pH dependent releasing agent has a melting point above 37° C. In some embodiments, the pH dependent releasing agent has a melting point above 40° C. In some embodiments, the pH dependent releasing agent has a melting point above 45° C. In some embodiments, the pH dependent releasing agent has a melting point above 50° C. In some embodiments, the pH dependent releasing agent has a melting point above 55° C. In some embodiments, the pH dependent releasing agent has a melting point above 50° C. In some embodiments, the pH dependent releasing agent has a melting point above 65° C. In some embodiments, the pH dependent releasing agent has a melting point above 70° C. In some embodiments, the pH dependent releasing agent has a melting point above 75° C. In some embodiments, the pH dependent releasing agent is a carboxylic acid having at least 8 carbon atoms. In some embodiments, the carboxylic acid having at least 8 carbon atoms is a monocarboxylic acid.

IV. pH Dependent Assembly/Reassembly and Absorption/Reabsorption System pH dependent assembly and/or reassembly compounds (i.e., reconstitution agents) include groups that facilitate carrier reassembly or facilitate the formation a new carrier upon duodenal reflux, i.e., the components in the carrier either assist reassembly of the carrier into its low pH form from its high pH form or the components assist assembly of the carrier into a new carrier form in low pH environments. In either case, the reassembled carrier or newly assembled carrier is capable of reabsorbing or absorbing the biologically active agents upon transition from its high pH form to its low pH form. The absorption or reabsorption of the biologically active agents has a number of advantageous properties: (a) further protection of the stomach from biologically active agents injurious to the stomach, and (b) further prevention of the loss of biologically active agents due to decomposition in the stomach, e.g., reduced loss of acid labile biologically active agents.

Exemplary pH dependent reassembly compounds include, without limitation, neutral lipids, surfactants, polymers including ionizable groups, other compound capable of carrier reassembly or capable of new carrier formation in low pH environments that tend to absorb or reabsorb biologically active agents, or mixtures and combinations thereof. Of course, the pH dependent assembly or reassembly compounds should be selected that do not adversely affect the pH dependent release properties of the carrier.

In some embodiments, reconstituting agents are designed to either facilitate oil matrix reconstitution and/or facilitate drug reabsorption into reconstituted carrier such as sorbitan and/or sorbitol esters, poloxamers, nonionic neutral polymers, and mixtures of combinations thereof.

In other embodiments, the non-aqueous pH dependent reassembly/assembly and reabsorption/absorption system comprises: (a) one or more polyacids, (b) one or more polymers including a plurality of carboxylic acid moieties, (c) one or more water insoluble surfactants, (d) one or more water insoluble oligomers or lower molecular weight polymers, (e) one or more water insoluble polymers (higher molecular weight polymers than the oligomer), and (f) any combination thereof. In some embodiments, the non-aqueous pH dependent reassembly/assembly and reabsorption/ absorption system comprises: (a) one or more polyacids, (b) one or more water insoluble oligomers (lower molecular weight polymers), (c) one or more water insoluble polymers (higher molecular weight polymers than the oligomer), and (d) any combination thereof.

In some embodiments, the non-aqueous pH dependent reassembly/assembly and reabsorption/absorption system comprises one or more surfactants (e.g., nonionic surfactants and/or zwitterionic surfactants), one or more neutral lipids, and optionally: (a) one or more polyacids, (b) one or more water insoluble oligomers (lower molecular weight polymers), (c) one or more water insoluble polymers (higher molecular weight polymers than the oligomer), and (d) any combination thereof.

In some embodiments, the one or more polyacids comprise a biocompatible fatty poly acid. In some embodiments, the one or more polyacids comprise glutaric acid (GA), poly(methacrylic acid-co-methyl methacrylate), or hypromellose phthalate (HPMC-P), or a combination of two or more thereof.

In some embodiments, the one or more polyacids are present in the carrier in an amount of about 1 wt. % to about 10 wt. %. This includes about 1, 2, 3, 4, 5, 6, 7, 8, 9, or 10 wt. % of the carrier, including increments therein.

In some embodiments, the one or more water insoluble oligomers comprise low molecular weight poly(hexyl substituted lactides) (PHLA) (e.g., having between 10 and 100 hexyl substituted lactide units), low molecular weight polyethylene (e.g., having between 10 and 100 ethylene units), polyvinyl chloride, ethyl cellulose, or acrylate polymers and copolymers thereof, or a combination of two or more thereof.

In some embodiments, the one or more water insoluble oligomers are present in the carrier in an amount of about 1 wt. % to about 5 wt. %. This includes about 1.0, 1.25, 1.50, 1.75, 2.0, 2.25, 2.50, 2.75, 3.0, 3.25, 3.50, 3.75, 4.0, 4.25, 4.50, 4.75, or 5.0 wt. % of the carrier, including increments therein.

In some embodiments, the one or more water insoluble polymers comprise a copolymer of ethyl acrylate and methyl methacrylate, lactide-coglycolide, cellulose, or ethyl cellulose, or a combination of two or more thereof.

In some embodiments, the one or more water insoluble polymers are present in the carrier in an amount of about 1 wt. % to about 5 wt. %. This includes about 1.0, 1.25, 1.50, 1.75, 2.0, 2.25, 2.50, 2.75, 3.0, 3.25, 3.50, 3.75, 4.0, 4.25, 4.50, 4.75, or 5.0 wt. % of the carrier, including increments therein.

It has been found that free fatty acids are subject to esterification in the duodenum. If this process is facile, then considerable free fatty acid would be lost in the duodenum reducing the ability for matrix to reform and absorb BAI with minimal loss of BAI once reabsorbed. These additives including a plurality of carboxylic acid moieties are designed to act as sacrificial agents to reduce the amount of free fatty acid from being esterified in the duodenum allowing the reassembly of the oil matrix with sufficient free fatty acid to minimize loss of absorbed BAI. The water insoluble surfactants, especially nonionic surfactants, are believed to be capable of stabilizing oil matrices, especially during reassembly or reformation due to duodenal reflux. In an analogous manner, the water insoluble oligomers or polymers are also believed to stabilize oil matrices, especially during reassembly or reformation due to duodenal reflux. Thus, by engineering the carrier to include one or more of these agents, the matrix structure may be stabilized initially and more importantly during reconstitution.

In other embodiments, the carrier further comprise less than 10 wt. % of one or more selected from (1) fatty acid salts, (2) secondary complexing agents, (3) protective agents, (4) excipients, (5) adjuvants, (6) drying agents, (7) antioxidants, (8) preservatives, (9) chelating agents, (10) viscomodulators, (11) tonicifiers, (12) flavorants and taste masking agents, (13) colorants, (14) odorants, (15) opacifiers, (16) suspending agents, and (17) binders. This includes an amount of about 9, 8, 7, 6, 5, 4, 3, 2, 1, 0.8, 0.5, 0.3, 0.1, 0.08, 0.05, 0.03 wt. % of the carrier, or less, including increments therein.

In some embodiments, the reconstitution agent comprises one or more polyacids. In some embodiments, the polyacid is a biocompatible fatty poly acid.

In some embodiments, the reconstitution agent comprises one or more polymers including a plurality of carboxylic acid moieties. In some embodiments, the reconstitution agent comprises one or more surfactants.

In some embodiments, the reconstitution agent comprises one or more water insoluble oligomers. In some embodiments, a water-insoluble oligomer is a pre-polymer having 2 to about 15 recurring monomeric units, which can be the same or different. Exemplary examples including, without limitation, low molecular weight poly(hexyl substituted lactides) (PHLA), low molecular weight polyethylene, polyvinyl chloride, ethyl cellulose, acrylate polymers and copolymers thereof.

In some embodiments, the reconstitution agent comprises one or more water insoluble polymers. In some embodiments, a water insoluble polymer is based on acrylic of methacrylic esters. In some embodiments, the one or more water insoluble polymers include EUDRAGIT® L30D a copolymer of methacrylic acid and ethyl acrylate. In some embodiments, the one or more water insoluble polymers include EUDRAGIT® NE30D a copolymer of ethyl acrylate and methyl methacrylate. In some embodiments, the water insoluble polymer is a biodegradable polymer. In some embodiments, the water insoluble polymer includes lactide-coglycolide. In some embodiments, the water-insoluble polymer is selected from cellulose and ethyl cellulose.

In some embodiments, the non-aqueous carrier comprises a reconstitution agent that has a low melting point (i.e., a temperature less than or equal to room temperature). In some embodiments, the reconstitution agent has a melting point below 25° C. In some embodiments, the reconstitution agent has a melting point below 20° C. In some embodiments, the reconstitution agent has a melting point below 15° C. In some embodiments, the reconstitution agent has a melting point below 10° C. In some embodiments, the reconstitution agent has a melting point below 5° C. In some embodiments, the reconstitution agent has a melting point below 0° C.

In some embodiments, the reconstitution agent has a medium melting point (i.e., melting point temperatures greater than room temperature and less than or equal to a body temperature of an animal, a mammal, or a human). In some embodiments, the melting point of the agent is above room temperature and less than or equal to a body temperature of a mammal. In some embodiments, the melting point of the agent is above room temperature and less than or equal to a body temperature of a human. In some embodiments, the reconstitution agent has a melting point above 25° C. and below 37° C. In some embodiments, the reconstitution agent has a melting point below 37° C. and above 30° C. In some embodiments, the reconstitution agent has a melting point below 30° C. and above 25° C.

In some embodiments, the reconstitution agent has a high melting point (i.e., the melting point is above the body temperature of an animal, a mammal, or a human). In some embodiments, the reconstitution agent has a melting point above 37° C. In some embodiments, the reconstitution agent has a melting point above 40° C. In some embodiments, the reconstitution agent has a melting point above 45° C. In some embodiments, the reconstitution agent has a melting point above 50° C. In some embodiments, the reconstitution agent has a melting point above 55° C. In some embodiments, the reconstitution agent has a melting point above 50° C. In some embodiments, the reconstitution agent has a melting point above 65° C. In some embodiments, the reconstitution agent has a melting point above 70° C. In some embodiments, the reconstitution agent has a melting point above 75° C.

Fatty Acid, Fatty Acid Ester, and Triglyceride Melting Point Data:

The following tables list physical properties, especially melting point temperatures of a number of fatty acids, fatty acid esters, and triglycerides for use in the present disclosure.

TABLE I

Melting Point Data (° C.) for Certain Free Fatty Acids

| Name | Formula | Structural Formula | mp (° C.) |
|---|---|---|---|
| lauric acid | $C_{11}H_{23}COOH$ | $CH_3(CH_2)_{10}COOH$ | 44 |
| myristic acid | $C_{13}H_{27}COOH$ | $CH_3(CH_2)_{12}COOH$ | 58 |
| palmitic acid | $C_{15}H_{31}COOH$ | $CH_3(CH_2)_{14}COOH$ | 63 |
| palmitoleic acid | $C_{15}H_{29}COOH$ | $CH_3(CH_2)_5CH=CH(CH_2)_7COOH$ | 0.5 |
| stearic acid | $C_{17}H_{35}COOH$ | $CH_3(CH_2)_{16}COOH$ | 70 |
| oleic acid | $C_{17}H_{33}COOH$ | $CH_3(CH_2)_7CH=CH(CH_2)_7COOH$ | 16 |
| linoleic acid | $C_{17}H_{31}COOH$ | $CH_3(CH_2)_3(CH_2CH=CH)_2(CH_2)_7COOH$ | 5 |
| α-linolenic acid | $C_{17}H_{29}COOH$ | $CH_3(CH_2CH=CH)_3(CH_2)_7COOH$ | −11 |
| arachidonic acid | $C_{19}H_{31}COOH$ | $CH_3(CH_2)_4(CH_2CH=CH)_4(CH_2)_2COOH$ | −50 |

TABLE II

Melting Point Data (° C.) of Saturated Free Fatty Acids and Fatty Acid Esters

| Chain | Free Fatty Acid | Methyl Ester | Ethyl Ester | Propyl Ester | Butyl Ester |
|---|---|---|---|---|---|
| 8:0 | 15.41 | −37.43 | −44.74 | −45.68 | −43.33 |
| 9:0 | 11.28 | −34.99 | −43.56 | −41.81 | −43.10 |
| 10:0 | 30.80 | −13.48 | −20.44 | −21.84 | −22.96 |
| 11:0 | 27.32 | −12.17 | −19.43 | −19.70 | −23.69 |
| 12:0 | 43.29 | 4.30 | −1.78 | −4.35 | −6.53 |
| 13:0 | 41.37 | 5.17 | −2.07 | −8.48 | |
| 14:0 | 53.47 | 18.09 | 12.52 | 9.24 | 5.57 |
| 15:0 | 52.15 | 18.47 | 11.81 | 6.26 | |
| 16:0 | 62.20 | 28.48 | 23.23 | 20.27 | 16.07 |
| 17:0 | 60.85 | 28.58 | 24.70 | 22.32 | 19.68 |
| 18:0 | 69.29 | 37.66 | 32.98 | 28.10 | 25.63 |
| 19:0 | 67.76 | 38.03 | 35.28 | 32.94 | 30.71 |
| 20:0 | 74.76 | 46.43 | 41.33 | 37.15 | 35.14 |
| 21:0 | 73.69 | 47.58 | 43.66 | | |
| 22:0 | 79.54 | 53.22 | 48.64 | 45.29 | |
| 23:0 | 78.74 | 53.38 | 51.22 | | |
| 24:0 | 83.82 | 58.61 | 55.92 | 52.32 | |

TABLE III

Melting Point Data (° C.) of Unsaturated Free Fatty Acids and Fatty Acid Esters

| Chain | FFA | Methyl Ester | Ethyl Ester | Propyl Ester | Butyl Ester |
|---|---|---|---|---|---|
| 11:1 Δ10 | 23.91 | −24.63 | −32.24 | | |
| 14:1 Δ9c | −3.91 | −52.26 | −65.35 | −66.19 | |
| 16:1 Δ9c | 1.22 | −34.10 | −36.65 | −52.61 | |

TABLE III-continued

Melting Point Data (° C.) of Unsaturated Free Fatty Acids and Fatty Acid Esters

| Chain | FFA | Methyl Ester | Ethyl Ester | Propyl Ester | Butyl Ester |
|---|---|---|---|---|---|
| 16:1 Δ9t | 32.22 | −2.99 | −10.99 | −12.83 | |
| 17:1 Δ10c | 15.05 | −16.02 | −20.02 | −24.35 | |
| 18:1 Δ6c | 29.11 | −0.97 | −7.74 | | |
| 18:1 Δ6t | 52.38 | 19.16 | 9.45 | | |
| 18:1 Δ9c | 12.82 | −20.21 | −20.32 | −30.50 | −34.76 |
| 18:1 Δ9t | 43.35 | 9.94 | 4.17 | | −0.03 |
| 18:1 Δ11c | 15.40 | −24.29 | −36.49 | | |
| 18:1 Δ11t | 43.37 | 9.94 | 4.10 | −0.23 | |
| 18:2 Δ9c, Δ12c | −7.15 | −43.09 | −56.72 | −51.50 | |

TABLE IV

Melting Point Data (° C.) of Unsaturated Free Fatty Acids and Fatty Acid Esters

| Chain | FFA | Methyl Ester | Ethyl Ester | Propyl Ester | Butyl Ester |
|---|---|---|---|---|---|
| 18:3 Δ9c, Δ12c, Δ15c | −11.58 | −61.71 | −57.63 | −58.61 | |
| 19:1 Δ10c | 22.47 | −2.33 | −7.51 | | |
| 20:1 Δ5c | 26.61 | 2.39 | −8.57 | | |
| 20:1 Δ8c | 35.13 | 9.11 | 3.14 | | |
| 20:1 Δ11c | 23.37 | −7.79 | −8.80 | −22.69 | |
| 20:1 Δ11t | 51.94 | 20.76 | 14.11 | | |
| 21:1 Δ12 | 32.96 | 8.47 | 5.63 | | |
| 22:1 Δ13c | 32.18 | −3.05 | | | |
| 22:1 Δ13t | 59.16 | 29.36 | 24.50 | | |
| 23:1 Δ14c | 43.23 | 18.22 | 13.27 | | |
| 24:1 Δ15c | 42.87 | 9.49 | 1.21 | | |

TABLE V

Melting Point Data (° C.) of Some Branched Free Fatty Acids (FFA) and Fatty Acid Methyl Esters

| Chain | FFA | Methyl Ester |
|---|---|---|
| Iso Acids | | |
| 10-Methyl C11 | 40.28 | −13.02 |
| 11-Methyl C12 | 40.57 | −6.87 |
| 12-Methyl C13 | 53.13 | 3.48 |
| 13-Methyl C14 | 51.35 | 6.37 |
| 14-Methyl C15 (isopalmitic) | 61.94 | 16.80 |
| 15-Methyl C16 | 59.78 | 17.55 |
| 16-Methyl C17 (isostearic) | 69.23 | 26.82 |
| 17-Methyl C18 | 66.34 | 27.98 |

TABLE V-continued

Melting Point Data (° C.) of Some Branched Free Fatty Acids (FFA) and Fatty Acid Methyl Esters

| Chain | FFA | Methyl Ester |
|---|---|---|
| 18-Methyl C19 | 74.68 | |
| 19-Methyl C20 | 72.51 | 36.43 |
| Anteiso Acids | | |
| 12-Methyl C14 | 24.05 | −5.29 |
| 13-Methyl C15 | −13.34 | |
| 14-Methyl C16 | 37.10 | 7.62 |

TABLE VI

Melting Point Data (° C.) of Certain Triglycerides

| Chain | mp |
|---|---|
| Saturated Triglycerides | |
| 8:0 | 9.44 |
| 9:0 | 9.46 |

TABLE VII

Melting Point Data (° C.) of Certain Triglycerides

| Chain | mp |
|---|---|
| Saturated Triglycerides | |
| 10:0 | 30.37 |
| 11:0 | 27.98 |
| 12:0 | 46.29 |
| 13:0 | 44.60 |
| 14:0 | 57.35 |
| 15:0 | 55.46 |
| 16:0 | 65.45 |
| 17:0 | 64.11 |
| 18:0 | 72.67 |
| 19:0 | 71.31 |
| 20:0 | 77.67 |
| 21:0 | 76.36 |
| 22:0 | 82.50 |
| 23:0 | 81.85 |
| Unsaturated Triglycerides | |
| 16:1 Δ9c | −22.75 |
| 18:1 Δ6c | 26.24 |
| 18:1 Δ9c | 3.98 |
| 18:1 Δ11c | 1.04 |
| 18:2 Δ9c, Δ12c | −12.70 |
| 19:1 Δ10c | 26.12 |
| 20:1 Δ11c | 10.11 |
| 21:1 Δ12c | 37.97 |
| Saturated Triglycerides | |
| 22:1 Δ13c | 29.78 |
| 24:1 Δ15c | 41.43 |

TABLE VIII

Melting Point Data (° C.) and Fatty Acid Compositions of Certain Vegetable Oils

| Oil | MP | % Monounsaturated | % Polyunsaturated | % Saturated |
|---|---|---|---|---|
| Cottonseed Oil | −48 | 18 | 54 | 28 |
| Flax Seed Oil | −24 | 21 | 71 | 8 |
| Almond Oil | −18 | 73 | 19 | 8 |
| Sunflower Oil | −17 | 20 | 69 | 11 |
| Safflower Oil | −17 | 14 | 78 | 8 |
| Soybean Oil | −16 | 24 | 61 | 15 |
| Corn Oil | −11 | 25 | 61 | 14 |
| Canola Oil | −10 | 58 | 35 | 7 |
| Grapeseed Oil | −10 | 57 | 29 | 14 |

TABLE IX

Melting Point Data (° C.) and Fatty Acid Compositions of Certain Vegetable Oils

| Oil | MP | % Monounsaturated | % Polyunsaturated | % Saturated |
|---|---|---|---|---|
| Rice Bran Oil | −5 to −10 | 38 | 37 | 25 |
| Hemp Seed Oil | −8 | 13 | 63 | 9 |
| Olive Oil | −6 | 79 | 8 | 11 |
| Sesame Oil | −6 | 40 | 42 | 14 |
| Peanut Oil | 3 | 48 | 34 | 18 |
| Palm Kernel Oil | 24 | 12 | 2 | 86 |
| Coconut Oil | 25 | 6 | 2 | 92 |
| Cocoa Butter | 34 to 38 | 20 to 43 | 0 to 5 | 57 to 64 |
| Palm Oil | 35 | 38 | 10 | 52 |

Surfactants

Suitable surfactants include, without limitation, cationic surfactants, anionic surfactants, nonionic surfactants, zwitterionic surfactants, and mixtures or combinations thereof.

Cationic Surfactants

Suitable cationic surfactants include, without limitation, $RN^+H_3Cl^-$ (salt of a long-chain amine), $RN^+(CH_3)_3Cl^-$ (quaternary ammonium chloride, also known as quats), and mixtures or combinations thereof.

One or more cationic surfactants may be present in the carrier in an amount of about 0.1 wt. % to about 5 wt. %. This includes an amount of about 0.10, 0.20, 0.30, 0.40, 0.50, 0.60, 0.70, 0.80, 0.90, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 wt. %, including increments therein. In some embodiments, the one or more cationic surfactants are present in the carrier in an amount of about 0.1 wt. % to about 4 wt. %, about 0.1 wt. % to about 3 wt. %, about 0.1 wt. % to about 2 wt. %, about 0.1 wt. % to about 1 wt. %, about 0.5 wt. % to about 5 wt. %, about 0.5 wt. % to about 4 wt. %, about 0.5 wt. % to about 3 wt. %, about 0.5 wt. % to about 2 wt. %, about 1 wt. % to about 5 wt. %, about 1 wt. % to about 4 wt. %, or about 1 wt. % to about 3 wt. %.

Anionic Surfactants

Suitable anionic surfactants include, without limitation, anionic surfactants include (a) carboxylates: alkyl carboxylates-fatty acid salts; carboxylate fluoro surfactants, (b) sulfates: alkyl sulfates (e.g., sodium lauryl sulfate); alkyl ether sulfates (e.g., sodium laureth sulfate), (c) sulfonates: docusates (e.g., dioctyl sodium sulfosuccinate); alkyl benzene sulfonates, (d) phosphate esters: alkyl aryl ether phosphates; alkyl ether phosphates. Sodium lauryl sulphate BP (a mixture of sodium alkyl sulfates, mainly sodium dodecyl sulfate, $C_{12}H_{25}SO_4Na^+$), alkyl sulfates, alkyltrimethylammonium bromides, and alcohol ethoxylates.

One or more anionic surfactants may be present in the carrier in an amount of about 0.1 wt. % to about 5 wt. %. This includes an amount of about 0.10, 0.20, 0.30, 0.40, 0.50, 0.60, 0.70, 0.80, 0.90, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 wt. %, including increments therein. In some embodiments, the one or more anionic surfactants are present in the carrier in an amount of about 0.1 wt. % to about 4 wt. %, about 0.1 wt. % to about 3 wt. %, about 0.1 wt. % to about 2 wt. %, about 0.1 wt. % to about 1 wt. %, about 0.5 wt. % to about 5 wt. %, about 0.5 wt. % to about 4 wt. %, about 0.5 wt. % to about 3 wt. %, about 0.5 wt. % to about 2 wt. %, about 1 wt. % to about 5 wt. %, about 1 wt. % to about 4 wt. %, or about 1 wt. % to about 3 wt. %.

Zwitterionic Surfactants

Suitable zwitterionic surfactants include, without limitation, phospholipids, betaines, sulfobetaines, or mixtures and combinations thereof. Exemplary examples include, without limitation, $RN^+H_2CH_2COO^-$, $RN^+(CH_3)_2CH_2CH_2SO_3^-$, where R is linear, branched, saturated, or unsaturated alkyl groups; linear, branched, saturated, or unsaturated $C_8$-$C_{19}$ alkyl groups; linear, branched, saturated, or unsaturated $C_{20}$-$C_{40}$ alkyl groups; sterol or steroid groups, or mixtures and combinations thereof, CHAPS zwitterionic surfactants such as 3-[(3-cholamidopropyl)dimethylammonio]-1-propanesulfonate or related CHAPSO surfactants, phospholipids, phospholipid containing oils such as lecithins, cocamidopropyl betaine, cocamidopropyl hydroxysultaine, hydroxysultaine, miltefosine, lipophilic peptitergents, or mixtures and combinations.

One or more zwitterionic surfactants may be present in the carrier in an amount of at least 5 wt. %. In some embodiments, the one or more zwitterionic surfactants are present in the carrier in an amount of at least 10 wt. %. In some embodiments, the one or more zwitterionic surfactants are present in the carrier in an amount of about 5 wt. % to about 25 wt. %. This includes about 5, 6, 7, 8, 9, 10, 11, 12, 13, 14, 15, 16, 17, 18, 19, 20, 21, 22, 23, 24, and 25 wt. %, including increments therein. In some embodiments, the one or more zwitterionic surfactants are present in the carrier in an amount of about 10 wt. % to about 25 wt. %, or about 15 wt. % to about 25 wt. %.

In some embodiments, the one or more zwitterionic surfactants are present in the carrier in an amount of less than about 10 wt %. This includes about 9, 8, 7, 6, 5, 4, 3, 2, 1 wt. %, or less, including increments therein. In some embodiments, the carrier is devoid of zwitterionic surfactants. In some embodiments, the carrier includes less than 10 wt. %, or less than 5 wt. %, or less than 2.5 wt. % of one or more phospholipids.

Phospholipids

Suitable secondary complexing agents and/or secondary anti-toxicity agents for use in the compositions of this disclosure include, without limitation, phospholipids, amphoteric agents and/or zwitterionic agents or mixtures or combinations thereof. Phospholipids include any phospholipid or mixtures and combinations thereof such as (1) diacylglyceride phospholipids or glycerophospholipids including, without limitation, phosphatidic acid (phosphatidate) (PA), phosphatidylethanolamine (cephalin) (PE), phosphatidylcholine (lecithin) (PC), phosphatidylserine (PS), phosphoinositides such as phosphatidylinositol (PI), phosphatidylinositol phosphate (PIP), phosphatidylinositol bisphosphate (PIP2) and phosphatidylinositol triphosphate (PIP3), and (2) phosphosphingolipids such as ceramide phosphorylcholine (Sphingomyelin) (SPH), ceramide phosphorylethanolamine (Sphingomyelin) (Cer-PE), and ceramide phosphorylglycerol. Amphoteric agents include acetates, betaines, glycinates, imidazolines, propionates, other amphoteric agents or mixtures thereof. Zwitterionic agents include, without limitation, biocompatible zwitterionic phospholipids, biocompatible zwitterionic betaines, biocompatible amphoteric/zwitterionic surfactants, biocompatible quaternary salts, biocompatible amino acids, other biocompatible compounds capable of forming or in the form of a zwitterion, and mixtures or combinations thereof.

Suitable biocompatible zwitterionic phospholipids for use in this disclosure include, without limitation, a phospholipid of general formula:

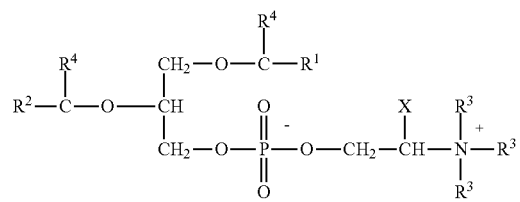

where $R^1$ and $R^2$ are saturated or unsaturated substitutions ranging from 8 to 32 carbon atoms; $R^3$ is H or $CH_3$, and X is H or COOH; and $R^4$ is =O or $H_2$. Mixtures and combinations of the zwitterionic phospholipids of the general formula and mixtures and combinations of NSAIDs can be used as well.

Exemplary examples of zwitterionic phospholipid of the above formula include, without limitation, phosphatidylcholines such as phosphatidyl choline (PC), dipalmitoylphosphatidylcholine (DPPC), other disaturated phosphatidylcholines, phosphatidylethanolamines, phosphatidylinositol, phosphatidylserines sphingomyelin or other ceramides, or various other zwitterionic phospholipids, phospholipid containing oils such as lecithin oils derived from soy beans, dimyristoylphosphatidylcholine, di stearoylphosphatidylcholine, dilinoleoylphosphatidylcholine (DLL-PC), dipalmitoylphosphatidylcholine (DPPC), soy phophatidylchloine (Soy-PC or PCS) and egg phosphatidycholine (Egg-PC or PCE). In DPPC, a saturated phospholipid, the saturated aliphatic substitution $R^1$ and $R^2$ are $CH_3(CH_2)_{14}$, $R^3$ is $CH_3$ and X is H. In DLL-PC, an unsaturated phospholipid, $R^1$ and $R^2$ are $CH_3(CH_2)_4CH=CHCH_2CH=CH(CH_2)_7$, R3 is $CH_3$ and X is H. In Egg PC, which is a mixture of unsaturated phospholipids, $R^1$ primarily contains a saturated aliphatic substitution (e.g., palmitic or stearic acid), and $R^2$ is primarily an unsaturated aliphatic substitution (e.g., oleic or arachidonic acid). In Soy-PC, which in addition to the saturated phospholipids (palmitic acid and stearic acid) is a mixture of unsaturated phospholipids (oleic acid, linoleic acid and linolenic acid). In certain embodiments, the phospholipids are zwitterionic phospholipid include, without limitation, dipalmitoyl phosphatidylcholine, phosphatidyl choline, or a mixture thereof.

In some embodiments, the carrier comprises one or more zwitterionic surfactants, wherein the one or more zwitterionic surfactants comprise phosphatidic acid, phosphatidylethanolamine, phosphatidylcholine, phosphatidylserine, phosphatidylinositol, phosphatidylinositol phosphate, phosphatidylinositol bisphosphate, phosphatidylinositol triphosphate, ceramide phosphorylcholine, ceramide phosphorylethanolamine, ceramide phosphorylglycerol, dimyristoylphosphatidylcholine, di stearoylphosphatidylcholine, dilinoleoylphosphatidylcholine, dipalmitoylphosphatidylcholine, or a combination of two or more thereof. In some embodiments, the carrier comprises one or more zwittterionic surfactants, wherein the one or more zwitterionic surfactants comprise lecithin.

Nonionic Surfactants

Suitable nonionic surfactants are categorized by their hydrophilic-lipophilic balance (HLB) number, with a low value (<10) corresponding to greater lipophilicity and a higher value (>10) corresponding to higher hydrophilicity. Low HLB (<10) emulsifier include, without limitation, (a) alkylene glycol esters of fatty acids such as ethylene glycol esters of saturated and unsaturated C8-C24 fatty acids, propylene glycol esters of saturated and unsaturated C8-C24 fatty acids, butylene glycol esters of saturated and unsaturated C8-C24 fatty acids, high alkylene glycols of esters of saturated and unsaturated C8-C24 fatty acids, and mixtures or combinations thereof, (b) unsaturated polyglycolized glycerides such as oleoyl macrogolglycerides and linoleoyl macrogolglycerides, (c) sorbitan esters such as sorbitan monooleate, sorbitan monostearate, sorbitan monolaurate, and sorbitan monopalmitate; or (d) mixtures or combinations thereof. High HLB (>10) emulsifier include, without limitation, (a) polyoxyethylene sorbitan esters such as polysorbate 20, polysorbate 40, polysorbate 60, and polysorbate 80; (b) polyoxyl castor oil derivatives such as Polyoxyl 35 castor oil and Polyoxyl 40 hydrogenated castor oil; (c) polyoxyethylene polyoxypropylene block copolymer such as Poloxamer 188 and Poloxamer 407; (d) saturated polyglycolized glycerides such as lauroyl macrogolglycerides and stearoyl macrogolglycerides; (e) PEG-8 caprylic/capric glycerides such as caprylocaproyl macrogolglycerides; (f) vitamin E derivative such as tocopherol PEG succinate; or (g) mixtures or combinations thereof. Other suitable nonionic surfactants include, without limitation, polyolesters, cyclic polyol esters, polyethylene glycol (PEG) esters, or mixtures and combination thereof. Exemplary examples include, without limitation, sorbitan monofatty and/or polyfatty acid esters, sorbitoal monofatty and/or polyfatty acid esters, mono fatty acid glycerides, polyethylene glycol (PEG) ester surfactants including hydrophilic and/or hydrophobic gelucires such as hydrophilic GELUCIRE® 44/14, lauroyl macrogol glyceride type 1500, hydrophobic GELUCIRE® 43/01, GELUCIRE® 39/01, GELUCIRE® 33/01, or other gelucires; polyglycol modified castor oils such as polyoxyl 35 hydrogenated castor oil, polyoxyl 40 hydrogenated castor oil; polyethylene oxides; polypropylene oxides; poly(ethylene oxide and propylene oxide) polymers; polysorbates such as polysorbate 20, 40, 60, 80, etc., and TWEEN® surfactants; and mixtures or combinations thereof.

Exemplary examples of suitable nonionic surfactants include, without limitation, SPAN® surfactants (available from Sigma-Aldrich) such as SPAN® 20—sorbitan laurate, sorbitan monolaurate, SPAN® 40—sorbitan monopalmitate, SPAN® 60—sorbitan stearate, sorbitane monostearate, SPAN® 80—sorbitane monooleate, sorbitan oleate, or other Span surfactants, TWEEN® surfactants such as TWEEN® 40—polyoxyethylene sorbitan monopalmitate, TWEEN® 60—polyethylene glycol sorbitan monostearate, TWEEN® 80—polyoxyethylene-sorbitan-20 monooleate, POE (20) sorbitan monooleate, polyethylene glycol sorbitan monooleate, polyoxyethylene sorbitan monooleate, polysorbate 80, BRIJ™ surfactants such as BRIJ™ 58—polyoxyethylene-20 hexadecyl ether, BRIJ™ 92-2-[(Z)-octadec-9-enoxy]ethanol, BRIJ™ 35—polyethoxylated lauryl alcohol (yielding a lauryl ether), BRIJ™ 700—polyetholylated stearyl alcohol, BRIJ™ 700—polyoxyethylene stearyl ether (HLB 18.8), or the other BRIJ™ surfactants, SOLULAN™ $C^{24}$-2-[[10,13-dimethyl-17-(6-methylheptan-2-yl)-2,3,4,7,8,9,11,12,14,15, 16,17-dodecahydro-1H-cyclopenta[a]phenanthren-3-yl]oxy]ethanol or polyoxyethylene-24-cholesterol ether, PEG surfactants—polyethylene oxides, TRITON™ surfactants such as TRITON™ X-100—octylphenol ethoxylate polyoxyethylene 9.5-octlphenol, TRITON™ X-80N—alkyl-oxy-polyethylene-oxy-polypropylene-oxyethanol, or other TRITON™ surfactants, PLURONIC™ surfactants from Thermo Fisher, TERGITOL™ surfactants from Dow Chemicals, SURFONIC™ JL-80X—alkoxylated linear alcohol, ETHOFAT™ 242/25—ethoxylated tall oil, alkyl polyglycoside, polyethylene glycol hexadecyl ether (CETOMACROGOL™ 1000), cetostearyl alcohol, cetyl alcohol, cocamide DEA, cocamide MEA, decyl glucoside, decyl polyglucose, glycerol monostearate, IGEPAL® alkylphenoxypoly(ethyleneoxy)ethanols surfactants from Cameo such as IGEPAL® CA-630, ethoxylated iso-cetyl alcohol (Isoceteth-20), lauryl glucoside or dodecyl β-d-glucopyranoside, maltoside or maltose glycosides, Mycosubtilin, nonylphenoxypolyethoxyethanol (NONIDET™ P-40 from Shell), 26-(4-nonylphenoxy)-3,6,9,12,15,18,21,24-octaoxahexacosan-1-ol (Nonoxynol-9), nonaethylene glycol or polyethylene glycol nonyl phenyl ether (Nonoxynols), 4-nonylphenyl-polyethylene glycol (NP-40), octaethylene glycol monododecyl ether, N-octyl beta-d-thioglucopyranoside, octyl glucoside, oleyl alcohol, PEG-10 sunflower glycerides, pentaethylene glycol monododecyl ether, ethoxylated dodecanol (Polidocanol), polyethoxylated tallow amine, polyglycerol polyricinoleate, stearyl alcohol, and mixtures or combinations thereof. In some embodiments, one or more nonionic surfactants comprise an ethylene glycol mono fatty acid ester, a propylene glycol mono fatty acid ester, or a combination of two or more thereof. In some embodiments, one or more nonionic surfactants comprise one or more selected from sorbitan mono-, di-, and tri-fatty acid esters. In some embodiments, one or more nonionic surfactants comprise sorbitan trioleate (STO), sorbitan monooleate, or sorbitan tristearate, or a combination thereof. In some embodiments, one or more nonionic surfactants comprise propylene glycol monolaurate.

One or more nonionic surfactants may be present in the carrier in an amount of about 0.05 wt. % to about 20 wt. %. This includes about 0.05, 0.06, 0.07, 0.08, 0.09, 0.10, 0.20, 0.30, 0.40, 0.50, 0.60, 0.70, 0.80, 0.90, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, 10.0, 10.2, 10.4, 10.6, 10.8, 11.0, 11.2, 11.4, 11.6, 11.8, 12.0, 12.2, 12.4, 12.6, 12.8, 13.0, 13.2, 13.4, 13.6, 13.8, 14.0, 14.2, 14.4, 14.6, 14.8, 15.0, 15.2, 15.4, 15.6, 15.8, 16.0, 16.2, 16.4, 16.6, 16.8, 17.0, 17.2, 17.4, 17.6, 17.8, 18.0, 18.2, 18.4, 18.6, 18.8, 19.0, 19.2, 19.4, 19.6, 19.8, or 20.0 wt. %, including increments thereof. In some embodiments, the one or more nonionic surfactants are present in the carrier in an amount of about 0.05 wt. % to about 15 wt. %, about 0.05 wt. % to about 10 wt. %, about 0.05 wt. % to about 5 wt. %, about 0.05 wt. % to about 1 wt. %, about 0.1 wt. % to about 20 wt. %, about 0.1 wt. % to about 15 wt. %, about 0.1 wt. % to about 10 wt. %, about 0.1 wt. % to about 5 wt. %, about 0.1 wt. % to about 1 wt. %, about 0.5 wt. % to about 20 wt. %, about 0.5 wt. % to about 15 wt. %, about 0.5 wt. % to about 10 wt. %, about 0.5 wt. % to about 5 wt. %, or about 0.5 wt. % to about 1 wt. %.

Sorbitan and Sorbitol Esters

Suitable sorbitan and/or sorbitol esters for use in this disclosure include, without limitation, sorbitan mono ester such as sorbitan caprylate, sorbitan undecylenate, sorbitan laurate, sorbitan palmitate, sorbitan isostearate, sorbitan oleate, sorbitan stearate, etc.; sorbitan sesquiesters such as sesquicaprylate, sorbitan sesquiisostearate, sorbitan sesquioleate, sorbitan sesquistearate, etc.; sorbitan diesters such as sorbitan diisostearate, sorbitan dioleate, sorbitan distearate, etc.; sorbitan triesters such as sorbitan triisostearate, sorbitan trioleate, sorbitan tristearate, etc.; mixed-chain sorbitan esters such as sorbitan cocoate, sorbitan olivate, sorbitan palmate, sorbitan Theobroma grandiflorum seedate, etc.; or mixtures and combinations thereof. Other sorbitan or sorbitol esters include, without limitation, PEGs sorbitan and sorbitol fatty acid esters including PEG-20 sorbitan cocoate, PEG-40 sorbitan diisostearate, PEG-2 sorbitan isostearate, PEG-5 sorbitan isosteatate, PEG-20 sorbitan isostearate, PEG-40 sorbitan lanolate, PEG-75 sorbitan lanolate, PEG-10 sorbitan laurate, PEG-40 sorbitan laurate, PEG-44 sorbitan laurate, PEG-75 sorbitan laurate, PEG-80 sorbitan laurate, PEG-3 sorbitan oleate, PEG-6 sorbitan oleate, PEG-80 sorbitan palmitate, PEG-40 sorbitan perisostearate, PEG-40 sorbitan peroleate, PEG-3 sorbitan stearate, PEG-6 sorbitan stearate, PEG-40 sorbitan stearate, PEG-60 sorbitan stearate, PEG-30 sorbitan tetraoleate, PEG-40 sorbitan tetraoleate, PEG-60 sorbitan tetraoleate, PEG-60 sorbitan tetrasterate, PEG-160 sorbitan triisostearate; PEG-20 sorbitan triisostearate, Sorbeth-40 hexaoleate, Sorbeth-50 hexaoleate, Sorbeth-30 tetraoleate laurate, Sorbeth-60 tetrastearate, and any mixture thereof. These PEG sorbitans or sorbitols range from tan, waxy solids and amber-colored pastes to clear yellow liquids. Other exemplary nonionic surfactants include, without limitation, polyoxyethylene surfactants such as POE sorbitan monolaurate (TWEEN® 20, HLB 17), POE sorbitan monopalmitate (TWEEN® 40, HLB 15.6), POE sorbitan monostearate (TWEEN® 60, HLB 15.0), POE sorbitan monooleate (TWEEN® 80, HLB 15.0), POE sorbitan tristearate (TWEEN® 65, HLB 10.5), POE sorbitan trioleate (TWEEN® 85, HLB 11.0), POE glycerol trioleate (TAGAT® TO, HLB 11.5), POE-40-hydrogenated castor oil (solid) Cremophor RH 40, HLB 14.0 to 16.0), POE-35-castor oil (Cremophor EL (liquid), HLB 12.0-14.0), POE (10) oleyl ether (BRIJ® 96, HLB 12.4), POE (23) lauryl ether (BRIJ® 35, HLB 16.9), POE-vitamin E (Alpha-tocopherol TPGS, HLB 13.0), and mixtures or combinations thereof.

Poloxamers

Suitable poloxamers include, without limitation, are nonionic triblock copolymers composed of a central hydrophobic chain of polyoxypropylene (poly(propylene oxide)) flanked by two hydrophilic chains of polyoxyethylene (poly(ethylene oxide)). Poloxamers are also known by the tradenames SYNPERONIC®, PLURONIC®, and KOLLIPHOR®. Because the lengths of the polymer blocks can be customized, many different poloxamers exist that have slightly different properties. For the generic term poloxamer, these copolymers are commonly named with the letter P (for poloxamer) followed by three digits: the first two digits multiplied by 100 give the approximate molecular mass of the polyoxypropylene core, and the last digit multiplied by 10 gives the percentage polyoxyethylene content (e.g., P407=poloxamer with a polyoxypropylene molecular mass of 4000 g/mol and a 70% polyoxyethylene content). For the PLURONIC® and SYNPERONIC® tradenames, coding of these copolymers starts with a letter to define its physical form at room temperature (L=liquid, P=paste, F=flake (solid)) followed by two or three digits, The first digit (two digits in a three-digit number) in the numerical designation, multiplied by 300, indicates the approximate molecular weight of the hydrophobe; and the last digit x 10 gives the percentage polyoxyethylene content (e.g., L61 indicates a polyoxypropylene molecular mass of 1800 g/mol and a 10% polyoxyethylene content). In the example given, poloxamer 181 (P181)=PLURONIC® L61 and SYNPERONIC® PE/L 61.

Nonionic Neutral Polymers

Suitable nonionic neutral polymers include, without limitation, pH responsive nonionic polymers and temperature sensitive nonionic polymers. Exemplary examples of such pH responsive nonionic polymers include, without limitation, pH responsive dendrimers such as poly-amidoamide (PAMAM), dendrimers, poly(propyleneimine) dendrimers, poly(-lisine) ester, poly(hydroxyproline), Poly(propyl acrylic acid), poly(methacrylic acid), CARBOPOL®, EUDRAGIT® S-100, EUDRAGIT® L-100, chitosan, poly(methacrylic acid) (PMMA), PMAA-PEG copolymer, N,N-dimethylaminoethyl methacrylate (DMAEMA), and any mixture thereof. Exemplary examples of temperature sensitive polymer include, without limitation, poloxamers, prolastin, poly(n-substituted acrylamide), poly(organophosphazene), cyclotriphosphazenes with poly(ethyleneglycol) and amino acid esters, block copolymers of poly(ethylene glycol)/poly(lactic-co-glycolic acid), poly(ethylene glycol) (PEG), poly(propylene glycol) (PPG), PMAA, poly(vinyl alcohol) (PVA), various silk-elastin-like polymers, poly(silamine), poly(vinyl methyl ether) (PVME), poly(vinyl methyl oxazolidone) (PVMO), poly(vinyl pyrrolidone) (PVP), poly(n-vinylcaprolactam), poly(N-vinyl isobutyl amid), poly(vinyl methyl ether), poly(N-vinylcaprolactam) (PVCL), poly(siloxyethylene glycol), poly(dimethylamino ethyl methacrylate), triblock copolymer poly(DL-lactide-co-glycolide-b-ethylene glycol-b-DL-lactide-co-glycolide) (PLGA-PEG-PLGA), cellulose derivatives, alginate, gellan, xyloglucan, and any mixture thereof.

Neutral Lipids

Fatty Acid Esters

In some embodiments, a neutral lipid disclosed herein comprise at least one fatty acid ester. Fatty acid esters comprise esters of any of the fatty acids listed above including, without limitation, mono-alcohol esters, where the mono-alcohol or polyols including 1 carbon atom to 20 carbon atoms, where one or more of the carbon atoms may be replace by O, NR (R is a hydrocarbyl group having between 1 and 5 carbon atoms), or S. Exemplary mono-alcohols used to from the free fatty acid esters include methanol, ethanol, propanol, butanol, pentanol or mixtures thereof.

Biocompatible Oils

Suitable biocompatible oils include, without limitation, any oil approved for a human, mammal or animal consumption by the FDA or other governmental agency. Exemplary biocompatible oils include, without limitation, plant derived oils or animal derived oils or their derivatives or synthetic oils. In certain embodiments, the natural oils are oils rich in phospholipids such as lecithin oils from soybeans. Exemplary examples of plant derived oils or animal derived oils or their derivatives or synthetic oils include, without limitation, essential oils, vegetable oils an hydrogenated vegetable oils such as peanut oil, canola oil, avocado oil, safflower oil, olive oil, corn oil, soy bean oil, sesame oil, vitamin A, vitamin D, vitamin E, or the like, animal oils, fish oils, krill oil, or the like or mixture thereof.

In certain embodiments, the biocompatible oil includes a neutral lipid. Suitable neutral lipids include, without limitation, any neutral lipid such as the fatty acid esters, monoglyceride, diglyceride, and/or triglyceride. For a partial listing of representative neutral lipids, such as the triglycerides, reference is specifically made to U.S. Pat. Nos. 4,950,656 and 5,043,329, incorporated by reference herein. Both saturated and unsaturated triglycerides may be employed in the present compositions, and include such triglycerides as tripalmitin (saturated), triolein and trilinolein (unsaturated). However, these particular triglycerides are listed here for convenience only, and are merely representative of a variety of useful triglycerides and is further not intended to be inclusive.

Animal fats include, without limitation, lard, duck fat, butter, or mixture or combination thereof.

Vegetable fats include, without limitation, coconut oil, palm oil, cottonseed oil, wheat germ oil, soya oil, olive oil, corn oil, sunflower oil, safflower oil, hemp oil, canola/rapeseed oil, or mixture and combinations thereof.

One or more neutral lipids may be present in the carrier in an amount of about 30 wt. % to about 75 wt. %. This includes about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 wt. %, including increments therein. In some embodiments, the one or more neutral lipids may be present in the carrier in an amount of about 30 wt. % to about 70 wt. %, about 30 wt. % to about 60 wt. %, about 30 wt. % to about 55 wt. %, about 35 wt. % to about 75 wt. %, about 35 wt. % to about 70 wt. %, about 35 wt. % to about 65 wt. %, about 35 wt. % to about 60 wt. %, about 35 wt. % to about 55 wt. %, about 40 wt. % to about 75 wt. %, about 40 wt. % to about 70 wt. %, about 40 wt. % to about 65 wt. %, about 40 wt. % to about 60 wt. %, or about 40 wt. % to about 55 wt. %.

In some embodiments, the carrier comprises one or more neutral lipids, wherein the one or more neutral lipids comprise a fatty acid ester. In some embodiments, the fatty acid ester is a fatty acid methyl ester. In some embodiments, the fatty acid methyl ester is methyl linolenate, methyl oleate, or methyl palmitate, or a combination of thereof.

V. Excipients or Adjuvants

The formulation or compositions of this disclosure can also include other chemicals, such as anti-oxidants (e.g., Vitamin A, C, D, E, etc.), trace metals and/or polyvalent cations (aluminum, gold, copper, zinc, calcium, etc.), surface-active agents and/or solvents (e.g., propylene glycol/PPG, dimethyl sulfoxide/DMSO, medium chain triglycerides/MCT, etc.), non-toxic dyes and flavor enhancers may be added to the formulation as they are being prepared to improve stability, fluidity/spreadability, permeability, effectiveness and consumer acceptance. These additives, excipients, and/or adjuvants may also function as active agents.

VI. BAI and Pharmaceutical Agents

Suitable pharmaceutical agents for use in the compositions of this disclosure include, without limitation, any pharmaceutical agent capable of being dispersed in a carrier of this disclosure. In certain embodiments, the pharmaceutical agents are solids. In other embodiments, the pharmaceutical agents are liquids. In other embodiments, the pharmaceutical agents are weak acid pharmaceutical agents. In other embodiments, the pharmaceutical agents are weak base pharmaceutical agents. In some embodiments, the biologically active agent comprises at least one agent selected from the group consisting of an acid-labile pharmaceutical agent, an anti-depressant, an anti-diabetic agent, an anti-epileptic agent, an anti-fungal agent, an anti-malarial agent, an anti-muscarinic agent, an anti-neoplastic agent, an immunosuppressant, an anti-protozoal agent, an anti-tussive, a neuroleptics, a beta-blocker, a cardiac inotropic agent, a corticosteroid, an anti-parkinsonian agent, a gastro-intestinal agent, histamine, a histamine receptor antagonist, a keratolytic, a lipid regulating agent, a muscle relaxant, a nitrate, an anti-anginal agent, a non-steroidal anti-inflammatory agent, a nutritional agent, an opioid analgesic, a sex hormone, a stimulant, a nutraceutical, a peptide, a protein, a therapeutic protein, a nucleoside, a nucleotide, DNA, RNA, a glycosaminoglycan, an acid-labile drug, (+)-N{3-[3-(4-fluorophenoxy)phenyl]-2-cyclopenten-1-yl}-N-hydroxyurea, amylase, aureomycin, bacitracin, beta carotene, cephalosporins, chloromycetin, cimetidine, cisapride, cladribine, clorazepate, deramciclane, didanosine, digitalis glycosides, dihydrostreptomycin, erythromycin, etoposide, famotidine, a hormone, estrogen, insulin, adrenalin, heparin, lipase, milameline, novobiocin, pancreatin, penicillin salts, polymyxin, pravastatin, progabide, protease, quinapril, quinoxaline-2-carboxylic acid, [4-(R)carbamoyl-1-(S-3-fluorobenzyl-2-(S),7-dihydroxy-7-methyloctyl]amide, quinoxaline-2-carboxylic acid[1-benzyl-4-(4,4-difluoro-1-hydroxycyclohexyl)-2-hydroxy-4-hydroxycarbamoyl-butyl]-amide ranitidine, streptomycin, subtilin, sulphanilamide, a proton pump inhibitors, esomeprazole, lansoprazole, minoprazole, omeprazole, pantoprazole and rabeprazole.

Hydrophobic Pharmaceutical and/or Nutraceutical Agents

Hydrophobic therapeutic agents suitable for use in the pharmaceutical compositions of the present disclosure are not particularly limited, as the carrier is surprisingly capable of solubilizing and delivering a wide variety of hydrophobic therapeutic agents. Hydrophobic therapeutic agents are compounds with little or no water solubility. Intrinsic water solubilities (i.e., water solubility of the unionized form) for hydrophobic therapeutic agents usable in the present disclosure are less than about 1% by weight, and typically less than about 0.1% or 0.01% by weight. Such therapeutic agents can be any agents having therapeutic or other value when administered to an animal, particularly to a mammal, such as drugs, nutrients, and cosmetics (cosmeceuticals). It should be understood that while the disclosure is described with particular reference to its value in the form of aqueous dispersions, the disclosure is not so limited. Thus, hydrophobic drugs, nutrients or cosmetics which derive their therapeutic or other value from, for example, topical or transdermal administration, are still considered to be suitable for use in the present disclosure.

Specific non-limiting examples of hydrophobic therapeutic agents that can be used in the pharmaceutical compositions of the present disclosure include the following representative compounds, as well as their pharmaceutically acceptable salts, isomers, esters, ethers and other derivatives: analgesics and anti-inflammatory agents, such as aloxiprin, auranofin, azapropazone, benorylate, capsaicin, celecoxib, diclofenac, diflunisal, etodolac, fenbufen, fenoprofen calcium, flurbiprofen, ibuprofen, indomethacin, ketoprofen, ketorolac, leflunomide, meclofenamic acid, mefenamic acid, nabumetone, naproxen, oxaprozin, oxyphenbutazone, phenylbutazone, piroxicam, refocoxib, sulindac, tetrahydrocannabinol, tramadol and tromethamine; antihelminthics, such as albendazole, bephenium hydroxynaphthoate, cambendazole, dichlorophen, ivermectin, mebendazole, oxamniquine, oxfendazole, oxantel embonate, praziquantel, pyrantel embonate and thiabendazole; anti-arrhythmic agents, such as amiodarone HCl, disopyramide, flecainide acetate and quinidine sulfate; anti-asthma agents, such as zileuton, zafirlukast, terbutaline sulfate, montelukast, and albuterol; anti-bacterial agents such as alatrofloxacin, azithromycin, baclofen, benzathine penicillin, cinoxacin, ciprofloxacin HCl, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin HCl, nalidixic acid, nitrofurantoin, norfloxacin, ofloxacin, rifampicin, rifabutine, rifapentine, sparfloxacin, spiramycin, sulphabenzamide, sulphadoxine, sulphamerazine, sulphacetamide, sulphadiazine, sulphafurazole, sulphamethoxazole, sulphapyridine, tetracycline, trimethoprim, trovafloxacin, and vancomycin; anti-viral agents, such as abacavir, amprenavir, delavirdine, efavirenz, indinavir, lamivudine, nelfinavir, nevirapine, ritonavir, saquinavir, and stavudine; anti-coagulants, such as cilostazol, clopidogrel, dicumarol, dipyridamole, nicoumalone, oprelvekin, phenindione, ticlopidine, and tirofiban; anti-depressants, such as amoxapine, bupropion, citalopram, clomipramine, fluoxetine HCl, maprotiline HCl, mianserin HCl, nortriptyline HCl, paroxetine HCl, sertraline HCl, trazodone HCl, trimipramine maleate, and venlafaxine HCl; anti-diabetics, such as acetohexamide, chlorpropamide, glibenclamide, gliclazide, glipizide, glimepiride, miglitol, pioglitazone, repaglinide, rosiglitazone, tolazamide, tolbutamide and troglitazone; anti-epileptics, such as beclamide, carbamazepine, clonazepam, ethotoin, felbamate, fosphenytoin sodium, lamotrigine, methoin, methsuximide, methylphenobarbitone, oxcarbazepine, paramethadione, phenacemide, phenobarbitone, phenytoin, phensuximide, primidone, sulthiame, tiagabine HCl, topiramate, valproic acid, and vigabatrin; anti-fungal agents, such as amphotericin, butenafine HCl, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, terbinafine HCl, terconazole, tioconazole and undecenoic acid; anti-gout agents, such as allopurinol, probenecid and sulphinpyrazone; anti-hypertensive agents, such as amlodipine, benidipine, benezepril, candesartan, captopril, darodipine, dilitazem HCl, diazoxide, doxazosin HCl, elanapril, eposartan, losartan mesylate, felodipine, fenoldopam, fosenopril, guanabenz acetate, irbesartan, isradipine, lisinopril, minoxidil, nicardipine HCl, nifedipine, nimodipine, nisoldipine, phenoxybenzamine HCl, prazosin HCl, quinapril, reserpine, terazosin HCl, telmisartan, and valsartan; anti-malarials, such as amodiaquine, chloroquine, chlorproguanil HCl, halofantrine HCl, mefloquine HCl, proguanil HCl, pyrimethamine and quinine sulfate; anti-migraine agents, such as dihydroergotamine mesylate, ergotamine tartrate, frovatriptan, methysergide maleate, naratriptan HCl, pizotyline malate, rizatriptan benzoate, sumatriptan succinate, and zolmitriptan; anti-muscarinic agents, such as atropine, benzhexol HCl, biperiden, ethopropazine HCl, hyoscyamine, mepenzolate bromide, oxyphencyclimine HCl and tropicamide; anti-neoplastic agents and immunosuppressants, such as aminoglutethimide, amsacrine, azathioprine, bicalutamide, bisantrene, busulfan, camptothecin, cytarabine, chlorambucil, cyclosporin, dacarbazine, ellipticine, estramustine, etoposide, irinotecan, lomustine, melphalan, mercaptopurine, methotrexate, mitomycin, mitotane, mitoxantrone, mofetil mycophenolate, nilutamide, paclitaxel, procarbazine HCl, sirolimus, tacrolimus, tamoxifen citrate, teniposide, testolactone, topotecan HCl, and toremifene citrate; antiprotozoal agents, such as atovaquone, benznidazole, clioquinol, decoquinate, diiodohydroxyquinoline, diloxanide furoate, dinitolmide, furazolidone, metronidazole, nimorazole, nitrofurazone, ornidazole and tinidazole; anti-thyroid agents, such as carbimazole, paracalcitol, and propylthiouracil; anti-tussives, such as benzonatate; anxiolytics, sedatives, hypnotics and neuroleptics, such as alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, diazepam, droperidol, ethinamate, flunanisone, flunitrazepam, triflupromazine, fluphenthixol decanoate, fluphenazine decanoate, flurazepam, gabapentin, haloperidol, lorazepam, lormetazepam, medazepam, meprobamate, mesoridazine, methaqualone, methylphenidate, midazolam, molindone, nitrazepam, olanzapine, oxazepam, pentobarbitone, perphenazine pimozide, prochlorperazine, pseudoephedrine, quetiapine, rispiridone, sertindole, sulpiride, temazepam, thioridazine, triazolam, zolpidem, and zopiclone; .beta.-Blockers, such as acebutolol, alprenolol, atenolol, labetalol, metoprolol, nadolol, oxprenolol, pindolol and propranolol; cardiac inotropic agents, such as amrinone, digitoxin, digoxin, enoximone, lanatoside C and medigoxin; corticosteroids, such as beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone and triamcinolone; diuretics, such as acetazolamide, amiloride, bendroflumethiazide, bumetanide, chlorothiazide, chlorthalidone, ethacrynic acid, frusemide, metolazone, spironolactone and triamterene. antiparkinsonian agents, such as bromocriptine mesylate, lysuride maleate, pramipexole, ropinirole HCl, and tolcapone; gastrointestinal agents, such as bisacodyl, cimetidine, cisapride, diphenoxylate HCl, domperidone, famotidine, lansoprazole, loperamide, mesalazine, nizatidine, omeprazole, ondansetron HCl, rabeprazole sodium, ranitidine HCl and sulphasalazine; histamine H, and H,-receptor antagonists, such as acrivastine, astemizole, chlorpheniramine, cinnarizine, cetrizine, clemastine fumarate, cyclizine, cyproheptadine HCl, dexchlorpheniramine, dimenhydrinate, fexofenadine, flunarizine HCl, loratadine, meclizine HCl, oxatomide, and terfenadine; keratolytics, such as such as acetretin, calcipotriene, calcifediol, calcitriol, cholecalciferol, ergocalciferol, etretinate, retinoids, targretin, and tazarotene; lipid regulating agents, such as atorvastatin, bezafibrate, cerivastatin, ciprofibrate, clofibrate, fenofibrate, fluvastatin, gemfibrozil, pravastatin, probucol, and simvastatin; muscle relaxants, such as dantrolene sodium and tizanidine HCl; nitrates and other anti-anginal agents, such as amyl nitrate, glyceryl trinitrate, isosorbide dinitrate, isosorbide mononitrate and pentaerythritol tetranitrate; nutritional agents, such as calcitriol, carotenes, dihydrotachysterol, essential fatty acids, nonessential fatty acids, phytonadiol, vitamin A, vitamin B2, vitamin D, vitamin E and vitamin K. opioid analgesics, such as codeine, codeine, dextropropoxyphene, diamorphine, dihydrocodeine, fentanyl, meptazinol, methadone, morphine, nalbuphine and pentazocine; sex hormones, such as clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, norethisterone, norgestrel, oestradiol, conjugated estrogens, progesterone, rimexolone, stanozolol, stilbestrol, testosterone and tibolone; stimulants, such as amphetamine, dexamphetamine, dexfenfluramine, fenfluramine and mazindol; and others, such as becaplermin, donepezil HCl, L-thryroxine, methoxsalen, verteporfin, physostigmine, pyridostigmine, raloxifene HCl, sibutramine HCl, sildenafil citrate, tacrine, tamsulosin HCl, and tolterodine.

Exemplary examples of hydrophobic therapeutic agents include sildenafil citrate, amlodipine, tramadol, celecoxib, rofecoxib, oxaprozin, nabumetone, ibuprofen, terbenafine, itraconazole, zileuton, zafirlukast, cisapride, fenofibrate, tizanidine, nizatidine, fexofenadine, loratadine, famotidine, paricalcitol, atovaquone, nabumetone, tetrahydrocannabinol, megestrol acetate, repaglinide, progesterone, rimexolone, cyclosporin, tacrolimus, sirolimus, teniposide, paclitaxel, pseudoephedrine, troglitazone, rosiglitazone, finasteride, vitamin A, vitamin D, vitamin E, and pharmaceutically acceptable salts, isomers and derivatives thereof Particularly preferred hydrophobic therapeutic agents are progesterone and cyclosporin.

Suitable proton pump inhibitors for use in the present disclosure include, without limitation, omeprazole, lansoprazole, rabeprazole, pantoprazole, esomeprazole, and mixtures thereof.

It should be appreciated that this listing of hydrophobic therapeutic agents and their therapeutic classes is merely illustrative. Indeed, a particular feature and surprising advantage, of the compositions of the present disclosure is the ability of the present compositions to solubilize and deliver a broad range of hydrophobic therapeutic agents, regardless of functional class. Of course, mixtures of hydrophobic therapeutic agents may also be used where desired. These carrier attributes will also be equally effective as a delivery vehicle for yet to be developed hydrophobic therapeutic agents.

In certain embodiments, the suitable pharmaceutical agents for use in the compositions of this disclosure include, without limitation, weak acid pharmaceuticals, weak acid pharmaceuticals or mixtures and combinations thereof. Exemplary weak acid pharmaceuticals include, without limitation, anti-inflammatory pharmaceuticals, steroids, sterols, NSAID, COX-2 inhibitors, or mixture thereof. Exemplary weak base pharmaceuticals include, without limitation, weak base antibiotics, caffeine, codiene, ephedrine, chlordiazepoxide, morphine, pilocarpine, quinine, tolbutamine, other weak base pharmaceutical agents and mixtures or combinations thereof. Exemplary anti-inflammatory pharmaceuticals include steroidal anti-inflammatory drugs, non-steroidal anti-inflammatory drugs, acetaminophen and COX-2 inhibitors or mixtures and combinations thereof.

Suitable NSAIDS include, without limitation: (a) propionic acid drugs including fenoprofen calcium, flurbiprofen, suprofen, benoxaprofen, ibuprofen, ketoprofen, naproxen, and/or oxaprozin; (b) acetic acid drug including diclofenac sodium, diclofenac potassium, aceclofenac, etodolac, indomethacin, ketorolac tromethamine, and/or ketorolac; (c) ketone drugs including nabumetone, sulindac, and/or tolmetin sodium; (d) fenamate drugs including meclofenamate sodium, and/or mefenamic acid; (e) oxicam drugs piroxicam, lornoxicam and meloxicam; (f) salicylic acid drugs including diflunisal, aspirin, magnesium salicylate, bismuth subsalicylate, and/or other salicylate pharmaceutical agents; (g) pyrazolin acid drugs including oxyphenbutazone, and/or phenylbutazone; and (h) mixtures or combinations thereof.

Suitable COX-2 inhibitors include, without limitation, celecoxib, rofecoxib, or mixtures and combinations thereof.

Acid Labile Pharmaceuticals

Suitable acid labile pharmaceutical active agents include, without limitation, peptides, proteins, nucleosides, nucleotides, DNA, RNA, glycosaminoglyacan, any other acid labile pharmaceuticals, or mixtures or combinations thereof. Examples of acid-labile drugs which may be used in the carrier systems disclosed herein are, e.g., (+)-N{3-[3-(4-fluorophenoxy)phenyl]-2-cyclopenten-1-yl}-N-hydroxyurea, amylase, aureomycin, bacitracin, beta carotene, cephalosporins, chloromycetin, cimetidine, cisapride, cladribine, clorazepate, deramciclane, didanosine, digitalis glycosides, dihydrostreptomycin, erythromycin, etoposide, famotidine, hormones (in particular estrogens, insulin, adrenalin and heparin), lipase, milameline, novobiocin, pancreatin, penicillin salts, polymyxin, pravastatin, progabide, protease, quinapril, quinoxaline-2-carboxylic acid, [4-(R) carbamoyl-1-(S-3-fluorobenzyl-2-(S),7-dihydroxy-7-methyloctyl]amide, quinoxaline-2-carboxylic acid [1-benzyl-4-(4,4-difluoro-1-hydroxy-cyclohexyl)-2-hydroxy-4-hydroxycarbamoyl-butyl]amide, ranitidine, streptomycin, subtilin, sulphanilamide and acid-labile proton pump inhibitors like esomeprazole, lansoprazole, minoprazole, omeprazole, pantoprazole or rabeprazole. Digestive proteins such as amylase, lipase and protease may be included in disclosed carrier systems. Amylases, lipases and proteases which are suitable as digestive enzyme supplement or digestive enzyme substitute in mammals, particularly humans, are preferred. Amylase, lipase and/or protease may be derived from microbial or animal, in particular, mammalian sources. Pancreatin is an acid-labile drug. Other therapeutic proteins or peptides may be used with the disclosed carriers to increase bioavailability. Other therapeutic proteins may include, without limitation, insulin, erythropoietin, or fragments or derivatives thereof. Example of glycosaminoglycan include, without limitation, heparin, or fragments thereof. The foregoing list of acid-labile drugs is not meant to be exhaustive, but merely illustrative as a person of ordinary skill in the art would understand that many other acid-labile drugs or combination of acid-labile drugs could also be used.

Nutraceutical Agents

Suitable nutraceuticals for use in the compositions of this disclosure include, without limitation, any nutraceutical agent that is capable with the carriers of this disclosure. In certain embodiments, the nutraceutical agents are solid. In other embodiments, the nutraceutical agents are oil soluble liquids or oil miscible liquids.

Additionally, or alternatively, suitable pharmaceutical agents for use in the compositions of this disclosure may be categorized as class I, II, III, or IV pharmaceuticals, defined as follows.

Class I pharmaceuticals are characterized in that the API has a higher concentration in oil phases in the initial pH 1 solution and final pH 1 solution compared to the concentration of the API in oil phase in the pH 7 solution. Class I pharmaceuticals are small molecule pharmaceuticals characterized in that the pharmaceuticals do not include functional groups that protonate at pH less than about 2 or 3; such groups include primary, secondary and tertiary amines, guanidines, pyridines, imidazole, benzimidazole, histidine, phosphazene, similar or mixtures and combinations thereof. Class I pharmaceuticals may include linear, branched, cyclic, saturated and/or unsaturated alkyl groups, aralkyl groups, aralkyl groups, aryl groups, hydroxy groups, alkoxy groups, carbonyl group, carboxylic acid groups, carboxylic ester groups, acetate groups, amide groups, sulfone groups, sulfonamide groups, cyclic rings, or heterocyclic groups that do not protonate at pH less than about 2 or 3, or mixtures and combinations thereof. Exemplary examples of class I pharmaceutical include, 5-alpha-reductase inhibitors, ACE inhibitors with calcium channel blocking agents, aldosterone receptor antagonists, adrenal cortical steroids, group V anti-arrhythmics, fatty acid derivative anti-convulsants, fabric acid derivatives, mitotic inhibitors, MTOR inhibitors, NSAIDs (such as ibuprofen and aspirin), COX-2 inhibitors, otic steroids, sterols, steroids, transthyretin stabilizers, uterotonic agents, vasopressin antagonists, or mixtures and combination thereof.

Class II pharmaceuticals are characterized in that the API has lower concentration in oil phases in the initial pH 1 solution and final pH 1 solution compared to the concentration of the API in oil phase in the pH 7 solution. Class II pharmaceuticals are small molecule pharmaceuticals characterized in that the pharmaceuticals include functional groups that protonate at pH less than about 3 or less than about 2; functional groups include primary, secondary and tertiary amines, guanidines, pyridines, imidazole, benzimidazole, histidine, phosphazene, similar or mixtures and combinations thereof. Exemplary examples of class II pharmaceuticals include proton-pump inhibitors (such as omeprazole), or mixtures and combination thereof.

Class III pharmaceuticals are characterized in that the API has a higher concentration in oil phases in the initial pH 1 solution and final pH 1 solution compared to the concentration of the API in oil phase in the pH 7 solution. Exemplary examples of class III pharmaceuticals include proteins, polypeptides, enzymes, ribozymes, RNA, DNA, or mixtures and combination thereof.

Class IV pharmaceuticals are characterized in that the API has lower concentration in oil phases in the initial pH 1 solution and final pH 1 solution compared to the concentration of the API in oil phase in the pH 7 solution. This class may include carbohydrates, polysaccharides, other highly water soluble macromolecules.

VII. Pharmaceutical or Nutraceutical Dosages

In pharmaceutical compositions, the compositions generally contain from about 1 mg to about 5000 mg per dose depending on the pharmaceutical agent(s). In other pharmaceutical compositions, the compositions contain from about 10 mg to about 2500 mg per dose depending on the pharmaceutical agent(s). In other pharmaceutical compositions, the compositions contain from about 250 mg to about 2500 mg per dose depending on the pharmaceutical agent(s). In other pharmaceutical compositions, the compositions contain from about 500 mg to about 2500 mg per dose depending on the pharmaceutical agent(s). In other pharmaceutical compositions, the compositions contain from about 500 mg to about 2000 mg per dose depending on the pharmaceutical agent(s). In other pharmaceutical compositions, the compositions contain from about 1 mg to about 2000 mg per dose depending on the pharmaceutical agent(s). In other pharmaceutical compositions, the compositions contain from about 1 mg to about 1000 mg per dose depending on the pharmaceutical agent(s). Of course, the exact dosage for each composition depends on the pharmaceutical agent(s) used and the potency of the pharmaceutical agent(s).

In nutraceutical compositions, the compositions generally contain from about 1 mg to about 5000 mg per dose depending on the nutraceutical agent(s). In other nutraceutical compositions, the compositions contain from about 10 mg to about 2500 mg per dose depending on the nutraceutical agent(s). In other nutraceutical compositions, the compositions contain from about 250 mg to about 2500 mg per dose depending on the nutraceutical agent(s). In other nutraceutical compositions, the compositions contain from about 500 mg to about 2500 mg per dose depending on the nutraceutical agent(s). In other nutraceutical compositions, the compositions contain from about 500 mg to about 2000 mg per dose depending on the nutraceutical agent(s). In other nutraceutical compositions, the compositions contain from about 1 mg to about 2000 mg per dose depending on the nutraceutical agent(s). In other nutraceutical compositions, the compositions contain from about 1 mg to about 1000 mg per dose depending on the nutraceutical agent(s). Of course, the exact dosage for each composition depends on the pharmaceutical agent(s) used and the potency of the pharmaceutical agent(s).

VIII. Methods for Making the Carriers and Compositions

Some embodiments of the present disclosure relate broadly to methods for making the carriers of this disclosure including contacting (1) a pH dependent release system and (2) a pH dependent carrier reassembly/assembly and reabsorption/absorption system under conditions of mixing, temperature, pressure, and time sufficient to form a carrier having tailored properties. The pH dependent release system is capable of targeting the release of one or more biologically active agents at a desired pH and the pH dependent carrier reassembly/assembly and reabsorption/absorption system is capable of reforming or forming a carrier due to duodenal reflux and a reabsorption/absorption of the biologically active agents in the low pH environment of the stomach. In certain embodiments, the mixing contacting occur in the presence of a solvent followed by solvent removal so that the resulting carrier is substantially free of solvent.

In certain embodiments, the methods for making the carriers of this disclosure including contacting (1) pH dependent release system, (2) a pH dependent carrier reassembly/assembly and biologically active agent reabsorption/absorption due to duodenal reflux, (3) optionally one or more neutral lipids, (4) optionally one or more surfactants, (5) optionally a biologically active agent complexing agent, and (6) optionally a protective system including agents to reduce and/or eliminate biologically active agent toxicities, irritations or side-effects. The carriers are generally viscous fluids capable of being orally administered, directly administered, internally administered and/or topically administered. Again, in certain embodiments, the mixing contacting occur in the presence of a solvent followed by solvent removal so that the resulting carrier is substantially free of solvent.

In other embodiments, the carriers are generally prepared at room temperature, at atmospheric pressure with mixing for a time sufficient to render the carrier uniform and/or homogeneous or substantially uniform and/or substantially homogeneous. However, the carrier may be prepared and higher or lower pressures. In other embodiments, the mixing may be performed at an elevated temperature up to a melting point of the highest melting component, but below a decomposition temperature of any of the carrier components. In other embodiments, the temperature is elevated to a temperature up to about 130° C. In other embodiments, the temperature is elevated to a temperature up to about 80° C. In other embodiments, the temperature is elevated to a temperature up to about 60° C. In other embodiments, the temperature is elevated to a temperature up to about 40° C.

In other embodiments, the pressure at or near atmospheric pressure. In other embodiments, the pressure is above atmospheric pressure. In other embodiments, the pressure is below atmospheric pressure.

In other embodiments, the time is for a period between about 5 minutes and about 12 hours. In other embodiments, the time is for a period between about 10 minutes and about 8 hours. In other embodiments, the time is for a period between about 20 minutes and about 4 hours. In other embodiments, the time is for a period between about 30 minutes and about 2 hours. In other embodiments, the time is for a period between about 30 minutes and about 1 hour.

In other embodiments, the mixing is performed by low shear mixing such as paddle mixers. In other embodiments, the mixing is performed by high shear mixing such as extruders, internal mixers, etc. In certain embodiments, the mixing is performed by a combination of low shear mixing and high shear mixing. In certain embodiments, the mixing is performed by sonication with or without low shear and/or high shear mixing. In certain embodiments, the mixing is performed by vortex mixing in the presence or absence of sonication.

In other embodiments, the present disclosure relates broadly to methods for making the compositions of this disclosure by contacting a carrier of this disclosure and an effective amount of at least one biologically active agent under conditions of mixing, temperature, pressure and time sufficient to form a composition having tailored properties, wherein the carrier includes (1) pH dependent release system, (2) a pH dependent carrier reassembly/assembly and biologically active agent reabsorption/absorption due to duodenal reflux, (3) optionally one or more neutral lipids, (4) optionally one or more surfactants, (5) optionally a biologically active agent complexing agent, and (6) optionally a protective system including agents to reduce and/or eliminate biologically active agent toxicities, irritations or side-effects. In certain embodiments, the compositions may also include a secondary complexing agent for the active agent under conditions of mixing, temperature, pressure, and time sufficient to form a composition having tailored properties in the presence or absence of a solvent system. If solvent system is used, then the system is generally removed prior to use. In certain embodiments, the compositions may also include a protective agent for the active agents. In certain embodiments, the active agents include pharmaceutical agents, nutraceutical agent or mixtures and combinations thereof. In certain embodiments, the compositions are made at room temperature, at atmospheric pressure with mixing until the carrier is uniform and/or homogeneous. In other embodiments, the mixing may be performed at an elevated temperature up to a melting point of the highest melting component, but below a decomposition temperature of any of the carrier components. In other embodiments, the temperature is elevated to a temperature up to about 130° C. In other embodiments, the temperature is elevated to a temperature up to about 80° C. In other embodiments, the temperature is elevated to a temperature up to about 60° C. In other embodiments, the temperature is elevated to a temperature up to about 40° C. In certain embodiments, the pressure at or near atmospheric pressure. In other embodiments, the pressure is above atmospheric pressure. In other embodiments, the pressure is below atmospheric pressure.

In certain embodiments, the mixture is mixed for a time between about 5 minutes and about 12 hours. In other embodiments, the time is for a period between about 10 minutes and about 8 hours. In other embodiments, the time is for a period between about 20 minutes and about 4 hours. In other embodiments, the time is for a period between about 30 minutes and about 2 hours. In other embodiments, the time is for a period between about 30 minutes and about 1 hour.

In certain embodiments, the mixing is performed by low shear mixing such as paddle mixers. In other embodiments, the mixing is performed by high shear mixing such as extruders, internal mixers, etc. In certain embodiments, the mixing is performed by a combination of low shear mixing and high shear mixing. In certain embodiments, the mixing is performed by sonication with or without low shear and/or high shear mixing. In certain embodiments, the mixing is performed by vortex mixing in the presence or absence of sonication. Of course, the compositions may be prepared by mixing the active agents and the carrier components in any order, thus, the carrier does not have to be pre-made prior to adding the active agents. Additionally, the order of addition is not critical and may vary depending on components, mixers, desired final properties, or operator choice.

IX. Methods for Using the Carriers and Compositions

Some embodiments of the present disclosure broadly relate to methods of targeting release of a biologically active agent at specific portion of a tract such as the gastrointestinal (GI) tract, wherein the methods comprise the step of orally administering a composition comprising a carrier and at least one biologically active agent. The carrier includes an effective amount of a pH dependent release system and an effective amount of a pH dependent carrier assembly or reassembly system. The pH dependent release system is designed to release the at least one biologically active agent in pH sensitive manner characterized in that less than 20% of the at least one biologically active agent is released into gastric fluid and greater than 50% of the at least one biologically active agent is released in intestinal fluid having a pH value greater than pH 3. In certain embodiments, pH dependent release system includes compounds that are uncharged in gastric fluid and charged in intestinal fluids, which is responsible for the pH dependent release of the at least one biologically active agent.

Some embodiments of the present disclosure relate broadly to methods for using the compositions of this disclosure by administering a composition of this disclosure to a human, a mammal or an animal at a dose sufficient to illicit at least one therapeutic effect such as treatment and/or prevention of pain, fever, inflammation, cancer, inflammatory bowel syndrome, crones disease, cardiovascular disease, infections, brain and spinal cord injury, Alzheimer's disease, other neurologic diseases diabetes, and/or any other disease or malady treatable via the administration of an active agent such as a pharmaceutical and/or nutraceutical agents. In other embodiments, the compositions treat, prevent and/or ameliorate symptoms of diseases and/or maladies.

Some embodiments of the present disclosure relate broadly to methods including orally or internally administering a composition including a carrier of this disclosure and a therapeutically effective amount of a composition of this disclosure to increase transport of the pharmaceutical or nutraceutical agent across the blood-brain barrier or into the central nervous system (CNS) or peripheral nervous system (PNS) allowing more pharmaceutical or nutraceutical agent to get to the trauma site and reduce inflammation, platelet aggregation, pain (nociceptive) sensation, cell death and/or apoptosis due to inflammation and/or inducing competitive cell death of cancer cells in preventing or treating cancers.

Some embodiments of the present disclosure relate broadly to methods including orally or internally administering a composition including a carrier of this disclosure and a therapeutically effective amount of a composition of this disclosure to prevent, treat and/or ameliorate symptoms associated with Alzheimer's disease.

Some embodiments of the present disclosure relate broadly to methods including administering a composition of this disclosure to a human, mammal or animal. The carriers may be tailored so that the compositions have good pharmaceutical and/or nutraceutical release characteristics, have reduced pharmaceutical and/or nutraceutical toxicity or irritation, have increased pharmaceutical and/or nutraceutical bioavailability and have increased pharmaceutical or nutraceutical availability across relatively hydrophobic barriers in a human, mammal or animal. For example, pharmaceuticals and/or nutraceuticals that have GI toxicity and/or GI irritation, the carriers of this disclosure may be tailored to ameliorate, reduce, or eliminate the GI toxicity and/or GI irritation of the pharmaceuticals and/or nutraceuticals. In certain embodiments, the pharmaceutical and/or nutraceutical agents reduce, ameliorate, or treat inflammation. In other embodiments, the pharmaceutical and/or nutraceutical agents reduce, ameliorate, or treat platelet aggregation. In other embodiments, the pharmaceutical and/or nutraceutical agents reduce, ameliorate, or treat pyretic activity. In other embodiments, the pharmaceutical and/or nutraceutical agents reduce, ameliorate, or treat ulcerated regions of the tissue. Of course, the pharmaceutical and/or nutraceutical agents reduce, ameliorate, or treat combinations of these symptoms as well.

The disclosure is further described by reference to the following examples, which are provided for illustration only. The disclosed is not limited to the examples, but rather includes all variations that are evident from the teachings provided herein. All publicly available documents referenced herein, including but not limited to U.S. patents, are specifically incorporated by reference.

X. Definitions

The following terms have the meanings set forth below. In the present disclosure, singular and plural forms of words are used and should not be seen to be expressly limited to the singular or plural form. Thus, reference to a carrier would also include reference to more the one carrier and reference to carriers would include reference to a single carrier.

All ranges are inclusive meaning that they cover all subranges. For example, a range between about 10 and about 20 means any subrange between about 10 and about 20 such as about 10 to about 19, about 18, about 17, about 16, about 15, about 14, about 13, about 12, and about 11 or about 11, about 12, about 13, about 14, about 15, about 16, about 17, about 18, about 19 to about 20 and any fraction range such as about 10.1 to about 19.9, etc.

The term "mixture" means a blend of one or more ingredients, where the ingredients may interact at the molecular level, e.g., a homogeneous mixture is a mixture, where the ingredients are uniformly and homogeneously distributed, while an inhomogeneous mixture is a mixture, where the ingredients are not uniformly and homogeneously distributed.

The term "combination" means one or more ingredients that are combined, but not mixed.

The term "about" means 20% of an indicated value, within 15% of an indicated value, within 10% of an indicated value, within 5% of an indicated value, and/or within 1% of an indicated value. It should be recognized that the language of within 10% encompasses all values between 0% and 10% or $\forall 0$ to $\forall 10\%$ and is true for all of the other ranges.

The term "substantially" or "essentially" means that the attribute, condition or value is within 10% of an indicated value, within 7.5% of an indicated value, within 5% of an indicated value, within 2.5% of an indicated value, within 1% of an indicated value, within 0.5% of an indicated value, within 0.1% of an indicated value, within 0.05% of an indicated value, within 0.01% of an indicated value, within 0.005% of an indicated value, within 0.001% of an indicated value, within 0.0005% of an indicated value, and/or within 0.0001% of an indicated value. It should be recognized that the language of within 10% encompasses all values between 0% and 10% or $\forall 0$ to $\forall 10\%$ and is true for all of the other ranges.

The term "essentially free" or "substantially free" means compositions include less than or equal to about 5% (wt. % or vol. %) of a given ingredient, less than or equal to about 2.5% (wt. % or vol. %) of a given ingredient, less than or equal to about 1% (wt. % or vol. %) of a given ingredient, less than or equal to about 0.5% (wt. % or vol. %) of a given ingredient, less than or equal to about 0.1% (wt. % or vol. %) of a given ingredient, less than or equal to about 0.05% (wt. % or vol. %) of a given ingredient, less than or equal to about 0.01% (wt. % or vol. %) of a given ingredient, less than or equal to about 0.005% (wt. % or vol. %) of a given ingredient, less than or equal to about 0.001% (wt. % or vol. %) of a given ingredient, less than or equal to about 0.0005% (wt. % or vol. %) of a given ingredient, or less than or equal to about 0.0001.% (wt. % or vol. %) of a given ingredient. Such ingredient may include, without limitation, water, solvents, or any other ingredient that is to be substantially excluded from the desired composition. Again, it should be recognized that the language of less than or equal to about 5% encompasses all values between about 0% and about 5% of the given ingredient.

The term "relatively high concentration" means that the pharmaceutical or nutraceutical agents comprise greater than or equal to about 50 wt. % of the final composition, greater than or equal to about 55 wt. % of the final composition, greater than or equal to about 60 wt. % of the final composition, greater than or equal to about 65 wt. % of the final composition, greater than or equal to about 70 wt. % of the final composition, greater than or equal to about 75 wt. % of the final composition, greater than or equal to about 80 wt. % of the final composition or greater than or equal to about 85 wt. % of the final composition.

The term "major component" means a component present in a composition in an amount of at least about 33% (vol. % or wt. %) based on 100% of the formulations (vol. % or wt. %). In other embodiments, the term means at least about 51% (vol. % or wt. %).

The term "minimally released" or "inefficiently released" means that less than about 20% of a biologically active agent is released.

The term "maximally released" or "efficiently released" means that greater than about 50% of a biologically active agent is released or greater than the amount released in low pH environments.

The term "association complex" or "associated complex" means a non-covalent association between two or more compounds, where the compounds are held together by non-covalent chemical and/or physical interactions including hydrogen bonding, ionic bonding, dipolar interactions, hyperpolarizible interactions, van der Waals interaction, electrostatic interaction, a polar bonding or interaction, or any other chemical and/or physical attractive interaction.

The term "hydrophilic" means a compound having a strong affinity for water; are soluble in water; tend to dissolve in, mix with, miscible with water, or are wetted by water.

The term "hydrophobic" means a compound lacking affinity for water; insoluble in water; tends to repel water; or tends not to dissolve in, mix with, dissolve with, or are wetted by water.

The term "zwitterion" means a molecule that has a positively charged and a negatively charged functional group or moiety in the molecular structure at biological pH levels.

The term "relatively hydrophobic barriers" means any external, internal, cellular or subcellular barrier that has hydrophobic properties, which generally resists or reduces transport and/or partitioning of hydrophilic reagents across the barrier. Such barriers include, without limitation, a mucosal gel layer (e.g., gastric, duodenal, or colonic mucosal gel layers, vaginal mucosal gel layers, esophagus mucosal gel layers, nasal mucosal gel layers, lung mucosal gel layers, etc.), a plasma lemma (cellular membrane), the blood-brain barrier, placental barrier, testicular barrier, or any other barrier of a human, mammal or animal, through which partitioning and/or transporting of hydrophobic materials more easily occurs than hydrophilic materials.

The term "residual water" means water remaining in components used to make the compositions of this disclosure. Generally, the residual water comprises a small impurity in the components of the compositions of this disclosure.

The term "minimal residual water" means that the compositions of this disclosure include less than about 5% (wt. % or vol. %) residual water, less than about 4% (wt. % or vol. %) residual water, less than about 3% (wt. % or vol. %) residual water, less than about 2% (wt. % or vol. %) residual water, less than about 1% (wt. % or vol. %) residual water, less than about 0.5% (wt. % or vol. %) residual water, less than about 0.1% (wt. % or vol. %) residual water, less than about 0.05% (wt. % or vol. %) residual water, less than about 0.01% (wt. % or vol. %) residual water, less than about 0.005% (wt. % or vol. %) residual water, or less than about 0.001% (wt. % or vol. %) residual water.

The term "low moisture" means that the compositions only include residual water found in the components used to make the compositions of this disclosure.

The term "targeted manner" or "targeted release" means that one or more biologically active agents targeted for release into a desired biological environment.

The term "pH dependent manner" or "pH dependent release" means that one or more biologically active agents for release into a desired biological pH environment. That is, the compositions release one or more biologically active agents based on the pH of the biological environment. The carriers of the present disclosure operate to modify, alter, change, or augment chemical and/or physical characteristics of the one or more biologically active agents by providing an immiscible/different environment compared to an aqueous biofluid such as blood, gastric fluids, duodenal fluids, small intestinal fluids, large intestinal fluids, vaginal fluids, rectal solids/fluids, or any other biofluid setting up a situation where the active agent is free to partition between the two immiscible environments. Additionally, properties of the carriers of this disclosure such as viscosity, lipophilicity, hydrophobicity, dispersibility, dispensability, softening temperature, melting temperature, etc. also act to modify, alter, change, or augment the rate of partitioning of the one or more biologically active agents by sequestering the one or more biologically active agents in the immiscible carrier until the carrier matrix is dispersed to small enough particles to facilitate mass transfer from the immiscible carrier to the biofluid. For solid active agents sequestered in a carrier matrix of this disclosure, an added reduction in partitioning rate ensues because the solid must dissolve out of the matrix as the particle size of the matrix reduces in the biofluid due to mechanic actions of the tissue and/or organ and/or due to biochemical processes occurring in the tissue and/or organ. Thus, the pH of the biofluid changes the rate at which the immiscible carrier matrix disperses in the biofluid and the mass transfer rates of the one or more biologically active agents out of the carrier matrix. For weak acid active agents and weak base active agents, the carrier may be designed to reduce release of the active agent until the pH of the biofluid is at or near (within about 1 pH unit or less) of the pKa or pKb of the active agent. For a weak acid active agent, the carrier reduces release of the active agent in low pH environments such as in gastric fluid, which showing increased release in pH environments at or near (within about 1 pH unit or less) of the pKa of the weak acid active agent.

The term "one or more", "at least one", "one . . . or a plurality of . . . " all mean a singular or more than one articles, components, ingredients, devices, etc.

The term "active agent" or "biologically active agent" or "active ingredient" or "biologically active ingredient", which may be abbreviated as BAI or BAIs, means any pharmaceutical agent or active pharmaceutical ingredients (API) and/or any nutraceutical agent as defined by the United State Food and Drug Administration (FDA).

The term "pharmaceutical agent" or "active pharmaceutical ingredients (APIs)" means any compound or composition that has been or will be approved for human, mammal, and/or animal administration for treating some malady, disease, syndrome, dysfunction, etc.

The term "nutraceutical agent" means any compound or composition for human, mammal, and/or animal administration for nutritional supplementation or other uses.

The term "weak acid active agents or ingredients", "weak acid biologically active agents", "weak base active agents or ingredients", or "weak base biologically active agents or ingredients" or "weak acid or base active pharmaceutical ingredients (APIs)" are active agents that are only partially ionized in aqueous solutions and the extent of ionization depends on the pH of the aqueous solution.

The term "anti-inflammatory drugs" mean any of a variety of drugs that reduce or inhibit inflammation in tissue, organs, or the like. Anti-inflammatory drugs including non-steroidal, anti-inflammatory drugs (COX1 and/or COX2 inhibitors), drugs for treating irritable bowel disorder or disease (IBD) represents a family of ulcerative diseases including Ulcerative Colitis and Crohn's Disease that affect the colon and distal small bowel, and other drugs that have anti-inflammatory activity in humans, mammals and/or animals. The present targeted delivery systems may also find utility in treating conditions evidencing a pH imbalance in animal, mammals, and human GI, urinary, and reproductive tracts.

The term "NSAID" refers any of a variety of drugs generally classified as non-steroidal, anti-inflammatory drugs, including, without limitation, ibuprofen, piroxicam, salicylate, aspirin, naproxen, indomethacin, diclofenac, COX2 inhibitors or any mixture thereof.

The term "oil" means any of numerous animal oils, vegetable oils, synthetic oils, animal fats, vegetable fats or synthetic fats that are generally slippery, combustible, viscous, liquid, or liquefiable at room temperature, soluble in various organic solvents such as ether, but not soluble in or miscible with water.

The term "lipid" means any organic compounds including fats, oils, waxes, sterols, monoglycerides, di-glycerides, triglycerides, fatty acid esters, or the like that are insoluble in water but soluble in nonpolar organic solvents and are oily to the touch.

The term "neutral lipid" (NL) as used in this application is not the traditional meaning known in the art, but here means an uncharged, non-phosphoglyceride lipid, which includes triglycerides, fatty acid esters, other biocompatible oils, or any mixture thereof. In some embodiments, the term neutral lipid refers exclusively to triglycerides (TGs).

The term "phospholipid" (PL) means any naturally occurring or synthetic phospholipid.

The term "zwitterionic phospholipid" means any phospholipid bearing a positive and an negative charge at biological pHs including, without limitation, phosphatidylcholine, phosphatidylserine, phosphalidylethanolamine, sphingomyelin and other ceramides, as well as various other zwitterionic phospholipids.

The term "biocompatible" means being compatible with living cells, tissues, organs, or systems, and posing no, minimal, or acceptable risk of injury, toxicity, or rejection by the immune system of a human, mammal, or animal.

The term "biocompatible agent" means any compound that is compatible with living cells, tissues, organs, or systems, and posing no risk of injury, toxicity, or rejection by the immune system of a human, mammal, or animal. There are a number of classes of biocompatible agents suitable for use in the disclosure including hydrophobic biocompatible agents, biocompatible oils, pH dependent biocompatible release agents such as biocompatible fatty acids or biocompatible fatty polyacids, and lecithin oils.

The term "biocompatible oil" means any oil that is compatible with living cells, tissues, organs, or systems, and posing no risk of injury, toxicity, or rejection by the immune system of a human, mammal, or animal. In certain embodiments, biocompatible oils are any oil that has been approved for human consumption by the FDA or other governmental agents or approved for of a human, mammal, or animal consumption, where the compound may be a solid or liquid at room temperature or biological temperatures. In certain embodiments, the term means any oil that is a fluid at biological temperatures. In other embodiments, the term means any oil that is a fluid at room temperature. In the disclosure, when oils are referenced, the term should be interpreted as biocompatible oils.

The term "biocompatible fatty acid or biocompatible free fatty acid" means any fatty acid or free fatty acid (FFA) that is compatible with living cells, tissues, organs, or systems of a human, mammal, or animal. In certain embodiments, biocompatible fatty acids are mono-carboxylic acids. In certain embodiments, the biocompatible fatty acids have at least 8 carbon atoms. In other embodiments, the biocompatible fatty acids have at least 10 carbon atoms. In other embodiments, the biocompatible fatty acids have at least 12 carbon atoms. In other embodiments, the biocompatible fatty acids have at least 14 carbon atoms. In other embodiments, the biocompatible fatty acids have at least 16 carbon atoms. In other embodiments, the biocompatible fatty acids have at least 18 carbon atoms. In certain embodiments, the biocompatible fatty acids may be unsaturated fatty acids. In certain embodiments, the biocompatible fatty acids may be saturated fatty acids. In certain embodiments, the biocompatible fatty acids may be a mixture of saturated and unsaturated fatty acids. The term "free fatty acid" is used sometimes as a term to fully distinguish between a fatty acid (a carboxylic acid) and a fatty acid ester, a mono-glyceride, di-glyceride, and triglyceride. Again, the terms fatty acid or free fatty acid are used, the terms should be interpreted as biocompatible fatty acid or biocompatible free fatty acid.

The term "biocompatible fatty acid ester" means any fatty acid ester that is compatible with living cells, tissues, organs, or systems of a human, mammal, or animal. In certain embodiments, the biocompatible carboxylic acid esters are esters of mono-alcohols or polyols. Again, the term fatty acid ester is used, the term should be interpreted as biocompatible fatty acid ester.

The term "biocompatible fatty acid salt" means any salt of a biocompatible fatty acid. In certain embodiments, the salts are salts of mono-carboxylic fatty acids. Again, if the term fatty acid salt is used, the term should be interpreted as biocompatible fatty acid salt.

The term "biocompatible fatty poly acids" means any biocompatible compound having more than one carboxylic acid moiety per compound that is compatible with living cells, tissues, organs, or systems of a human, mammal, or animal. In certain embodiments, the biocompatible poly acids have at least 8 carbon atoms. In other embodiments, the biocompatible poly acids have at least 10 carbon atoms. In other embodiments, the biocompatible poly acids have at least 12 carbon atoms. In other embodiments, the biocompatible poly acids have at least 14 carbon atoms. In other embodiments, the biocompatible poly acids have at least 16 carbon atoms. In other embodiments, the biocompatible fatty acids have at least 18 carbon atoms. In certain embodiments, the biocompatible fatty acids may be unsaturated fatty acids. In certain embodiments, the biocompatible fatty acids may be saturated fatty acids. In certain embodiments, the biocompatible fatty acids may be a mixture of saturated and unsaturated fatty acids. Again, the term fatty acid poly acids should be interpreted as biocompatible fatty acid poly acids.

The term "lecithin" means a yellow-brownish fatty substances derived from plant or animal and that is defined as complex mixture of acetone-insoluble phosphatides, which consist chiefly of phosphatidylcholine, phosphatidylethanolamine, phosphatidylserine, and phosphatidylinositol, combined with various amounts of other substances such as triglycerides, fatty acids, and carbohydrates, as separated from the crude vegetable oil source. It contains not less than 50.0% of acetone-insoluble matter. In certain embodiments, the lecithin may comprise lipids esterified with unsaturated fatty acid side chains. In other embodiments, the lecithin may be comprised of lipids with saturated lipids. In other embodiments, the lecithin may be comprised of lipids with mixtures thereof.

The term "crude lecithin" means a lecithin containing having about 10-15 wt. % phosphatidylcholine.

The term "semi crude or triple strength lecithin" means a lecithin where the phosphatidylcholine content has been increased to 35 wt. % to about 50 wt %.

The term "lecithin oil" means a liquid lecithin where lecithin is solubilized in oil and/or a free fatty acid. In certain embodiments, this lecithin oil is a semi crude or triple strength lecithin solubilized in a triglyceride and/or a free fatty acid.

The term "a purified phospholipid" means a naturally extracted or synthetic phospholipid having a purity above at least 90 wt. % of phospholipids, a single compound, or a class of closely related phospholipids such as phosphatidylcholine, phosphatidylethanol amine, dipalmitoylphosphatidylcholine (DPPC), or other similar phospholipids. Purified phospholipids are not lecithin, but may be derived from lecithin through extraction and purification.

The term "targeted biocompatible release agent" or "targeted release agent" means an agent that controls the release of one or more active agents in a targeted manner, i.e., release the active agents into a particular tissue or organ depending on the tissue or organ's physiological environment.

The term "pH dependent biocompatible release agent" or "pH dependent release agent" means a targeted release agent that controls the release of one or more active agents in a pH dependent manner.

The term "carrier" means a composition that is a base for active agents such as pharmaceutical and/or nutraceutical agents.

The term "hydrophobic carrier" means a composition that is a base for active agents such as pharmaceutical and/or nutraceutical agents, where the carrier including one or more or at least one hydrophobic biocompatible agents and where the carrier is immiscible in water.

The term "oil-based carrier" means an oil-based composition that is a base for active agents such as pharmaceutical and/or nutraceutical agents. The oil-based carriers comprise one or more biocompatible oils and/or biocompatible hydrophobic agents and is a water immiscible.

The term "internal administration", "internally administered" or "parenteral administration" means any non-enteral means of administration, but is generally interpreted as relating to injecting directly into the body, bypassing the skin and mucous membranes. The common parenteral routes are intramuscular (IM), subcutaneous (SC) and intravenous (IV).

The term "enteral administration" means any non-parenteral administration methods including oral administration (via the mouth), sublingual/buccal administration, rectal/vaginal administration, inhalation/inhaler administration, and/or topical administration.

EXPERIMENTS OF THE DISCLOSURE

Example 1

This example illustrates the change in the form of a composition of this disclosure comprising a carrier including a fatty acid and a triglyceride as the composition is first placed in simulated gastric fluid, a low pH environment having a pH less than pH 3, second a base is added to raise the pH to a high pH environment having a pH of 7, and third an acid is added to lower the pH back to a pH less than pH 3.

1 gram of oleic acid and 9 grams of soybean oil is added to a beaker and stirred with a magnetic stirrer for 1 minute.

Figure 2:
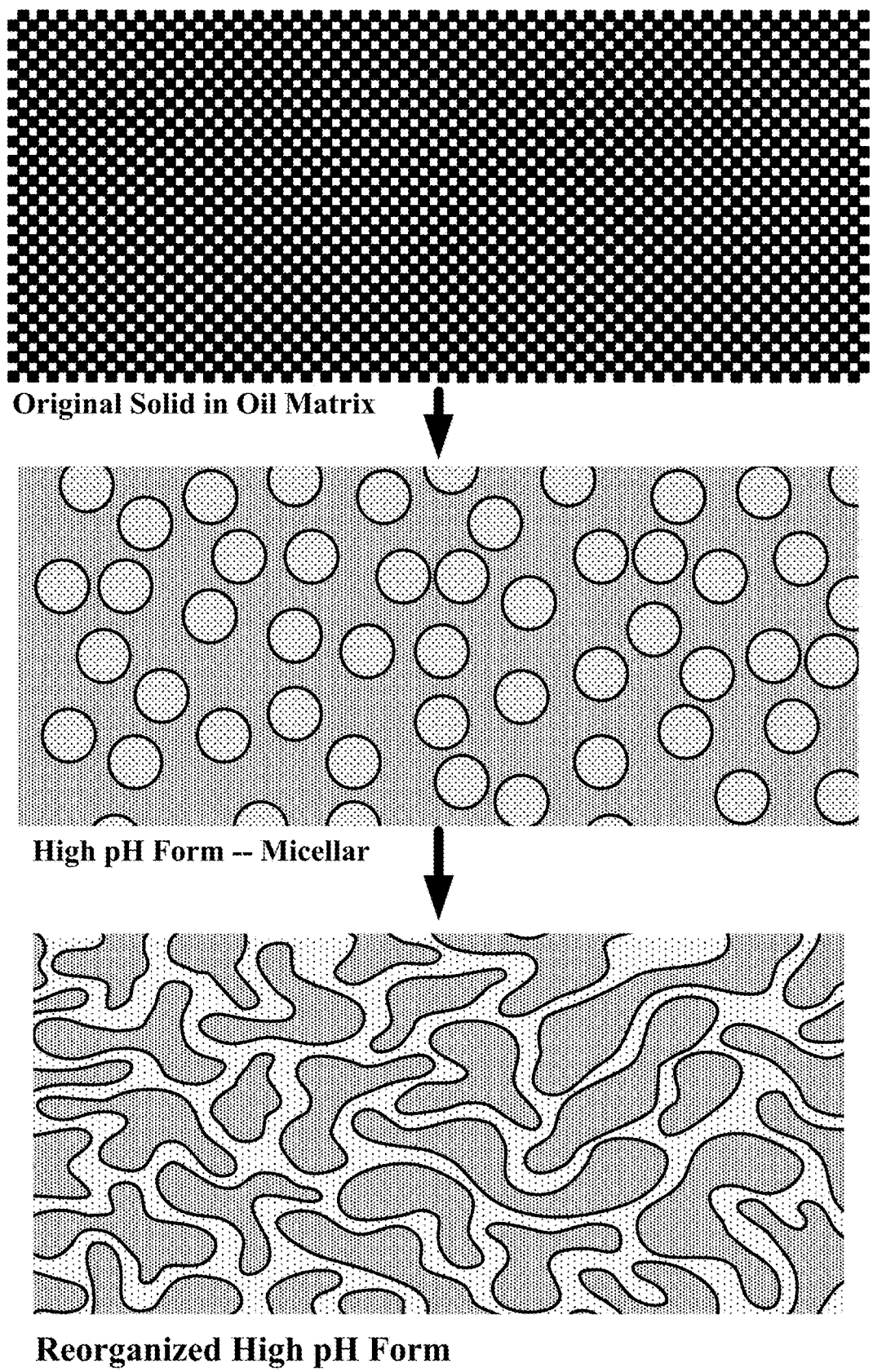
FIG. 2 illustrates matrix changes from the composition in its original form as a solid-in-oil suspension to a micellar solution, which is the form the composition likely takes when the composition proceeds from the stomach to the duodenum. The composition then reforms into oil globules distributed in gastric fluid. The globules may coalesce into a single continuous or into a semi-continuous phase. Again, the concentration of BAI is shown by the dot pattern shading: lower dot pattern shading for lower BAI concentration and higher dot pattern shading for higher BAI concentration. The BAI concentrations are likely controlled by partitioning, but when the free fatty acids become deprotonated, the free fatty acids are converted into anionic surfactants to stabilize the micelles.

5 grams of the composition is added to a beaker equipped with a magnetic stirrer and 50 mL of simulated gastric fluid is added with stirring. It is expected that the composition does not distribute in the simulated gastric fluid. To this material, a 1 N solution of sodium hydroxide is added slowly to bring the pH up to about pH 7 with stirring. Raising the pH to pH 7 gives rise to a change in the carrier in a high pH environment. To this material, a 1 N solution of hydrochloride acid is added slowly until the pH is lowered to the pH of the simulated gastric fluid. It is expected that the carrier will reorganize. Thus, a carrier comprising a sufficient amount of a fatty acid in a triglyceride is capable of reorganization in a low pH environment, here simulated gastric fluid. FIGS. 1 and 2 are designed to illustrate one possible sequence of changes the carriers would undergo in transitioning from a low pH environment to a high pH environment and back to a low pH environment. The examples included hereinbelow include photographs of actual changes in the compositions as they transition from a low pH environment to a high pH environment and back to a low pH environment evidencing the nature of the initial form, the high pH form and the reconstituted form, which may or may not resemble the illustration of FIGS. 1 and 2

Example 2

This example illustrates the change in the form of a composition of this disclosure comprising a carrier including a fatty acid and a triglyceride as the composition is first placed in simulated gastric fluid, a low pH environment having a pH less than pH 3, second a base is added to raise the pH to a high pH environment having a pH of 7, and third an acid is added to lower the pH back to a pH less than pH 3.

1 gram of oleic acid and 9 grams of soybean oil is added to a beaker and stirred with a magnetic stirrer for 1 minute.

5 grams of the composition is added to a beaker equipped with a magnetic stirrer and 50 mL of simulated gastric fluid is added with stirring. It is expected that the composition does not distribute in the simulated gastric fluid. To this material, a 1 N solution of sodium hydroxide is added slowly to bring the pH up to about pH 7 with stirring. Raising the pH to pH 7 gives rise to a change in the carrier in a high pH environment. To this material, a 1 N solution of hydrochloride acid is added slowly until the pH is lowered to the pH of the simulated gastric fluid. It is expected that the carrier will reorganize. To this solution is added 10 grams of powdered aspirin and the amount of aspirin in the simulated gastric fluid and reorganized carrier are measured showing that the aspirin partitions between the reorganized carrier and the simulated gastric fluid. Thus, a carrier comprising a sufficient amount of a fatty acid in a triglyceride is capable of reorganization and absorption of a BAI from the low pH fluid, here simulated gastric fluid.

Example 3

This example illustrates the change in the form of a composition of this disclosure comprising a carrier including a fatty acid and a triglyceride and aspirin in a 1:1 weight ratio as the composition is first placed in simulated gastric fluid, a low pH environment having a pH less than pH 3, second a base is added to raise the pH to a high pH environment having a pH of 7, and third an acid is added to lower the pH back to a pH less than pH 3.

1 gram of oleic acid, 9 grams of soybean oil, and 10 grams of aspirin powder is added to a beaker and stirred with a magnetic stirrer for 1 minute.

5 grams of the composition is added to a beaker equipped with a magnetic stirrer and 50 mL of simulated gastric fluid is added with stirring. It is expected that the composition does not distribute in the simulated gastric fluid. To this material, a 1 N solution of sodium hydroxide is added slowly to bring the pH up to about pH 7 with stirring showing the change in the carrier in a high pH environment and the release of aspirin into the high pH environment. To this material, a 1 N solution of hydrochloride acid is added slowly until the pH is lowered to the pH of the simulated gastric fluid. The carrier then reorganizes and the amount of aspirin in the simulated gastric fluid and reorganized carrier are measured showing that the aspirin partitions between the reorganized carrier and the simulated gastric fluid. Thus, a carrier comprising a sufficient amount of a free fatty acid in a triglyceride is capable of reorganization/reassembly in a low pH environment after BAI release in a high pH environment and the reorganized carrier is capable of reabsorption of a BAI from the low pH fluid, here simulated gastric fluid.

Example 4

This example illustrates the construction of a set of experiments designed to determine the influence of free fatty acid melting point, triglyceride melting point, nonionic surfactants and nonionic surfactant melting point has on pH dependent carrier BAI release, pH dependent carrier reorganization, reassembly, organization, or assembly and carrier BAI absorption upon reorganization, reassembly, organization, or assembly after the carrier transitions from a low pH environment, to a high pH environment, and back to a low pH environment.

The experiments are set forth in the following tables, Table X and Table XI. Table X lists the reagents to be tested and their melting point when available. Table XI tabulates the weight percentages of the reagents used in the each test sample.

TABLE X

| Reagents to Be Tested | | | |
|---|---|---|---|
| Acid | Triglyceride | Fatty Acid Methyl Esters | Nonionic Surfactant |
| oleic acid (OA) (mp = 16° C.) | soybean oil (SBO) (mp = −16° C.) | methyl linolenate (ML) (mp = −52° C.) | sorbitan monooleate (SMO) (liquid) |
| lauric acid (LA) (mp = 44° C.) | olive oil (OO) (mp = −6° C.) | methyl oleate (MO) (mp = −20° C.) | sorbitan trioleate (STO) (liquid) |
| stearic acid (SA) (mp = 70° C.) | palm oil (PO) (mp = 35° C.) | methyl palmitate (MP) (mp = 30.5° C.) | sorbitan tristearate (STS) (mp = 53° C.) |

TABLE XI

| Proposed Experiments Reagents Expressed in Percent Weight | | | | | | | | | | | | |
|---|---|---|---|---|---|---|---|---|---|---|---|---|
| run | OA | LA | SA | SBO | OO | PO | ML | MO | MP | SMO | STO | STS |
| 1 | 10 | 10 | 0 | 80 | 0 | 0 | 0 | 0 | 0 | 0 | 0 | 0 |
| 2 | 10 | 0 | 10 | 80 | 0 | 0 | 0 | 0 | 0 | 0 | 0 | 0 |
| 3 | 0 | 10 | 10 | 80 | 0 | 0 | 0 | 0 | 0 | 0 | 0 | 0 |
| 4 | 6.7 | 6.6 | 6.6 | 80 | 0 | 0 | 0 | 0 | 0 | 0 | 0 | 0 |
| 5 | 20 | 0 | 0 | 40 | 40 | 0 | 0 | 0 | 0 | 0 | 0 | 0 |
| 6 | 20 | 0 | 0 | 40 | 0 | 40 | 0 | 0 | 0 | 0 | 0 | 0 |
| 7 | 20 | 0 | 0 | 0 | 40 | 40 | 0 | 0 | 0 | 0 | 0 | 0 |
| 8 | 20 | 0 | 0 | 26.7 | 26.6 | 26.6 | 0 | 0 | 0 | 0 | 0 | 0 |
| 9 | 20 | 0 | 0 | 70 | 0 | 0 | 10 | 0 | 0 | 0 | 0 | 0 |

TABLE XII

| Proposed Experiments Reagents Expressed in Percent Weight | | | | | | | | | | | | |
|---|---|---|---|---|---|---|---|---|---|---|---|---|
| run | OA | LA | SA | SBO | OO | PO | ML | MO | MP | SMO | STO | STS |
| 10 | 20 | 0 | 0 | 70 | 0 | 0 | 0 | 10 | 0 | 0 | 0 | 0 |
| 11 | 20 | 0 | 0 | 70 | 0 | 0 | 0 | 0 | 10 | 0 | 0 | 0 |
| 12 | 20 | 0 | 0 | 70 | 0 | 0 | 6.7 | 6.6 | 6.6 | 0 | 0 | 0 |
| 13 | 20 | 0 | 0 | 70 | 0 | 0 | 0 | 0 | 0 | 10 | 0 | 0 |
| 14 | 20 | 0 | 0 | 70 | 0 | 0 | 0 | 0 | 0 | 0 | 10 | 0 |
| 15 | 20 | 0 | 0 | 70 | 0 | 0 | 0 | 0 | 0 | 0 | 0 | 10 |
| 16 | 20 | 0 | 0 | 70 | 0 | 0 | 0 | 0 | 0 | 6.7 | 6.6 | 6.6 |

Example 5

This example illustrates a designed set of experiments to illustrate the influence of polyacids on the assembly of carrier that transition from a low pH environment to a high pH environment and back.

The experiments are set forth in the following tables, Table XIII and Table XIV. Table XIII lists the reagents to be tested and their melting point when available. Table XIV tabulates the weight percentages of the reagents used in each test run.

TABLE XIII

Reagents to Be Tested

| Acid | Triglyceride | Poly Acids | Nonionic Surfactant |
|---|---|---|---|
| oleic acid (OA) | soybean oil (SBO) | Glutaric acid (GA)<br>EUDRAGIT ® L (EL)*<br>EUDRAGIT ® E (EE)**<br>HPMC-P | sorbitan trioleate (STO) |

*EUDRAGIT ® L: poly(methacrylic acid-co-methyl methacrylate)
**EUDRAGIT ® E: copolymer of dimethylaminoethyl methacrylate, butyl methacrylate, and methyl methacylate

TABLE XIV

Proposed Experimental Reagents Expressed in Weight Percent

| run | OA | SBO | GA | EL | EE | HPMC-P | STO |
|---|---|---|---|---|---|---|---|
| 1 | 20 | 80 | 0 | 0 | 0 | 0 | 0 |
| 2 | 20 | 70 | 10 | 0 | 0 | 0 | 0 |
| 3 | 20 | 70 | 0 | 10 | 0 | 0 | 0 |
| 4 | 20 | 70 | 0 | 0 | 10 | 0 | 0 |
| 5 | 20 | 70 | 0 | 0 | 0 | 10 | 0 |
| 6 | 20 | 70 | 2.5 | 2.5 | 2.5 | 2.5 | 0 |
| 7 | 20 | 70 | 5 | 0 | 0 | 0 | 5 |

TABLE XV

Proposed Experimental Reagents Expressed in Weight Percent

| run | OA | SBO | GA | EL | EE | HPMC-P | STO |
|---|---|---|---|---|---|---|---|
| 8 | 20 | 70 | 0 | 5 | 0 | 0 | 5 |
| 9 | 20 | 70 | 0 | 0 | 5 | 0 | 5 |
| 10 | 20 | 70 | 0 | 0 | 0 | 5 | 5 |
| 11 | 20 | 60 | 2.5 | 2.5 | 2.5 | 2.5 | 5 |

Example 6

This example illustrates whether the compositions of EXAMPLE 4 once reorganized, reassembled, organized, or assembled after the carrier transitions from a low pH environment, to a high pH environment, and back to a low pH environment, absorb aspirin via partitioning away from the simulated gastric fluid.

Example 7

This example illustrates whether the compositions of EXAMPLE 5 once reorganized, reassembled, organized, or assembled after the carrier transitions from a low pH environment, to a high pH environment, and back to a low pH environment, absorb aspirin via partitioning away from the simulated gastric fluid.

Example 8

This example illustrates the preparation of a set of examples designed to determine the relative concentrations of carrier ingredient to simultaneously optimize pH dependent BAI release and carrier reassembly or reformulation due to duodenal reflux. Each ingredient is designed to serve competing strategies including sacrificial agents, stabilization agents, and improved hydrophobic characteristic upon reassembly or reformulation in a low pH environment.

TABLE XVI

| Ingredient | wt. % | wt. % | wt. % | wt. % | wt. % | wt. % | wt. % | wt. % | wt. % |
|---|---|---|---|---|---|---|---|---|---|
| oleic acid | 20 | 30 | 40 | 40 | 20 | 40 | 20 | 35 | 17.5 |
| stearic acid | 5 | 0 | 0 | 0 | 0 | 0 | 0 | 0 | 0 |
| palmitic acid | 5 | 10 | 0 | 0 | 20 | 0 | 20 | 0 | 17.5 |
| a polymer including at least 20% acrylic acid remainder ethylene | 5 | 5 | 10 | 10 | 10 | 0 | 0 | 0 | 0 |
| soybean oil | 40 | 35 | 40 | 20 | 40 | 60 | 30 | 55 | 27.5 |
| coconut oil | 10 | 10 | 0 | 20 | 0 | 0 | 30 | 0 | 27.5 |
| phospholipid | 5 | 0 | 0 | 0 | 0 | 0 | 0 | 0 | 0 |
| lower MW nonionic surfactant | 5 | 5 | 5 | 5 | 5 | 0 | 0 | 5 | 5 |
| higher MW nonionic surfactant | 5 | 5 | 5 | 5 | 5 | 0 | 0 | 5 | 5 |
| Totals | 100 | 100 | 100 | 100 | 100 | 100 | 100 | 100 | 100 |

Experiments Designed to Simulate Duodenal Reflux and to Test Reconstitution and API Reabsorption The following examples describe a procedure to simulate duodenal reflux. Duodenal reflux is a process by which material from the stomach enters the duodenum through the pyloric sphincter and a portion of the material flows back into the stomach when the pyloric sphincter opens and closes. The simulated duodenal reflux procedure involves subjecting a sample of a suspension of an API in an oil based carrier to a pH cycle comprising adding the sample to an aqueous 0.1 N HCl solution having a pH of about pH 1 (simulated gastric fluid) with stirring, adding NaOH to the mixture with stirring to raise the pH to about pH 7 (simulated duodenal fluid), and finally adding concentrated HCl to the mixture with stirring to lower the pH to about pH 1 (simulated gastric fluid). Photographs are taken during all stages of the procedure to document changes in the sample during pH cycling. Analytical samples are taken from the oil phase and the aqueous phase of each of the solutions to determine API concentrations in oil phase and the aqueous phase of each of the solutions. The analytical samples were subjected to UV analysis to measure API concentrations in each of the phases of the solutions. UV analysis is suitable for APIs that include UV detectable groups such as carbonyl groups, carboxylic acid group, aromatic rings, or other group susceptible to UV analysis, especially APIs that include aromatic rings. Aspirin, ibuprofen and omeprazole are APIs that include aromatic rings that make UV analysis straight forward. Proteins are also APIs that are amendable to UV analysis as most proteins include at least one of the aromatic ring containing amino acids phenylalanine, tryptophan, and tyrosine.

Example 9. Control Composition Preparation and pH Cycle Testing

This example illustrates the preparation of a sample of a control composition subject to the duodenal reflux procedure outlined above.

The control composition included the following ingredients:

TABLE XVII

| Ingredient | Quantity per Unit (mg) | Quantity (g) |
|---|---|---|
| Citric Acid Anhydrous Powder USP/EP | 7.48 | 7.48 |
| Lecithin | 15.78 | 15.82 |
| Oleic Acid NF/EP | 19.27 | 19.27 |
| Soybean Oil-IV | 41.62 | 41.65 |
| Total | 84.15 | 84.22 |

Control Composition Preparation Procedure

The control composition was prepared as follows:
1. Screen citric acid through a 40 mesh hand screen;
2. Add oleic acid, soybean oil, and lecithin into a beaker and heat the mixture while stirring with a stir bar on a hot plate until the mixture achieves visual uniformity;
3. Add citric acid to the mixture while stirring with the stir bar on the hot plate until the mixture achieves visual uniformity; and
4. Continue stirring the mixture during testing to maintain uniformity.

Control Composition pH Cycle Test Procedure

The control composition pH cycle test was performed as follows:
1. Place 10 grams of the control composition in a 150 mL beaker containing 100 mL of a 0.1 N HCl solution having a pH of about 1, simulated gastric fluid;
2. Observe and photograph the control composition in the pH 1 solution;
3. Add concentrated NaOH to the beaker with stirring while monitoring the pH with a pH meter until the pH is about 7, simulated duodenal fluid;
4. Observe and photograph the control composition in the pH 7 solution;
5. Add concentrated HCl to the beaker with stirring while monitoring the pH with the pH meter until the pH is about 1, back to the simulated gastric fluid; and
6. Observe and photograph the control composition in the pH 1 solution.

Example 10. Aspirin-Containing Composition Preparation and pH Cycle Testing

This example illustrates the preparation of a sample of an aspirin-containing composition subject to the duodenal reflux procedure outlined above.

The aspirin-containing composition included the following ingredients:

TABLE XVIII

| Ingredient | Quantity per Unit (mg) | Quantity (g) |
|---|---|---|
| Aspirin (ASA) | 81 | 81 |
| Citric Acid Anhydrous Powder USP/EP | 7.48 | 7.48 |
| Lecithin | 15.78 | 15.82 |
| Oleic Acid NF/EP | 19.27 | 19.27 |
| Soybean Oil-TV | 41.62 | 41.62 |
| Total | 165.15 | 165.19 |

Aspirin-Containing Composition Preparation Procedure

The aspirin-containing composition was prepared as follows:
1. Screen citric acid and aspirin (ASA) through a 40 mesh hand screen;
2. Add oleic acid, soybean oil, and lecithin into a 150 mL beaker and heat the mixture while stirring with a stir bar on a hot plate to until the mixture achieves visual uniformity;
3. Add citric acid to the mixture while stirring with the stir bar on the hot plate until the mixture achieves visual uniformity;
4. Add aspirin to the mixture while stirring with a Caframo mixer until the mixture achieves visual uniformity; and
5. Continue stirring the mixture during testing to maintain uniformity.

Aspirin-Containing Composition pH Cycle Test Procedure

The aspirin-containing composition pH cycle test was performed as follows:
1. Place 10 g of the aspirin-containing composition in a 150 mL beaker containing 100 mL of a 0.1 N HCl solution having a pH of about 1, simulated gastric fluid;
2. Observe and photograph the aspirin-containing composition in the pH 1 solution;
3. Collect a sample of the oil phase and the aqueous phase from the pH 1 solution for UV analysis;

4. Add concentrated NaOH to the beaker with stirring while monitoring the pH with a pH meter until the pH is about 7, simulated duodenal fluid;

5. Observe and photograph the aspirin-containing composition in the pH 7 solution;

6. Collect a sample of the oil phase and aqueous phase from the pH 7 solution for UV analysis;

7. Add concentrated HCl to the beaker with stirring while monitoring the pH with the pH meter until the pH is about 1;

8. Observe and photograph the aspirin-containing composition in the pH 1 solution, back to simulated gastric fluid; and 9. Collect a sample of the oil phase and aqueous phase from the pH 1 solution for UV analysis.

Photographs of Control and Aspirin-Containing Samples

Photographs of Mixing, pH Monitoring, and Temperature Monitoring

Figure 3:
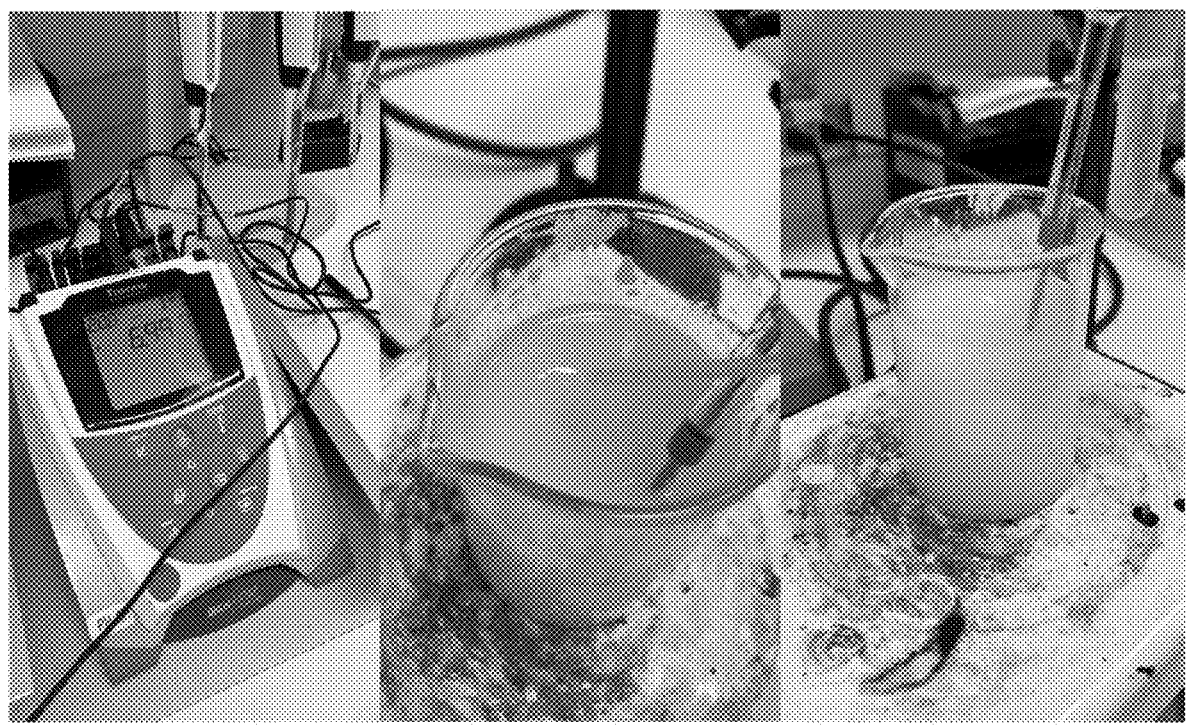
FIG. 3 depicts photographs illustrating the mixing, the temperature monitoring, and the pH monitoring of a sample undergoing a pH cycle.

Referring now to FIG. 3, photographs are shown the illustrate the mixing and monitoring procedures described above. FIG. 3 includes a photograph showing a pH meter and two photographs showing how the samples were mixed and how sample temperature and pH were monitored. Heating was controlled using a hot plate and monitored by a thermometer, and pH monitoring was monitored by the pH meter.

Photographs of Control Composition During pH Cycle

Figure 4:
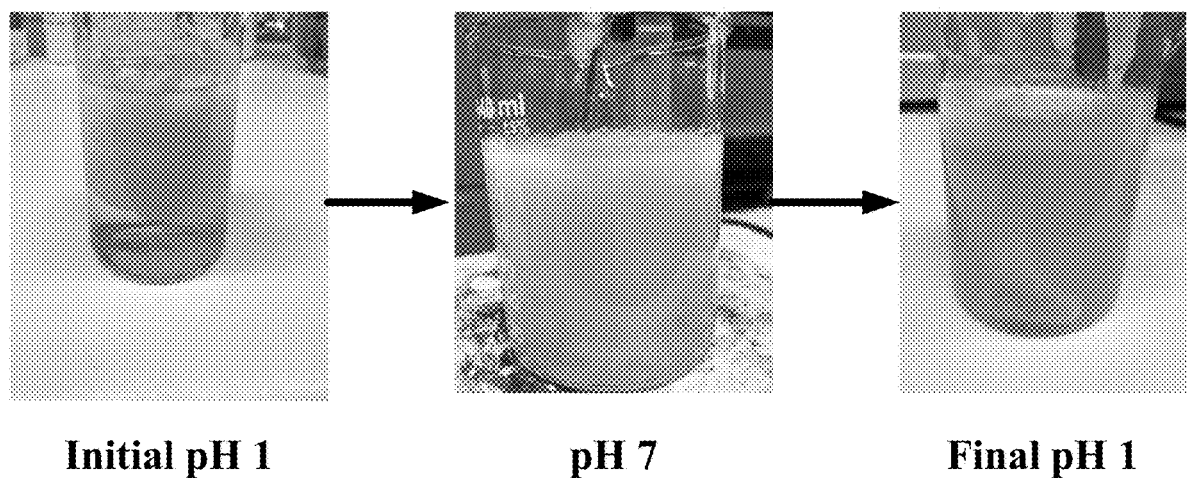
FIG. 4 depicts photographs of the control composition during a pH cycle simulating simulate duodenal reflux: the left photograph shows the control composition in the initial pH 1 solution (simulated gastric fluid), the middle photograph shows the control composition in the pH 7 solution (simulated duodenal fluid) after concentrated NaOH addition to the initial pH 1 solution, and the right photograph shows the control composition in the final pH 1 solution (simulated gastric fluid) after concentrated HCl addition to the pH 7 solution.

Referring now to FIG. 4, photographs show the control composition in an initial pH 1 solution (left photograph), in a pH 7 solution after concentrated NaOH addition to the initial pH 1 solution (middle photograph), and in a final pH 1 solution after concentrated HCl addition to the pH 7 aqueous solution (right photograph). The control composition is clearly immiscible in the initial pH 1 solution. When the pH is raised to pH 7, a change in the look of the control composition may be seen: compare the far left photograph to the middle photograph. At pH 7, the control composition appears to break apart in several oil phases, a lower density oil phase and a higher density oil phase and the aqueous phase appears slightly cloudy. The oil and aqueous phases still appear to be substantially immiscible in the pH 7 solution. When the pH of the pH 7 solution is lowered back to pH 1, the aqueous phase clarifies, while the oil phase now appears similar to its starting form.

Photographs of Aspirin-Containing Composition During pH Cycle

Figure 5:
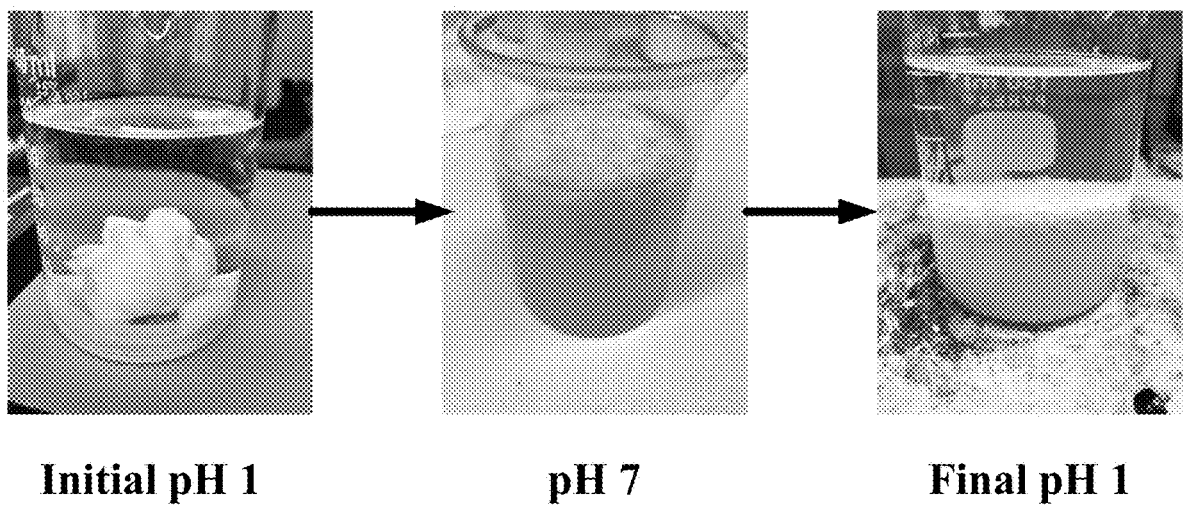
FIG. 5 depicts photographs of the aspirin-containing composition during a pH cycle simulating simulate duodenal reflux: the left photograph shows the aspirin-containing composition in the initial pH 1 solution (simulated gastric fluid), the middle photograph shows the aspirin-containing composition in the pH 7 solution (simulated duodenal fluid) after concentrated NaOH addition to the initial pH 1 solution, and the right photograph shows the aspirin-containing composition in the final pH 1 solution (simulated gastric fluid) after concentrated HCl addition to the pH 7 solution.

Referring now to FIG. 5, photographs show the aspirin-containing composition in an initial pH 1 solution, in a pH 7 solution after concentrated NaOH addition to the initial pH 1 solution, and in a final pH 1 solution after concentrated HCl addition to the pH 7 solution. Note that the aspirin-containing composition is denser than the initial pH 1 aqueous solution, a difference from the control composition. When the pH of the initial pH 1 solution is raised to pH 7, a change in the look of the aspirin-containing composition may be seen: compare the far left photograph to the middle photograph. At pH 7, the aspirin-containing composition is still immiscible in the aqueous phase, but now is less dense than the pH 7 aqueous phase and the aqueous phase of the pH 7 solution is slightly cloudy. When the pH of the pH 7 solution is lowered back to pH 1, the aqueous phase still slightly cloudy, while the oil phase appears lighter in color than at the start, but after sitting for a while, the oil phase gains back is normal color, but remains lighter than the final pH 1 aqueous phase.

Clearly, the control composition and the aspirin-containing composition maintain their essential immiscible in the aqueous phases during a pH cycle.

Figure 6:
FIG. 6 depicts photographs of the aspirin-containing composition during two pH 7 adjustment cycles.

Referring now to FIG. 6, photographs show the aspirin-containing composition after concentrated NaOH addition to raise the pH back to pH 7. The aqueous phase is still slightly cloudy, while the oil phase remains less dense than the aqueous solutions in both pH 7 solutions.

Referring now to FIG. 7, photographs show a comparison of various samples including from left to right: the control composition (Control) in the initial pH 1 solution, the aspirin-containing composition (ASA) in the pH 7 solution, the aspirin-containing composition (ASA) in the initial pH 1 aqueous solution, the aspirin-containing composition (ASA) in the first pH 7 solution, the aspirin-containing composition (ASA) in the final pH 1 solution, and the aspirin-containing composition (ASA) in the second pH 7 solution. In all cases, the pH 7 solutions are slightly cloudy, while the pH 1 aqueous solution are clear.

UV Analysis of Aspirin-Containing Samples

Aspirin (ASA) UV Analysis

The samples taken from the oil and aqueous phases during the pH cycling were analyzed using UV spectral analysis. Aspirin (ASA) is the only ingredient in the sample that includes an aromatic ring and has a distinct UV absorption; as aspirin is known to hydrolysis in water to salicylic acid (SA), SA was also analyzed. UV spectral analysis was used to determine the concentration of ASA and SA in the UV detection samples. The following table includes ASA/SA concentrations as determined by UV spectral analysis:

TABLE XIX

UV Aspirin (ASA) Phase Concentration Data in mg/mL

| Samples | pH of Solutions | | |
|---|---|---|---|
| | 1 (start) | 7 | 1 (end) |
| Oil Phase: ASA analysis | 0.8392 | 0.3182 | 0.6500 |
| Aqueous Phase: ASA analysis | 0.2092 | 0.3653 | 0.2751 |
| Oil Phase: SA analysis | 0.1013 | 0.0417 | 0.0780 |
| Aqueous Phase: SA analysis | 0.0042 | 0.1382 | 0.0231 |
| Oil Phase: ASA + SA analysis | 0.9405 | 0.3599 | 0.7280 |
| Aqueous Phase: ASA + SA analysis | 0.2135 | 0.5034 | 0.2982 |
| Total ASA + SA in both phases | 1.1539 | 0.8633 | 1.0262 |

Figure 8:
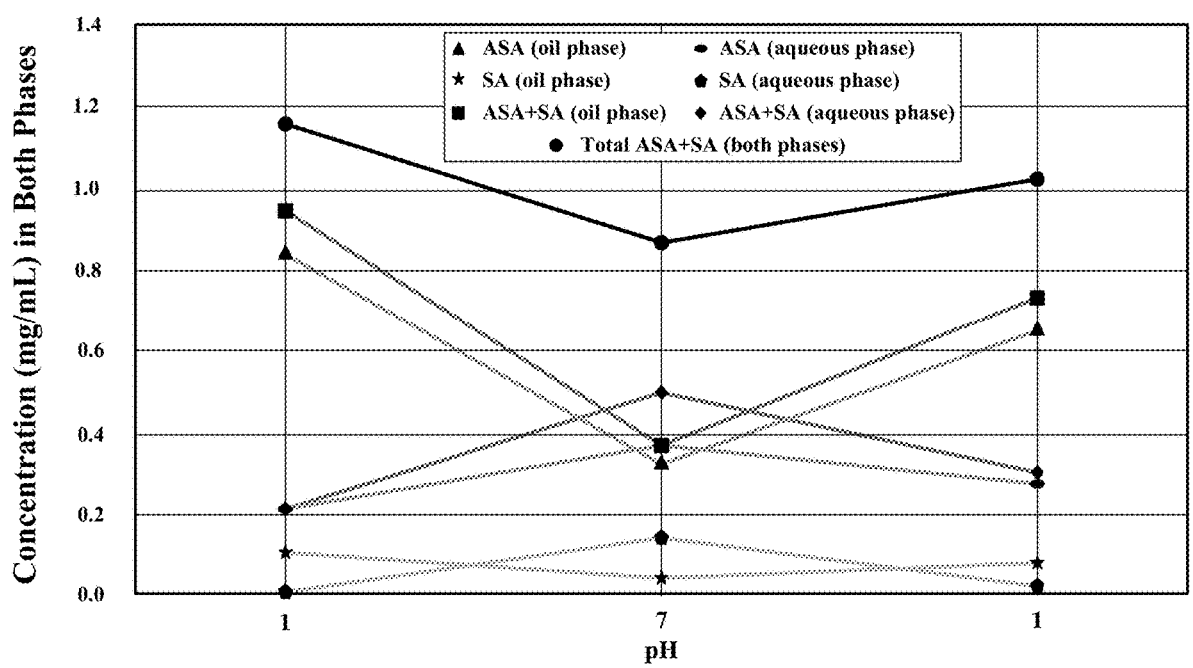
FIG. 8 depicts a plot of UV aspirin (ASA) and salicylic acid (SA) concentration values of the aspirin-containing composition during a pH cycles, showing release, reconstitution and reabsorption of aspirin.

Referring now to FIG. 8, a plot of the UV aspirin (ASA) and salicylic acid (SA) concentration values for the various phases of the aspirin-containing composition during the pH cycle experiment is shown. Initially, the ASA (aspirin) and SA (salicylic acid) are primarily in the oil phase with 0.9405 mg/mL (81.5%) in the oil phase compared to 0.2135 mg/mL (18.5%) in the aqueous phase. When the pH is raised to pH 7, the ASA (aspirin) and SA (salicylic acid) are present in the aqueous phase to a greater degree than in the oil phase with 0.5034 mg/mL (58.3%) in the aqueous phase compared to 0.3599 mg/mL (41.7%) in the oil phase. When the pH is lowered back to pH 1, a large amount of the ASA (aspirin) and SA (salicylic acid) from the aqueous phase is reabsorbed into the oil phase with 0.7280 mg/mL (70.9%) in the oil phase compared to 0.2982 mg/mL (29.1%) in the aqueous phase.

The inventors believe that this reconstitution and reabsorption is a contributing factor to the superior GI safety of the NSAID formulations of this disclosure. It appears that a sufficient amount of a free carboxylic acid in the carrier is responsible not only for the carrier's extreme hydrophobicity as evidenced that the carrier is immiscible in pH 1 aqueous solutions, where the API, here aspirin, is primarily present in the oil phase. The data also show that in the pH 7 solution, the API, aspirin here, is released into the aqueous phase, where a larger amount of aspirin is now present in the pH 7 aqueous phase. The data also clearly show that the API, aspirin here, is reabsorbed into the carrier when the pH is lowered back to pH of about 1 reducing the amount of API in the aqueous phase. These findings are consistent with the improved GI safety of the compositions of this disclosure including an effective amount of free carboxylic acids, as the reconstitution and reabsorption decreases aspirin concentration in the stomach during duodenal reflux.

Example 11. Ibuprofen-Containing Composition Preparation and pH Cycle Testing

This example illustrates the preparation of a sample of an ibuprofen-containing composition subject to the duodenal reflux procedure outlined above.

The ibuprofen-containing composition included the following ingredients:

TABLE XX

| Ingredient | Quantity per Unit (mg) | Quantity (g) |
|---|---|---|
| Ibuprofen (IBU) | 81 | 81 |
| Citric Acid Anhydrous Powder USP/EP | 7.48 | 7.48 |
| Lecithin | 15.78 | 16.04 |
| Oleic Acid NF/EP | 19.27 | 19.29 |
| Soybean Oil-IV | 41.62 | 41.62 |
| Total | 165.15 | 165.43 |

Ibuprofen-Containing Composition Preparation Procedure

The ibuprofen-containing composition was prepared as follows:
1. Screen citric acid and ibuprofen (IBU) through a 40 mesh hand screen;
2. Add oleic acid, soybean oil, and lecithin into a 150 mL beaker and heat the mixture while stirring with a stir bar on a hot plate to until the mixture achieves visual uniformity;
3. Add citric acid to the mixture while stirring with the stir bar on the hot plate until the mixture achieves visual uniformity;
4. Add ibuprofen to the mixture while stirring with a Caframo mixer until the mixture achieves visual uniformity; and
5. Continue stirring the mixture during testing to maintain uniformity.

Ibuprofen-Containing Composition pH Cycle Test Procedure

The ibuprofen-containing composition pH cycling was performed as follows:
1. Place 10 grams ibuprofen-containing composition in a 150 mL beaker including 100 mL of a 0.1 N HCl solution having a pH of about 1;
2. Observe and photograph the ibuprofen-containing composition in the pH 1 solution;
3. Collect a sample of the oil phase and the aqueous phase from the pH 1 solution for UV analysis;
4. Add concentrated NaOH to the beaker with stirring while monitoring the pH with a pH meter until the pH is about 7;
5. Observe and photograph the ibuprofen-containing composition in the pH 7 solution;
6. Collect a sample of the oil phase and aqueous phase from the pH 7 solution for UV analysis;
7. Add concentrated HCl to the beaker with stirring while monitoring the pH with a pH meter until the pH is about 1;
8. Observe and photograph the ibuprofen-containing composition in the pH 1 solution; and
9. Collect a sample of the oil phase and aqueous phase from the pH 1 solution for UV analysis.

Photographs of Ibuprofen-Containing Composition

Figure 9:
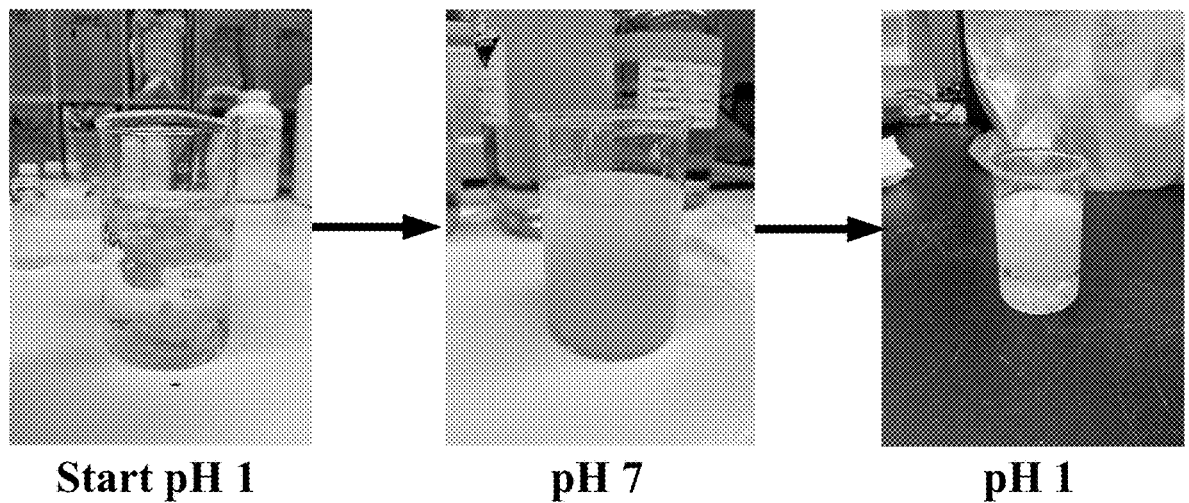
FIG. 9 depicts photographs of the ibuprofen-containing composition during a pH cycle.

Referring now to FIG. 9, photographs show the ibuprofen-containing sample in an initial pH 1 solution (left photograph), in the pH 7 solution after concentration NaOH addition to the initial pH 1 solution, (middle photograph), and in the final pH 1 solution after concentration HCl addition to the pH 7 solution (right photograph). The ibuprofen-containing composition is also clearly immiscible in the initial pH 1 solution. Note that a majority of the ibuprofen-containing composition is slightly less dense than the initial pH 1 solution. When the pH is raised to pH 7, a significant change in the look of the ibuprofen-containing composition may be seen: compare the left photograph to the middle photograph. At pH 7, the ibuprofen-containing composition appears to form a mixture of the oils phase dispersed in the aqueous phase similar to an emulsion. When the pH is lowered back to pH 1, the aqueous phase of the final pH 1 solution clarifies, while the oil phase appears to reconstitute into two phases, one less dense than the aqueous phase and one more dense than the aqueous phase.

Figure 10:
FIG. 10 depicts photographs of the ibuprofen-containing composition after undergoing a pH cycle after sitting for one day (Day 1) and for four additional days (Day 4).

Referring now to FIG. 10, photographs show the pH cycle ibuprofen-containing samples after 1 day and after 4 days. The day 4 photograph clearly show that the oil has reconstituted into two phases, one less dense than the aqueous phase and one more dense than the aqueous phase and the aqueous phase is clarified. Again, the photographs clearly show that the oil have is immiscible in the pH 1 solutions.

UV Analysis of Ibuprofen-Containing Composition

Ibuprofen (IBU) UV Analysis

The samples taken from the oil and aqueous phases during the pH cycling were analyzed using UV spectral analysis as aspirin (ASA) is the only group that absorbs UV light due to the presence of an aromatic ring. The following table includes the ASA UV results:

TABLE XXI

UV Ibuprofen (IBU) Phase Concentration Data in mg/mL and Percentages

| Solution | IBU in Less Dense Oil Phase | IBU in Aqueous Phase | IBU in Denser Oil Phase | IBU Total in Both Phases | Percent IBU in Oil Phase |
|---|---|---|---|---|---|
| pH 1 | 1.5918 | 0.0040 | | 1.5923 | 99.97% |
| pH 7 | 0.6373 | 0.5752 | | 1.2125 | 52.56% |
| pH 1 | 1.0010 | 0.2280 | 0.0255 | 1.2545 | 79.79% |

Figure 11:
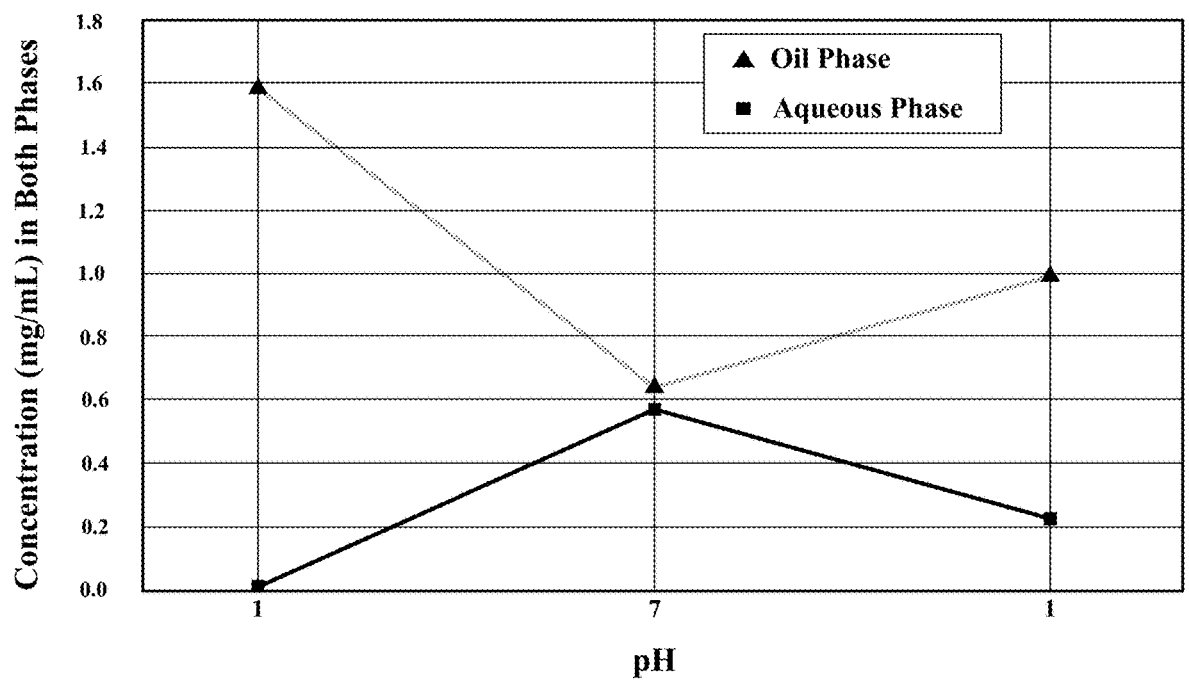
FIG. 11 depicts a plot of UV ibuprofen concentration values for the ibuprofen-containing composition during a pH cycle.

Referring now to FIG. 11, the UV ibuprofen concentration values for the ibuprofen-containing composition in the pH 1 solutions and the pH 7 solution during the pH cycle experiment. Initially, essentially all of the ibuprofen is in the oil phase: 1.5918 mg/mL (99.97%) of ibuprofen in the oil phase compared to 0.0040 mg/mL (0.03%) in the aqueous phase. When the pH is raised to pH 7, the ibuprofen partitions almost equally in the aqueous phase and the oil phase: 0.6373 mg/mL (52.56%) in the oil phase compared to 0.5752 mg/mL (47.44%) in the aqueous phase. When the pH is lowered back to pH 1, a large amount of the ibuprofen is reabsorbed into the oil phase: 1.0010 (79.79%) in the oil phase compared to 0.2280 (20.21%) in the aqueous phase.

Again, the inventors believe that this reconstitution and reabsorption is a contributing factor to the superior GI safety of carriers of this disclosure. It appears that a sufficient amount of a free carboxylic acid in the carrier is responsible not only for the carrier's extreme hydrophobicity as carrier is essentially immiscible in the initial pH 1 aqueous solution, where the API, here ibuprofen, is primarily present in the oil phase. The data also show that in the pH 7 solution, the API, ibuprofen here, is released into the aqueous phase, where almost equal amounts of ibuprofen are found in the two phases. The data also clearly show that the API, ibuprofen here, is reabsorbed into the carrier when the pH is lowered back to pH of about 1 reducing the amount of API in the aqueous phase. These findings are consistent with the improved GI safety of the compositions of this disclosure including an effective amount of free carboxylic acids.

Example 12. Omeprazole-Containing Composition Preparation and pH Cycle Testing This example illustrates the preparation of a sample of an omeprazole-containing composition subject to the duodenal reflux procedure outlined above.

The omeprazole-containing composition included the following ingredients:

TABLE XXII

| Ingredient | Quantity per Unit (mg) | Quantity (g) |
|---|---|---|
| Omeprazole (OZ) | 81 | 81 |
| Citric Acid Anhydrous Powder USP/EP | 7.48 | 7.48 |
| Lecithin | 15.78 | 16.04 |
| Oleic Acid NF/EP | 19.27 | 19.29 |
| Soybean Oil-IV | 41.62 | 41.62 |
| Total | 165.15 | 165.43 |

Omeprazole-Containing Composition Preparation Procedure

The omeprazole-containing composition was prepared as follows:
1. Screen citric acid and omeprazole (OZ) through a 40 mesh hand screen;
2. Add oleic acid, soybean oil, and lecithin into a 150 mL beaker and heat the mixture while stirring with a stir bar on a hot plate to until the mixture achieves visual uniformity;
3. Add citric acid to the mixture while stirring with the stir bar on the hot plate until the mixture achieves visual uniformity;
4. Add omeprazole to the mixture while stirring with a Caframo mixer until the mixture achieves visual uniformity; and
5. Continue stirring the mixture during testing to maintain uniformity.

Omeprazole-Containing Composition pH Cycle Test Procedure

The omeprazole-containing composition pH cycling was performed as follows:
1. Place 10 grams omeprazole-containing composition in a 150 mL beaker including 100 mL of a 0.1 N HCl solution having a pH of about 1;
2. Observe and photograph the omeprazole-containing composition in the pH 1 solution;
3. Collect a sample of the oil phase and the aqueous phase from the pH 1 solution for UV analysis;
4. Add concentrated NaOH to the beaker with stirring while monitoring the pH with a pH meter until the pH is about 7;
5. Observe and photograph the omeprazole-containing composition in the pH 7 solution;
6. Collect a sample of the oil phase and aqueous phase from the pH 7 solution for UV analysis;
7. Add concentrated HCl to the beaker with stirring while monitoring the pH with a pH meter until the pH is about 1;
8. Observe and photograph the omeprazole-containing composition in the pH 1 solution; and
9. Collect a sample of the oil phase and aqueous phase from the pH 1 solution for UV analysis.

Photographs of the Omeprazole-Containing Composition

Figure 12:
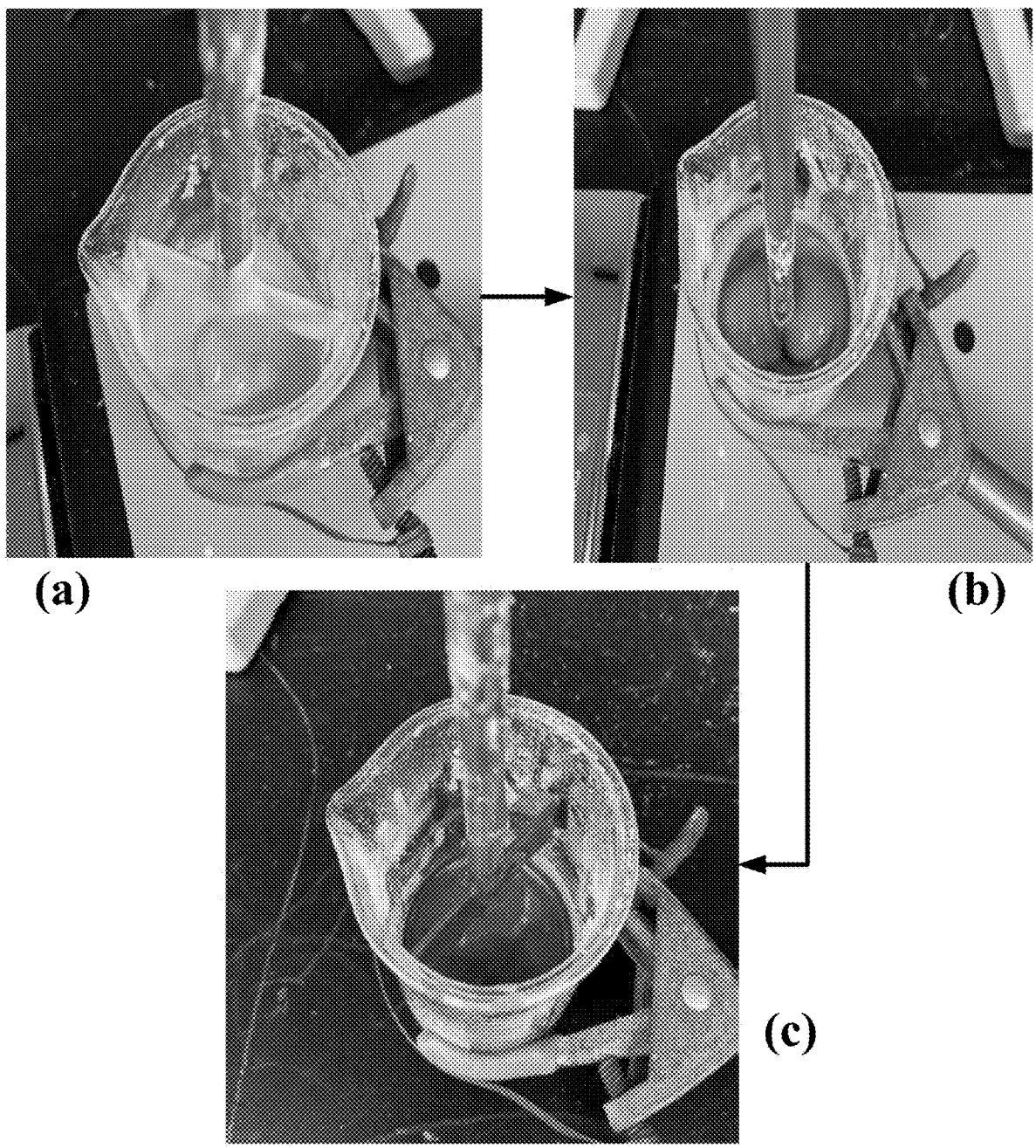
FIG. 12 depicts photographs of the preparation of the omeprazole-containing composition showing initial color and color change upon addition of citric acid.

Referring now to FIG. 12, photographs of the preparation of the omeprazole-containing composition. Photograph (a) shows omeprazole into the carrier to form the omeprazole-containing composition. Initially, the omeprazole-containing composition is a brown and upon citric acid addition, the omeprazole-containing composition begins to turn purple and after a little stirring turned deep purple. The inventors believe that the color change in due to the protonation of omeprazole. The inventors do not know why the color change happened only after citric acid addition as the matrix includes a large amount of oleic acid.

Referring now to FIG. 13, photographs of the omeprazole-containing composition after initial addition to the pH 1 solution, after pH adjustment of the pH 1 solution, and one minute after pH adjustment. Upon initial addition of the omeprazole-containing composition to the pH 1 solution, the omeprazole-containing composition sinks to the bottom and the aqueous phase turns brown. The initial pH of the solution was not at pH 1, but was at a pH about 2. The inventors believe that the rise in pH was due to the protonation of omeprazole. After adjusting the pH to 1, the solution turned darker, but after setting for about one minute, the omeprazole-containing composition is still at the bottom, and the aqueous phase is still brown.

Figure 14:
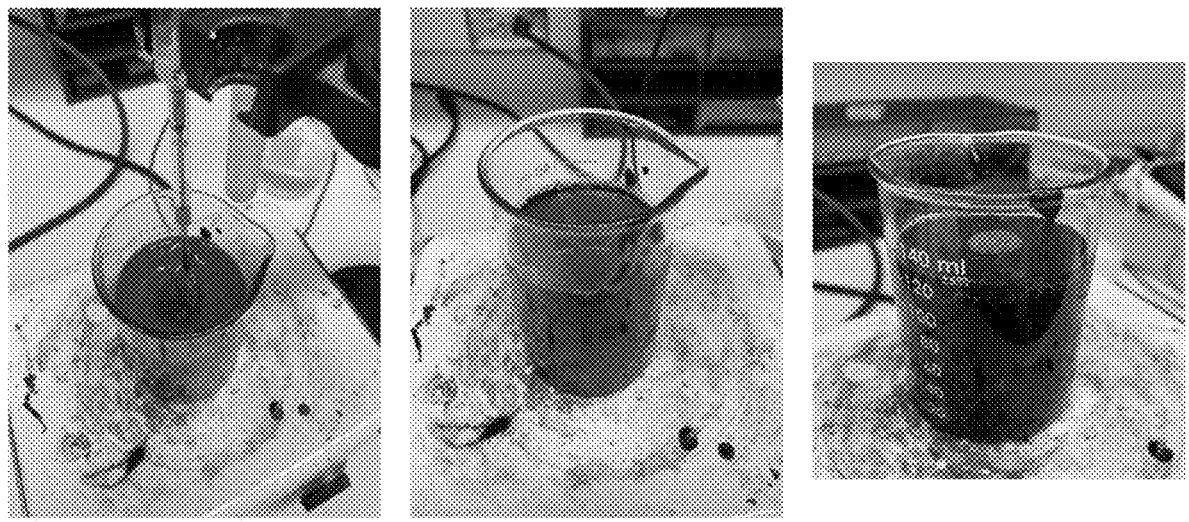
FIG. 14 depicts photographs of the omeprazole-containing composition in the pH 1 solution during concentrated NaOH addition to adjust the pH to pH 7.

Referring now to FIG. 14, photographs of the omeprazole-containing composition show the omeprazole-containing composition as the pH of the pH 1 solution is raised to pH 7. The solution turned purple with the oil phase distributed in the solution.

Referring now to FIG. 15, photographs of the control composition prior to addition to a solution (left photograph), the omeprazole-containing composition prior to addition to a solution (next photograph), the omeprazole-containing composition after addition to the pH 1 solution (next photograph), the omeprazole-containing composition after raising the pH to pH 7 (next photograph), and the omeprazole-containing composition after lowering the pH to pH 1 (next photograph): a pH cycle. The control composition is a light yellow oil. The omeprazole-containing composition is a deep purple. The omeprazole-containing composition after addition to the pH 1 solution settled to the bottom and the aqueous solution is a brown color. The omeprazole-containing composition after raising the pH to pH 7 is distributed throughout the aqueous solution and the mixture is deep purple in color. The omeprazole-containing composition after lowering the pH of the solution back to pH 1 settled to the bottom and the aqueous solution is a dark brown to purple color.

UV Analysis of the Omeprazole-Containing Composition

Omeprazole (OZ) UV Analysis of the Omeprazole-Containing Composition

The samples taken from the oil and aqueous phases during the pH cycling were analyzed using UV spectral analysis as omeprazole (OZ) is the only group that absorbs UV light due to the presence of an aromatic ring. The following table includes the OZ UV results:

TABLE XXIII

UV Omeprazole (OZ) Phase Concentration Data in mg/mL and Percentages

| Solution | OZ in Oil Phase (mg/mL) | OZ Aqueous Phase (mg/mL) | OZ in Oil Phase (%) | OZ in Aqueous Phase (%) |
|---|---|---|---|---|
| pH 1 | 3.2 | 1.78 | 64.40 | 35.60 |
| pH 1-7 | 4.50 | 0.50 | 90.00 | 10.00 |
| pH 1-7-1 | 1.97 | 3.03 | 39.40 | 61.60 |

Figure 16:
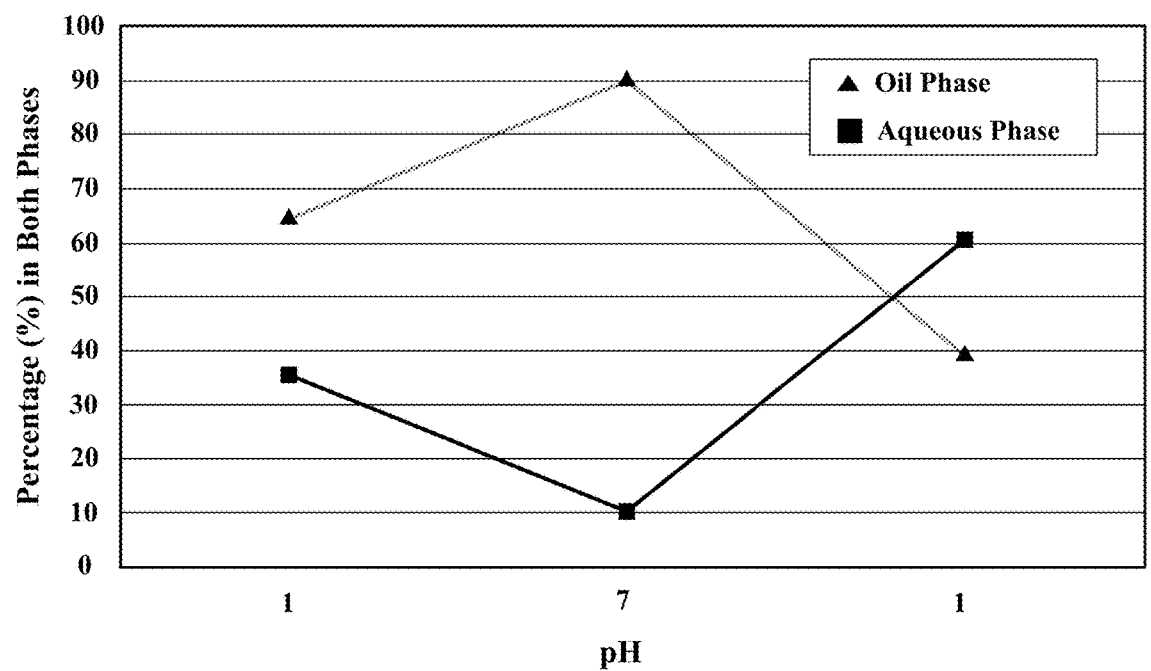
FIG. 16 depicts a plot of UV omeprazole concentration values for the omeprazole-containing composition during a pH cycle.

Referring now to FIG. 16, a plot of UV omeprazole (OZ) concentration values of the omeprazole-containing composition in the oil and aqueous phases during a pH cycle. Initially, 3.2 mg/mL (64.40%) of omeprazole is in the oil phase and 1.78 mg/mL (35.60%) of omeprazole in the aqueous phase. When the pH is raised to pH 7, the omeprazole partitions from the aqueous phase and the oil phase resulting in 4.50 mg/mL (90.00%) in the oil phase compared to 0.50 mg/mL (10.00%) in the aqueous phase. When the pH is lowered back to pH 1, the concentration in the aqueous phase is now larger the composition of omeprazole in the oil phase: 1.97 mg/mL (39.40%) in the oil phase compared to 3.03 (61.60%) in the aqueous phase.

The behavior of the omeprazole during preparation and during pH cycle testing is fundamentally different from the behavior of aspirin and ibuprofen. The inventors believe that the difference in behavior is due to the fact that omeprazole has groups that may be protonated or deprotonated as shown below:

The inventors believe that the cation form of omeprazole may be responsible for the deep purple color in the oil matrix and may be reason for the brown color of the pH 1 solution and the color of the pH 7 solution. Interestingly, omeprazole partitions into the oil phase once the pH is raised to pH 7 and the omeprazole is in its neutral form. While the pH behavior of omeprazole is not the same as the pH behavior of aspirin and ibuprofen, the behavior of omeprazole still shows pH dependent release. The more significant observation is the fact that omeprazole is almost exclusively in the oil phase at pH 7. Based on the chemistry of omeprazole shown above, this behavior is not inconsistent with the UV determined concentrations of omeprazole during pH cycling. While the direction of the pH dependent phase concentration is different from aspirin and ibuprofen, the inventors believe that the absorption of omeprazole into the oil phase at pH 7 may increase the absorption of omeprazole in the duodenum.

Figure 17:
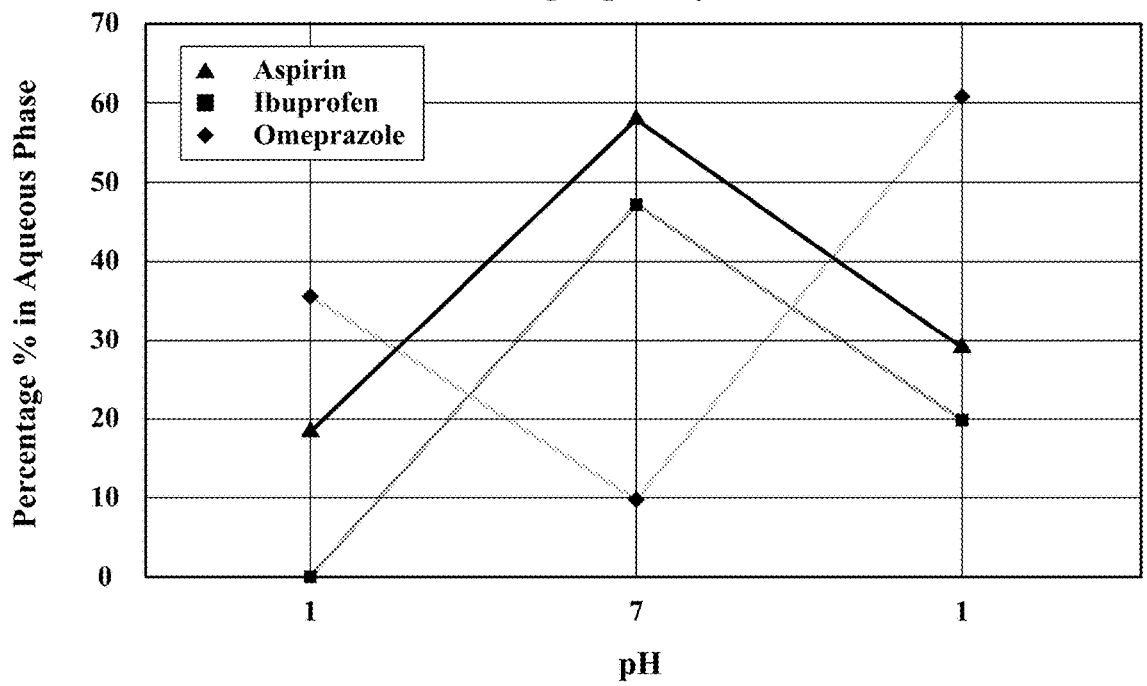
FIG. 17 depicts a plot of a comparison of UV aspirin, ibuprofen, and omeprazole concentration values in the water phase during a pH cycle.

Referring now to FIG. 17, a plot comparing UV aspirin, ibuprofen, and omeprazole concentration during a pH cycle. The plot clearly shows the difference in pH cycle behavior during pH cycling. Thus, the inventors believe that the pH behavior of pharmaceuticals in the oil carriers of this disclosure may be determined based on the structure of the pharmaceutical. If the structure includes a group that protonates at pH 1 and deprotonates at pH 7, the pH dependent behavior should mimic omeprazole. If the structure does not include a protonatable group at pH 1, then the pH dependent behavior should mimic aspirin and ibuprofen. If the structure includes a group that deprotonates at pH 7, then the pH dependent behavior should show much greater release at pH 7 than aspirin or ibuprofen. Thus, pharmaceutical compounds may be easily separated into three classes: class 1 pharmaceutical compounds are compounds that include a group that protonates at pH 1 and deprotonates at pH 7, class 2 pharmaceutical compounds are compounds that do not include a group that protonates at pH 1 and deprotonates at pH 7, and class 3 pharmaceutical compounds are compounds that a group that deprotonates at pH 7. However, the inventors believe that this classification scheme may only be amenable to simple pharmaceutical compounds. More complex pharmaceutical compounds such as proteins, polypeptide, DNA, RNA, enzymes, or the like may have different pH dependent behavior, which may be elucidated based on the pH dependent behavior of soy isolate described herein.

Example 13. High Oleic Acid-Ibuprofen-Containing Composition Preparation and pH Cycle Testing This example illustrates the preparation of a sample of a ibuprofen-containing composition, where the oil matrix includes 50% oleic acid and 50% soybean oil and the pH cycle behavior during the duodenal reflux procedure outlined above.

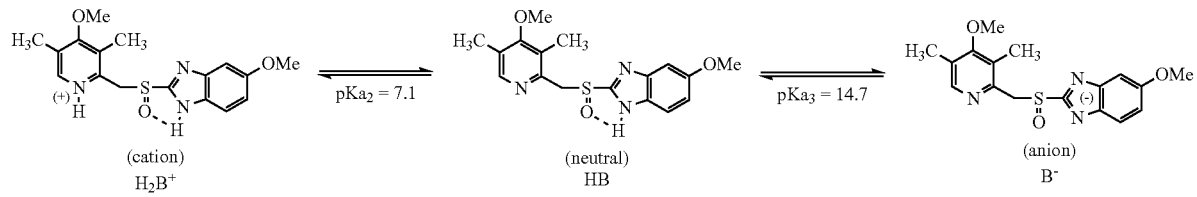

The high oleic acid-ibuprofen-containing composition included the following ingredients:

TABLE XXIV

| Ingredient | Quantity per Unit (mg) | Quantity (g) |
|---|---|---|
| ibuprofen | 20.25 | 20.25 |
| citric acid anhydrous powder USP/EP | 1.87 | 1.87 |
| lecithin | 3.95 | 3.95 |
| oleic acid NF/EP | 7.61 | 7.61 |
| soybean oil-IV | 7.61 | 7.61 |
| Total | 41.29 | 41.29 |

High Oleic Acid-Ibuprofen-Containing Composition Preparation

The high oleic acid-ibuprofen-containing composition was prepared as follows:

1. Screen citric acid and ibuprofen (IBU) through a 40 mesh hand screen;
2. Add oleic acid, soybean oil, and lecithin into a 150 mL beaker and heat the mixture while stirring with a stir bar on a hot plate to until the mixture achieves visual uniformity;
3. Add citric acid to the mixture while stirring with the stir bar on the hot plate until the mixture achieves visual uniformity;
4. Add ibuprofen to the mixture while stirring with a Caframo mixer until the mixture achieves visual uniformity; and
5. Continue stirring the mixture during testing to maintain uniformity.

High Oleic Acid-Ibuprofen-Containing Composition pH Cycle Test

The high oleic acid-ibuprofen-containing composition pH cycling was performed as follows:

1. Place 10 grams the high oleic acid-ibuprofen-containing composition in a 150 mL beaker including 100 mL of a 0.1 N HCl solution having a pH of about 1;
2. Observe and photograph the high oleic acid-ibuprofen-containing composition in the pH 1 solution;
3. Collect a sample of the oil phase and the aqueous phase from the pH 1 solution for UV analysis;
4. Add concentrated NaOH to the beaker with stirring while monitoring the pH with a pH meter until the pH is about 7;
5. Observe and photograph the high oleic acid-ibuprofen-containing composition in the pH 7 solution;
6. Collect a sample of the oil phase and aqueous phase from the pH 7 solution for UV analysis;
7. Add concentrated HCl to the beaker with stirring while monitoring the pH with a pH meter until the pH is about 1;
8. Observe and photograph the high oleic acid-ibuprofen-containing composition in the pH 1 solution; and
9. Collect a sample of the oil phase and aqueous phase from the pH 1 solution for UV analysis.

Photographs of High Oleic Acid-Ibuprofen-Containing Composition

Figure 18:
FIG. 18 depicts photographs of the high oleic acid-ibuprofen-containing composition during a pH cycle.
Figure 19:
FIG. 19 depicts photographs of the control composition (no ibuprofen) and the high oleic acid-ibuprofen-containing composition after the concentrated NaOH addition to adjust the pH to pH 7, showing that both the control composition and the ibuprofen-containing composition formed very stable emulsions at pH 7.

Referring now to FIG. 18, photographs of the high oleic acid-ibuprofen-containing composition in the pH 1 solution, the high oleic acid-ibuprofen-containing composition in the solution after concentrated NaOH addition to raise the pH to pH 7, and the high oleic acid-ibuprofen-containing composition in the solution after concentrated HCl addition to lower the pH back to pH 1. The photographs show that the high oleic acid-ibuprofen-containing composition is immiscible in the pH 1 solutions and forms an emulsion in the pH 7 solution. The high oleic acid-ibuprofen-containing composition behaves a little differently from the low oleic acid-ibuprofen composition in the pH 7 solution as the emulsion seems to be a little better formed. In fact, FIG. 19 shows that the high oleic acid-ibuprofen-containing composition forms an emulsion very similar to the emulsion produced when the control composition in the pH 7 solution after concentrated NaOH addition to raise the pH of the pH 1 solution to pH 7.

UV Analysis of High Oleic Acid-Ibuprofen-Containing Composition

Ibuprofen (IBU) UV Analysis of the High Oleic Acid-Ibuprofen-Containing Composition The samples taken from the oil and aqueous phases during the pH cycling were analyzed using UV spectral analysis as ibuprofen (IBU) is the only compound that having an aromatic ring. The following table includes the IBU UV concentration results:

TABLE XXV

UV Ibuprofen (IBU) Phase Concentration Data in mg/mL and Percentages

| Solution | IBU in Oil Phase (mg/mL) | IBU Aqueous Phase (mg/mL) | IBU in Both Phases (mg/mL) | IBU in Oil Phase (%) |
|---|---|---|---|---|
| pH 1 | 0.5840 | 0.0078 | 0.5918 | 98.69% |
| pH 1-7 | 0.3515 | 0.2092 | 0.5608 | 62.68% |
| pH 1-7-1 | 0.3736 | 0.0077 | 0.3812 | 97.99% |

Figure 20:
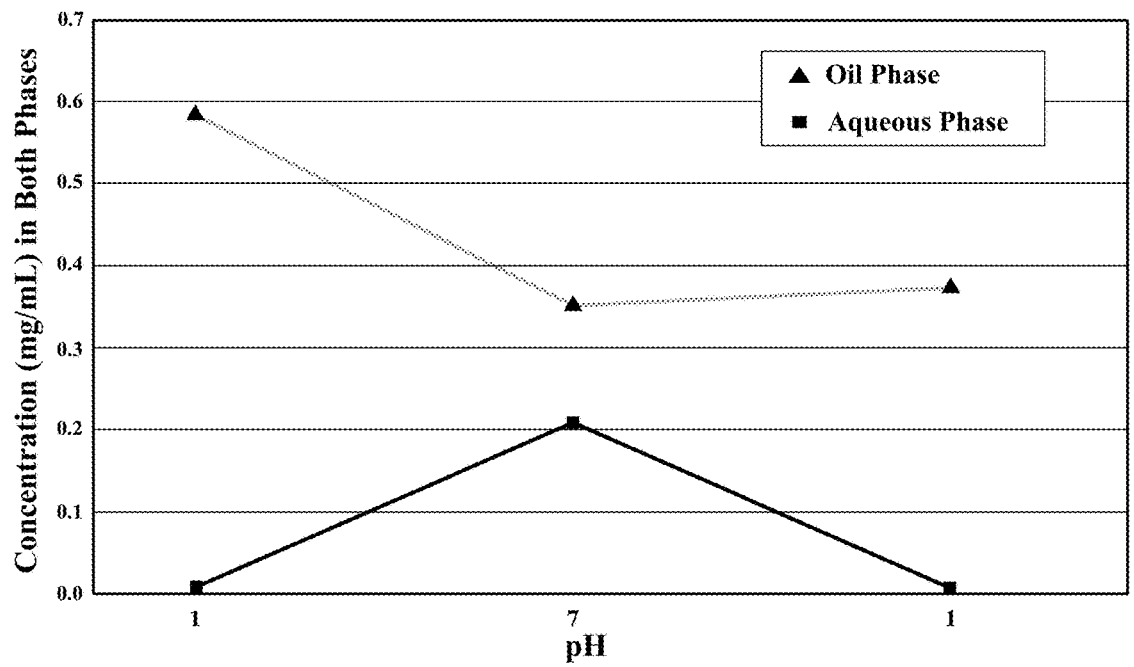
FIG. 20 depicts a plot of UV ibuprofen concentration values for the high oleic acid-ibuprofen-containing composition during a pH cycle.

Referring now to FIG. 20, the UV ibuprofen concentration values for the ibuprofen-containing sample in the pH 1 solutions and the pH 7 solution during the pH cycle. Initially, essentially all of the ibuprofen is in the oil phase: 0.5840 mg/mL (98.69%) of ibuprofen in the oil phase compared to 0.0078 mg/mL (1.31%) in the aqueous phase. When the pH is raised to pH 7, the ibuprofen partitions between the phases with 0.3515 mg/mL (62.68%) in the oil phase compared to 0.2092 mg/mL (37.32%) in the aqueous phase. When the pH is lowered back to pH 1, a large amount of the ibuprofen is reabsorbed into the oil phase: 0.3786 (97.99%) in the oil phase compared to 0.0077 (2.01%) in the aqueous phase. The high amount of oleic acid in the composition resulted in a larger reabsorption compared to the lower amount of oleic acid in the composition.

Again, the inventors believe that this reconstitution and reabsorption is a contributing factor to the superior GI safety of carriers of this disclosure. It appears that a sufficient amount of a free carboxylic acid in the carrier is responsible not only for the carrier's extreme hydrophobicity as carrier is essentially immiscible in the initial pH 1 aqueous solution, where the API, here ibuprofen, is primarily present in the oil phase. The data also show that in the pH 7 solution, the API, ibuprofen here, is released into the aqueous phase, where almost equal amounts of ibuprofen are found in the two phases. The data also clearly show that the API, ibuprofen here, is reabsorbed into the carrier when the pH is lowered back to pH of about 1 reducing the amount of API in the aqueous phase. These findings are consistent with the improved GI safety of the compositions of this disclosure including an effective amount of free carboxylic acids.

Example 14. Nonionic Surfactant-Ibuprofen-Containing Composition Preparation and pH Cycle Testing This example illustrates the preparation of a sample of a nonionic surfactant-ibuprofen-containing composition subject to the duodenal reflux procedure outlined above.

The nonionic surfactant-ibuprofen-containing composition included the following ingredients:

TABLE XXVI

| Ingredient | Quantity per Unit (mg) | Quantity (g) |
| --- | --- | --- |
| Ibuprofen (IBU) | 81 | 81 |
| Citric Acid Anhydrous Powder USP/EP | 7.48 | 7.48 |
| Lecithin | 15.78 | 16.04 |
| GATTEFOSSÉ LAUROGLYCOL ™ 90 Nonionic Surfactant | 0.52 | 0.52 |
| Oleic Acid NF/EP | 19.27 | 19.29 |
| Soybean Oil-IV | 41.62 | 41.62 |
| Total | 165.67 | 165.95 |

Nonionic Surfactant-Ibuprofen-Containing Composition Preparation Procedure

The nonionic surfactant-ibuprofen-containing composition was prepared as follows:
1. Screen citric acid and ibuprofen (IBU) through a 40 mesh hand screen;
2. Add oleic acid, soybean oil, nonionic surfactant (GATTEFOSSÉ LAUROGLYCOL™ 90), and lecithin into a 150 mL beaker and heat the mixture while stirring with a stir bar on a hot plate to until the mixture achieves visual uniformity;
3. Add citric acid to the mixture while stirring with the stir bar on the hot plate until the mixture achieves visual uniformity;
4. Add ibuprofen to the mixture while stirring with a Caframo mixer until the mixture achieves visual uniformity; and
5. Continue stirring the mixture during testing to maintain uniformity.

Nonionic Surfactant-Ibuprofen-Containing Composition pH Cycle Test Procedure

The nonionic surfactant-ibuprofen-containing composition pH cycling was performed as follows:
1. Place 10 grams nonionic surfactant-ibuprofen-containing composition in a 150 mL beaker including 100 mL of a 0.1 N HCl solution having a pH of about 1;
2. Observe and photograph the nonionic surfactant-ibuprofen-containing composition in the pH 1 solution;
3. Collect a sample of the oil phase and the aqueous phase from the pH 1 solution for UV analysis;
4. Add concentrated NaOH to the beaker with stirring while monitoring the pH with a pH meter until the pH is about 7;
5. Observe and photograph the nonionic surfactant-ibuprofen-containing composition in the pH 7 solution;
6. Collect a sample of the oil phase and aqueous phase from the pH 7 solution for UV analysis;
7. Add concentrated HCl to the beaker with stirring while monitoring the pH with a pH meter until the pH is about 1;
8. Observe and photograph the nonionic surfactant-ibuprofen-containing composition in the pH 1 solution; and
9. Collect a sample of the oil phase and aqueous phase from the pH 1 solution for UV analysis.

Photographs of Nonionic Surfactant-Ibuprofen-Containing Composition

Figure 21:
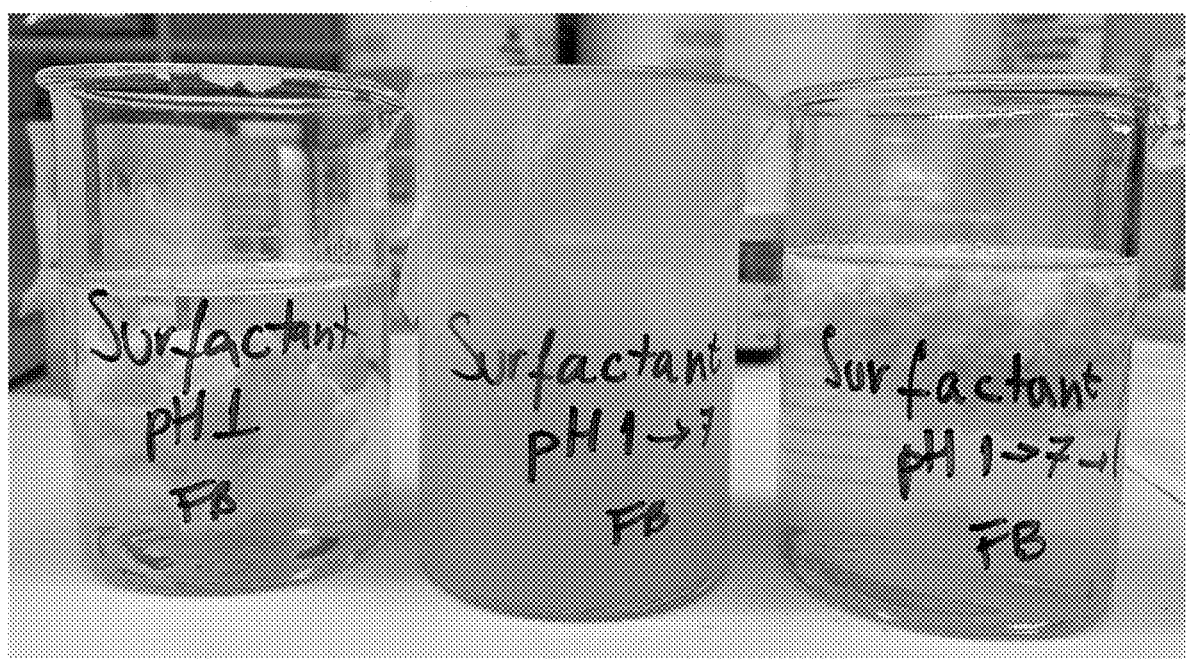
FIG. 21 depicts photographs of the surfactant-ibuprofen-containing composition during a pH cycle.

Referring now to FIG. 21, photographs of the nonionic surfactant-ibuprofen-containing composition in the pH 1 solution, the nonionic surfactant-ibuprofen-containing composition in the solution after concentrated NaOH addition to raise the pH to pH 7, and the nonionic surfactant-ibuprofen-containing composition in the solution after concentrated HCl addition to lower the pH back to pH 1. The photographs show that the nonionic surfactant-ibuprofen-containing composition is immiscible in the pH 1 solutions and forms an emulsion with an oil phase on top in the pH 7 solution. The nonionic surfactant-ibuprofen-containing composition behaves similarly to the low oleic acid-ibuprofen composition in the pH 7 solution, which also showed an emulsion with an oil layer on top. The nonionic surfactant-ibuprofen-containing is fully reconstituted in the final pH 1 solution, but now being a little less dense than the aqueous phase, where it was a little more dense in the pH 1 solution.

UV Analysis of Nonionic Surfactant-Ibuprofen-Containing Samples

Ibuprofen (IBU) UV Analysis of the Nonionic Surfactant-Ibuprofen-Containing Composition The samples taken from the oil and aqueous phases during the pH cycling were analyzed using UV spectral analysis as aspirin (ASA) is the only group that absorbs UV light due to the presence of an aromatic ring. The following table includes the ASA UV results:

TABLE XXVII

| | UV Ibuprofen (IBU) Phase Concentration Data in mg/mL and Percentages | | | |
| --- | --- | --- | --- | --- |
| Solution | IBU in Oil Phase (mg/mL) | IBU Aqueous Phase (mg/mL) | IBU in Both Phases (mg/mL) | IBU in Oil Phase (%) |
| pH 1 | 0.9825 | 0.0156 | 0.9981 | 98.44% |
| pH 1-7 | 0.5033 | 0.2160 | 0.7193 | 69.96% |
| pH 1-7-1 | 0.7369 | 0.0119 | 0.7487 | 98.42% |

Figure 22:
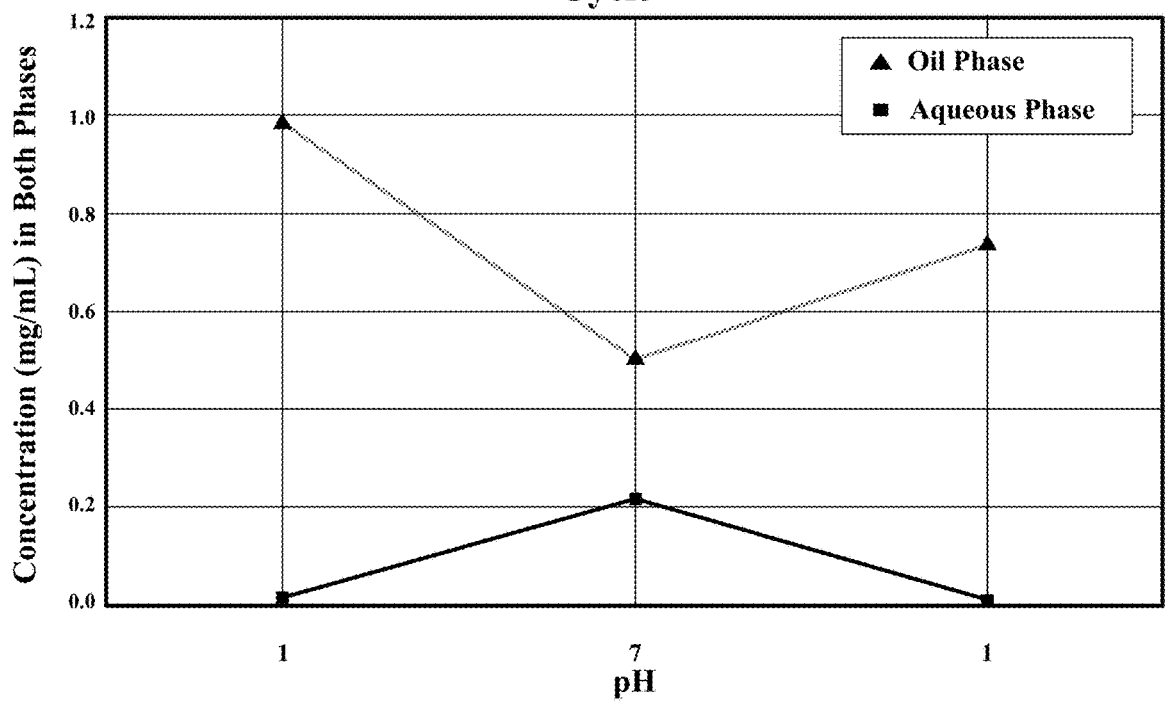
FIG. 22 depicts a plot of UV ibuprofen concentration values for the surfactant-ibuprofen-containing composition during a pH cycle.

Referring now to FIG. 22, the UV ibuprofen concentration values for the nonionic surfactant-ibuprofen-containing composition in the pH 1 solutions and the pH 7 solution during the pH cycle experiment. Initially, essentially all of the ibuprofen is in the oil phase: 0.9825 (98.44%) of ibuprofen in the oil phase compared to 0.0156 mg/mL (1.56%) in the aqueous phase. When the pH is raised to pH 7, the ibuprofen partitions with 0.5033 mg/mL (69.96%) in the oil phase compared to 0.2160 mg/mL (30.04%) in the aqueous phase. When the pH is lowered back to pH 1, a large amount of the ibuprofen is reabsorbed into the oil phase: 0.7369 (98.42%) in the oil phase compared to 0.0119 mg/mL (1.58%) in the aqueous phase.

Again, the inventors believe that this reconstitution and reabsorption is a contributing factor to the superior GI safety of carriers of this disclosure. It appears that a sufficient amount of a free carboxylic acid in the carrier is responsible not only for the carrier's extreme hydrophobicity as carrier is essentially immiscible in the initial pH 1 aqueous solution, where the API, here ibuprofen, is primarily present in the oil phase. The data also show that in the pH 7 solution, the API, ibuprofen here, is released into the aqueous phase, where almost equal amounts of ibuprofen are found in the two phases. The data also clearly show that the API, ibuprofen here, is reabsorbed into the carrier when the pH is lowered back to pH of about 1 reducing the amount of API in the aqueous phase. These findings are consistent with the improved GI safety of the compositions of this disclosure including an effective amount of free carboxylic acids.

Comparison of UV Ibuprofen Concentration Values for the Three Ibuprofen Compositions The three ibuprofen compositions were designed to determine whether changing the composition of the carrier would change the reconstitution and API reabsorption properties of the matrix. To make the comparison easier, the UV ibuprofen (IBU) concentration values are tabulated below.

TABLE XXVIII

UV Ibuprofen (IBU) Phase Concentration Percentage Data for the Three IBU Compositions

|  | Standard Composition | | High Oleic Acid Composition | | Nonionic Surfactant Composition | |
| --- | --- | --- | --- | --- | --- | --- |
| Solution | Oil Phase | Aqueous Phase | Oil Phase | Aqueous Phase | Oil Phase | Aqueous Phase |
| pH 1 | 99.97% | 0.03% | 98.69% | 1.31% | 98.44% | 1.56% |
| pH 1!7 | 52.56% | 47.44% | 62.68% | 37.32% | 69.96% | 30.04% |
| pH 7!1 | 79.79% | 20.21% | 97.99% | 2.01% | 98.42% | 1.58% |

Figure 23:
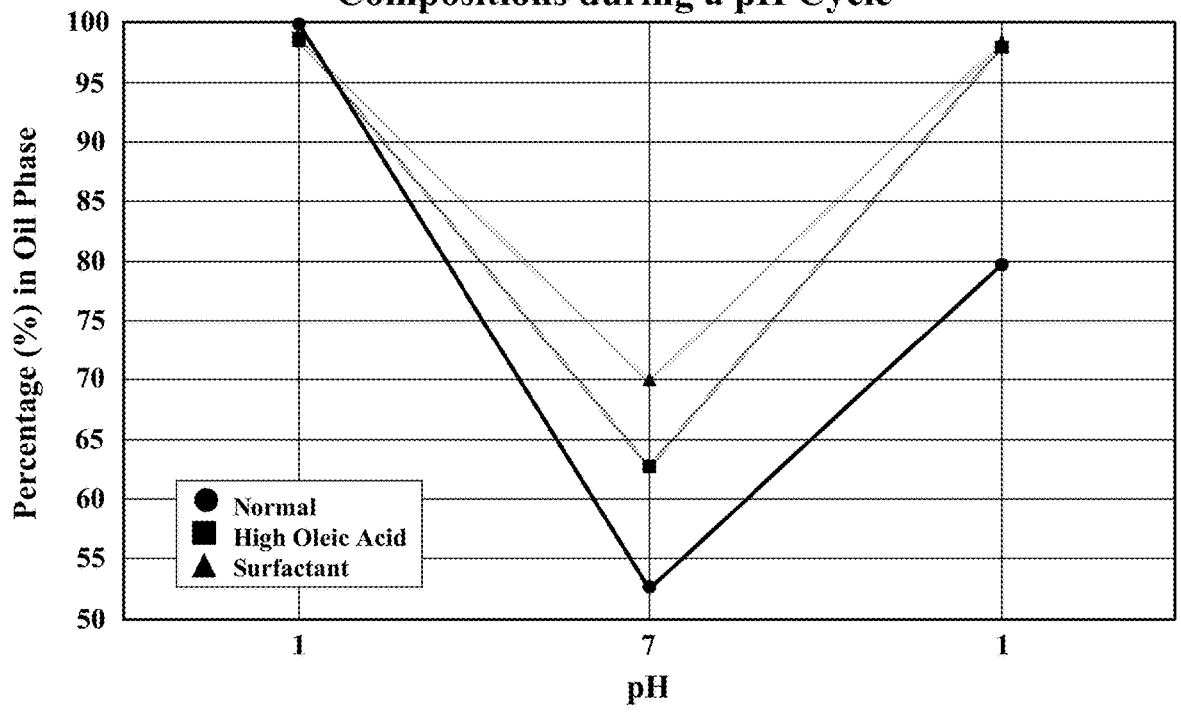
FIG. 23 depicts a plot of comparing UV ibuprofen concentration values for the ibuprofen-containing composition, the high oleic acid-ibuprofen-containing composition, and surfactant-ibuprofen-containing composition during a pH cycle.

Additionally, referring now to FIG. 23, the tabulated data is plotted. A review of the data in Table XV and shown in FIG. 23 clearly evidence that the reconstitution and API reabsorption properties of the oil carrier may be changed by changing the material composition of the carrier. The standard composition includes a weight ratio of oleic acid to soybean oil is about 1:2, while the weight ratio of oleic acid to soybean oil is about 1:1, a 50% increase on oleic acid and a 50% decrease on soybean oil. The consequences of the change in free fatty acid to triglyceride ratio caused a greater amount of the API to be in the oil phase at pH 7 and a greater reabsorption of the API when the pH is adjusted from pH 7 back to pH 1. The increase in reabsorption was about 20%. A similar effect is seen when 5 wt. % of the oil is replaced by a nonionic surfactant also showing a 20% increase in API reabsorption. Interestingly, the high oleic acid composition showed about a 10% increase of the API in the oil phase at pH 7, while the surfactant composition showed about a 15% increase of the API in the oil phase at pH 7. Thus, the carrier may be tailored to change API partitioning upon initial digestion (initial pH 1 data) and upon progression into the duodenum (pH 7 solution) and finally, the amount of API reabsorption during duodenal reflux.

Example 15 Whey Isolate Protein-Containing Composition Preparation and pH Cycle Testing This example illustrates the preparation of a sample of a whey isolate protein-containing composition subject to the duodenal reflux procedure outlined above.

The whey isolate protein-containing composition included the following ingredients:

TABLE XXIX

| Ingredient | Quantity per Unit (mg) | Quantity (g) |
| --- | --- | --- |
| Whey Isolate Protein | 20.25 | 20.26 |
| Citric Acid Anhydrous Powder USP/EP | 1.87 | 1.87 |
| Lecithin | 3.95 | 3.98 |
| Oleic Acid NF/EP | 4.81 | 4.81 |
| Soybean Oil-IV | 10.41 | 10.42 |
| Total | 41.29 | 41.34 |

Whey Isolate Protein-Containing Preparation

The whey isolate protein-containing composition was prepared as follows:

1. Screen citric acid and whey isolate protein (WIP) through a 40 mesh hand screen;

2. Add oleic acid, soybean oil, and lecithin into a 150 mL beaker and heat the mixture while stirring with a stir bar on a hot plate to until the mixture achieves visual uniformity;

3. Add citric acid to the mixture while stirring with the stir bar on the hot plate until the mixture achieves visual uniformity;

4. Add whey isolate protein (WIP) to the mixture while stirring with a Caframo mixer until the mixture achieves visual uniformity; and 5. Continue stirring the mixture during testing to maintain uniformity.

Whey Protein Isolate-Containing Composition pH Cycle Test

The whey isolate protein-containing composition pH cycling was performed as follows:

1. Place 10 grams whey isolate protein in a 150 mL beaker including 100 mL of a 0.1 N HCl solution having a pH of about 1;

2. Observe and photograph the whey isolate protein-containing composition in the pH 1 solution;

3. Collect a sample of the oil phase and the aqueous phase from the pH 1 solution for UV analysis;

4. Add concentrated NaOH to the beaker with stirring while monitoring the pH with a pH meter until the pH is about 7;

5. Observe and photograph the whey isolate protein-containing composition in the pH 7 solution;

6. Collect a sample of the oil phase and aqueous phase from the pH 7 solution for UV analysis;

7. Add concentrated HCl to the beaker with stirring while monitoring the pH with a pH meter until the pH is about 1;

8. Observe and photograph the whey isolate protein-containing composition in the pH 1 solution; and 9. Collect a sample of the oil phase and aqueous phase from the pH 1 solution for UV analysis.

Photographs of Whey Isolate Protein-Containing Composition

Figure 24:
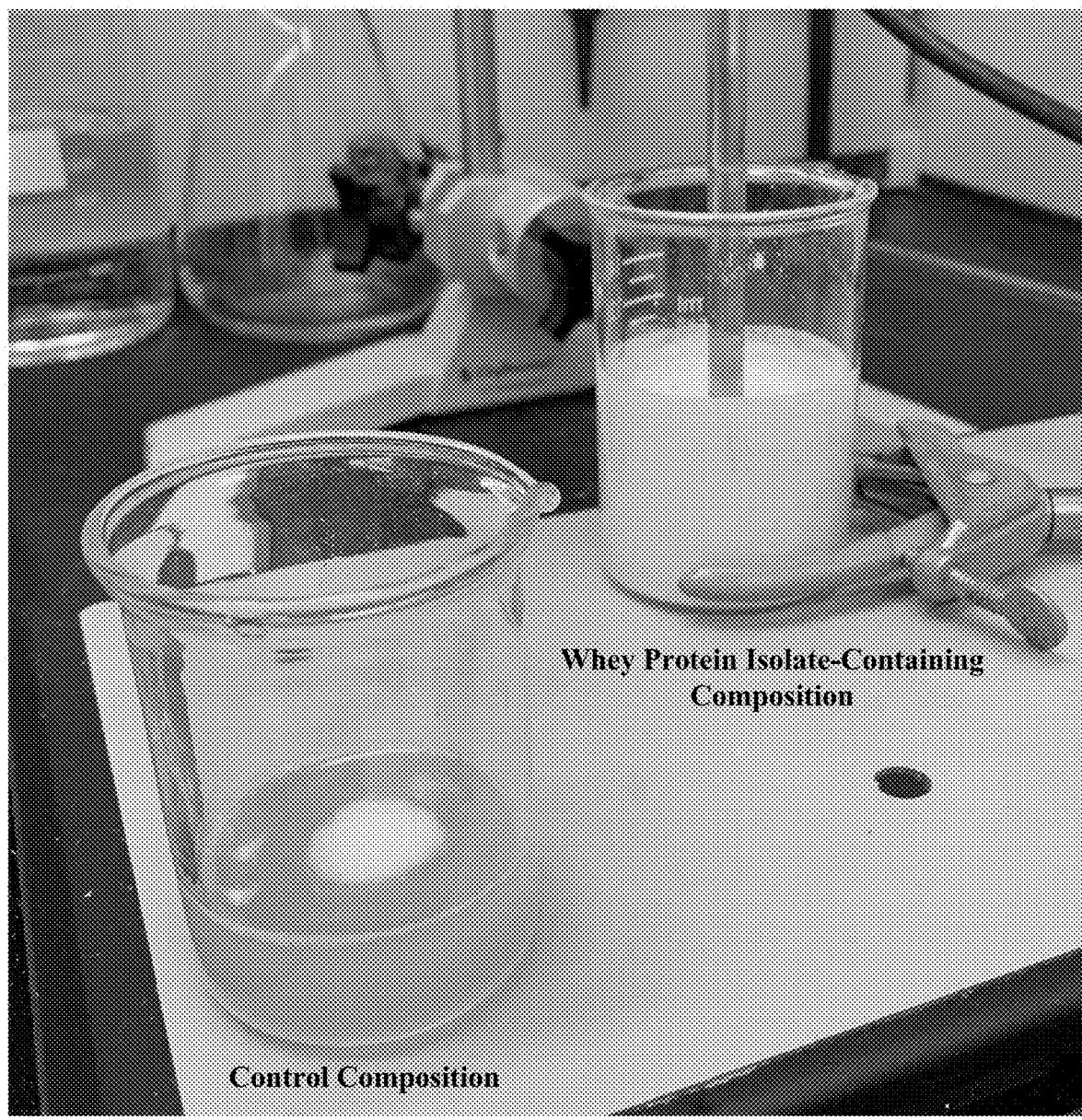
FIG. 24 depicts photographs of the control composition (no whey isolate protein) and the whey isolate protein-containing composition during preparation.
Figure 25:
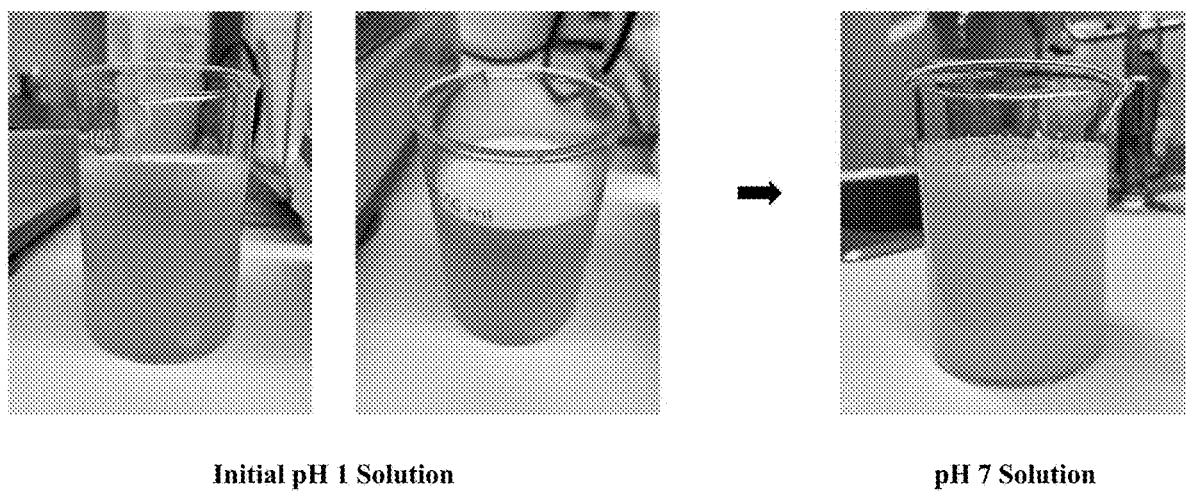
FIG. 25 depicts photographs of a sample of the whey isolate protein-containing composition in the initial pH 1 solution and in the NaOH adjusted pH 7 solution.
Figure 26:
FIG. 26 depicts photographs of the sample of the whey isolate protein-containing composition in all three solution of a pH cycle.

Referring now to FIG. 24, a photograph of the placebo and the whey isolate protein-containing composition. The whey protein isolate-containing composition was very thick. Visually, all three pH solutions looked very similar. The whey isolate protein-containing composition did not hold a clearly observed form at the initial pH 1 solution. The aqueous phases of all three solution, initial pH 1 solution, pH 7 solution and final pH 1 solution, looked turbid. Some foaming was noticed in the initial pH 1 solution. Looking at FIG. 25, three photographs are shown. The left two photographs shows the sample of the whey isolate protein-containing composition after being added to the simulated gastric fluid, initial pH 1 solution, where some foaming was observed. The right photograph shows the sample of the whey isolate protein-containing composition after concentrated NaOH was added to the initial pH 1 solution to raise the pH to pH ~7. The oil phase is not as distinct as in the case of NSAID, but there still does appear to be two phases. Looking at FIG. 26, three photographs are shown. The left photograph shows the sample of the whey isolate protein-containing composition in the initial pH 1 solution; the middle photograph shows the sample of the whey protein isolate-containing composition in the pH 7 solution; and the right photograph shows the sample of the whey isolate protein-containing composition after concentrated HCl was added to lower the pH to pH ~1. In all three photographs the aqueous phase appeared cloudy, and the oil phase appeared cloudy as well. Although the results are not as pronounced as for NSAIDs, the data does show partitioning, release in the pH 7 solution and some reabsorption in the final pH 1 solution. As noted above, the nature of the matrix is capable of changing the relative amounts of API in each phase at the two different pH values, pH 1 and pH 7 suggesting that the matrix is capable of being optimized for different type of drugs or pharmaceutical that evidence release and reabsorption dynamic in the same direction as observed for the NSAIDs, or any small molecule pharmaceutical compound that does not include an amino group or an group that is easily protonated at pH values less than pH 3.

Uv Analysis of Whey Isolate Protein-Containing Samples

Whey Isolate Protein UV Analysis

The samples taken from the oil and aqueous phases during the pH cycling were analyzed using UV spectral analysis as whey isolate protein includes amino acids that absorb UV light due to the presence of an aromatic ring. The following table includes the whey isolate protein UV concentration results:

TABLE XXX

UV Whey Isolate Protein (WIP)
Concentration Data in mg/mL and Percentages

| Solution | WIP in Oil Phase (mg/mL) | WIP Aqueous Phase (mg/mL) | WIP in Both Phases (mg/mL) | WIP in Oil Phase (%) |
|---|---|---|---|---|
| pH 1 | 0.24 | 0.33 | 0.57 | 42.42 |
| pH 1-7 | 0.08 | 0.49 | 0.57 | 14.24 |
| pH 1-7-1 | 0.15 | 0.42 | 0.57 | 26.69 |

Figure 27:
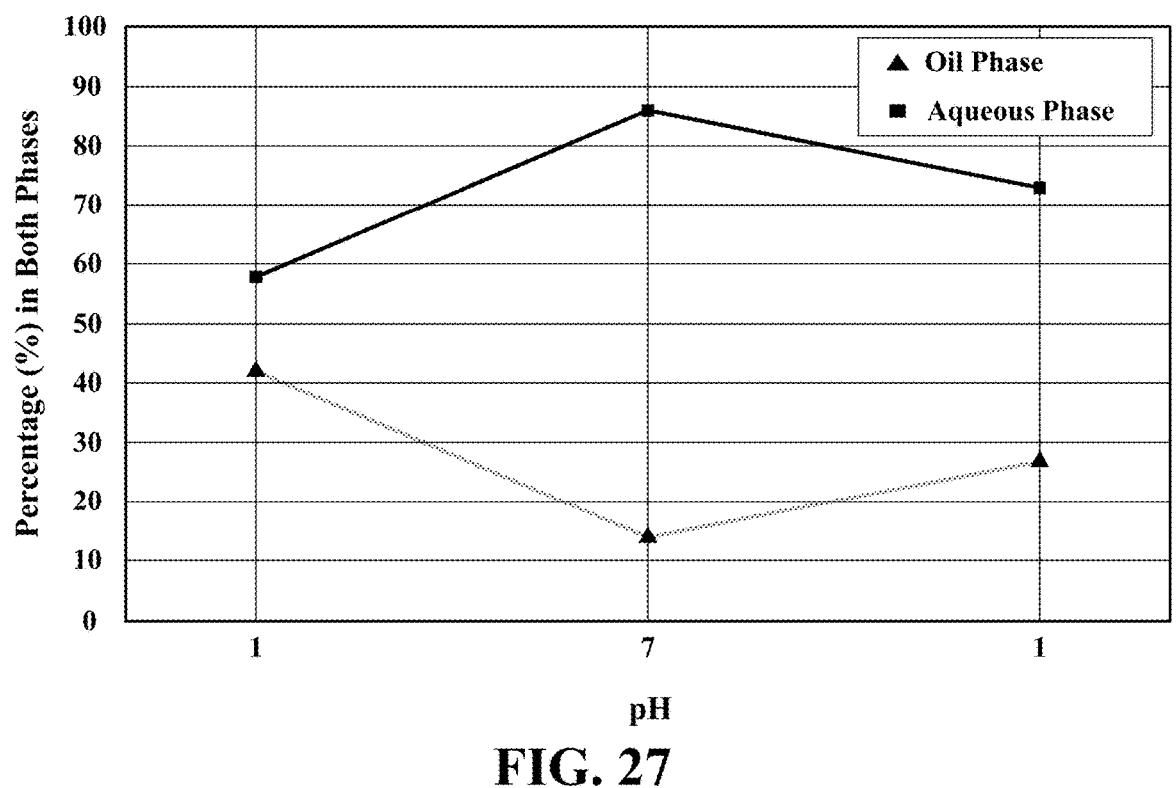
FIG. 27 depicts a plot of UV whey isolate protein percentage values for the whey isolate protein-containing composition during a pH cycle.

Referring now to FIG. 27, a plot of UV percentage values of whey isolate protein in both phases for the whey isolate protein-containing composition in the pH 1 solutions and the pH 7 solution during the pH cycle. In the initial pH 1 solution, about 60% of the whey isolate protein (WIP) was in the aqueous phase and 40% in the oil phase. In the pH 7 solution, about 86% of the WIP was in the aqueous phase and 14% in the oil phase. In the final pH 1 solution, about 73% was in the aqueous phase and 27% in the oil phase. While the results are not as pronounced as in the case of aspirin and ibuprofen, the trends are similar and opposite of omeprazole suggesting that the matrix may be able to be modified to reduce initial protein partitioning from the oil phase to the aqueous phase in the stomach, increase release in the duodenum, and increase reconstitution and reabsorption during duodenal reflux.

Figure 28:
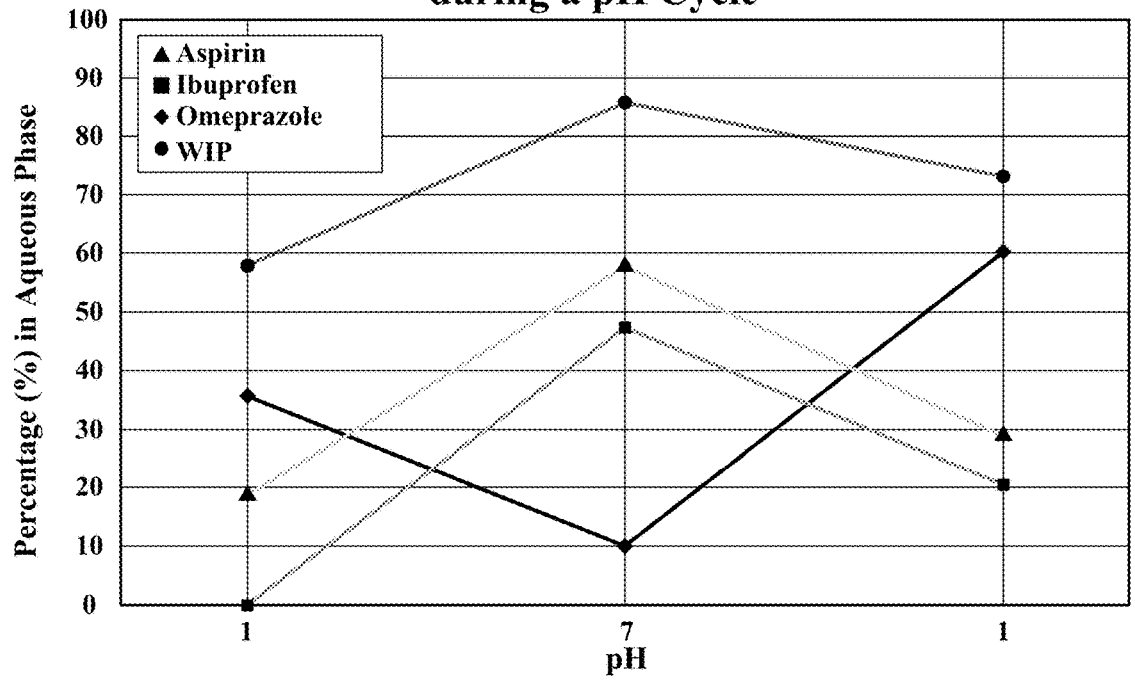
FIG. 28 depicts a plot of a comparison of UV aspirin, ibuprofen, whey isolate protein, and omeprazole percentage values for their respective compositions in the aqueous phase during a pH cycle.

Referring now to FIG. 28, a plot of a comparison of UV percentage values in the aqueous phase of aspirin, ibuprofen, whey isolate protein, and omeprazole compositions during a pH cycle. The plot shows that aspirin, ibuprofen and whey isolate protein behave in a similar manner, with the protein being absorbed to a higher extent in the aqueous phase, with omeprazole behaving the an opposite behavior compared to the other APIs.

Example 16. High Oleic Acid, Nonionic Surfactant Whey Isolate Protein-Containing Composition Preparation and pH Cycle Testing This example illustrates the preparation of a sample of a high oleic acid, nonionic surfactant (HA, NIS) whey isolate protein-containing composition subject to the duodenal reflux procedure outlined above.

The HA, NIS whey isolate protein-containing composition included the following ingredients:

TABLE XXXI

| Ingredient | Quantity per Unit (mg) | Quantity (g) |
|---|---|---|
| Whey Isolate Protein | 20.25 | 20.27 |
| Lecithin | 3.95 | 3.97 |
| Oleic Acid NF/EP | 6.85 | 6.85 |
| Soybean Oil-IV | 6.85 | 6.86 |
| Nonionic Surfactant (LAUROGLYCOL ™ 90)* | 1.52 | 1.52 |
| Total | 39.42 | 39.47 |

*LAUROGLYCOL ™ 90 (propylene glycol monolaurate) is a nonionic water-insoluble surfactant.

High Oleic Acid, Nonionic Surfactant Whey Isolate Protein-Containing Preparation The HA, NIS whey isolate protein-containing composition was prepared as follows:

1. Screen citric acid and whey isolate protein (WIP) through a 40 mesh hand screen;
2. Add oleic acid, soybean oil, lecithin, and nonionic surfactant (LAUROGLYCOL™ 90) into a 150 mL beaker and heat the mixture while stirring with a stir bar on a hot plate to until the mixture achieves visual uniformity;
3. Add citric acid to the mixture while stirring with the stir bar on the hot plate until the mixture achieves visual uniformity;
4. Add whey protein isolate to the mixture while stirring with a Caframo mixer until the mixture achieves visual uniformity; and
5. Continue stirring the mixture during testing to maintain uniformity.

HA, NIS Whey Isolate Protein-Containing Composition pH Cycle Test

The HA, NIS whey protein isolate-containing composition pH cycling was performed as follows:

1. Place 10 grams whey protein isolate in a 150 mL beaker including 100 mL of a 0.1 N HCl solution having a pH of about 1;

2. Observe and photograph the HA, NIS whey protein isolate-containing composition in the pH 1 solution;

3. Collect a sample of the oil phase and the aqueous phase from the pH 1 solution for UV analysis;

4. Add concentrated NaOH to the beaker with stirring while monitoring the pH with a pH meter until the pH is about 7;

5. Observe and photograph the HA, NIS whey protein isolate-containing composition in the pH 7 solution;

6. Collect a sample of the oil phase and aqueous phase from the pH 7 solution for UV analysis;

7. Add concentrated HCl to the beaker with stirring while monitoring the pH with a pH meter until the pH is about 1;

8. Observe and photograph the HA, NIS whey protein isolate-containing composition in the pH 1 solution; and 9. Collect a sample of the oil phase and aqueous phase from the pH 1 solution for UV analysis.

Photographs of Whey Isolate Protein-Containing Composition

Figure 29:
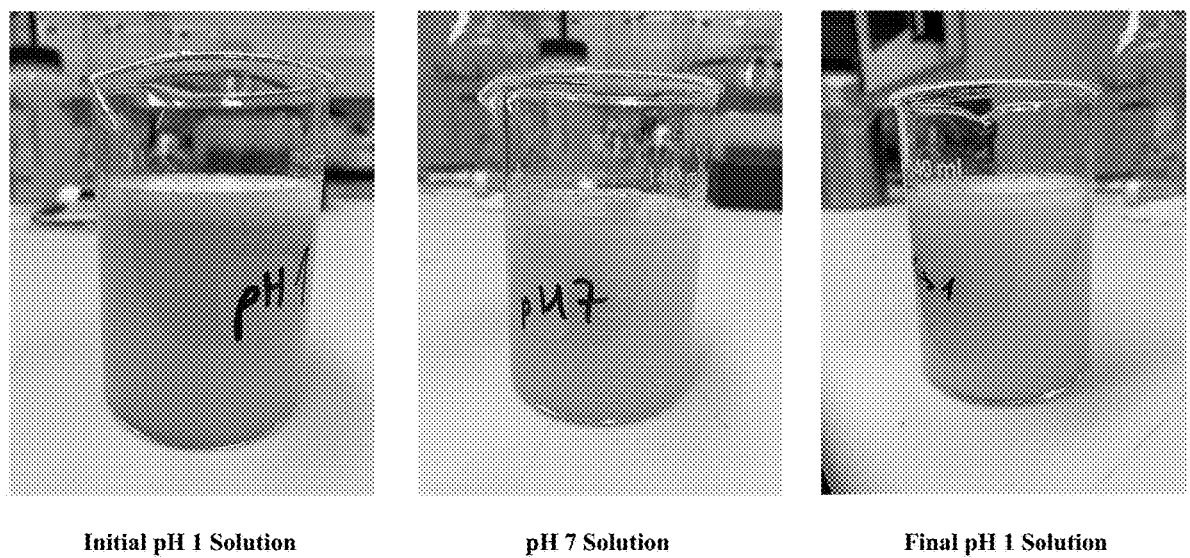
FIG. 29 depicts photographs of a sample of the high acid (HA), nonionic surfactant (NIS) whey isolate protein-containing composition in all three solution during a pH cycle.

Referring now to FIG. 29, three photographs of the HA, NIS whey protein isolate-containing composition are shown. The left photograph shows the sample of the HA, NIS whey protein isolate-containing composition in the initial pH 1 solution; the middle photograph shows the sample of the HA, NIS whey protein isolate-containing composition after the pH 1 solution was NaOH pH adjusted to pH 7; and the middle photograph shows the sample of the HA, NIS whey protein isolate-containing composition after the pH 7 solution was HCl pH adjusted back to pH 1. The whey protein isolate-containing composition was thinner than the whey isolate protein-containing composition of Example 15. Visually and similar to the whey isolate protein-containing composition of Example 15, all three pH solutions looked very similar. The HA, NIS whey protein isolate-containing composition also did not hold a clearly observed form at the initial pH 1 solution. The aqueous phases of all three solution, initial pH 1 solution, pH 7 solution and final pH 1 solution, looked turbid. Some foaming was noticed in the initial pH 1 solution.

UV Analysis of HA, NIS Whey Protein Isolate-Containing Samples

Whey Protein Isolate UV Analysis

The samples taken from the oil and aqueous phases during the pH cycling were analyzed using UV spectral analysis as whey isolate protein includes amino acids that absorb UV light due to the presence of an aromatic ring. The following table includes the whey protein isolate UV concentration results:

TABLE XXXII

UV Whey Isolate Protein (WIP) Concentration Data in mg/mL and Percentages

| Solution | WIP in Oil Phase (mg/mL) | WIP in Aqueous Phase (mg/mL) | WIP in Both Phases (%) |
|---|---|---|---|
| pH 1 | 0.48 | 0.09 | 83.45 |
| pH 1-7 | 0.33 | 0.42 | 43.81 |
| pH 1-7-1 | 0.51 | 0.23 | 68.84 |

Figure 30:
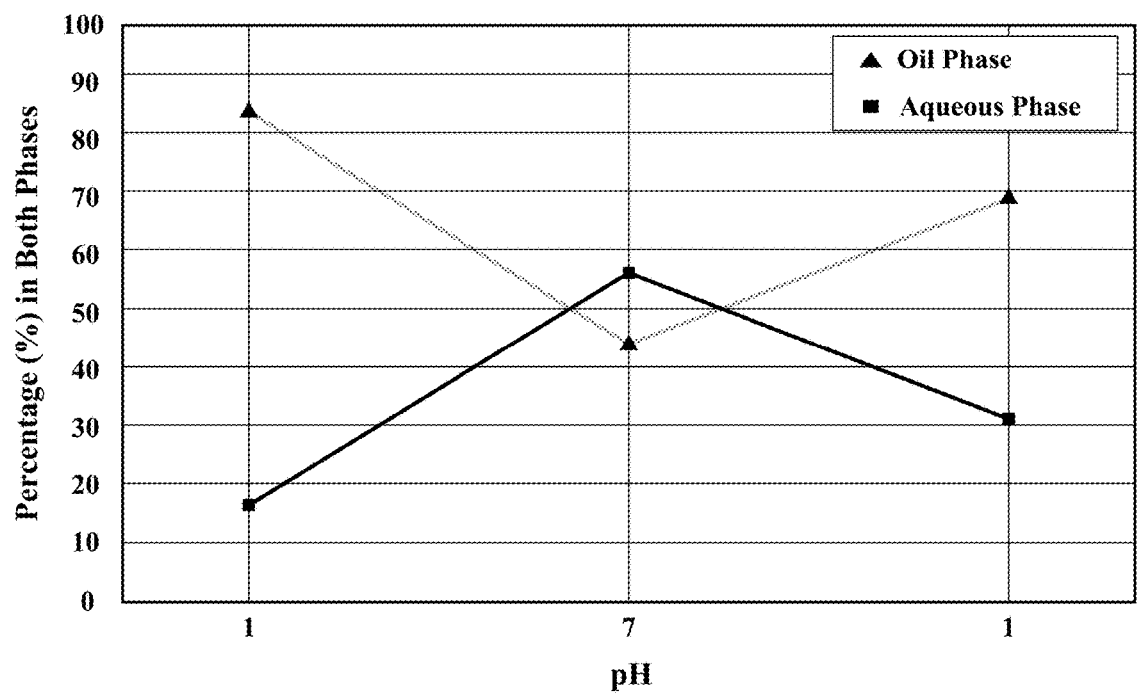
FIG. 30 depicts a plot of UV WIP percentage values for the HA, NIS whey isolate protein-containing composition during a pH cycle.

Referring now to FIG. 30, a plot of UV percentage values for the whey isolate protein from the HA, NIS whey isolate protein-containing composition in the pH 1 solutions and the pH 7 solution during the pH cycle. In the initial pH 1 solution, about 83.45% of the whey isolate protein (WIP) was in the oil phase and 16.55% in the aqueous phase. In the pH 7 solution, about 43.81% of the WIP was in the oil phase and 56.19% in the aqueous phase. In the final pH 1 solution, about 68.84% of the WIP was in the oil phase and 31.16% in the aqueous phase.

Figure 31:
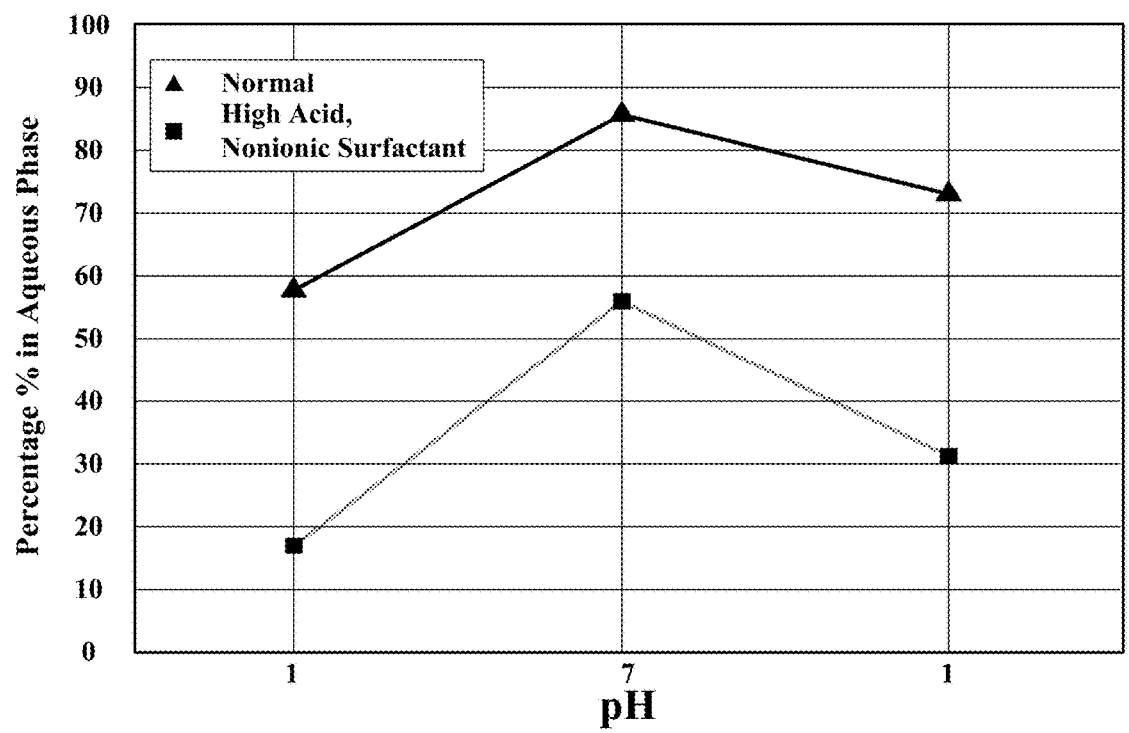
FIG. 31 depicts a plot of a comparison of UV WIP percentage values for the two whey isolate protein-containing compositions during a pH cycle evidencing a significant change in release and reabsorption properties of the oil matrix used for the proteins.

Referring now to FIG. 31, a plot of a comparison of UV percentage values in the aqueous phase for the whey isolate protein-containing composition of Example 15 and the UV percentage values for the HA, NIS whey isolate protein-containing composition is shown. The plot clearly shows that increasing the amount of oleic acid and adding a nonionic surfactant lowered the amount of WIP in the aqueous of the initial pH 1 solution, also lowers the amount of WIP released into the aqueous phase at pH 7 and lowered the amount of WIP in the aqueous phase of the final pH 1 solution. While the whey isolate protein has lower amount of WIP released at pH 7 compared to the whey isolate protein-containing composition of Example 15, the change in the matrix provides a composition that reduces that amount of protein released in the initial pH 1 solution to less than 20% and near 40% reduction in WIP in the initial pH 1 solution compared to the whey isolate protein-containing composition of Example 15. Additionally, the HA, NIS matrix showed a greater than 40% increase in reabsorption of the whey isolate protein compared to the whey isolate protein-containing composition of Example 15. Clearly, the oil carrier or matrix may be modified to prepare a protein composition that releases minimally at pH 1, releases at a higher rate at pH 7 and have enhanced reconstitution and API reabsorption properties. Applying the matrix to proteins such as heparin and insulin, oral formulations of these proteins may be formulated. It should also be recognized that duodenum reflux involves a small fraction of the material entering the duodenum from the stomach and the API delivered to the stomach will be absorbed from both the aqueous and oil phases in the duodenum. In fact, the oil phase may facilitate the absorption the API in the duodenum or at least on hinder the transport of the API into the blood stream or lymphatic system depending on the transportation mechanism for the API entering the blood stream or the lymphatic system.

Figure 32:
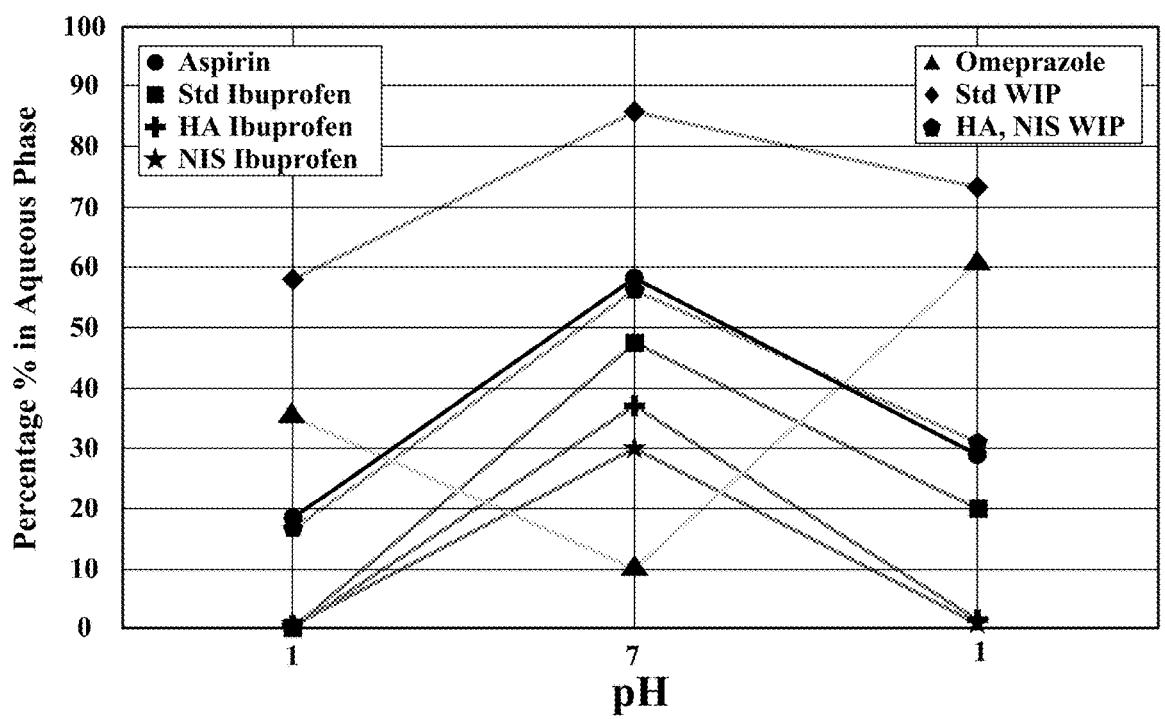
FIG. 32 depicts a plot of a comparison of UV API percentage values in the aqueous phase for aspirin-, ibuprofen-, omeprazole-, and whey isolate protein-containing compositions (with or without nonionic surfactant) during a pH cycle.

Referring now to FIG. 32, a plot of a comparison of UV percentage values in the aqueous phase of aspirin, standard ibuprofen (Std Ibuprofen), high oleic acid ibuprofen (HA Ibuprofen), nonionic surfactant ibuprofen (NIS Ibuprofen), standard whey isolate protein (Std WIP), high oleic acid, nonionic surfactant whey isolate protein (HA, NIS WIP), and omeprazole in the aqueous phase for their respective compositions is shown. The plot clearly shows that nonionic surfactants greatly modify API release amounts in the initial pH 1 solution, API release amounts in the pH 7 solution, mimicking duodenum fluid, and in API reabsorption amounts in the final pH 1 solution. It should be recognized that the behavior of ibuprofen to the different matrices, the inventors fully expect aspirin to behavior in a similar manner to ibuprofen. The inventors selected ibuprofen based on the fact ibuprofen is easier to analyze as it is not subject to hydrolysis like aspirin so only a single compound must be analyzed by UV spectrometry.

Example 17. Nonionic Surfactant-Aspirin-Containing Composition Preparation and pH Cycle Testing This example illustrates the preparation of a sample of an aspirin-containing composition subject to the duodenal reflux procedure outlined above, wherein the carrier includes 9 wt. % citric acid (drying agent), 15 wt. % lecithin, 15 wt. % nonionic surfactant (LAUROGLYCOL™ 90), 20 wt. % oleic acid, and 41 wt. % soybean oil.

The aspirin-containing composition included the following ingredients:

TABLE XXXIII

| Ingredient | Quantity per Unit (mg) | Quantity (g) |
|---|---|---|
| Aspirin (ASA) | 20.25 | 20.25 |
| Citric Acid Anhydrous Powder USP/EP | 1.89 | 1.89 |
| Lecithin | 3.16 | 3.16 |
| Oleic Acid NF/EP | 4.21 | 4.22 |
| Soybean Oil-IV | 8.63 | 8.64 |
| Nonionic Surfactant (LAUROGLYCOL ™ 90) | 3.16 | 3.17 |
| Total | 41.30 | 41.33 |

Nonionic Surfactant-Aspirin-Containing Composition Preparation Procedure

The aspirin-containing composition was prepared as follows:
1. Screen citric acid and aspirin (ASA) through a 40 mesh hand screen;
2. Add oleic acid, soybean oil, lecithin, and nonionic surfactant into a 150 mL beaker and heat the mixture while stirring with a stir bar on a hot plate to until the mixture achieves visual uniformity;
3. Add citric acid to the mixture while stirring with the stir bar on the hot plate until the mixture achieves visual uniformity;
4. Add aspirin to the mixture while stirring with a Caframo mixer until the mixture achieves visual uniformity; and
5. Continue stirring the mixture during testing to maintain uniformity.

Aspirin-Containing Composition pH Cycle Test Procedure

The aspirin-containing composition pH cycle test was performed as follows:
1. Place 10 g of the nonionic surfactant-aspirin-containing composition in a 150 mL beaker containing 100 mL of a 0.1 N HCl solution having a pH of about 1, simulated gastric fluid;
2. Observe and photograph the nonionic surfactant-aspirin-containing composition in the pH 1 solution;
3. Collect a sample of the oil phase and the aqueous phase from the pH 1 solution for UV analysis;
4. Add concentrated NaOH to the beaker with stirring while monitoring the pH with a pH meter until the pH is about 7, simulated duodenal fluid;
5. Observe and photograph the nonionic surfactant-aspirin-containing composition in the pH 7 solution;
6. Collect a sample of the oil phase and aqueous phase from the pH 7 solution for UV analysis;
7. Add concentrated HCl to the beaker with stirring while monitoring the pH with the pH meter until the pH is about 1;
8. Observe and photograph the nonionic surfactant-aspirin-containing composition in the pH 1 solution, back to simulated gastric fluid; and
9. Collect a sample of the oil phase and aqueous phase from the pH 1 solution for UV analysis.

Figure 33:
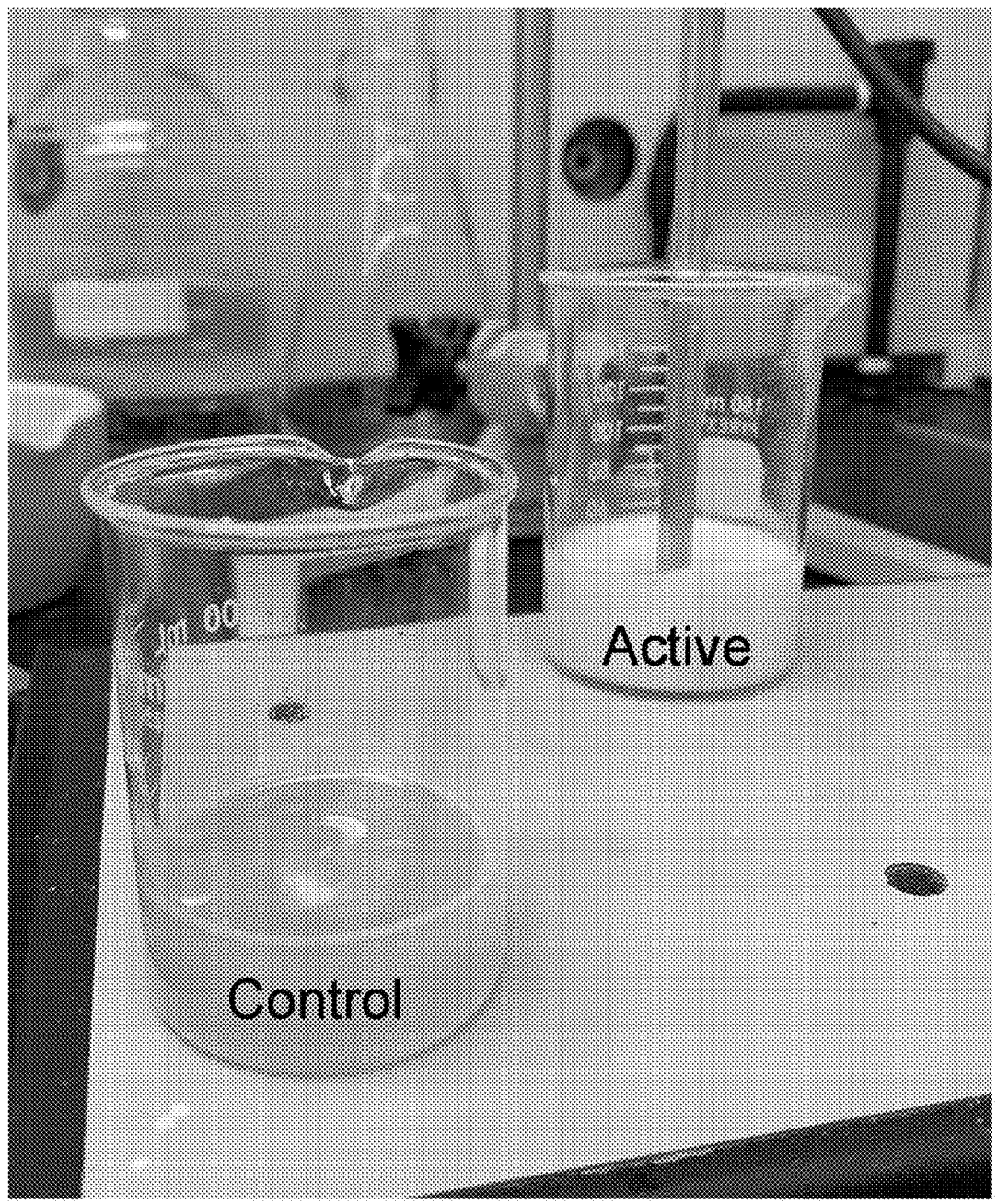
FIG. 33 depicts photographs of the preparation of the nonionic surfactant-aspirin-containing composition compared to the control composition.

Photographs of Control and Nonionic Surfactant-Aspirin-Containing Compositions
Photographs of Mixing, pH Monitoring, and Temperature Monitoring Referring now to FIG. 33, photographs are shown of the control composition compared to the nonionic surfactant-aspirin-containing composition.

Figure 34:
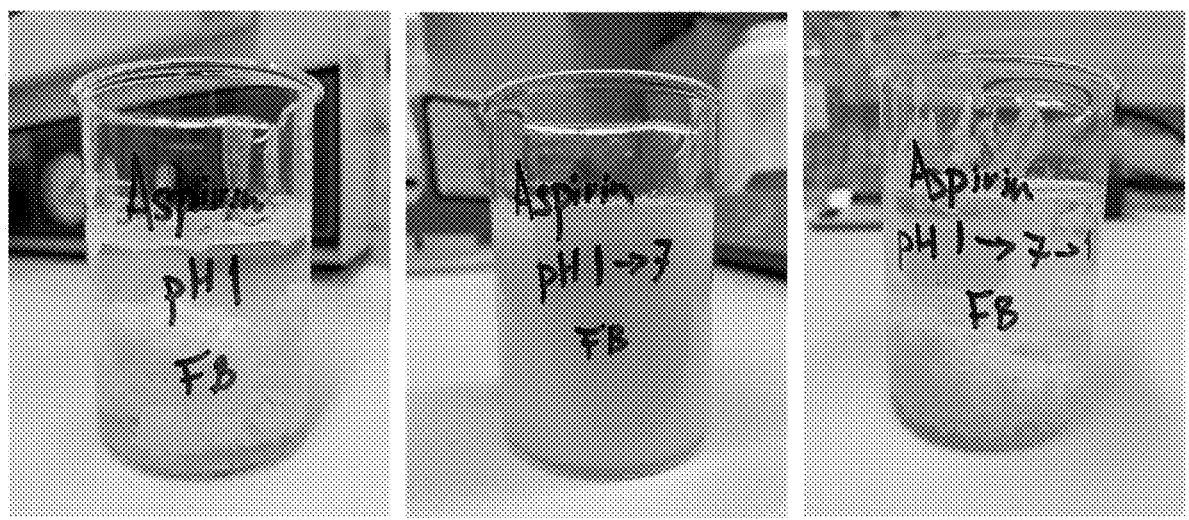
FIG. 34 depicts photographs of the nonionic surfactant-aspirin-containing composition during a pH cycle.

Photographs of Nonionic Surfactant-Aspirin-Containing Composition During a pH Cycle Referring now to FIG. 34, photographs show a sample of the nonionic surfactant-aspirin-containing composition in an initial pH 1 solution (left photograph), in a pH 7 solution after concentrated NaOH addition to the initial pH 1 solution (middle photograph), and in a final pH 1 solution after concentrated HCl addition to the pH 7 aqueous solution (right photograph). The nonionic surfactant-aspirin-containing composition is clearly immiscible in the initial pH 1 solution and is denser than the aqueous phase. When the pH is raised to pH 7, a change in the look of the control composition may be seen—compare the far left photograph to the middle photograph. At pH 7, the nonionic surfactant-aspirin-containing composition appears to include a top oil phase and a cloudy aqueous phase, likely an emulsion. When the pH of the pH 7 solution is lowered back to pH 1, the aqueous phase clarifies, while the oil phase now appears similar to its starting form.

UV Analysis of Nonionic Surfactant-Aspirin-Containing Samples Aspirin (ASA) UV Analysis The samples taken from the oil and aqueous phases during the pH cycling were analyzed using UV spectral analysis. Aspirin (ASA) is the only ingredient in the sample that includes an aromatic ring and has a distinct UV absorption. UV spectral analysis was used to determine the concentration of ASA in the UV detection samples. The following table includes ASA concentrations as determined by UV spectral analysis:

TABLE XXXIV

| UV Aspirin (ASA) Phase Concentration Data in mg/mL | | | |
|---|---|---|---|
| Solution | ASA in Oil Phase (mg/mL) | ASA Aqueous Phase (mg/mL) | ASA in Oil Phase (%) |
| pH 1 | 0.77 | 0.03 | 96.69 |
| pH 1-7 | 0.20 | 0.24 | 45.41 |
| pH 1-7-1 | 0.98 | 0.04 | 96.06 |

Figure 35:
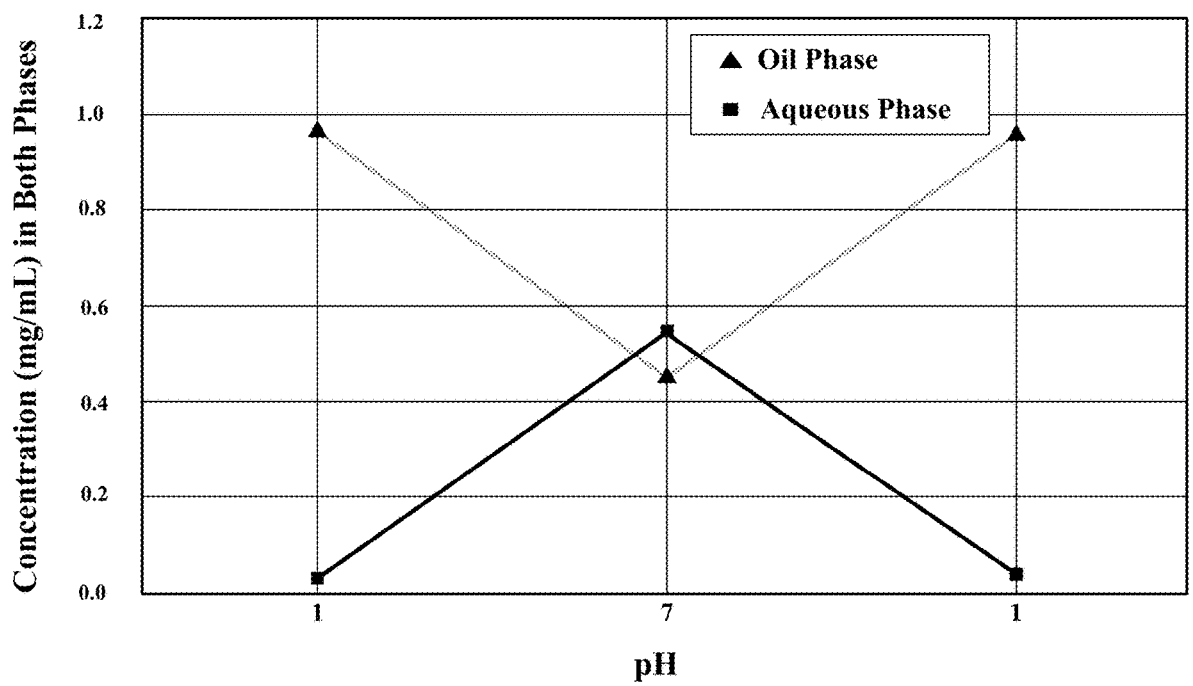
FIG. 35 depicts a plot of UV aspirin concentration values for the NIS-ASA-containing composition during a pH cycle.

Referring now to FIG. 35, a plot of the UV aspirin (ASA) concentration values (mg/mL) for the oil phase and the aqueous phase from the sample of the nonionic surfactant-aspirin-containing composition during the pH cycle experiment is shown. Initially, the ASA (aspirin) is almost exclusively in the oil phase with 0.77 mg/mL (96.69%) in the oil phase compared to 0.03 mg/mL (3.31%) in the aqueous phase. When the pH is raised to pH 7, the ASA (aspirin) is present in the aqueous phase to a greater degree than in the oil phase with 0.24 mg/mL (54.59%) in the aqueous phase compared to 0.20 mg/mL (45.41%) in the oil phase. When the pH is lowered back to pH 1, a large amount of the ASA (aspirin) from the aqueous phase was almost completely reabsorbed into the oil phase with 0.98 mg/mL (96.06%) in the oil phase compared to 0.04 mg/mL (3.94%) in the aqueous phase. Clearly, the carrier of this disclosure may be tailored to significantly decrease the amount of API releases in the stomach and significantly increase the amount of API reabsorbed into the carrier during duodenal reflux, a completely unexpected result.

Figure 36:
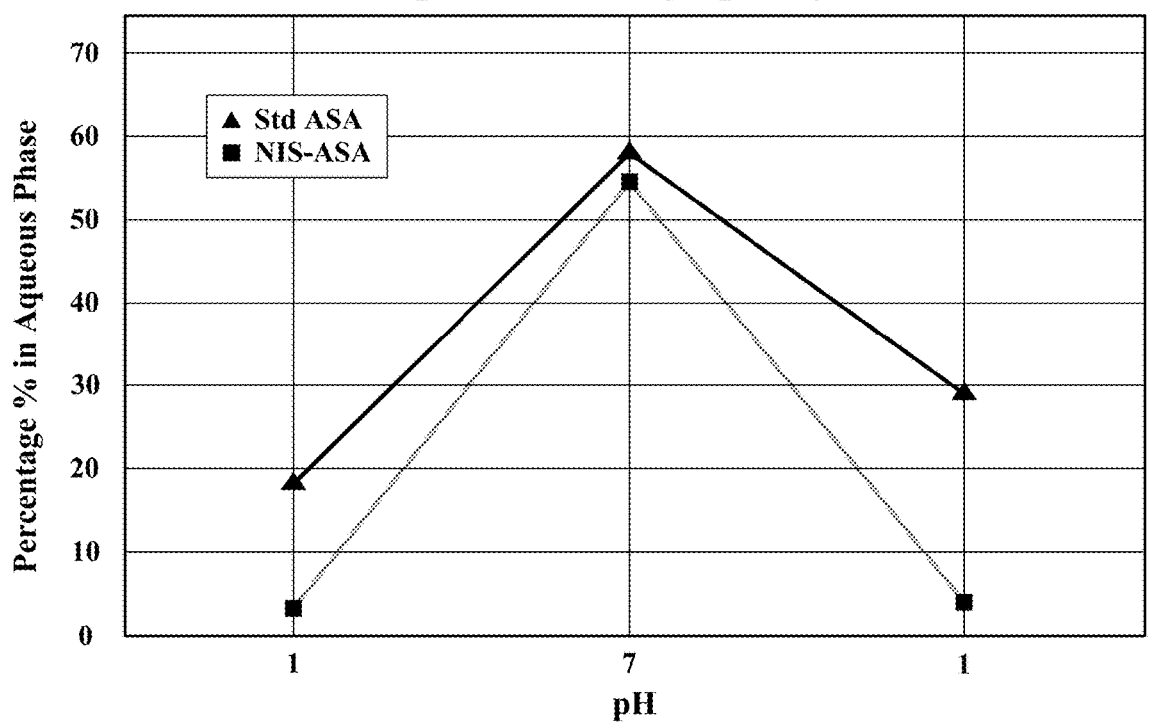
FIG. 36 depicts a plot comparison of UV aspirin concentration values for the two aspirin-containing compositions (with or without nonionic surfactant) during a pH cycle.

Referring now to FIG. 36, a plot comparing the UV aspirin (ASA) percentage concentration values for the aqueous phase of the aspirin-containing composition of Example 10 and the aspirin (ASA) percentage concentration values for the aqueous phase of the nonionic surfactant-aspirin-containing composition of this Example 17 during the pH cycle experiment is shown. The addition of the nonionic surfactant to the aspirin-containing composition of Example 10 resulted in a 77.78% decrease in the amount of aspirin (~18% to ~4%) in the initial pH 1 aqueous phase and a 86.21% increase in the amount of aspirin (~30% to ~4%) reabsorbed in the final pH 1 aqueous phase during the pH cycle. These results, as in the ibuprofen and whey isolate protein examples, are significant and unexpected as there is no guidance from the prior art that the addition of a nonionic surfactant would result in such as marked increase in concentration of the API in the oil phase in the initial pH 1 solution and the marked increase in the concentration of the API in the oil phase in the final pH 1 solution.

Figure 37:
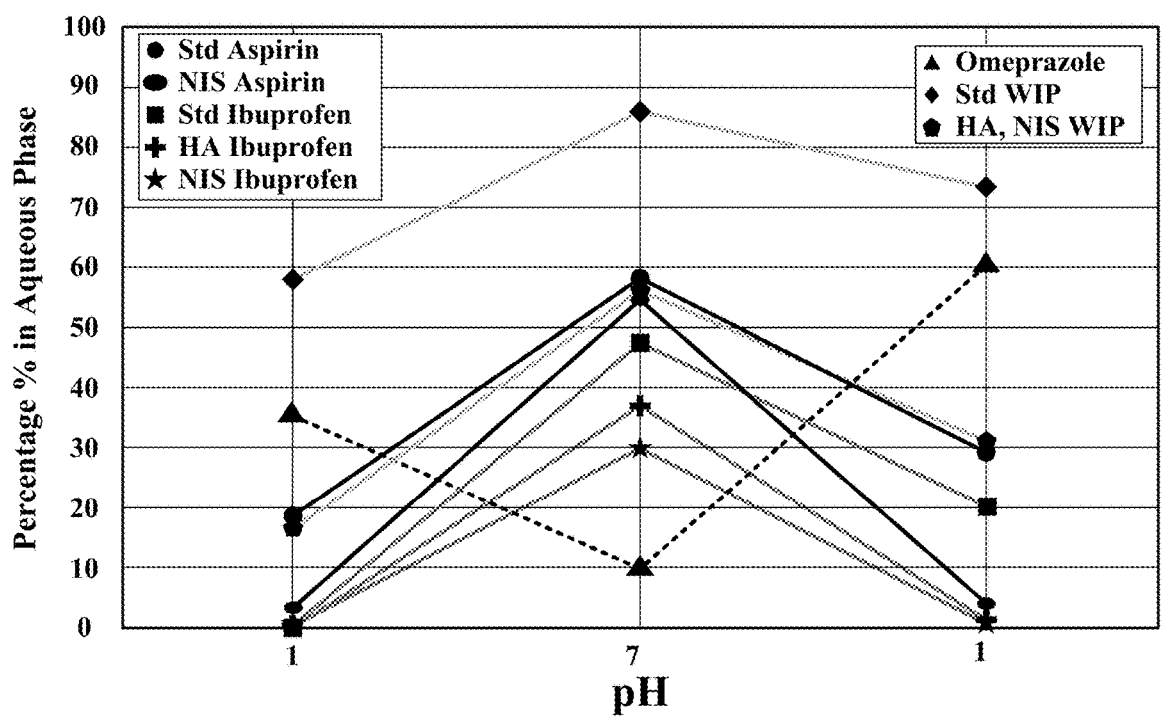
FIG. 37 depicts a plot of a comparison of UV API percentage values in the aqueous phase for aspirin-, ibuprofen-, omeprazole-, and whey isolate protein-containing compositions (with or without nonionic surfactant) during a pH cycle.

Referring now to FIG. 37, a plot of a comparison of UV percentage values in the aqueous phase of standard aspirin (Std ASA), nonionic surfactant aspirin (NIS ASA), standard ibuprofen (Std Ibuprofen), high oleic acid ibuprofen (HA Ibuprofen), nonionic surfactant ibuprofen (NIS Ibuprofen), standard whey isolate protein (Std WIP), high oleic acid, nonionic surfactant whey isolate protein (HA, NIS WIP), and omeprazole in the aqueous phase for their respective compositions is shown. The plot clearly shows that nonionic surfactants greatly modify API release amounts in the initial pH 1 solution, API release amounts in the pH 7 solution, mimicking duodenum fluid, and in API reabsorption amounts in the final pH 1 solution. The data clearly shows that the carrier may be tailored to significantly reduce the amount of API reduced in the initial pH 1 solution and significantly increase the amount of API reabsorbed in the final pH 1 solution.

All references cited herein are incorporated by reference. Although the disclosure has been disclosed with reference to its preferred embodiments, from reading this description those of skill in the art may appreciate changes and modification that may be made which do not depart from the scope and spirit of the disclosure as described above and claimed hereafter.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Embodiment 1. A pharmaceutical carrier composition comprising:
  (a) a non-aqueous pH dependent release system; and
  (b) a non-aqueous pH dependent reassembly/assembly and reabsorption/absorption system,
    wherein:
      (i) the carrier composition has a low pH form and a high pH form;
      (ii) the carrier composition is formulated to release one or more biologically active agents minimally from a low pH form and maximally from a high pH form due to the non-aqueous pH dependent release system;

(iii) the carrier composition is formulated to either reassemble into the low pH form or assembly into a new low pH form due to the non-aqueous pH dependent reassembly/assembly and reabsorption/absorption system; and (iv) the carrier is formulated to either reabsorb the one or more biologically active agents in its reassembled form or absorb the one or more biologically active agents in the newly assembled form.

Embodiment 2. The composition of Embodiment 1, wherein the non-aqueous pH dependent reassembly/assembly and reabsorption/absorption system comprises:

(a) one or more polyacids, (b) one or more polymers including a plurality of carboxylic acid moieties, (c) one or more surfactants, (d) one or more water insoluble oligomers, (e) one or more water insoluble polymers, and any combination thereof.

Embodiment 3. The composition of Embodiment 1 or 2, wherein the pH dependent release system comprises at least 5 wt. % of a carboxylic acid having at least 8 carbon atoms.

Embodiment 4. The composition of Embodiment 3, wherein the pH dependent release system comprises at least 8 wt. % of a carboxylic acid having at least 8 carbon atoms.

Embodiment 5. The composition of Embodiment 4, wherein the pH dependent release system comprises at least 10 wt. % of a carboxylic acid having at least 8 carbon atoms.

Embodiment 6. The composition of Embodiment 5, wherein the pH dependent release system comprises at least 15 wt. % of a carboxylic acid having at least 8 carbon atoms.

Embodiment 7. The composition of any one of Embodiments 1 to 6, wherein the carboxylic acid having at least 8 carbon atoms is a monocarboxylic acid.

Embodiment 8. The composition of any one of Embodiments 1 to 7, wherein the pH dependent release system comprises a carboxylic acid having at least 8 carbon atoms with a low melting point.

Embodiment 9. The composition of any one of Embodiments 1 to 8, wherein the pH dependent release system comprises a carboxylic acid having at least 8 carbon atoms with a medium melting point.

Embodiment 10. The composition of any one of Embodiments 1 to 9, wherein the pH dependent release system comprises a carboxylic acid having at least 8 carbon atoms with a high melting point.

Embodiment 11. The composition of any one of Embodiments 1 to 10, wherein the non-aqueous pH dependent reassembly/assembly and reabsorption/absorption system comprises one or more poly acids.

Embodiment 12. The composition of Embodiment 11, wherein the one or more polyacids comprises a biocompatible fatty poly acid.

Embodiment 13. The composition of Embodiment 11 or 12, wherein the one or more polyacids comprise Glutaric acid (GA).

Embodiment 14. The composition of any one of Embodiments 11 to 13, wherein the one or more polyacids comprise EUDRAGIT® L (EL).

Embodiment 15. The composition of any one of Embodiments 11 to 14, wherein the one or more polyacids comprise EUDRAGIT® E (EE).

Embodiment 16. The composition of any one of Embodiments 11 to 15, wherein the one or more polyacids comprise Hypromellose Phtalate (HPMC-P).

Embodiment 17. The composition of any one of Embodiments 1 to 16, wherein the non-aqueous pH dependent reassembly/assembly and reabsorption/absorption system comprises one or more polymers including a plurality of carboxylic acid moieties.

Embodiment 18. The composition of any one of Embodiments 1 to 17, wherein the non-aqueous pH dependent reassembly/assembly and reabsorption/absorption system comprises one or more surfactants.

Embodiment 19. The composition of Embodiment 18, wherein the one or more surfactants comprise a nonionic surfactant.

Embodiment 20. The composition of Embodiment 18 or 19, wherein the one or more surfactants comprise sorbitan trioleate (STO).

Embodiment 21. The composition of any one of Embodiments 18 to 20, wherein the one or more surfactants comprise sorbitan monooleate.

Embodiment 22. The composition of any one of Embodiments 18 to 21, wherein the one or more surfactants comprise sorbitan tristearate.

Embodiment 23. The composition of any one of Embodiments 1 to 22, wherein the non-aqueous pH dependent reassembly/assembly and reabsorption/absorption system comprises one or more water insoluble oligomers.

Embodiment 24. The composition of any one of Embodiments 1 to 23, wherein the non-aqueous pH dependent reassembly/assembly and reabsorption/absorption system comprises one or more water insoluble polymers.

Embodiment 25. The composition of any one of Embodiments 1 to 24, wherein the non-aqueous pH dependent reassembly/assembly and reabsorption/absorption system comprises a reconstitution agent with a low melting point.

Embodiment 26. The composition of any one of Embodiments 1 to 25, wherein the non-aqueous pH dependent reassembly/assembly and reabsorption/absorption system comprises a reconstitution agent with a medium melting point.

Embodiment 27. The composition of any one of Embodiments 1 to 26, wherein the non-aqueous pH dependent reassembly/assembly and reabsorption/absorption system comprises a reconstitution agent with a high melting point.

Embodiment 28. The composition of any one of Embodiments 1 to 27, wherein:

(a) the non-aqueous pH dependent release system is present in an amount between 10 wt. % and 95 wt. %; and (b) the non-aqueous pH dependent reassembly/assembly and reabsorption/absorption system is present in an amount between about 5 wt. % and 90 wt. %.

Embodiment 29. The composition of any one of Embodiments 1 to 28, wherein:

(a) the non-aqueous pH dependent release system is present in an amount between 20 wt. % and 95 wt. %; and (b) the non-aqueous pH dependent reassembly/assembly and reabsorption/absorption system is present in an amount between about 5 wt. % and 80 wt. %.

Embodiment 30. The composition of any one of Embodiments 1 to 29, wherein:

(a) the non-aqueous pH dependent release system is present in an amount between 30 wt. % and 95 wt. %; and (b) the non-aqueous pH dependent reassembly/assembly and reabsorption/absorption system is present in an amount between about 5 wt. % and 70 wt. %.

Embodiment 31. The composition of any one of Embodiments 1 to 30, wherein:

(a) the non-aqueous pH dependent release system is present in an amount between 40 wt. % and 95 wt. %; and (b) the non-aqueous pH dependent reassembly/assembly and reabsorption/absorption system is present in an amount between about 5 wt. % and 60 wt. %.

Embodiment 32. The composition of any one of Embodiments 1 to 31, wherein the non-aqueous pH dependent release system comprises:
(a) at least 15 wt. % of one or more monocarboxylic acids having at least 8 carbon atoms,
(b) at least 20 wt. % of one or more monocarboxylic acids having at least 8 carbon atoms, or
(c) at least 30 wt. % of one or more monocarboxylic acids having at least 8 carbon atoms.

Embodiment 33. The composition of any one of Embodiments 1 to 32, wherein the non-aqueous pH dependent release system comprises:
(a) at least 15 wt. % of a mixture of (i) one or more low melting point monocarboxylic acids, (ii) one or more medium melting point monocarboxylic acids, (iii) one or more high melting point monocarboxylic acids, or (iv) any combination thereof, and
(b) wherein:
(i) the low melting point monocarboxylic acids have melting point temperatures less than or equal to room temperature,
(ii) the medium melting point monocarboxylic acids have melting point temperatures greater than room temperature and less than or equal to a body temperature of a mammal, or a human, and
(iii) the high melting point monocarboxylic acids have melting point temperatures above the body temperature of a mammal, or a human.

Embodiment 34. The composition of any one of Embodiments 1 to 33, wherein the non-aqueous pH dependent release system further comprises one or more neutral lipids.

Embodiment 35. The composition of Embodiment 34, wherein the one or more neutral lipids comprise a fatty acid ester.

Embodiment 36. The composition of Embodiment 35, wherein the fatty acid ester is a fatty acid methyl ester.

Embodiment 37. The composition of Embodiment 35, wherein the fatty acid methyl ester is methyl linolenate.

Embodiment 38. The composition of Embodiment 35, wherein the fatty acid methyl ester is methyl oleate.

Embodiment 39. The composition of Embodiment 35, wherein the fatty acid methyl ester is methyl palmitate.

Embodiment 40. The composition of any one of Embodiments 33 to 39, wherein the non-aqueous pH dependent release system further comprises one or more low melting point neutral lipids.

Embodiment 41. The composition of any one of Embodiments 33 to 40, wherein the non-aqueous pH dependent release system further comprises one or more medium melting point neutral lipids.

Embodiment 42. The composition of any one of Embodiments 33 to 41, wherein the non-aqueous pH dependent release system further comprises one or more high melting point neutral lipids.

Embodiment 43. The composition of any one of Embodiments 1 to 42, further comprising less than 10 wt. % of one or more selected from (1) fatty acid salts, (2) secondary complexing agents, (3) protective agents, (4) excipients, (5) adjuvants, (6) drying agents, (7) antioxidants, (8) preservatives, (9) chelating agents, (10) viscomodulators, (11) tonicifiers, (12) flavorants and taste masking agents, (13) colorants, (14) odorants, (15) opacifiers, (16) suspending agents, and (17) binders.

Embodiment 44. The carrier composition according to any one of Embodiments 1 to 43, wherein the composition comprises less than 10 wt. % zwittterionic phospholipid.

Embodiment 45. A pharmaceutical composition comprising:
(a) a carrier composition according to any one of Embodiments 1 to 44; and
(b) one or more biologically active agents,
wherein a weight ratio of the carrier composition to the one or more biologically active agents is between about 10:1 and about 1:2.

Embodiment 46. The pharmaceutical composition of Embodiment 45, wherein the one or more biologically active agents is suspended in the carrier composition.

Embodiment 47. The pharmaceutical composition of Embodiment 45 or 46, wherein the one or more biologically active agents are crystalline solid particles.

Embodiment 48. The pharmaceutical composition of any one of Embodiments 45 to 47, wherein the biologically active agent comprises at least one agent selected from the group consisting of an acid-labile pharmaceutical agent, an anti-depressant, an anti-diabetic agent, an anti-epileptic agent, an anti-fungal agent, an anti-malarial agent, an anti-muscarinic agent, an anti-neoplastic agent, an immunosuppressant, an anti-protozoal agent, an anti-tussive, a neuroleptics, a beta-blocker, a cardiac inotropic agent, a corticosteroid, an anti-parkinsonian agent, a gastrointestinal agent, histamine, a histamine receptor antagonist, a keratolytic, a lipid regulating agent, a muscle relaxant, a nitrate, an anti-anginal agent, a nutritional agent, an opioid analgesic, a sex hormone, a stimulant, a nutraceutical, a peptide, a protein, a therapeutic protein, a nucleoside, a nucleotide, DNA, RNA, a glycosaminoglycan, an acid-labile drug, (+)-N{3-[3-(4-fluorophenoxy)phenyl]-2-cyclopenten-1-yl}-N-hydroxyurea, amylase, aureomycin, bacitracin, beta carotene, cephalosporins, chloromycetin, cimetidine, cisapride, cladribine, clorazepate, deramciclane, didanosine, digitalis glycosides, dihydrostreptomycin, erythromycin, etoposide, famotidine, a hormone, estrogen, insulin, adrenalin, heparin, lipase, milameline, novobiocin, pancreatin, penicillin salts, polymyxin, pravastatin, progabide, protease, quinapril, quinoxaline-2-carboxylic acid, [4-(R)carbamoyl-1-(S-3-fluorobenzyl-2-(S),7-dihydroxy-7-methyloctyl]amide, quinoxaline-2-carboxylic acid[1-benzyl-4-(4,4-difluoro-1-hydroxycyclohexyl)-2-hydroxy-4-hydroxycarbamoyl-butyl]-amide ranitidine, streptomycin, subtilin, sulphanilamide, a proton pump inhibitors, esomeprazole, lansoprazole, minoprazole, omeprazole, pantoprazole and rabeprazole.

Embodiment 49. The pharmaceutical composition of any one of Embodiments 45 to 48, wherein the one or more biologically active agents is hydrophobic.

Embodiment 50. The pharmaceutical composition of any one of Embodiments 45 to 49, wherein the one or more biologically active agents includes an acid labile drug.

Embodiment 51. The pharmaceutical composition of Embodiment 50, wherein the acid-labile drug is selected from the group consisting of heparin, insulin, erythropoietin, pancreatin, lansoprazole, omeprazole, pantoprazole, rabeprazole, penicillin salts, benzathine penicillin, polymyxin, sulphanilamide, and erythromycin.

Embodiment 52. The pharmaceutical composition of any one of Embodiments 45 to 48, wherein the one or more biologically active agents includes a non-steroidal anti-inflammatory agent (NSAID).

Embodiment 53. The pharmaceutical composition of Embodiment 52, wherein the NSAID is selected from the group consisting of ibuprofen, piroxicam, salicylate, aspirin, naproxen, indomethacin, diclofenac, mefenamic acid, COX2 inhibitors, and any mixture thereof.

Embodiment 54. The pharmaceutical composition of Embodiment 52, wherein the NSAID is selected from the group consisting of aspirin, naproxen, indomethacin and mefenamic acid.

Embodiment 55. The pharmaceutical composition of Embodiment 52, wherein the NSAID is aspirin.

Embodiment 56. A pharmaceutical carrier composition comprising:
(a) a non-aqueous pH dependent release system; and
(b) a non-aqueous pH dependent reassembly/assembly and reabsorption/absorption system,
wherein:
(i) the carrier composition has a low pH form and a high pH form;
(ii) the carrier composition is formulated to release one or more biologically active agents minimally from a low pH form and maximally from a high pH form due to the non-aqueous pH dependent release system;
(iii) the carrier composition is formulated to either reassemble into the low pH form or assembly into a new low pH form due to the non-aqueous pH dependent reassembly/assembly and reabsorption/absorption system; and
(iv) the carrier composition is formulated to either reabsorb the one or more biologically active agents in its reassembled form or absorb the one or more biologically active agents in the newly assembled form.

Embodiment 57. The composition of Embodiment 56, wherein the non-aqueous pH dependent reassembly/assembly and reabsorption/absorption system comprises one or more nonionic surfactants.

Embodiment 58. The composition of Embodiment 57, wherein the one or more nonionic surfactants are present in the composition in an amount of about 0.05 wt. % to about 20 wt. %.

Embodiment 59. The composition of Embodiments 57 or 58, wherein the one or more nonionic surfactants comprise an ethylene glycol mono fatty acid ester, a propylene glycol mono fatty acid ester, or a combination of two or more thereof.

Embodiment 60. The composition of Embodiments 57 or 58, wherein the one or more nonionic surfactants comprise one or more selected from sorbitan mono, di, and tri fatty acid esters.

Embodiment 61. The composition of Embodiments 57 or 58, wherein the one or more nonionic surfactants comprise propylene glycol monolaurate.

Embodiment 62. The composition of Embodiments 57 or 58, wherein the one or more nonionic surfactants comprise sorbitan trioleate (STO), sorbitan monooleate, or sorbitan tristearate, or a combination thereof.

Embodiment 63. The composition of any one of Embodiments 56 to 62, wherein the non-aqueous pH dependent reassembly/assembly and reabsorption/absorption system comprises one or more zwittterionic surfactants.

Embodiment 64. The composition of Embodiment 63, wherein the one or more zwittterionic surfactants comprise one or more zwittterionic phospholipids.

Embodiment 65. The composition of Embodiments 63 or 64, wherein the one or more zwitterionic surfactants comprise phosphatidic acid, phosphatidylethanolamine, phosphatidylcholine, phosphatidylserine, phosphatidylinositol, phosphatidylinositol phosphate, phosphatidylinositol bisphosphate, phosphatidylinositol triphosphate, ceramide phosphorylcholine, ceramide phosphorylethanolamine, ceramide phosphorylglycerol, dimyristoylphosphatidylcholine, distearoylphosphatidylcholine, dilinoleoylphosphatidylcholine, dipalmitoylphosphatidylcholine, or a combination of two or more thereof.

Embodiment 66. The composition of any one of Embodiments 63 to 65, wherein the one or more zwitterionic surfactants comprise lecithin.

Embodiment 67. The composition of any one of Embodiments 63 to 66, wherein the one or more zwittterionic surfactants are present in the composition in an amount of at least about 10 wt. %.

Embodiment 68. The composition of any one of Embodiments 63 to 66, wherein the one or more zwitterionic surfactants are present in the composition in an amount of about 5 wt. % to about 25 wt. %.

Embodiment 69. The composition of any one of Embodiments 56 to 68, wherein the pH dependent release system comprises a carboxylic acid having at least 8 carbon atoms.

Embodiment 70. The composition of Embodiment 69, wherein the carboxylic acid having at least 8 carbon atoms is present in the composition in an amount of at least about 5 wt. %.

Embodiment 71. The composition of Embodiment 69, wherein the carboxylic acid having at least 8 carbon atoms is present in the composition in an amount of at least about 10 wt. %.

Embodiment 72. The composition of Embodiment 69, wherein the carboxylic acid having at least 8 carbon atoms is present in the composition in an amount of at least about 15 wt. %.

Embodiment 73. The composition of Embodiment 69, wherein the carboxylic acid having at least 8 carbon atoms is present in the composition in an amount of at least about 20 wt. %.

Embodiment 74. The composition of Embodiment 69, wherein the carboxylic acid having at least 8 carbon atoms is present in the composition in an amount of about 5 wt. % to about 50 wt. %.

Embodiment 75. The composition of any one of Embodiments 69 to 74, wherein the carboxylic acid having at least 8 carbon atoms is a monocarboxylic acid.

Embodiment 76. The composition of any one of Embodiments 69 to 75, wherein the carboxylic acid having at least 8 carbon atoms is selected from the group consisting of as octenoic acid, decenoic acid, decadienoic acid, lauroleic acid, laurolinoleic acid, myristovaccenic acid, myristolinoleic acid, myristolinolenic acid, palmitolinolenic acid, palmitidonic acid, α-linolenic acid, stearidonic acid, dihomo-α-linolenic acid, eicosatetraenoic acid, eicosapentaenoic acid, clupanodonic acid, docosahexaenoic acid, 9,12,15,18,21-tetracosapentaenoic acid, 6,9,12,15,18,21-tetracosahexaenoic acid, myristoleic acid, palmitovaccenic acid, α-eleostearic acid, β-eleostearic acid, punicic acid, 7,10,13-octadecatrienoic acid, 9,12,15-eicosatrienoic acid, β-eicosatetraenoic acid, 8-tetradecenoic acid, 12-octadecenoic acid, linoleic acid, linolelaidic acid, γ-linolenic acid, calendic acid, pinolenic acid, dihomo-linoleic acid, dihomo-γ-linolenic acid, arachidonic acid, adrenic acid, osbond acid, palmitoleic acid, vaccenic acid, rumenic acid, paullinic acid, 7,10,13-eicosatrienoic acid, oleic acid, elaidic acid, gondoic acid, erucic acid, nervonic acid, 8,11-eicosadienoic acid, mead acid, sapienic acid, gadoleic acid, 4-hexadecenoic acid, petroselinic acid, and 8-eicosenoic acid, or a combination of two or more thereof.

Embodiment 77. The composition of any one of Embodiments 56 to 76, wherein the non-aqueous pH dependent reassembly/assembly and reabsorption/absorption system further comprises:
(a) one or more polyacids,
(b) one or more water insoluble oligomers,
(c) one or more water insoluble polymers, or
(d) any combination thereof.

Embodiment 78. The composition of Embodiment 77, wherein the one or more polyacids comprise a biocompatible fatty poly acid.

Embodiment 79. The composition of Embodiment 77, wherein the one or more polyacids comprise glutaric acid (GA), poly(methacrylic acid-co-methyl methacrylate), or hypromellose phthalate (HPMC-P), or a combination of two or more thereof.

Embodiment 80. The composition of any one of Embodiments 77 to 79, wherein the one or more polyacids are present in the composition in an amount of about 1 wt. % to about 10 wt. %.

Embodiment 81. The composition of any one of Embodiments 77 to 80, wherein the one or more water insoluble oligomers comprise low molecular weight poly(hexyl substituted lactides) (PHLA), low molecular weight polyethylene, polyvinyl chloride, ethyl cellulose, or acrylate polymers and copolymers thereof, or a combination of two or more thereof.

Embodiment 82. The composition of any one of Embodiments 77 to 81, wherein the one or more water insoluble oligomers are present in the composition in an amount of about 1 wt. % to about 5 wt. %.

Embodiment 83. The composition of any one of Embodiments 77 to 82, wherein the one or more water insoluble polymers comprise a copolymer of ethyl acrylate and methyl methacrylate, lactide-coglycolide, cellulose, or ethyl cellulose, or a combination of two or more thereof.

Embodiment 84. The composition of any one of Embodiments 77 to 83, wherein the one or more water insoluble polymers are present in the composition in an amount of about 1 wt. % to about 5 wt. %.

Embodiment 85. The composition of any one of Embodiments 56 to 84, wherein:
(a) the non-aqueous pH dependent release system is present in an amount between 10 wt. % and 95 wt. %; and
(b) the non-aqueous pH dependent reassembly/assembly and reabsorption/absorption system is present in an amount between about 5 wt. % and 90 wt. %.

Embodiment 86. The composition of any one of Embodiments 56 to 84, wherein:
(a) the non-aqueous pH dependent release system is present in an amount between 20 wt. % and 95 wt. %; and
(b) the non-aqueous pH dependent reassembly/assembly and reabsorption/absorption system is present in an amount between about 5 wt. % and 80 wt. %.

Embodiment 87. The composition of any one of Embodiments 56 to 84, wherein:
(a) the non-aqueous pH dependent release system is present in an amount between 30 wt. % and 95 wt. %; and
(b) the non-aqueous pH dependent reassembly/assembly and reabsorption/absorption system is present in an amount between about 5 wt. % and 70 wt. %.

Embodiment 88. The composition of any one of Embodiments 56 to 84, wherein:
(a) the non-aqueous pH dependent release system is present in an amount between 40 wt. % and 95 wt. %; and
(b) the non-aqueous pH dependent reassembly/assembly and reabsorption/absorption system is present in an amount between about 5 wt. % and 60 wt. %.

Embodiment 89. The composition of any one of Embodiments 56 to 88, wherein the non-aqueous pH dependent release system comprises:
(a) at least 15 wt. % of one or more monocarboxylic acids having at least 8 carbon atoms,
(b) at least 20 wt. % of one or more monocarboxylic acids having at least 8 carbon atoms, or
(c) at least 30 wt. % of one or more monocarboxylic acids having at least 8 carbon atoms.

Embodiment 90. The composition of any one of Embodiments 56 to 89, wherein the non-aqueous pH dependent release system comprises:
(a) at least 15 wt. % of a mixture of (i) one or more low melting point monocarboxylic acids, (ii) one or more medium melting point monocarboxylic acids, (iii) one or more high melting point monocarboxylic acids, or (iv) any combination thereof, and
(b) wherein:
(i) the low melting point monocarboxylic acids have melting point temperatures less than or equal to room temperature,
(ii) the medium melting point monocarboxylic acids have melting point temperatures greater than room temperature and less than or equal to a body temperature of a mammal, or a human, and
(iii) the high melting point monocarboxylic acids have melting point temperatures above the body temperature of a mammal, or a human.

Embodiment 91. The composition of any one of Embodiments 56 to 90, wherein the non-aqueous pH dependent release system further comprises one or more neutral lipids.

Embodiment 92. The composition of Embodiment 91, wherein the one or more neutral lipids comprise one or more biocompatible oils.

Embodiment 93. The composition of Embodiment 92, wherein the one or more biocompatible oils comprise peanut oil, canola oil, avocado oil, safflower oil, olive oil, corn oil, soybean oil, sesame oil, vitamin A, vitamin D, vitamin E, animal oils, fish oils, or krill oil, or a combination of two or more thereof.

Embodiment 94. The composition of Embodiment 91, wherein the one or more neutral lipids comprise a fatty acid ester.

Embodiment 95. The composition of Embodiment 94, wherein the fatty acid ester is a fatty acid methyl ester.

Embodiment 96. The composition of Embodiment 95, wherein the fatty acid methyl ester is methyl linolenate, methyl oleate, or methyl palmitate, or a combination of thereof.

Embodiment 97. The composition of any one of Embodiments 91 to 96, wherein the one or more neutral lipids are present in the composition in an amount of about 30 wt. % to about 75 wt. %.

Embodiment 98. The composition of any one of Embodiments 56 to 90, wherein the non-aqueous pH dependent release system further comprises one or more low melting point neutral lipids.

Embodiment 99. The composition of any one of Embodiments 56 to 90, wherein the non-aqueous pH dependent release system further comprises one or more medium melting point neutral lipids.

Embodiment 100. The composition of any one of Embodiments 56 to 90, wherein the non-aqueous pH dependent release system further comprises one or more high melting point neutral lipids.

Embodiment 101. The composition of any one of Embodiments 56 to 100, further comprising less than 10 wt. % of one or more selected from (1) fatty acid salts, (2) secondary complexing agents, (3) protective agents, (4) excipients, (5) adjuvants, (6) drying agents, (7) antioxidants, (8) preservatives, (9) chelating agents, (10) viscomodulators, (11) tonicifiers, (12) flavorants and taste masking agents, (13) colorants, (14) odorants, (15) opacifiers, (16) suspending agents, and (17) binders.

Embodiment 102. A pharmaceutical composition comprising, consisting essentially of, or consisting of:
  (a) a carrier composition according to any one of Embodiments 56 to 101; and
  (b) one or more biologically active agents,
wherein a weight ratio of the carrier composition to the one or more biologically active agents is between about 10:1 and about 1:2.

Embodiment 103. The pharmaceutical composition of Embodiment 102, wherein the one or more biologically active agents is suspended in the carrier composition.

Embodiment 104. The pharmaceutical composition of Embodiments 102 or 103, wherein the one or more biologically active agents are crystalline solid particles.

Embodiment 105. The pharmaceutical composition of any one of Embodiments 102 to 104, wherein the biologically active agent comprises at least one agent selected from the group consisting of an acid-labile pharmaceutical agent, an anti-depressant, an anti-diabetic agent, an anti-epileptic agent, an anti-fungal agent, an anti-malarial agent, an anti-muscarinic agent, an anti-neoplastic agent, an immunosuppressant, an anti-protozoal agent, an anti-tussive, a neuroleptics, a beta-blocker, a cardiac inotropic agent, a corticosteroid, an anti-parkinsonian agent, a gastrointestinal agent, histamine, a histamine receptor antagonist, a keratolytic, a lipid regulating agent, a muscle relaxant, a nitrate, an anti-anginal agent, a non-steroidal anti-inflammatory agent, a nutritional agent, an opioid analgesic, a sex hormone, a stimulant, a nutraceutical, a peptide, a protein, a therapeutic protein, a nucleoside, a nucleotide, DNA, RNA, a glycosaminoglycan, an acid-labile drug, (+)-N{3-[3-(4-fluorophenoxy)phenyl]-2-cyclopenten-1-yl}-N-hydroxyurea, amylase, aureomycin, bacitracin, beta carotene, cephalosporins, chloromycetin, cimetidine, cisapride, cladribine, clorazepate, deramciclane, didanosine, digitalis glycosides, dihydrostreptomycin, erythromycin, etoposide, famotidine, a hormone, estrogen, insulin, adrenalin, heparin, lipase, milameline, novobiocin, pancreatin, penicillin salts, polymyxin, pravastatin, progabide, protease, quinapril, quinoxaline-2-carboxylic acid, [4-(R)carbamoyl-1-(S-3-fluorobenzyl-2-(S),7-dihydroxy-7-methyloctyl]amide, quinoxaline-2-carboxylic acid[1-benzyl-4-(4,4-difluoro-1-hydroxycyclohexyl)-2-hydroxy-4-hydroxycarbamoyl-butyl]-amide ranitidine, streptomycin, subtilin, sulphanilamide, a proton pump inhibitors, esomeprazole, lansoprazole, minoprazole, omeprazole, pantoprazole and rabeprazole.

Embodiment 106. The pharmaceutical composition of any one of Embodiments 102 to 105, wherein the one or more biologically active agents is hydrophobic.

Embodiment 107. The pharmaceutical composition of any one of Embodiments 102 to 106, wherein the one or more biologically active agents includes an acid labile drug.

Embodiment 108. The pharmaceutical composition of Embodiment 107, wherein the acid-labile drug is selected from the group consisting of heparin, insulin, erythropoietin, pancreatin, lansoprazole, omeprazole, pantoprazole, rabeprazole, penicillin salts, benzathine penicillin, polymyxin, sulphanilamide, and erythromycin.

Embodiment 109. The pharmaceutical composition of any one of Embodiments 102 to 105, wherein the one or more biologically active agents includes a non-steroidal anti-inflammatory agent (NSAID).

Embodiment 110. The pharmaceutical composition of Embodiment 109, wherein the NSAID is selected from the group consisting of ibuprofen, piroxicam, salicylate, aspirin, naproxen, indomethacin, diclofenac, mefenamic acid, COX2 inhibitors, and any mixture thereof.

Embodiment 111. The pharmaceutical composition of Embodiment 110, wherein the NSAID is selected from the group consisting of aspirin, naproxen, indomethacin and mefenamic acid.

Embodiment 112. The pharmaceutical composition of Embodiment 110, wherein the NSAID is aspirin.

Embodiment 113. A pharmaceutical carrier composition consisting essentially of or consisting of:
  (a) a non-aqueous pH dependent release system;
  (b) a non-aqueous pH dependent reassembly/assembly and reabsorption/absorption system; and
  (c) optionally less than 10 wt. % of one or more selected from (1) fatty acid salts, (2) secondary complexing agents, (3) protective agents, (4) excipients, (5) adjuvants, (6) drying agents, (7) antioxidants, (8) preservatives, (9) chelating agents, (10) viscomodulators, (11) tonicifiers, (12) flavorants and taste masking agents, (13) colorants, (14) odorants, (15) opacifiers, (16) suspending agents, and (17) binders;
wherein:
  (i) the carrier composition has a low pH form and a high pH form;
  (ii) the carrier composition is formulated to release one or more biologically active agents minimally from a low pH form and maximally from a high pH form due to the non-aqueous pH dependent release system;
  (iii) the carrier composition is formulated to either reassemble into the low pH form or assembly into a new low pH form due to the non-aqueous pH dependent reassembly/assembly and reabsorption/absorption system; and
  (iv) the carrier composition is formulated to either reabsorb the one or more biologically active agents in its reassembled form or absorb the one or more biologically active agents in the newly assembled form.

Embodiment 114. The composition of Embodiment 113, wherein the non-aqueous pH dependent reassembly/assembly and reabsorption/absorption system comprises one or more nonionic surfactants.

Embodiment 115. The composition of Embodiment 114, wherein the one or more nonionic surfactants are present in the composition in an amount of about 0.05 wt. % to about 20 wt. %.

Embodiment 116. The composition of Embodiments 114 or 115, wherein the one or more nonionic surfactants comprise an ethylene glycol mono fatty acid ester, a propylene glycol mono fatty acid ester, or a combination of two or more thereof.

Embodiment 117. The composition of Embodiments 114 or 115, wherein the one or more nonionic surfactants comprise one or more selected from sorbitan mono, di, and tri fatty acid esters.

Embodiment 118. The composition of Embodiments 114 or 115, wherein the one or more nonionic surfactants comprise propylene glycol monolaurate.

Embodiment 119. The composition of Embodiments 114 or 115, wherein the one or more nonionic surfactants comprise sorbitan trioleate (STO), sorbitan monooleate, or sorbitan tristearate, or a combination thereof.

Embodiment 120. The composition of any one of Embodiments 113 to 119, wherein the non-aqueous pH dependent reassembly/assembly and reabsorption/absorption system comprises one or more zwittterionic surfactants.

Embodiment 121. The composition of Embodiment 120, wherein the one or more zwittterionic surfactants comprise one or more zwittterionic phospholipids.

Embodiment 122. The composition of Embodiments 120 or 121, wherein the one or more zwitterionic surfactants comprise phosphatidic acid, phosphatidylethanolamine, phosphatidylcholine, phosphatidylserine, phosphatidylinositol, phosphatidylinositol phosphate, phosphatidylinositol bisphosphate, phosphatidylinositol triphosphate, ceramide phosphorylcholine, ceramide phosphorylethanolamine, ceramide phosphorylglycerol, dimyristoylphosphatidylcholine, di stearoylphosphatidylcholine, dilinoleoylphosphatidylcholine, dipalmitoylphosphatidylcholine, or a combination of two or more thereof.

Embodiment 123. The composition of any one of Embodiments 120 to 122, wherein the one or more zwitterionic surfactants comprise lecithin.

Embodiment 124. The composition of any one of Embodiments 120 to 123, wherein the one or more zwittterionic surfactants are present in the composition in an amount of at least about 10 wt. %.

Embodiment 125. The composition of any one of Embodiments 120 to 123, wherein the one or more zwitterionic surfactants are present in the composition in an amount of about 5 wt. % to about 25 wt. %.

Embodiment 126. The composition of any one of Embodiments 113 to 125, wherein the pH dependent release system comprises a carboxylic acid having at least 8 carbon atoms.

Embodiment 127. The composition of Embodiment 126, wherein the carboxylic acid having at least 8 carbon atoms is present in the composition in an amount of at least about 5 wt. %.

Embodiment 128. The composition of Embodiment 126, wherein the carboxylic acid having at least 8 carbon atoms is present in the composition in an amount of about 5 wt. % to about 50 wt. %.

Embodiment 129. The composition of any one of Embodiments 126 to 128, wherein the carboxylic acid having at least 8 carbon atoms is a monocarboxylic acid.

Embodiment 130. The composition of any one of Embodiments 126 to 129, wherein the carboxylic acid having at least 8 carbon atoms is selected from the group consisting of as octenoic acid, decenoic acid, decadienoic acid, lauroleic acid, laurolinoleic acid, myristovaccenic acid, myristolinoleic acid, myristolinolenic acid, palmitolinolenic acid, palmitidonic acid, α-linolenic acid, stearidonic acid, dihomo-α-linolenic acid, eicosatetraenoic acid, eicosapentaenoic acid, clupanodonic acid, docosahexaenoic acid, 9,12,15,18,21-tetracosapentaenoic acid, 6,9,12,15,18,21-tetracosahexaenoic acid, myristoleic acid, palmitovaccenic acid, α-eleostearic acid, β-eleostearic acid, punicic acid, 7,10,13-octadecatrienoic acid, 9,12,15-eicosatrienoic acid, β-eicosatetraenoic acid, 8-tetradecenoic acid, 12-octadecenoic acid, linoleic acid, linolelaidic acid, γ-linolenic acid, calendic acid, pinolenic acid, dihomo-linoleic acid, dihomo-γ-linolenic acid, arachidonic acid, adrenic acid, osbond acid, palmitoleic acid, vaccenic acid, rumenic acid, paullinic acid, 7,10,13-eicosatrienoic acid, oleic acid, elaidic acid, gondoic acid, erucic acid, nervonic acid, 8,11-eicosadienoic acid, mead acid, sapienic acid, gadoleic acid, 4-hexadecenoic acid, petroselinic acid, and 8-eicosenoic acid, or a combination of two or more thereof.

Embodiment 131. The composition of any one of Embodiments 113 to 130, wherein the non-aqueous pH dependent reassembly/assembly and reabsorption/absorption system further comprises:
(a) one or more polyacids,
(b) one or more water insoluble oligomers,
(c) one or more water insoluble polymers, or
(d) any combination thereof.

Embodiment 132. The composition of Embodiment 131, wherein the one or more polyacids comprise a biocompatible fatty poly acid.

Embodiment 133. The composition of Embodiment 131, wherein the one or more polyacids comprise glutaric acid (GA), poly(methacrylic acid-co-methyl methacrylate), or hypromellose phthalate (HPMC-P), or a combination of two or more thereof.

Embodiment 134. The composition of any one of Embodiments 131 to 133, wherein the one or more polyacids are present in the composition in an amount of about 1 wt. % to about 10 wt. %.

Embodiment 135. The composition of any one of Embodiments 131 to 134, wherein the one or more water insoluble oligomers comprise low molecular weight poly(hexyl substituted lactides) (PHLA), low molecular weight polyethylene, polyvinyl chloride, ethyl cellulose, or acrylate polymers and copolymers thereof, or a combination of two or more thereof.

Embodiment 136. The composition of any one of Embodiments 131 to 135, wherein the one or more water insoluble oligomers are present in the composition in an amount of about 1 wt. % to about 5 wt. %.

Embodiment 137. The composition of any one of Embodiments 131 to 136, wherein the one or more water insoluble polymers comprise a copolymer of ethyl acrylate and methyl methacrylate, lactide-coglycolide, cellulose, or ethyl cellulose, or a combination of two or more thereof.

Embodiment 138. The composition of any one of Embodiments 131 to 137, wherein the one or more water insoluble polymers are present in the composition in an amount of about 1 wt. % to about 5 wt. %.

Embodiment 139. The composition of any one of Embodiments 113 to 138, wherein the non-aqueous pH dependent release system further comprises one or more neutral lipids.

Embodiment 140. The composition of Embodiment 139, wherein the one or more neutral lipids comprise one or more biocompatible oils.

Embodiment 141. The composition of Embodiment 140, wherein the one or more biocompatible oils comprise peanut oil, canola oil, avocado oil, safflower oil, olive oil, corn oil, soybean oil, sesame oil, vitamin A, vitamin D, vitamin E, animal oils, fish oils, or krill oil, or a combination of two or more thereof.

Embodiment 142. The composition of Embodiment 139, wherein the one or more neutral lipids comprise a fatty acid ester.

Embodiment 143. The composition of Embodiment 142, wherein the fatty acid ester is a fatty acid methyl ester.

Embodiment 144. The composition of Embodiment 143, wherein the fatty acid methyl ester is methyl linolenate, methyl oleate, or methyl palmitate, or a combination of thereof.

Embodiment 145. The composition of any one of Embodiments 139 to 144, wherein the one or more neutral lipids are present in the composition in an amount of about 30 wt. % to about 75 wt. %.

Embodiment 146. A pharmaceutical composition comprising, consisting essentially of, or consisting of:
(a) a carrier composition according to any one of Embodiments 113 to 145; and
(b) one or more biologically active agents,
wherein a weight ratio of the carrier composition to the one or more biologically active agents is between about 10:1 and about 1:2.

Embodiment 147. The pharmaceutical composition of Embodiment 146, wherein the one or more biologically active agents is suspended in the carrier composition.

Embodiment 148. The pharmaceutical composition of Embodiments 146 or 147, wherein the one or more biologically active agents are crystalline solid particles.

Embodiment 149. The pharmaceutical composition of any one of Embodiments 146 to 148, wherein the biologically active agent comprises at least one agent selected from the group consisting of an acid-labile pharmaceutical agent, an anti-depressant, an anti-diabetic agent, an anti-epileptic agent, an anti-fungal agent, an anti-malarial agent, an anti-muscarinic agent, an anti-neoplastic agent, an immunosuppressant, an anti-protozoal agent, an anti-tussive, a neuroleptics, a beta-blocker, a cardiac inotropic agent, a corticosteroid, an anti-parkinsonian agent, a gastrointestinal agent, histamine, a histamine receptor antagonist, a keratolytic, a lipid regulating agent, a muscle relaxant, a nitrate, an anti-anginal agent, a non-steroidal anti-inflammatory agent, a nutritional agent, an opioid analgesic, a sex hormone, a stimulant, a nutraceutical, a peptide, a protein, a therapeutic protein, a nucleoside, a nucleotide, DNA, RNA, a glycosaminoglycan, an acid-labile drug, (+)-N{3-[3-(4-fluorophenoxy)phenyl]-2-cyclopenten-1-yl}-N-hydroxyurea, amylase, aureomycin, bacitracin, beta carotene, cephalosporins, chloromycetin, cimetidine, cisapride, cladribine, clorazepate, deramciclane, didanosine, digitalis glycosides, dihydrostreptomycin, erythromycin, etoposide, famotidine, a hormone, estrogen, insulin, adrenalin, heparin, lipase, milameline, novobiocin, pancreatin, penicillin salts, polymyxin, pravastatin, progabide, protease, quinapril, quinoxaline-2-carboxylic acid, [4-(R)carbamoyl-1-(S-3-fluorobenzyl-2-(S),7-dihydroxy-7-methyloctyl]amide, quinoxaline-2-carboxylic acid[1-benzyl-4-(4,4-difluoro-1-hydroxycyclohexyl)-2-hydroxy-4-hydroxycarbamoyl-butyl]-amide ranitidine, streptomycin, subtilin, sulphanilamide, a proton pump inhibitors, esomeprazole, lansoprazole, minoprazole, omeprazole, pantoprazole and rabeprazole.

Embodiment 150. The pharmaceutical composition of any one of Embodiments 146 to 149, wherein the one or more biologically active agents is hydrophobic.

Embodiment 151. The pharmaceutical composition of any one of Embodiments 146 to 150, wherein the one or more biologically active agents includes an acid labile drug.

Embodiment 152. The pharmaceutical composition of Embodiment 151, wherein the acid-labile drug is selected from the group consisting of heparin, insulin, erythropoietin, pancreatin, lansoprazole, omeprazole, pantoprazole, rabeprazole, penicillin salts, benzathine penicillin, polymyxin, sulphanilamide, and erythromycin.

Embodiment 153. The pharmaceutical composition of any one of Embodiments 146 to 149, wherein the one or more biologically active agents includes a non-steroidal anti-inflammatory agent (NSAID).

Embodiment 154. The pharmaceutical composition of Embodiment 153, wherein the NSAID is selected from the group consisting of ibuprofen, piroxicam, salicylate, aspirin, naproxen, indomethacin, diclofenac, mefenamic acid, COX2 inhibitors, and any mixture thereof.

Embodiment 155. The pharmaceutical composition of Embodiment 154, wherein the NSAID is selected from the group consisting of aspirin, naproxen, indomethacin and mefenamic acid.

Embodiment 156. The pharmaceutical composition of Embodiment 154, wherein the NSAID is aspirin.

Other embodiments are set forth in the following claims.

We claim:

1. A pharmaceutical carrier composition comprising:
(a) a non-aqueous pH dependent release system comprising oleic acid; and
(b) a non-aqueous pH dependent reassembly/assembly and reabsorption/absorption system comprising:
(1) one or more nonionic surfactants comprising propylene glycol monolaurate, sorbitan trioleate (STO), sorbitan monooleate, or sorbitan tristearate, or a combination thereof, and
(2) one or more neutral lipids comprising one or more biocompatible oils selected from peanut oil, canola oil, avocado oil, safflower oil, olive oil, corn oil, soybean oil, sesame oil, vitamin A, vitamin D, vitamin E, animal oils, fish oils, or krill oil, or a combination of two or more thereof,
wherein:
the oleic acid is present in the carrier composition in an amount of about 5 wt. % to about 50 wt. %, the one or more nonionic surfactants are present in the carrier composition in an amount of about 0.05 wt. % to about 20 wt. %, and the one or more neutral lipids are present in the carrier composition in an amount of about 30 wt. % to about 75 wt. %;
(ii) the carrier composition is capable of adopting:
(a) a low pH form at a pH less than or equal to about pH 3, and
(b) a high pH form at a pH greater than about pH 3, and
(iii) the carrier composition is capable of:
(a) releasing one or more biologically active agents minimally from the low pH form of the carrier composition in a low pH environment;
(b) either reassembling into the low pH form or assembling into a new low pH form; and
(c) either reabsorbing the one or more biologically active agents into the low pH form or the new low pH form.

2. The composition of claim 1, wherein the composition protects the stomach from injury and/or protects the one or more biologically active agents from degradation during duodenal reflux.

3. The composition of claim 1, wherein the non-aqueous pH dependent reassembly/assembly and reabsorption/absorption system further comprises one or more zwitterionic surfactants, one or more anionic surfactants, one or more cationic surfactants, or any combination of two or more thereof; wherein:

(a) the one or more zwitterionic surfactants comprise:
   (i) zwitterionic phospholipids,
   (ii) betaines,
   (iii) sulfobetaines, or
   (iv) any combination of two or more thereof;
(b) the one or more anionic surfactants comprise:
   (i) carboxylate anionic surfactants,
   (ii) sulfate anionic surfactants,
   (iii) sulfonates anionic surfactants,
   (iv) phosphate esters anionic surfactants, or
   (v) any combination of two or more thereof; and
(c) the one or more cationic surfactants comprise quaternary ammonium salts.

4. The composition of claim 3, wherein:
(a) the one or more zwitterionic phospholipids comprise phosphatidic acid, phosphatidylethanolamine, phosphatidylcholine, phosphatidylserine, phosphatidylinositol, phosphatidylinositol phosphate, phosphatidylinositol bisphosphate, phosphatidylinositol triphosphate, ceramide phosphorylcholine, ceramide phosphorylethanolamine, ceramide phosphorylglycerol, dimyristoylphosphatidylcholine, di stearoylphosphatidylcholine, dilinoleoylphosphatidylcholine, dipalmitoylphosphatidylcholine, or a combination of two or more thereof;
(b) the one or more anionic surfactants comprise sodium lauryl sulfate; sodium laureth sulfate, dioctyl sodium sulfosuccinate, or sodium dodecyl sulfate; and
(c) the one or more cationic surfactants comprise alkyltrimethylammonium chlorides or alkyltrimethylammonium bromides.

5. The composition of claim 4, wherein the one or more zwitterionic surfactants are comprised in lecithin.

6. The composition of claim 4, wherein:
(a) the one or more nonionic surfactants are present in the composition in an amount of about 10 wt. % to about 20 wt. %;
(b) the one or more zwitterionic surfactants are present in the composition in an amount of at least about 10 wt. %;
(c) the one or more anionic surfactants are present in the composition in an amount of at least about 5 wt. %; and
(d) the one or more cationic surfactants are present in the composition in an amount of at least about 5 wt. %.

7. The composition of claim 3, wherein:
(a) the one or more nonionic surfactants are present in the composition in an amount of between about 0.05 wt. % and about 20 wt. %;
(b) the one or more zwitterionic surfactants are present in the composition in an amount of about 5 wt. % to about 25 wt. %;
(c) the one or more anionic surfactants are present in the composition in an amount of at least about 0.1 wt. % to about 5 wt. %; and
(d) the one or more cationic surfactants are present in the composition in an amount of at least about 0.1 wt. % to about 5 wt. %.

8. The composition of claim 1, wherein the oleic acid is present in the composition in an amount of between about 10 wt. % and about 50 wt. %, between about 15 wt. % and about 50 wt. %, or between about 20 wt. % and about 50 wt. %.

9. The composition of claim 1, wherein the non-aqueous pH dependent reassembly/assembly and reabsorption/absorption system further comprises:

(a) one or more polyacids comprising glutaric acid (GA), poly(methacrylic acid-co-methyl methacrylate), or hypromellose phthalate (HPMC-P), or a combination of two or more thereof,
(b) one or more water insoluble oligomers comprising low molecular weight poly(hexyl substituted lactides) (PHLA), low molecular weight polyethylene, polyvinyl chloride, ethyl cellulose, or acrylate polymers and copolymers thereof, or a combination of two or more thereof,
(c) one or more water insoluble polymers comprising a copolymer of ethyl acrylate and methyl methacrylate, lactide-coglycolide, cellulose, or ethyl cellulose, or a combination of two or more thereof, or
(d) any combination thereof.

10. The composition of claim 9, wherein the one or more polyacids are present in the composition in an amount of about 1 wt. % to about 10 wt. % or in an amount of about 1 wt. % to about 5 wt. %.

11. The composition of claim 9, wherein the one or more water insoluble polymers are present in the composition in an amount of about 1 wt. % to about 5 wt. %.

12. The composition of claim 1, further comprising less than 10 wt. % of one or more selected from the group consisting of (1) fatty acid salts, (2) secondary complexing agents, (3) protective agents, (4) excipients, (5) adjuvants, (6) drying agents, (7) antioxidants, (8) preservatives, (9) chelating agents, (10) viscomodulators, (11) tonicifiers, (12) flavorants and taste masking agents, (13) colorants, (14) odorants, (15) opacifiers, (16) suspending agents, and (17) binders.

13. A pharmaceutical composition comprising:
(a) a carrier composition according to claim 1; and
(b) one or more biologically active agents,
wherein the weight ratio of the carrier composition to the one or more biologically active agents is between about 10:1 and about 1:2.

14. The pharmaceutical composition of claim 13, wherein the one or more biologically active agents is suspended in the carrier composition.

15. The pharmaceutical composition of claim 13, wherein the one or more biologically active agents are crystalline solid particles.

16. The pharmaceutical composition of claim 13, wherein the biologically active agent comprises at least one agent selected from the group consisting of a non-steroidal anti-inflammatory agent, a peptide, and a protein.

17. The pharmaceutical composition of claim 13, wherein the one or more biologically active agents is hydrophobic.

18. The pharmaceutical composition of claim 13, wherein the one or more biologically active agents comprises an acid labile drug.

19. The pharmaceutical composition of claim 18, wherein the acid-labile drug is selected from the group consisting of heparin, insulin, erythropoietin, pancreatin, lansoprazole, omeprazole, pantoprazole, rabeprazole, penicillin salts, benzathine penicillin, polymyxin, sulphanilamide, and erythromycin.

20. The pharmaceutical composition of claim 13, wherein the one or more biologically active agents comprises a non-steroidal anti-inflammatory agent (NSAID) selected from the group consisting of ibuprofen, piroxicam, salicylate, aspirin, naproxen, indomethacin, diclofenac, mefenamic acid, COX2 inhibitors, and any mixture thereof.

* * * * *